United States Patent [19]

Mueller et al.

[11] Patent Number: 5,451,604
[45] Date of Patent: Sep. 19, 1995

[54] HALOGENATED PHENYLACETONITRILE ALKYLAMINOALKYLPHENYL COMPOUNDS AS IMMUNOSUPPRESSIVES

[75] Inventors: Richard A. Mueller, Glencoe; Thomas E. Barta, Evanston, both of Ill.; John P. McKearn, Pacific; Susan A. Gregory, St. Louis, both of Mo.; Richard A. Partis, Evanston; Francis J. Koszyk, Prospect Heights, both of Ill.

[73] Assignee: G. D. Searle & Co., Chicago, Ill.

[21] Appl. No.: 97,809

[22] Filed: Jul. 26, 1993

[51] Int. Cl.$^6$ .................. A61K 31/275; C07C 247/06; C07C 255/35
[52] U.S. Cl. .................. 514/423; 514/150; 552/8; 558/390; 558/426
[58] Field of Search .................. 558/408, 390, 426; 552/8; 514/150, 523

[56] References Cited

U.S. PATENT DOCUMENTS

| | | | |
|---|---|---|---|
| 3,261,859 | 7/1966 | Dengel | 260/465 |
| 4,593,042 | 6/1986 | Liang | 514/523 |
| 4,681,970 | 7/1987 | Liang | 558/408 |

FOREIGN PATENT DOCUMENTS 2014166  4/1990  Canada.
1069921  5/1967  United Kingdom.

OTHER PUBLICATIONS

G. Walz et al, *Transplantation*, 47, pp. 331–334 (1989).
A, E. Nel et al, *Scan. J. Immunology*, 24, pp. 283–290 (1986).
W. R. Chen, et al, *Acta. Pharmacologica Sinica*, 11(3), pp. 281–285, (1990).

*Primary Examiner*—Joseph Paul Brust
*Attorney, Agent, or Firm*—J. Timothy Keane

[57] ABSTRACT

A class of halogenated phenylacetonitrile alkylaminoalkylphenyl compounds having immunosuppressive properties is described. Compounds of this class would be useful in reducing recipient rejection of transplanted organs and for treatment of autoimmune or inflammatory diseases. Compounds of particular interest are of the formula

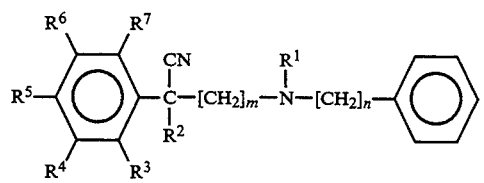

wherein m is a number selected from three to five, inclusive; wherein n one or two; wherein $R^1$ is selected from methyl, ethyl, n-propyl, isopropyl, n-butyl, sec-butyl, tert-butyl, iso-butyl, n-pentyl, isopentyl, cyclopropyl, cyclobutyl, cyclopentyl, cyclohexyl, cyclopropylmethyl, cyclobutylmethyl, cyclopentylmethyl, cyclohexylmethyl, benzyl and phenethyl; wherein $R^2$ is selected from methyl, ethyl, n-propyl, isopropyl, n-butyl, sec-butyl, tert-butyl, iso-butyl, n-pentyl, isopentyl, cyclopropyl, cyclobutyl, cyclopentyl, cyclohexyl, cyclopropylmethyl, cyclobutylmethyl, cyclopentylmethyl, cyclohexylmethyl, benzyl and phenethyl; wherein each of $R^3$ through $R^7$ is selected from hydrido, fluoro, chloro, bromo, azide, trifluoromethyl, difluorochloromethyl, 1,1-difluoroethyl, 2,2,2-trifluoroethyl, perfluoroethyl and 2,2,2-tetrafluoropropyl; with the proviso that at least one of $R^3$ through $R^7$ is selected from fluoro and trifluoromethyl; or a tautomer thereof or a pharmaceutically-acceptable salt thereof.

4 Claims, No Drawings

HALOGENATED PHENYLACETONITRILE ALKYLAMINOALKYLPHENYL COMPOUNDS AS IMMUNOSUPPRESSIVES

FIELD OF THE INVENTION

This invention is in the field of clinical immunology and relates to compounds having immunosuppressive properties. Of particular interest is a family of halogenated phenylacetonitrile alkylaminoalkylphenyl compounds for reducing recipient acute or chronic rejection of transplanted cells or organs, and for treatment of autoimmune or inflammatory diseases, hypersensitivity reactions of the acute or delayed type, allergic or asthmatic disorders, contact dermatitis, granulomas, meningitis, arthritis, and septic shock.

BACKGROUND OF THE INVENTION

Successful organ transplantation requires effective physiological and pharmacological intervention of the immune system of an organ recipient. Immunologic mechanisms are universal within the human species. But histocompatibility variations between donor and recipient lead inevitably to rejection of donor tissue by stimulation of the recipient's immune system except, perhaps, in donor-recipient pairing of the monozygotic type. One approach to intervention of immune response in an organ transplant recipient, especially a recipient targeted for an allogenic or homologous graft, is by the use of immunosuppressive drugs. These drugs have been used to prolong survival of transplanted organs in recipients in cases involving, for example, transplants of kidney, liver, heart, bone marrow and pancreas.

There are several types of immunosuppressive drugs available for use in reducing organ rejection in transplantation. Such drugs fall within three major classes, namely: antiproliferative agents, antiinflammatory-acting compounds and inhibitors of lymphocyte activation.

Examples of the class of cytotoxic or antiproliferative agents are azathioprine, cyclophosphamide and methotrexate. The compound azathioprine acts by interrupting DNA synthesis through inhibition of purine metabolism. The compound cyclophosphamide is an alkylating agent which interferes with enzyme actions and cell proliferation and interrupts DNA synthesis by binding to cellular DNA, RNA, and proteins. The compound methotrexate is a folic acid antagonist which interferes with nucleotide and protein synthesis. Drugs of the antiproliferative class may be effective immunosuppressives in patients with chronic inflammatory disorders and in organ transplant recipients by limiting cell proliferation. These drugs which abrogate mitosis and cell division have severe cytotoxic side effects on normal cell populations which have a high turn-over rate, such as bone marrow cells and cells of the gastrointestinal (GI) tract lining. Accordingly, such drugs often have severe side effects, particularly, lymphopenia, neutropenia, bone marrow depression, hemorrhagic cystitis, liver damage, increased incidence of malignancy, hair loss, GI tract disturbances, and infertility.

A second class of immunosuppressive drugs for use in transplantation is provided by compounds having antiinflammatory action. Representatives of this drug class are generally known as adrenal corticosteroids and have the advantage of not exerting globally systemic cytotoxic effects. These compounds usually act by preventing or inhibiting inflammatory responses or by reducing cytokine production, or by reducing chemotaxis, or by reducing neutrophil or macrophage activation or effector function. Typical examples of adrenal corticosteroids are prednisone and prednisolone which affect carbohydrate and protein metabolism as well as immune functions. Compounds of this class are sometimes used in combination with cytotoxic agents, such as compounds of the antiproliferative class because the corticosteroids are significantly less toxic. But the adrenal corticosteroids lack specificity of effect and can exert a broad range of metabolic, antiinflammatory and auto-immune effects. Typical side effects of this class include increased organ-recipient infections and interference with wound healing, as well as disturbing hemodynamic balance, carbohydrate and bone metabolism and mineral regulation.

A third class of immunosuppressive drugs for use in organ transplantation is provided by compounds which are immunomodulatory and generally prevent or inhibit leukocyte activation. Such compounds usually act by blocking activated T-cell effector functions or proliferation, or by inhibiting cytokine production, or by preventing or inhibiting activation, differentiation or effector functions of platelet, granulocyte, B-cell, or macrophage actions. The cyclosporin family of compounds is the leading example of drugs in this class. Such compounds are polypeptide fungal metabolites which have been found to be very effective in suppressing helper T cells so as to reduce both cellular and humoral responses to newly-encountered antigens. Cyclosporins alter macrophage and lymphocyte activity by reducing cytokine production or secretion and, in particular, by interfering with activation of antigen-specific CD-4 cells, by preventing IL-2 secretion and secretion of many T-cell products, as well as by interfering with expression of receptors for these lymphokines on various cell types. Cyclosporin A, in particular, has been used extensively as an immunosuppressive agent in organ transplantation. Other microbial metabolites include cyclosporins such as cyclosporin B and cyclosporin G, and another microbial product known as FK-506. Cyclosporin A suppresses humoral immunity as well as cell-mediated reactions. Cyclosporin A is indicated for organ rejection in kidney, liver, heart, pancreas, bone-marrow and heart-lung transplants. Cyclosporin A is also useful in the treatment of autoimmune and inflammatory diseases, including rheumatoid arthritis, Crohn's disease, Graves ophthalmopathy, severe psoriasis, aplastic anemia, multiple-sclerosis, alopecia areata, penphigus and penphigoid, dermatomyositis, polymyositis, Behcet's disease, uveitis, pulmonary sarcocidiosis, biliary cirrhosis, myasthenia gravis and atopic dermatitis.

Cyclosporins do possess several significant disadvantages. Firstly, while cyclosporins have provided significant benefits in organ transplantation, cyclosporins are non-specific immunosuppressives. Thus, immunologic reactions to transplanted tissue are not totally impeded, requiring concomitant treatment with prednisone methylprednisolone and/or other immunosuppression agents including monoclonal antibodies such as anti-CD3 or anti-CD5/CD7. Desirable immune reactions may be reduced against other foreign antigens. Secondly, cyclosporins can produce severe side effects in many organ recipients. And cyclosporins show host-variable effects on the liver, the CNS and GI tract. Significant among the adverse side effects are damage to the kidney and liver, hyperplasia of gum tissue, refractory hypertension and increased incidence of infections and malignancy.

Thus, the need remains for efficacious, selective immunosuppressive drugs in organ transplantation, especially for grafts between less-than-perfectly matched donor-recipient pairs.

Phenylacetonitrile compounds are known for use in treatment of cardiovascular diseases. For example, U.S. Pat. No. 3,261,859 describes phenylacetonitrile compounds, including the well-known compound verapamil, for use as coronary dilators. U.S. Pat. No. 4,593,042 describes certain bicycloamino-substituted phenylacetonitrilealkyl compounds, including several specific compounds having an isopropyl group attached to the alkylene alpha carbon of the phenylacetonitrile nucleus. Such compounds are characterized as calcium ion channel blockers for use in treatment of hypertension. U.S. Pat. No. 4,681,970 describes bicycloamino-substituted phenylacetonitrilealkyl compounds, several specific compounds of which have a long chain alkyl group (i.e., twelve carbons) attached to the alkylene alpha carbon of the phenylacetonitrile nucleus. These compounds are characterized as calcium channel blockers for treatment of hypertension.

Phenylacetonitrile compounds have been investigated for other pharmaceutical purposes. For example, certain calcium channel blocking agents, including verapamil, have been investigated for antiproliferative effects on T-cell mitogenesis [G. Walz et al, *Transplantation*, 47, 33–334 (1989)]. Various calcium channel blockers, including verapamil and nifedipine, have been studied for interaction with stimulated T-lymphocytes [A. Nell et al, *Scan. J. Immunolgy*, 24, 283–290 (1986)]. German Offen. 3,826,796 published 8 Feb. 1990 describes substituted phenylacetonitrile compounds for use in overcoming resistance to antimalarial or anticancer agents. The calcium antagonists verapamil, nifedipine and nicardipine were compared and found to produce dose-dependent acute and chronic antiinflammatory effects [W. R. Chen et al, *Acta. Pharmacologica Sinica*, 11(3), 281–285 (1990)]. A description of the preparation of substituted phenylacetonitriles was disclosed in United Kingdom Patent No. 1,069,921. The patent, however, failed to describe any utility for the compounds.

DESCRIPTION OF INVENTION

Reduction in recipient rejection of a transplanted organ, or treatment of an autoimmune or inflammatory disease, or a hypersensitivity reaction of the acute or delayed type, an allergic reaction or asthmatic disorder, or treatment of dermatitis, arthritis, meningitis, granulomas, vasculitis or septic shock may be accomplished by a method to prevent or suppress immune responses in a recipient or treatment subject, which method comprises administering to the subject a therapeutically-effective amount of an immunosuppressive compound of Formula I:

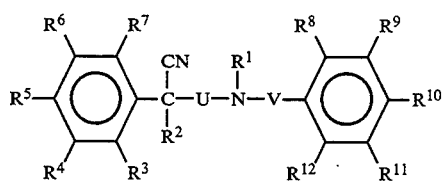

wherein each of U and V is independently selected from divalent alkyl, divalent alkenylalkyl and divalent alkynylalkyl;

wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkylaryloxycarbonylalkyl, alkenylalkyl, cycloalkenyl, aralkoxycarbonylalkyl, alkynylalkyl, alkylthiocarbonylalkyl, alkylthiothiocarbonylalkyl, arylthiocarbonylalkyl, arylthiothiocarbonylalkyl, aralkylthiocarbonylalkyl, alkylarylthiocarbonylalkyl, alkylsulfonylalkyl, aralkylsulfonylalkyl and arylsulfonylalkyl;

wherein $R^2$ is selected from hydrido, alkyl, hydroxyalkyl, cycloalkyl, cycloalkylalkyl, aralkyl, aroyl, aryloxyalkyl, alkoxyalkyl, alkylcarbonyl, alkylcarbonylalkyl, alkoxycarbonyl, alkenylalkyl, cycloalkenylalkyl, alkynylalkyl, carboxyalkyl, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkylthiocarbonyl, alkylthiothiocarbonyl, arylthiocarbonyl, arylcarbonylthio, arylthiocarbonyloxy, arylthiothiocarbonyl, aralkylthiocarbonyl, alkylthiocarbonylalkyl, alkylsulfinyl, alkylsulfonylalkyl, aralkylsulfinylalkyl, aralkylsulfonylalkyl, arylsulfinylalkyl and arylsulfonylalkyl;

wherein each of $R^3$, through $R^{12}$ is independently selected from hydrido, hydroxy, alkyl, hydroxyalkyl, halo, haloalkyl, halocycloalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonylalkyl, mercapto, alkylsulfinyl, alkylsulfonyl, aralkylsulfinyl, aralkylsulfonyl, arylsulfinyl, arylsulfonyl, and wherein each of $R^3$ through $R^{12}$ may be further independently selected from radicals of the formula

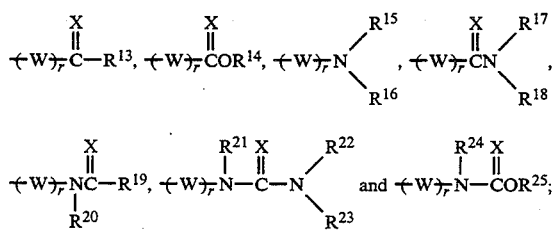

wherein W is selected from divalent alkyl, divalent alkenyl and divalent alkynyl groups; wherein X is oxygen atom or sulfur atom; wherein each r is a number independently selected from zero and one; wherein each of $R^{13}$ through $R^{25}$ is independently selected from hydrido, alkyl, cycloalkyl, cycloalkylalkyl, aralkyl and aryl;

and wherein any of the foregoing U, V, W and $R^1$ through $R^{25}$ groups having a substitutable position may be substituted by one or more groups independently selected from alkyl, halo, haloalkyl, halocycloalkyl, alkenyl, alkynyl, aralkyl, hydroxyalkyl, cyano, oxo, alkoxyalkyl, cycloalkyl, cycloalkylalkyl, aryl, aroylalkyl, cycloalkenyl, cyanoamino, alkylcarbonylalkyl, alkoxycarbonylalkyl, aralkoxycarbonylalkyl, carboxyalkyl, alkylthiocarbonylalkyl and alkylsulfonylalkyl;

with the proviso that at least one of $R^3$ through $R^{12}$ must be selected from halo, haloalkyl and halocycloalkyl;

or a tautomer thereof or a pharmaceutically-acceptable salt thereof.

Compounds of Formula I would provide suppression of an immune response in a human or animal subject. Immune suppression is therapeutically beneficial in organ transplantation procedures and to treat a variety of disease states. For example, compounds of Formula I would be useful to treat a recipient of a graft of a transplanted organ to reduce recipient rejection of the graft. Such compounds would be useful, in particular, for transplants of bone marrow, kidney, liver, heart-lung and pancreas organs. Compounds of Formula I would also be useful in suppressing immune response in a human or animal subject susceptible to or afflicted with an autoimmune disease or inflammatory disease. Examples of such treatable disease are systemic lupus erythematosis, multiple sclerosis, myesthenia gravis, thyroiditis, Grave's disease, autoimmune hemolytic anemia, autoimmune hemolytic anemia, autoimmune thrombocytopenia purpura, mixed connective tissue disease, idiopathic Addism's disease, Sjogren's syndrome, insulin dependent diabetes mellitus, rheumatoid arthritis, psoriasis, glomerulonephritis, inflammatory bowel disease and Crohn's Disease. Compounds of Formula I would also be useful in suppressing immune response in a human or animal subject susceptible to or afflicted with an allergy, such as an asthmatic condition or reaction, urticaria or with airway hypersensitivity. Compounds of Formula I would also be useful in suppressing immune response in a human or animal subject afflicted with or susceptible to septic shock. Compounds of Formula I would also be useful in preventing or suppressing acute or delayed-type hypersensitivity responses or conditions resulting from or associated with hypersensitivity responses such as contact dermatitis, hemolytic anemias, antibody-induced thrombocytopenia, Goodpasture's syndrome, hypersensitivity, pneumonitis, glomerulonephritis, granulomas, thyroiditis, encephelomyelitis, and meningitis.

The immunosuppressive effect of compounds of Formula I arises from inhibition of regulatory, effector, or accessory cells. For example, the immunosuppression of granulocytes, typically the neutrophil, eosinophil and basophil sub-types, as well as mononuclear phagocytic cells, such as monocytes, macrophages and histiocytes, may provide therapeutic benefits for transplantation and in treatment of the above-mentioned disease states. Immunosuppression of lymphocytes, such as T- and B-cell sub-types, likewise can produce therapeutic benefit.

Compounds of Formula I would be useful in treating organs prior to transplant. For example, an organ removed from a donor could be stored or transported in a bath containing an immunosuppressive compound of Formula I. The immunosuppressive compound would act to inhibit donor leukocyte reactivity.

Compounds of Formula I would also be useful in adjunct therapy involving, typically, coadministration of a second immunosuppressive compound of Formula I or coadministration of an immunosuppressive agent of a different class of compounds, such as a cyclosporin compound, or a Fujisawa FK-506 (macrolide lactone) compound or rapamycin, or a glucocorticoid, or an antiproliferative agent, or a monoclonal antibody such as an anti-CD3 (anti-T cell receptor antibody) or anti-CD5/CD7 or anti-CD4 agent, or an anti-IL-2 receptor (anti-cytokine receptor antibody) agent or an anti-IL-2 (anti-cytokine antibody), or a Nippon NKT-01 (15-deoxyspergualin) or a Syntex RS-61443.

A preferred class consists of compounds within Formula I wherein each of U and V is independently selected from divalent alkyl, divalent alkenylalkyl and divalent alkynylalkyl groups;

wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkylaryloxycarbonylalkyl, alkenylalkyl, cycloalkenylalkyl, aralkoxycarbonylalkyl and alkynylalkyl;

wherein $R^2$ is selected from hydrido, alkyl, hydroxyalkyl, cycloalkyl, cycloalkylalkyl, aralkyl, aroyl, aryloxyalkyl, alkoxyalkyl, alkylcarbonyl, alkylcarbonylalkyl, alkoxycarbonyl, alkenylalkyl, cycloalkenylalkyl, alkynylalkyl, carboxyalkyl, alkylcarbonyloxyalkyl, alkoxycarbonylalkyl, aralkoxycarbonylalkyl, aralkylcarbonyloxyalkyl and mercaptoalkyl;

wherein each of $R^3$ through $R^{12}$ is independently selected from hydrido, hydroxy, alkyl, hydroxyalkyl, halo, haloalkyl, halocycloalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonylalkyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, arylthio, mercapto, and wherein each of $R^3$ through $R^{12}$ may be further independently selected from radicals of the formula

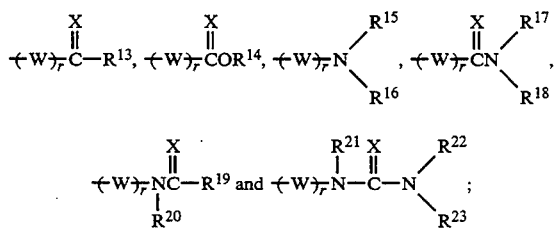

wherein W is selected from divalent alkyl, divalent alkenyl and divalent alkynyl groups; wherein X is oxygen atom or sulfur atom; wherein each r is a number independently selected from zero and one; wherein each of $R^{13}$ through $R^{23}$ is independently selected from hydrido, alkyl, cycloalkyl, cycloalkylalkyl, aralkyl and aryl;

and wherein any of the foregoing U, V, W and $R^1$ through $R^{23}$ groups having a substitutable position may be substituted by one or more groups independently selected from alkyl, halo, haloalkyl, halocycloalkyl, alkenyl, alkynyl, aralkyl, hydroxyalkyl, cyano, oxo, alkoxyalkyl, cycloalkyl, cycloalkylalkyl, aryl, aroylalkyl, alkylcarbonylalkyl, alkoxycarbonylalkyl, aralkoxycarbonylalkyl and carboxylalkyl;

with the proviso that at least one of $R^3$ through $R^{12}$ must be selected from halo, haloalkyl and halocycloalkyl;

or a tautomer thereof or a pharmaceutically-acceptable salt thereof.

A more preferred class consists of compounds within Formula I wherein each of U and V is independently selected from divalent alkyl, divalent alkenylalkyl and divalent alkynylalkyl groups, wherein said divalent groups are linear and contain from one to about twelve carbon atoms;

wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkenyl and alkynyl, wherein each of $R^3$ through $R^{12}$ is independently selected from hydrido, hydroxy, alkyl, hydroxyalkyl, halo, haloalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonylalkyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkoxycarbonyloxy, and wherein each of and $R^3$ through $R^{12}$ may be further independently selected from radicals of the formula

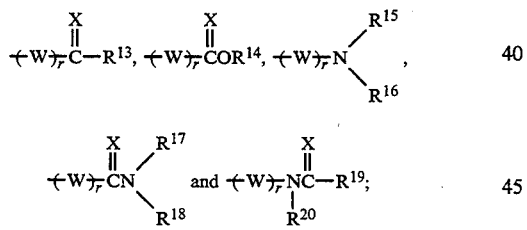

wherein W is selected from divalent alkyl, divalent alkenyl and divalent alkynyl groups; wherein said divalent groups are linear and contain from one to about twelve carbon atoms; wherein X is oxygen atom or sulfur atom; wherein each is a number independently selected from zero and one; wherein each of $R^{13}$ through $R^{20}$ is independently selected from hydrido, alkyl, cycloalkyl, cycloalkylalkyl, aralkyl and aryl;

wherein $R^2$ is selected from hydrido, alkyl, hydroxyalkyl, cycloalkyl, cycloalkylalkyl, aralkyl, aryloxyalkyl, aralkoxy, alkoxyalkyl, alkylcarbonylalkyl, alkenylalkyl, cycloalkenylalkyl, alkynylalkyl, carboxyalkyl, alkylcarbonyloxyalkyl, alkoxycarbonylalkyl, aralkoxycarbonylalkyl, aralkylcarbonyloxyalkyl and mercaptoalkyl;

and wherein any of the foregoing U, V, W and $R^1$ through $R^{20}$ groups having a substitutable position may be substituted by one or more groups independently selected from alkyl, halo, haloalkyl, halocycloalkyl, alkenyl, alkynyl, aralkyl, hydroxyalkyl, cyano, oxo, alkoxyalkyl, cycloalkyl, cycloalkylalkyl, aryl, aroylalkyl, cyanoamino, alkylcarbonylalkyl, alkoxycarbonylalkyl, aralkoxycarbonylalkyl and carboxylalkyl;

with the proviso that at least one of $R^3$ through $R^{12}$ must be selected from halo, haloalkyl and halocycloalkyl;

or a tautomer thereof or a pharmaceutically-acceptable salt thereof.

An even more preferred class consists of compounds within Formula I wherein $R^1$ is selected from hydrido, alkyl, hydroxyalkyl, cycloalkyl, cycloalkylalkyl, alkoxyalkyl, alkylcarbonylalkyl, alkoxycarbonylalkyl, alkenyl and alkynyl;

wherein $R^2$ is selected from hydrido, alkyl, hydroxyalkyl, cycloalkyl, cycloalkylalkyl, phenylalkyl, phenoxyalkyl, alkoxyalkyl, alkylcarbonylalkyl, alkenylalkyl, alkynylalkyl, carboxyalkyl, alkylcarbonyloxyalkyl and alkoxycarbonylalkyl;

wherein each of $R^3$ through $R^{12}$ is independently selected from hydrido, hydroxy, alkyl, halo, haloalkyl, halocycloalkyl, hydroxyalkyl, cycloalkyl, cycloalkylalkyl, cycloalkyloxy, alkoxy, phenylalkyl, phenyl, benzoyl, phenoxy, phenoxyalkyl, alkoxyalkyl, alkylcarbonylalkyl, alkynyl, carboxyl, carboxyalkyl, alkylcarbonyloxy, alkylcarbonyloxyalkyl, alkoxycarbonylalkyl, alkoxycarbonyloxy, and wherein each of $R^3$ through $R^{12}$ may be further independently selected from radicals of the formula

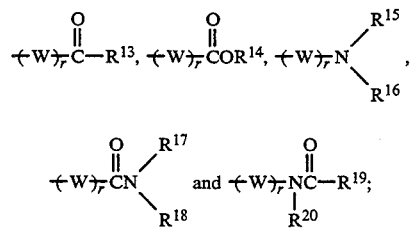

wherein each r is a number independently selected from zero and one; wherein each of $R^{13}$ through $R^{20}$ is independently selected from hydrido, alkyl, cycloalkyl, cycloalkylalkyl, phenylalkyl and phenyl;

wherein each of U, V and N independently is a linear divalent group consisting of one or more divalent groups selected from

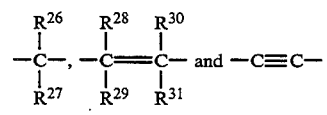

wherein each of $R^{26}$ and $R^{27}$ is independently selected from hydrido, alkyl, cycloalkyl, phenyl, benzyl, hydroxy, hydroxyalkyl, alkoxy, phenoxy, alkoxyalkyl, benzyloxy, cyano, alkanoyl,

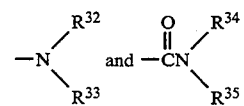

wherein each of $R^{32}$, $R^{33}$, $R^{34}$ and $R^{35}$ is independently selected from hydrido, alkyl and phenyl; wherein $R^{26}$ and $R^{27}$ may be taken together to form oxo or exomethylene; wherein each of $R^{28}$, $R^{29}$, $R^{30}$ and $R^{31}$ is independently selected from hydrido, alkyl, hydroxyalkyl and alkoxyalkyl;

and wherein any of the foregoing U, V, W and $R^1$ through $R^{35}$ groups having a substitutable position may be substituted by one or more groups independently selected from alkyl, halo, haloalkyl, halocycloalkyl, alkenyl, alkynyl, phenylalkyl, hydroxyalkyl, cyano, oxo, alkoxyalkyl, cycloalkyl, cycloalkylalkyl, phenyl, alkylcarbonylalkyl, alkoxycarbonylalkyl and carboxylalkyl;

with the proviso that at least one of $R^3$ through $R^{12}$ is selected from halo, haloalkyl and halocycloalkyl;

or a tautomer thereof or a pharmaceutically-acceptable salt thereof.

An even more highly preferred class consists of compounds within Formula I selected from compounds of Formula II:

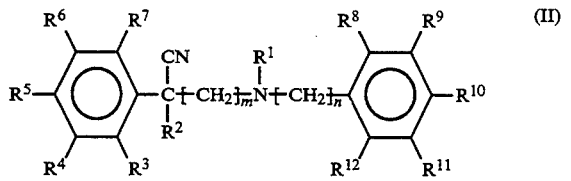
(II)

wherein each of m and n is a number independently selected from one to ten, inclusive; wherein $R^1$ is selected from hydrido, alkyl, hydroxyalkyl, cycloalkyl, cycloalkylalkyl, alkoxyalkyl, alkenylalkyl and alkynylalkyl;

wherein $R^6$ is selected from hydrido, alkyl, hydroxyalkyl, cycloalkyl, cycloalkylalkyl, benzyl, alkenylalkyl and alkynylalkyl;

wherein each of $R^{13}$ through $R^{12}$ is independently selected from hydrido, hydroxy, alkyl, hydroxyalkyl, halo, haloalkyl, halocycloalkyl, cycloalkyl, cycloalkylalkyl, cycloalkyloxy, alkoxy, phenoxy, benzyloxy, and radicals of the formula

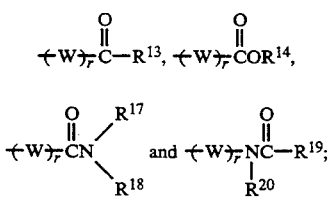

wherein W is a linear divalent group consisting of one or more divalent groups selected from

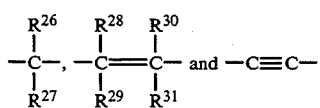

wherein each of $R^{26}$ and $R^{27}$ is independently selected from hydrido, alkyl, cycloalkyl, phenyl, benzyl, hydroxy, hydroxyalkyl, alkoxy, phenoxy, alkoxyalkyl, benzyloxy, cyano, alkanoyl,

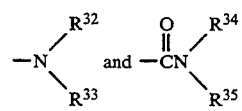

wherein each of $R^{32}$, $R^{33}$, $R^{34}$ and $R^{35}$ is independently selected from hydrido, alkyl and phenyl; wherein $R^{26}$ and $R^{27}$ may be taken together to form oxo or exomethylene; wherein each of $R^{28}$, $R^{29}$, $R^{30}$ and $R^{31}$ is independently selected from hydrido, alkyl, hydroxyalkyl and alkoxyalkyl;

wherein each of $R^{13}$, $R^{14}$, $R^{17}$, $R^{18}$, $R^{19}$ and $R^{20}$ is independently selected from hydrido, alkyl, cycloalkyl, cycloalkylalkyl and phenalkyl;

wherein each r is a number independently selected from zero and one;

and wherein any of the foregoing W and $R^1$ through $R^{14}$, $R^{17}$ through $R^{20}$ and $R^{26}$ through $R^{35}$ groups having a substitutable position may be substituted by one or more groups independently selected from alkyl, alkenyl, alkynyl, benzyl, hydroxyalkyl, alkoxyalkyl, cycloalkyl, oxo, cycloalkylalkyl and phenyl;

with the proviso that at least one of $R^3$ through $R^{12}$ must be selected from halo and haloalkyl;

or a tautomer thereof or a pharmaceutically-acceptable salt thereof.

A more highly preferred class consists of compounds within Formula I wherein m is a number selected from one to eight, inclusive; wherein n is a number selected from one to five, inclusive;

wherein $R^1$ is selected from hydrido, alkyl, hydroxyalkyl, alkoxyalkyl, alkenylalkyl and alkynylalkyl;

wherein $R^2$ is selected from hydrido, alkyl, hydroxyalkyl, cycloalkyl, cycloalkylalkyl, benzyl, alkenyl and alkynyl;

wherein each of $R^{13}$ through $R^{12}$ is independently selected from hydrido, hydroxy, alkyl, hydroxyalkyl, halo, haloalkyl, alkoxy, and radicals of the formula

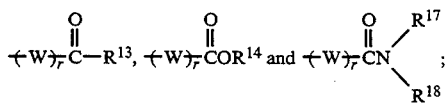

wherein W is a linear divalent group consisting of one or more divalent groups selected from

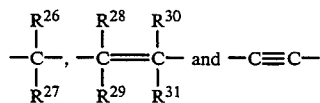

wherein each of $R^{26}$ and $R^{27}$ is independently selected from hydrido, alkyl, cycloalkyl, phenyl, benzyl, hydroxy, hydroxyalkyl, alkoxy and alkoxy and alkoxyalkyl;

wherein each of $R^{28}$, $R^{29}$, $R^{30}$ and $R^{31}$ is independently selected from hydrido, alkyl, hydroxyalkyl and alkoxyalkyl;

wherein each of $R^{13}$, $R^{14}$, $R^{17}$ and $R^{18}$ is independently selected from hydrido and alkyl;

wherein each r is a number independently selected from zero and one;

and wherein any of the foregoing W and $R^{12}$ through $R^{14}$, $R^{17}$, $R^{18}$ and $R^{26}$ through $R^{31}$ groups having a substitutable position may be substituted by one or more groups independently selected from alkyl, alkenyl, alkynyl, hydroxyalkyl and alkoxyalkyl;

with the proviso that at least one of $R^3$ through $R^{13}$ must be selected from halo and haloalkyl;

or a tautomer thereof or a pharmaceutically-acceptable salt thereof.

A much higher preferred class consists of compounds within Formula II selected from compounds of Formula III:

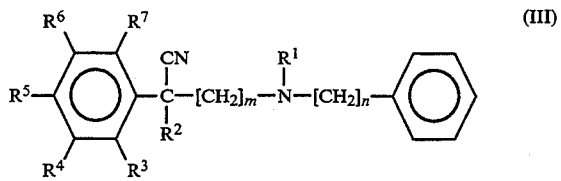

wherein m is a number selected from three to five, inclusive; wherein n one or two;

wherein $R^1$ is selected from methyl, ethyl, n-propyl, isopropyl, n-butyl, sec-butyl, tert-butyl, iso-butyl, n-pentyl, isopentyl, cyclopropyl, cyclobutyl, cyclopentyl, cyclohexyl, cyclopropylmethyl, cyclobutylmethyl, cyclopentylmethyl, cyclohexylmethyl, benzyl and phenethyl;

wherein $R^2$ is selected from methyl, ethyl, n-propyl, isopropyl, n-butyl, sec-butyl, tert-butyl, iso-butyl, n-pentyl, isopentyl, cyclopropyl, cyclobutyl, cyclopentyl, cyclohexyl, cyclopropylmethyl, cyclobutylmethyl, cyclopentylmethyl, cyclohexylmethyl, benzyl and phenethyl;

wherein each of $R^3$ through $R^7$ is selected from hydrido, fluoro, chloro, bromo, azide, trifluoromethyl, difluorochloromethyl, 1,1-difluoroethyl, 2,2,2-trifluoroethyl, perfluoroethyl and 2,2,3,3-tetrafluoropropyl;

with the proviso that at least one of $R^3$ through $R^7$ is selected from fluoro and trifluoromethyl;

or a tautomer thereof or a pharmaceutically-acceptable salt thereof.

The term "hydrido" denotes a single hydrogen atom (H). This hydrido group may be attached, for example, to a oxygen atom to form a hydroxyl group; or, as another example, two hydrido groups may be attached to a carbon atom to form a divalent —$CH_2$— group, that is, a "methylene" group; or, as another example, one hydrido group may be attached to a carbon atom to form a trivalent

group. Where the term "alkyl" is used either alone or within other terms such as "haloalkyl" and "hydroxyalkyl", the term "alkyl" embraces linear or branched radicals having one to about twenty carbon atoms or, preferably, one to about fifteen carbon atoms. For some substituents, more preferred alkyl radicals are "lower alkyl", that is, radicals having one to about ten carbon atoms. For some substituents, most preferred alkyl radicals are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The term "alkylthio" embraces radicals containing a linear or branched alkyl group, one to about ten carbon atoms attached to a divalent sulfur atom, such as a methythio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote, respectively, aryl groups having an oxygen or sulfur atom through which the radical is attached to a nucleus, examples of which are phenoxy and phenylthio. The terms "sulfinyl" and "sulfonyl" whether used alone or linked to other terms denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more preferred sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl, neopentyl, n-hexyl, n-heptyl, n-octyl, n-nonyl, n-decyl, n-undecyl, n-dodecyl, n-tridecyl, n-tetradecyl and n-hexadecyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

It is preferred that certain selections of radicals for $R^1$ be avoided. Radicals for $R^1$ which should preferably be avoided are alkyl, alkenyl and alkynyl moieties having a hydroxy, alkoxy or double or triple bond attached to the alpha carbon of the moiety, that is, the carbon attached to the nitrogen atom of Formula I on which $R^1$ is substituted. It is also preferred that certain selections of radicals for $R^6$ be avoided. Radicals for $R^4$ which should preferably be avoided are sulfhydryl, amino and mono- and di-substituted amino.

Also included in the family of compounds of Formula I are isomeric forms including diastereoisomers, regioisomers and the pharmaceutically-acceptable salts thereof. The term "pharmaceutically-acceptable salts" embraces salts commonly used to form alkali metal salts and to form addition salts of free acids or free bases, including quaternary ammonium salts. The nature of the salt is not critical, provided that it is pharmaceutically-acceptable. Suitable pharmaceutically-acceptable acid addition salts of compounds of Formulas I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, $\beta$-hydroxybutyric, malonic, galactaric and galacturonic acid. Suitable pharmaceutically-acceptable base addition salts of compounds of Formulas I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

A family of specific compounds of interest within Formula I consists of the following compounds and pharmaceutically-acceptable salts thereof, as follows:

($\pm$)-3,4-difluoro-$\alpha$-(1-methylethyl )-$\alpha$-[3-[methyl(-phenylmethyl)amino]propyl]benzeneacetonitrile;

($\pm$)-3,4-dichloro-$\alpha$-(1-methylethyl)-$\alpha$-[3-[methyl(-phenylmethyl)amino]propyl]benzeneacetonitrile;

($\pm$)-3,4-dibromo-$\alpha$-(1-methylethyl )-$\alpha$-[3-[methyl(-phenylmethyl)amino]propyl]benzeneacetonitrile;

($\pm$)-3,4-ditrifluoromethyl-$\alpha$-(1-methylethyl)-$\alpha$-[3-[methyl(phenylmethyl)amino]propyl]benzeneacetonitrile;

($\pm$)-3,4-difluoro-$\alpha$-(1-cyclopropyl)-$\alpha$-[3-[methyl(-phenylmethyl )amino]propyl]benzeneacetonitrile;

($\pm$)-3,4-difluoro-$\alpha$-(1-cyclobutyl)-$\alpha$-[3-[methyl(phenyl-methyl)amino]propyl]benzeneacetonitrile;

($\pm$)-3,4-difluoro-$\alpha$-(1-cyclopentyl)-$\alpha$-[3-[methyl(-phenylmethyl)amino]propyl]benzeneacetonitrile;

($\pm$)-3,4-difluoro-$\alpha$-(1-cyclohexyl)-$\alpha$-[3-[methyl(-phenylmethyl)amino]propyl]benezeneacetonitrile;

($\pm$)-3,4-difluoro-$\alpha$-(1-methylethyl)-$\alpha$-[3-[ethyl (phenyl-methyl)amino]propyl]benezeneacetonitrile;

($\pm$)-3,4-difluoro-$\alpha$-(1-methylethyl)-$\alpha$-[3-[n-propyl(-phenylmethyl)amino]propyl]benzeneacetonitrile;

(±)-3,4-difluoro-α-(1-methylethyl)-α-[3-[1-methylethyl(phenylmethyl)amino]propyl]benzeneacetonitrile;
(±)-3,4-difluoro-α-(1-methylethyl)-α-[3-[methyl(phenylethyl)amino]propyl]benzeneacetonitrile;
(±)-3,4-difluoro-α-(1-methylethyl)-α-[3-[methyl(phenylmethyl)amino]butyl]benzeneacetonitrile;
(±)-3,4-difluoro-α-(1-methylethyl)-5-[3-[methyl(phenylmethyl)amino]pentyl]benezeneacetonitrile;
(±)-3,4-difluoro-α-(1-cyclopropyl)-α-[3-[methyl(phenylmethyl)amino]propyl]benzeneacetonitrile;
(±)-3,4-difluoro-α-(1-cyclobutyl)-α-[3-[methyl(phenylmethyl)amino]propyl]benzeneacetonitrile;
(±)-3,4-difluoro-α-(1-cyclopentyl)-α-[3-[methyl(phenylmethyl)amino]propyl]benzeneacetonitrile;
(±)-3,4-difluoro-α-(1-cyclohexyl)-α-[3-[methyl(phenylmethyl)amino]propyl]benzeneacetonitrile;
(±)-3,4-dichloro-α-(1-cyclopropyl)-α-[3-[methyl(phenylmethyl)amino]propyl]benzeneacetonitrile;
(±)-3,4-dichloro-α-(1-cyclobutyl)-α-[3-[methyl(phenylmethyl)amino]propyl]benzeneacetonitrile;
(±)-3,4-dichloro-α-(1-cyclopentyl)-5-[3-[methyl(phenylmethyl)amino]propyl]benzeneacetonitrile;
(±)-3,4-dichloro-α-(1-cyclohexyl)-α-[3-[methyl(phenylmethyl)amino]propyl]benzeneacetonitrile;
(±)-3,4-dibromo-α-(1-cyclopropyl)-α-[3-[methyl(phenylmethyl)amino]propyl]benzeneacetonitrile;
(±)-3,4-dibromo-α-(1-cyclobutyl)-α-[3-[methyl(phenylmethyl)amino]propyl]benzeneacetonitrile;
(±)-3,4-dibromo-α-(1-cyclopentyl)-α-[3-[methyl(phenylmethyl)amino]propyl]benzeneacetonitrile;
(±)-3,4-dibromo-α-(1-cyclohexyl)-α-[3-[methyl(phenylmethyl)amino]propyl]benzeneacetonitrile;
(±)-3,4-ditrifluoromethyl-α-(1-cyclopropyl)-α-[3-[methyl(phenylmethyl)amino]propyl]benzeneacetonitrile;
(±)-3,4-ditrifluoromethyl-α-(1-cyclobutyl)-α-[3-[methyl(phenylmethyl)amino]propyl]benzeneacetonitrile;
(±)-3,4-ditrifluoromethyl-α-(1-cyclopentyl)-α-[3-[methyl(phenylmethyl)amino]propyl]benzeneacetonitrile;
(±)-3,4-ditrifluoromethyl-α-(1-cyclohexyl)-α-[3-[methyl(phenylmethyl)amino]propyl]benzeneacetonitrile;
(±)-3,4-difluoro-α-(1-methylethyl)-α-[3-[ethyl(phenylmethyl)amino]propyl]benzeneacetonitrile;
(±)-3,4-difluoro-α-(1-methylethyl)-α-[3-[n-propyl(phenylmethyl)amino]propyl]benzeneacetonitrile;
(±)-3,4-difluoro-α-(1-methylethyl)-α-[3-[1-methylethyl(phenylmethyl)amino]propyl]benzeneacetonitrile;
(±)-3,4-dichloro-α-(1-methylethyl)-α-[3-[ethyl(phenylmethyl)amino]propyl]benzeneacetonitrile;
(±)-3,4-dichloro-α-(1-methylethyl)-α-[3-[n-propyl(phenylmethyl)amino]propyl]benzeneacetonitrile;
(±)-3,4-dichloro-α-(1-methylethyl)-α-[3-[1-methylethyl(phenylmethyl)amino]propyl]benzeneacetonitrile;
(±)-3,4-dibromo-α-(1-methylethyl)-α-[3-[ethyl(phenylmethyl)amino]propyl]benzeneacetonitrile;
(±)-3,4-dibromo-α-(1-methylethyl)-α-[3-[n-propyl(phenylmethyl)amino]propyl]benzeneacetonitrile;
(±)-3,4-dibromo-α-(1-methylethyl)-α-[3-[1-methylethyl(phenylmethyl)amino]propyl]benzeneacetonitrile;
(±)-3,4-ditrifluoromethyl-α-(1-methylethyl)-α-[3-ethyl(phenylmethyl)amino]propyl]benzeneacetonitrile;
(±)-3,4-ditrifluoromethyl-α-(1-methylethyl)-α-[3-[n-propyl(phenylmethyl)amino]propyl]benzeneacetonitrile;
(±)-3,4-ditrifluoromethyl-α-(1-methylethyl)-α-[3-[1-methylethyl(phenylmethyl)amino]propyl]benzeneacetonitrile;
(±)-3,4-difluoro-α-(1-cyclohexyl)-α-[3-ethyl(phenylethyl)amino]propyl]benzeneacetonitrile;
(±)-3,4-dichloro-α-(1-methylethyl)-α-[3-methyl(phenylethyl)amino]propyl]benzeneacetonitrile;
(±)-3,4-dibromo-α-(1-methylethyl)-α-[3-methyl(phenylethyl)amino]propyl]benzeneacetonitrile;
(±)-3,4-ditrifluoromethyl-α-(1-methylethyl)-α-[3-methyl(phenylethyl)amino]propyl]benzeneacetonitrile;
(±)-3,4-difluoro-α-(1-cyclohexyl)-α-[3-[ethyl(phenylmethyl)amino]butyl]benzeneacetonitrile;
(±)-3,4-difluoro-α-(1-cyclohexyl)-α-[3-[ethyl(phenylmethyl)amino]pentyl]benzeneacetonitrile;
(±)-3,4-dichloro-α-(1-methylethyl)-α-[3-[methyl(phenylmethyl)amino]butyl]benzeneacetonitrile;
(±)-3,4-dichloro-α-(1-methylethyl)-α-[3-[methyl(phenylmethyl)amino]pentyl]benzeneacetonitrile;
(±)-3,4-dibromo-α-(1-methylethyl)-α-[3-[methyl(phenylmethyl)amino]butyl]benzeneacetonitrile;
(±)-3,4-dibromo-α-(1-methylethyl)-α-[3-[methyl(phenylmethyl)amino]pentyl]benzeneacetonitrile;
(±)-3,4-ditrifluoromethyl-α-(1-methylethyl)-α-[3-[methyl(phenylmethyl)amino]butyl]benzeneacetonitrile;
(±)-3,4-ditrifluoromethyl-α-(1-methylethyl)-α-[3-[methyl(phenylmethyl)amino]pentyl]benezeneacetonitrile;
(±)-3,4-difluoro-α-(1-cyclopropyl)-α-[3-[ethyl(phenylmethyl)amino]propyl]benzeneacetonitrile;
(±)-3,4-difluoro-α-(1-cyclopropyl)-α-[3 -[n-propyl(phenylmethyl)amino]propyl]benzeneacetonitrile;
(±)-3,4-difluoro-α-(1-cyclopropyl)-α-[3-[1-methylethyl(phenylmethyl)amino]propyl]benzeneacetonitrile;
(±)-3,4-difluoro-α-(1-cyclobutyl)-α-[3-[ethyl(phenylmethyl)amino]propyl]benzeneacetonitrile;
(±)-3,4-difluoro-α-(1-cyclobutyl)-α-[3-[nn-propyl(phenylmethyl)amino]propyl]benzeneacetonitrile;
(±)-3,4-difluoro-α-(1-cyclobutyl)-α-[3-[1-methylethyl(phenylmethyl)amino]propyl]benzeneacetonitrile;
(±)-3,4-difluoro-α-(1-cyclopentyl)-α-[3-[ethyl(phenylmethyl)amino]propyl]benzeneacetonitrile;
(±)-3,4-difluoro-α-(1-cyclopentyl)-α-[3-[n-propyl(phenylmethyl)amino]propyl]benzeneacetonitrile;
(±)-3,4-difluoro-α-(1-cyclopentyl)-α-[3-[1-methylethyl(phenylmethyl)amino]propyl]benzeneacetonitrile;
(±)-3,4-difluoro-α-(1-cyclohexyl)-α-[3-[1-ethyl(phenylmethyl)amino]propyl]benzeneacetonitrile;
(±)-3,4-difluoro-α-(1-cyclohexyl)-α-[3-[1-n-propyl(phenylmethyl)amino]propyl]benzeneacetonitrile;
(±)-3,4-difluoro-α-(1-cyclohexyl)-α-[3-[1-1-methylethyl(phenylmethyl)amino]propyl]benzeneacetonitrile;
(±)-3,4-difluoro-α-(1-cyclopropyl)-α-[3-[methyl(phenylethyl)amino]propyl]benzeneacetonitrile;
(±)-3,4-difluoro-α-(1-cyclobutyl)-α-[3-[methyl(phenylethyl)amino]propyl]benzeneacetonitrile;
(±)-3,4-difluoro-α-(1-cyclopentyl)-α-[3-[methyl(phenylethyl)amino]propyl]benzeneacetonitrile;

(±)-3,4-difluoro-α-(1-cyclohexyl)-α-[3-[methyl(-phenylethyl)amino]propyl]benzeneacetonitrile;
(±)-3,4-difluoro-α-(1-cyclopropyl)-α-[3-[methyl(-phenylmethyl)amino]propyl]benzeneacetonitrile;
(±)-3,4-difluoro-α-(1-cyclopropyl)-α-[3-[methyl(-phenylmethyl)amino]butyl]benzeneacetonitrile;
(±)-3,4-difluoro-α-(1-cyclopropyl)-α-[3-methyl(-phenylmethyl)amino]pentyl]benzeneacetonitrile;
(±)-3,4-difluoro-α-(1-cyclobutyl)-α-[3-methyl(phenylmethyl)amino]propyl]benzeneacetonitrile;
(±)-3,4-difluoro-α-(1-cyclobutyl)-α-[3-methyl(phenylmethyl)amino]butyl]benezeneacetonitrile;
(±)-3,4-difluoro-α-(1-cyclobutyl)-α-[3-methyl(phenylmethyl)amino]pentyl]benzeneacetonitrile;
(±)-3,4-difluoro-α-(1-cyclopentyl)-α-[3-methyl(-phenylmethyl)amino]propyl]benzeneacetonitrile;
(±)-3,4-difluoro-α-(1-cyclopentyl)-α-[3-methyl(-phenylmethyl)amino]butyl]benzeneacetonitrile;
(±)-3,4-difluoro-α-(1-cyclopentyl)-α-[3-methyl(-phenylmethyl)amino]pentyl]benzeneacetonitrile;
(±)-3,4-difluoro-α-(1-cyclohexyl)-α-[3-methyl(phenylmethyl)amino]propyl]benzeneacetonitrile;
(±)-3,4-difluoro-α-(1-cyclohexyl)-α-[3-methyl(phenylmethyl)amino]butyl]benzeneacetonitrile;
(±)-3,4-difluoro-α-(1-cyclohexyl)-α-[3-methyl(phenylmethyl)amino]pentyl]benzeneacetonitrile;
(±)-3,4-difluoro-α-(1-methylethyl)-α-[3-methyl(-phenylethyl)amino]propyl]benzeneacetonitrile;
(±)-3,4-difluoro-α-(1-methylethyl)-α-[3-[ethyl(-phenylethyl)amino]propyl]benzeneacetonitrile;
(±)-3,4-difluoro-α-(1-methylethyl)-α-[3-[n-propyl(-phenylethyl)amino]propyl]benzeneacetonitrile;
(±)-3,4-difluoro-α-(1-methylethyl)-α-[3-[1-methylethyl(phenylethyl)amino]propyl]benzeneacetonitrile;
(±)-3,4-difluoro-α-(1-methylethyl)-α-[3-[ethyl(phenylmethyl)amino]propyl]benzeneacetonitrile;
(±)-3,4-difluoro-α-(1-methylethyl)-α-[3-[ethyl(phenylmethyl)amino]butyl]benezeneacetonitrile;
(±)-3,4-difluoro-α-(1-methylethyl)-α-[3-[ethyl(phenylmethyl)amino]pentyl]benzeneacetonitrile;
(±)-3,4-difluoro-α-(1-methylethyl)-α-[n-propyl(-phenylmethyl)amino]propyl]benzeneacetonitrile;
(±)-3,4-difluoro-α-(1-methylethyl)-α-[3-[n-propyl(-phenylmethyl)amino]butyl]benzeneacetonitrile;
(±)-3,4-difluoro-α-(1-methylethyl)-α-[3-[n-propyl(-phenylmethyl)amino]pentyl]benezeneacetonitrile;
(±)-3,4-difluoro-α-(1-methylethyl)-α-[3-[methylethyl(-phenylmethyl)amino]propyl]benzeneacetonitrile;
(±)-3,4-difluoro-α-(1-methylethyl)-α-[3-[1-methylethyl(phenylmethyl)amino]butyl]benezeneacetonitrile;
(±)-3,4-difluoro-α-(1-methylethyl)-α-[3-[1-methylethyl(phenylmethyl)amino]pentyl]benzeneacetonitrile;
(±)-3,4-difluoro-α-(1-methylethyl)-α-[3-[methyl(-phenylethyl)amino]propyl]benzeneacetonitrile;
(±)-3,4-difluoro-α-(1-methylethyl)-α-[3-[methyl(-phenylethyl)amino]butyl]benezeneacetonitrile;
(±)-3,4-difluoro-α-(1-methylethyl)-α-[3-[methyl(-phenylethyl)amino]pentyl]benzeneacetonitrile;
(±)-3,4-difluoro-α-(1-cyclopropyl)-α-[3-[ethyl(phenylmethyl)amino]propyl]benezeneacetonitrile;
(±)-3,4-difluoro-α-(1-cyclopropyl)-α-[3-[n-propyl(-phenylmethyl)amino]propyl]benezeneacetonitrile;
(±)-3,4-difluoro-α-(1-cyclopropyl)-α-[3-[1-methylethyl(phenylmethyl)amino]propyl]benzeneacetonitrile;
(±)-3,4-difluoro-α-(1-cyclobutyl)-α-[3-[ethyl(phenylmethyl)amino]propyl]benzeneacetonitrile;

(±)-3,4-difluoro-α-(1-cyclobutyl)-α-[3-[n-propyl(-phenylmethyl)amino]propyl]benzeneacetonitrile;
(±)-3,4-difluoro-α-(1-cyclobutyl)-α-[3-[1-methylethyl(-phenylmethyl)amino]propyl]benzeneacetonitrile;
(±)-3,4-difluoro-α-(1-cyclopentyl)-α-[3-[ethyl(phenylmethyl)amino]propyl]benzeneacetonitrile;
(±)-3,4-difluoro-α-(1-cyclopentyl)-α-[3-[n-propyl(-phenylmethyl)amino]propyl]benzeneacetonitrile;
(±)-3,4-difluoro-α-(1-cyclopentyl)-α-[3-[1-methylethyl(phenylmethyl)amino]propyl]benzeneacetonitrile;
(±)-3,4-difluoro-α-(1-cyclohexyl)-α-[3-[ethyl(phenylmethyl)amino]propyl]benzeneacetonitrile;
(±)-3,4-difluoro-α-(1-cyclohexyl)-α-[3-[n-propyl(-phenylmethyl)amino]propyl]benzeneacetonitrile;
(±)-3,4-difluoro-α-(1-cyclohexyl)-α-[3-[1-methylethyl(phenylmethyl)amino]propyl]benzeneacetonitrile;
(±)-3,4-dichloro-α-(1-cyclopropyl)-α-[3-[ethyl(phenylmethyl)amino]propyl]benzeneacetonitrile;
(±)-3,4-dichloro-α-(1-cyclopropyl)-α-[3-[n-propyl(-phenylmethyl)amino]propyl]benezeneacetonitrile;
(±)-3,4-dichloro-α-(1-cyclopropyl)-α-[3-[1-methylethyl(phenylmethyl)amino]propyl]benzeneacetonitrile;
(±)-3,4-dichloro-α-(1-cyclobutyl)-α-[3[ethyl(phenylmethyl)amino]propyl]benzeneacetonitrile;
(±)-3,4-dichloro-α-(1-cyclobutyl)-α-[3-[n-propyl(-phenylmethyl)amino]propyl]benzeneacetonitrile;
(±)-3,4-dichloro-α-(1-cyclobutyl)-α-[3-[1-methylethyl(phenylmethyl)amino]propyl]benzeneacetonitrile;
(±)-3,4-dichloro-α-(1-cyclopentyl)-α-[3-[ethyl(phenylmethyl)amino]propyl]benzeneacetonitrile;
(±)-3,4-dichloro-α-(1-cyclopentyl)-α-[3-[n-propyl(-phenylmethyl)amino]propyl]benzeneacetonitrile;
(±)-3,4-dichloro-α-(1-cyclopentyl)-α-[3-[1-methylethyl(phenylmethyl)amino]propyl]benzeneacetonitrile;
(±)-3,4-dichloro-α-(1-cyclohexyl)-α-[3-[ethyl(phenylmethyl)amino]propyl]benzeneacetonitrile;
(±)-3,4-dichloro-α-(1-cyclohexyl)-α-[3-[n-propyl(-phenylmethyl)amino]propyl]benzeneacetonitrile;
(±)-3,4-dichloro-α-(1-cyclohexyl)-α-[3-[1-methylethyl(phenylmethyl)amino]propyl]benzeneacetonitrile;
(±)-3,4-dibromo-α-(1-cyclopropyl)-α-[3-[ethyl(phenylmethyl)amino]propyl]benzeneacetonitrile;
(±)-3,4-dibromo-α-(1-cyclopropyl)-α-[3-[n-propyl(-phenylmethyl)amino]propyl]benzeneacetonitrile;
(±)-3,4-dibromo-α-(1-cyclopropyl)-α-[3-[1-methylethyl(phenylmethyl)amino]propyl]benzeneacetonitrile;
(±)-3,4-dibromo-α-(1-cyclobutyl)-α-[3-[ethyl(phenylmethyl)amino]propyl]benzeneacetonitrile;
(±)-3,4-dibromo-α-(1-cyclobutyl)-α-[3-[n-propyl(-phenylmethyl)amino]propyl]benzeneacetonitrile;
(±)-3,4-dibromo-α-(1-cyclobutyl)-α-[3-[1-methylethyl(phenylmethyl)amino]propyl]benzeneacetonitrile;
(±)-3,4-dibromo-α-(1-cyclopentyl)-α-[3-[ethyl(phenylmethyl)amino]propyl]benzeneacetonitrile;
(±)-3,4-dibromo-α-(1-cyclopentyl)-α-[3-[n-propyl(-phenylmethyl)amino]propyl]benzeneacetonitrile;
(±)-3,4-dibromo-α-(1-cyclopentyl)-α-[3-[1-methylethyl(phenylmethyl)amino]propyl]benzeneacetonitrile;

(±)-3,4-dibromo-α-(1-cyclohexyl)-α-[3-[ethyl(phenylmethyl)amino]propyl]benzeneacetonitrile;
(±)-3,4-dibromo-α-(1-cyclohexyl)-α-[3-[n-propyl(phenylmethyl)amino]propyl]benzeneacetonitrile;
(±)-3,4-dibromo-α-(1-cyclohexyl)-α-[3-[1-methylethyl(phenylmethyl)amino]propyl]benzeneacetonitrile;
(±)-3,4-ditrifluoromethyl-α-(1-cyclopropyl)-α-[3-[ethyl(phenylmethyl)amino]propyl]benzeneacetonitrile;
(±)-3,4-ditrifluoromethyl-α-(1-cyclopropyl)-α-[3-[n-propyl(phenylmethyl)amino]propyl]benzeneacetonitrile;
(±)-3,4-ditrifluoromethyl-α-(1-cyclopropyl)-α-[3-[1-methylethyl(phenylmethyl)amino]propyl]benzeneacetonitrile;
(±)-3,4-ditrifluoromethyl-α-(1-cyclobutyl)-α-[3-[ethyl(phenylmethyl)amino]propyl]benzeneacetonitrile;
(±)-3,4-ditrifluoromethyl-α-(1-cyclobutyl)-α-[3-[n-propyl(phenylmethyl)amino]propyl]benzeneacetonitrile;
(±)-3,4-ditrifluoromethyl-α-(1-cyclobutyl)-α-[3-[1-methylethyl(phenylmethyl)amino]propyl]benzeneacetonitrile;
(±)-3,4-ditrifluoromethyl-α-(1-cyclopentyl)-α-[3-[ethyl(phenylmethyl)amino]propyl]benzeneacetonitrile;
(±)-3,4-ditrifluoromethyl-α-(1-cyclopentyl)-α-[3-[n-propyl(phenylmethyl)amino]propyl]benzeneacetonitrile;
(±)-3,4-ditrifluoromethyl-α-(1-cyclopentyl)-α-[3-[1-methylethyl(phenylmethyl)amino]propyl]benzeneacetonitrile;
(±)-3,4-ditrifluoromethyl-α-(1-cyclohexyl)-α-[3-[ethyl(phenylmethyl)amino]propyl]benzeneacetonitrile;
(±)-3,4-ditrifluoromethyl-α-(1-cyclohexyl)-α-[3-[n-propyl(phenylmethyl)amino]propyl]benzeneacetonitrile;
(±)-3,4-ditrifluoromethyl-α-(1-cyclohexyl)-α-[3-[1-methylethyl(phenylmethyl)amino]propyl]benzeneacetonitrile;
(±)-3,4-difluoro-α-(1-methylethyl)-α-[3-[ethyl(phenylethyl)amino]propyl]benzeneacetonitrile;
(±)-3,4-difluoro-α-(1-methylethyl)-α-[3-[n-propyl(phenylethyl)amino]propyl]benzeneacetonitrile;
(±)-3,4-difluoro-α-(1-methylethyl)-α-[3-[1-methylethyl(phenylethyl)amino]propyl]benzeneacetonitrile;
(±)-3,4-dichloro-α-(1-methylethyl)-α-[3-[ethyl(phenylethyl)amino]propyl]benzeneacetonitrile;
(±)-3,4-dichloro-α-(1-methylethyl)-α-[3-[n-propyl(phenylethyl)amino]propyl]benzeneacetonitrile;
(±)-3,4-dichloro-α-(1-methylethyl)-α-[3-[1-methylethyl(phenylethyl)amino]propyl]benzeneacetonitrile;
(±)-3,4-dibromo-α-(1-methyl ethyl)-α-[3-[ethyl(phenylethyl)amino]propyl]benzeneacetonitrile;
(±)-3,4-dibromo-α-(1-methylethyl)-α-[3-[n-propyl(phenylethyl)amino]propyl]benzeneacetonitrile;
(±)-3,4-dibromo-α-(1-methylethyl)-α-[3-[1-methylethyl(phenylethyl)amino]propyl]benezeneacetonitrile;
(±)-3,4-ditrifluoromethyl-α-(1-methylethyl)-α-[3-[ethyl(phenylethyl)amino]propyl]benzeneacetonitrile;
(±)-3,4-ditrifluoromethyl-α-(1-methylethyl)-α-[3-[n-propyl(phenylethyl)amino]propyl]benzeneacetonitrile;

(±)-3,4-ditrifluoromethyl-α-(1-methylethyl)-α-[3-[1-methylethyl(phenylethyl)amino]propyl]benzeneacetonitrile;
(±)-3,4-difluoro-α-(1-cyclopropyl)-α-[3-[methyl(phenylethyl)amino]propyl]benzeneacetonitrile;
(±)-3,4-difluoro-α-(1-cyclobutyl)-α-[3-[methyl(phenylethyl)amino]propyl]benzeneacetonitrile;
(±)-3,4-difluoro-α-(1-cyclopentyl)-α-[3-[methyl(phenylethyl)amino]propyl]benzeneacetonitrile;
(±)-3,4-difluoro-α-(1-cyclohexyl)-α-[3-[methyl(phenylethyl)amino]propyl]benzeneacetonitrile;
(±)-3,4-dichloro-α-(1-cyclopropyl)-α-[3-[methyl(phenylethyl)amino]propyl]benzeneacetonitrile;
(±)-3,4-dichloro-α-(1-cyclobutyl)-α-[3-[methyl(phenylethyl)amino]propyl]benzeneacetonitrile;
(±)-3,4-dichloro-α-(1-cyclopentyl)-α-[3-[methyl(phenylethyl)amino]propyl]benzeneacetonitrile;
(±)-3,4-dichloro-α-(1-cyclohexyl)-α-[3-[methyl(phenylethyl)amino]propyl]benzeneacetonitrile;
(±)-3,4-dibromo-α-(1-cyclopropyl)-α-[3-[methyl(phenylethyl)amino]propyl]benzeneacetonitrile;
(±)-3,4-dibromo-α-(1-cyclobutyl)-α-[3-[methyl(phenylethyl)amino]propyl]benzeneacetonitrile;
(±)-3,4-dibromo-α-(1-cyclopentyl)-α-[3-[methyl(phenylethyl)amino]propyl]benzeneacetonitrile;
(±)-3,4-dibromo-α-(1-cyclohexyl)-α-[3-[methyl(phenylethyl)amino]propyl]benzeneacetonitrile;
(±)-3,4-ditrifluoromethyl -α-(1-cyclopropyl)-α-[3-[methyl(phenylethyl)amino]propyl]benzeneacetonitrile;
(±)-3,4-ditrifluoromethyl-α-(1-cyclobutyl)-α-[3-[methyl(phenylethyl)amino]propyl]benzeneacetonitrile;
(±)-3,4-ditrifluoromethyl-α-(1-cyclopentyl)-α-[3-[methyl(phenylethyl)amino]propyl]benzeneacetonitrile;
(±)-3,4-ditrifluoromethyl-α-(1-cyclohexyl)-α-[3-[methyl(phenylethyl)amino]propyl]benzeneacetonitrile;
(±)-3,4-difluoro-α-(1-cyclopropyl)-α-[3-[methyl(phenylmethyl)amino]propyl]benzeneacetonitrile;
(±)-3,4-difluoro-α-(1-cyclopropyl)-α-[3-[methyl(phenylmethyl)amino]butyl]benzeneacetonitrile;
(±)-3,4-difluoro-α-(1-cyclopropyl)-α-[3-[methyl(phenylmethyl)amino]pentyl]benzeneacetonitrile;
(±)-3,4-difluoro-α-(1-cyclobutyl)-α-[3-[methyl(phenylmethyl)amino]propyl]benzeneacetonitrile;
(±)-3,4-difluoro-α-(1-cyclobutyl)-α-[3-[methyl(phenylmethyl)amino]butyl]benzeneacetonitrile;
(±)-3,4-difluoro-α-(1-cyclobutyl)-α-[3-[methyl(phenylmethyl)amino]pentyl]benzeneacetonitrile;
(±)-3,4-difluoro-α-(1-cyclopentyl)-α-[3-[methyl(phenylmethyl)amino]propyl]benzeneacetonitrile;
(±)-3,4-difluoro-α-(1-cyclopentyl)-α-[3-[methyl(phenylmethyl)amino]butyl]benzeneacetonitrile;
(±)-3,4-difluoro-α-(1-cyclopentyl)-α-[3-[methyl(phenylmethyl)amino]pentyl]benzeneacetonitrile;
(±)-3,4-difluoro-α-(1-cyclohexyl)-α-[3-[methyl(phenylmethyl)amino]propyl]benzeneacetonitrile;
(±)-3,4-difluoro-α-(1-cyclohexyl)-α-[3-[methyl(phenylmethyl)amino]butyl]benzeneacetonitrile;
(±)-3,4-difluoro-α-(1-cyclohexyl)-α-[3 -[methyl(phenylmethyl)amino]pentyl]benzeneacetonitrile;
(±)-3,4-dichloro-α-(1-cyclopropyl)-α-[3-[methyl(phenylmethyl)amino]propyl]benzeneacetonitrile;
(±)-3,4-dichloro-α-(1-cyclopropyl)-α-[3-[methyl(phenylmethyl)amino]butyl]benzeneacetonitrile;
(±)-3,4-dichloro-α-(1-cyclopropyl)-α-[3-[methyl(phenylmethyl)amino]pentyl]benzeneacetonitrile;
(±)-3,4-dichloro-α-(1-cyclobutyl)-α-[3-[methyl(phenylmethyl)amino]propyl]benzeneacetonitrile;

(±)-3,4-dichloro-α-(1-cyclobutyl)-α-[3-[methyl(phenylmethyl)amino]butyl]benzeneacetonitrile;
(±)-3,4-dichloro-α-(1-cyclobutyl)-α-[3-[methyl(phenylmethyl)amino]pentyl]benzeneacetonitrile;
(±)-3,4-dichloro-α-(1-cyclopentyl)-α-[3-[methyl(phenylmethyl)amino]propyl]benzeneacetonitrile;
(±)-3,4-dichloro-α-(1-cyclopentyl)-α-[3-[methyl(phenylmethyl)amino]butyl]benzeneacetonitrile;
(±)-3,4-dichloro-α-(1-cyclopentyl)-α-[3-[methyl(phenylmethyl)amino]pentyl]benzeneacetonitrile;
(±)-3,4-dichloro-α-(1-cyclohexyl)-α-[3-[methyl(phenylmethyl)amino]propyl]benzeneacetonitrile;
(±)-3,4-dichloro-α-(1-cyclohexyl)-α-[3-[methyl(phenylmethyl)amino]butyl]benzeneacetonitrile;
(±)-3,4-dichloro-α-(1-cyclohexyl)-α-[3-[methyl(phenylmethyl)amino]pentyl]benzeneacetonitrile;
(±)-3,4-ditrifluoromethyl-α-(1-cyclopropyl)-α-[3-[methyl(phenylmethyl)amino]propyl]benzeneacetonitrile;
(±)-3,4-ditrifluoromethyl-α-(1-cyclopropyl)-α-[3-[methyl(phenylmethyl)amino]butyl]benzeneacetonitrile;
(±)-3,4-ditrifluoromethyl-α-(1-cyclopropyl)-α-[3-[methyl(phenylmethyl)amino]pentyl]benzeneacetonitrile;
(±)-3,4-ditrifluoromethyl-α-(1-cyclobutyl)-α-[3-[methyl(phenylmethyl)amino]propyl]benzeneacetonitrile;
(±)-3,4-ditrifluoromethyl-α-(1-cyclobutyl)-α-[3-[methyl(phenylmethyl)amino]butyl]benzeneacetonitrile;
(±)-3,4-ditrifluoromethyl-α-(1-cyclobutyl)-α-[3-[methyl(phenylmethyl)amino]pentyl]benezeneacetonitrile;
(±)-3,4-ditrifluoromethyl-α-(1-cyclopentyl)-α-[3-[methyl(phenylmethyl)amino]propyl]benezeneacetonitrile;
(±)-3,4-ditrifluoromethyl-α-(1-cyclopentyl)-α-[3-[methyl(phenylmethyl)amino]butyl]benzeneacetonitrile;
(±)-3,4-ditrifluoromethyl-α-(1-cyclopentyl)-α-[3-[methyl(phenylmethyl)amino]pentyl]benzeneacetonitrile;
(±)-3,4-ditrifluoromethyl-α-(1-cyclohexyl)-α-[3-[methyl(phenylmethyl)amino]propyl]benzeneacetonitrile;
(±)-3,4-ditrifluoromethyl-α-(1-cyclohexyl)-α-[3-[methyl(phenylmethyl)amino]butyl]benzeneacetonitrile;
(±)-3,4-ditrifluoromethyl-α-(1-cyclohexyl)-α-[3-[methyl(phenylmethyl)amino]pentyl]benzeneacetonitrile;
(±)-3,4-difluoro-α-(1-methylethyl)-α-[3-[ethyl(phenylmethyl)amino]propyl]benzeneacetonitrile;
(±)-3,4-difluoro-α-(1-methylethyl)-α-[3-[n-propyl(phenylmethyl)amino]propyl]benzeneacetonitrile;
(±)-3,4-difluoro-α-(1-methylethyl)-α-[3-[1-methylethyl(phenylmethyl)amino]propyl]benzeneacetonitrile;
(±)-3,4-difluoro-α-(1-methylethyl)-α-[3-[ethyl(phenylmethyl)amino]butyl]benezeneacetonitrile;
(±)-3,4-difluoro-α-(1-methylethyl)-α-[3-[n-propyl(phenylmethyl)amino]butyl]benzeneacetonitrile;
(±)-3,4-difluoro-α-(1-methylethyl)-α-[3-[1-methylethyl(phenylmethyl)amino]butyl]benzeneacetonitrile;
(±)-3,4-difluoro-α-(1-methylethyl)-α-[3-[ethyl(phenylmethyl)amino]pentyl]benezeneacetonitrile;
(±)-3,4-difluoro-α-(1-methylethyl)-α-[3-[n-propyll(phenylmethyl)amino]pentyl]benzeneacetonitrile;
(±)-3,4-difluoro-α-(1-methylethyl)-α-[3-[1-methylethyl(phenylmethyl)amino]pentyl]benzeneacetonitrile;

(±)-3,4-dichloro-α-(1-methylethyl)-α-[3-[ethyl(phenylmethyl)amino]propyl]benzeneacetonitrile;
(±)-3,4-dichloro-α-(1-methylethyl)-α-[3-[n-propyl(phenylmethyl)amino]propyl]benzeneacetonitrile;
(±)-3,4-dichloro-α-(1-methylethyl)-α-[3-[1-methylethyl(phenylmethyl)amino]propyl]benzeneacetonitrile;
(±)-3,4-dichloro-α-(1-methylethyl)-α-[3-[ethyl(phenylmethyl)amino]butyl]benzeneacetonitrile;
(±)-3,4-dichloro-α-(1-methylethyl)-α-[3-[n-propyl(phenylmethyl)amino]butyl]benzeneacetonitrile;
(±)-3,4-dichloro-α-(1-methylethyl)-α-[3-[1-methylethyl(phenylmethyl)amino]butyl]benzeneacetonitrile;
(±)-3,4-dichloro-α-(1-methylethyl)-α-[3-[ethyl(phenylmethyl)amino]pentyl]benzeneacetonitrile;
(±)-3,4-dichloro-α-(1-methylethyl)-α-[3-[n-propyll(phenylmethyl)amino]pentyl]benzeneacetonitrile;
(±)-3,4-dichloro-α-(1-methylethyl)-α-[3-[1-methylethyl(phenylmethyl)amino]pentyl]benzeneacetonitrile;
(±)-3,4-dibromo-α-(1-methylethyl)-α-[3-[ethyl(phenylmethyl)amino]propyl]benezeneacetonitrile;
(±)-3,4-dibromo-α-(1-methylethyl)-α-[3-[n-propyll(phenylmethyl)amino]propyl]benzeneacetonitrile;
(±)-3,4-dibromo-α-(1-methylethyl)-α-[3-[1-methylethyl(phenylmethyl)amino]propyl]benzeneacetonitrile;
(±)-3,4-dibromo-α-(1-methylethyl)-α-[3-[ethyl(phenylmethyl)amino]butyl]benzeneacetonitrile;
(±)-3,4-dibromo-α-(1-methylethyl)-α-[3-[n-propyll(phenylmethyl)amino]butyl]benzeneacetonitrile;
(±)-3,4-dibromo-α-(1-methylethyl)-α-[3-[1-methylethyl(phenylmethyl)amino]butyl]benzeneacetonitrile;
(±)-3,4-dibromo-α-(1-methylethyl)-α-[3-[ethyl(phenylmethyl)amino]pentyl]benzeneacetonitrile;
(±)-3,4-dibromo-α-(1-methylethyl)-α-[3-[n-propyll(phenylmethyl)amino]pentyl]benzeneacetonitrile;
(±)-3,4-dibromo-α-(1-methylethyl)-α-[3-[1-methylethyl(phenylmethyl)amino]pentyl]benzeneacetonitrile;
(±)-3,4-ditrifluoromethyl-α-(1-methylethyl)-α-[3-[ethyl(phenylmethyl)amino]propyl]benzeneacetonitrile;
(±)-3,4-ditrifluoromethyl-α-(1-methylethyl)-α-[3-[n-propyll(phenylmethyl)amino]propyl]benzeneacetonitrile;
(±)-3,4-ditrifluoromethyl-α-(1-methylethyl)-α-[3-[1-methylethyl(phenylmethyl)amino]propyl]benzeneacetonitrile;
(±)-3,4-ditrifluoromethyl-(1-methylethyl)-α-[3-[ethyl(phenylmethyl)amino]butyl]benzeneacetonitrile;
(±)-3,4-ditrifluoromethyl-α-(1-methylethyl)-α-[3-[n-propyll(phenylmethyl)amino]butyl]benzeneacetonitrile;
(±)-3,4-ditrifluoromethyl-α-(1-methylethyl)-α-[3-[1-methylethyl(phenylmethyl)amino]butyl]benzeneacetonitrile;
(±)-3,4-ditrifluoromethyl-(1-methylethyl)-α-[3-[ethyl(phenylmethyl)amino]pentyl]benzeneacetonitrile;
(±)-3,4-ditrifluoromethyl-α-(1-methylethyl)-α-[3-[n-propyll(phenylmethyl)amino]pentyl]benzeneacetonitrile;
(±)-3,4-ditrifluoromethyl-α-(1-methylethyl)-α-[3-[1-methylethyl(phenylmethyl)amino]pentyl]benzeneacetonitrile;
(±)-3,4-difluoro-α-(1-methylethyl)-α-[3-[methyl(phenylethyl)amino]propyl]benzeneacetonitrile;

(±)-3,4-difluoro-α-(1-methylethyl)-α-[3-[methyl(phenylethyl)amino]butyl]benzeneacetonitrile;
(±)-3,4-difluoro-α-(1-methylethyl)-α-[3-[methyl(phenylethyl)amino]pentyl]benzeneacetonitrile;
(±)-3,4-dichloro-α-(1-methylethyl)-α-[3-[methyl(phenylethyl)amino]propyl]benzeneacetonitrile;
(±)-3,4-dichloro-α-(1-methylethyl)-α-[3-[methyl(phenylethyl)amino]butyl]benzeneacetonitrile;
(±)-3,4-dichloro-α-(1-methylethyl)-α-[3-[methyl(phenylethyl)amino]pentyl]benzeneacetonitrile;
(±)-3,4-dibromo-α-(1-methylethyl)-α-[3-[methyl(phenylethyl)amino]propyl]benzeneacetonitrile;
(±)-3,4-dibromo-α-(1-methylethyl)-α-[3-[methyl(phenylethyl)amino]butyl]benzeneacetonitrile;
(±)-3,4-dibromo-α-(1-methylethyl)-α-[3-[methyl(phenylethyl)amino]pentyl]benzeneacetonitrile;
(±)-3,4-ditrifluoromethyl-α-(1-methylethyl)-α-[3-[methyl(phenylethyl)amino]propyl]benzeneacetonitrile;
(±)-3,4-ditrifluoromethyl-α-(1-methylethyl)-α-[3-[methyl(phenylethyl)amino]butyl]benzeneacetonitrile;
(±)-3,4-ditrifluoromethyl-α-(1-methylethyl)-α-[3-[methyl(phenylethyl)amino]pentyl]benzeneacetonitrile;
(±)-3,4-difluoro-α-(1-cyclopropyl)-α-[3-[ethyl(phenylethyl)amino]propyl]benzeneacetonitrile;
(±)-3,4-difluoro-α-(1-cyclopropyl)-α-[3-[n-propyl(phenylethyl)amino]propyl]benzeneacetonitrile;
(±)-3,4-difluoro-α-(1-cyclopropyl)-α-[3-[1-methylethyl(phenylethyl)amino]propyl]benzeneacetonitrile;
(±)-3,4-difluoro-α-(1-cyclobutyl)-α-[3-[ethyl(phenylethyl)amino]propyl]benzeneacetonitrile;
(±)-3,4-difluoro-α-(1-cyclopbutyl)-α-[3-[n-propyl(phenylethyl)amino]propyl]benzeneacetonitrile;
(±)-3,4-difluoro-α-(1-cyclopbutyl)-α-[3-[1-methylethyl(phenylethyl)amino]propyl]benzeneacetonitrile;
(±)-3,4-difluoro-α-(1-cyclopentyl)-α-[3-[ethyl(phenylethyl)amino]propyl]benzeneacetonitrile;
(±)-3,4-difluoro-α-(1-cyclopentyl)-α-[3-[n-propyl(phenylethyl)amino]propyl]benzeneacetonitrile;
(±)-3,4-difluoro-α-(1-cyclopentyl)-α-[3-[1-methylethyl(phenylethyl)amino]propyl]benzeneacetonitrile;
(±)-3,4-difluoro-α-(1-cyclohexyl)-α-[3-[ethyl(phenylethyl)amino]propyl]benzeneacetonitrile;
(±)-3,4-difluoro-α-(1-cyclohexyl)-α-[3-[n-propyl(phenylethyl)amino]propyl]benzeneacetonitrile;
(±)-3,4-difluoro-α-(1-cyclohexyl)-α-[3-[1-methylethyl(phenylethyl)amino]propyl]benzeneacetonitrile;
(±)-3,4-difluoro-α-(1-cyclopropyl)-α-[3-[ethyl(phenylmethyl)amino]propyl]benzeneacetonitrile;
(±)-3,4-difluoro-α-(1-cyclopropyl)-α-[3-[n-propyl(phenylmethyl)amino]propyl]benzeneacetonitrile;
(±)-3,4-difluoro-α-(1-cyclopropyl)-α-[3-[1-methylethyl(phenylethyl)amino]propyl]benzeneacetonitrile;
(±)-3,4-difluoro-α-(1-cyclobutyl)-α-[3-[ethyl( phenylethyl)amino]propyl]benezeneacetonitrile;
(±)-3,4-difluoro-α-(1-cyclobutyl)-α-[3-[n-propyl(phenylethyl)amino]propyl]benzeneacetonitrile;
(±)-3,4-difluoro-α-(1-cyclobutyl)-α-[3-[1-methylethyl(phenylethyl)amino]propyl]benzeneacetonitrile;
(±)-3,4-difluoro-α-(1-cyclopentyl)-α-[3-[ethyl(phenylethyl)amino]propyl]benzeneacetonitrile;
(±)-3,4-difluoro-α-(1-cyclopentyl)-α-[3-[n-propyl(phenylethyl)amino]propyl]benzeneacetonitrile;
(±)-3,4-difluoro-α-(1-cyclopentyl)-α-[3-[1-methylethyl(phenylethyl)amino]propyl]benzeneacetonitrile;
(±)-3,4-difluoro-α-(1-cyclohexyl)-α-[3-[ethyl(phenylethyl)amino]propyl]benzeneacetonitrile;
(±)-3,4-difluoro-α-(1-cyclohexyl)-α-[3-[n-propyl(phenylethyl)amino]propyl]benzeneacetonitrile;

(±)-3,4-difluoro-α-(1-cyclohexyl)-α-[3-[1-methylethyl(phenylethyl)amino]propyl]benzeneacetonitrile;
(±)-3,4-difluoro-α-(1-cyclopropyl)-α-[3-[ethyl(phenylmethyl)amino]butyl]benzeneacetonitrile;
(±)-3,4-difluoro-α-(1-cyclopropyl)-α-[3-[n-propyl(phenylmethyl)amino]butyl]benzeneacetonitrile;
(±)-3,4-difluoro-α-(1-cyclopropyl)-α-[3-[1-methylethyl(phenylmethyl)amino]butyl]benzeneacetonitrile;
(±)-3,4-difluoro-α-(1-cyclopropyl)-α-[3-[ethyl(phenylmethyl)amino]pentyl]benzeneacetonitrile;
(±)-3,4-difluoro-α-(1-cyclopropyl)-α-[3-[n-propyl(phenylmethyl)amino]pentyl]benzeneacetonitrile;
(±)-3,4-difluoro-α-(1-cyclopropyl)-α-[3-[1-methylethyl(phenylmethyl)amino]pentyl]benzeneacetonitrile;
(±)-3,4-difluoro-α-(1-cyclobutyl)-α-[3-[ethyl(phenylmethyl)amino]butyl]benzeneacetonitrile;
(±)-3,4-difluoro-α-(1-cyclobutyl)-α-[3 -[n-propyl(phenylmethyl)amino]butyl]benzeneacetonitrile;
(±)-3,4-difluoro-α-(1-cyclobutyl)-α-[3-[1-methylethyl(phenylmethyl)amino]butyl]benzeneacetonitrile;
(±)-3,4-difluoro-α-(1-cyclobutyl)-α-[3-[ethyl(phenylmethyl)amino]pentyl]benzeneacetonitrile;
(±)-3,4-difluoro-α-(1-cyclobutyl)-α-[3-[n-propyl(phenylmethyl)amino]pentyl]benzeneacetonitrile;
(±)-3,4-difluoro-α-(1-cyclobutyl)-α-[3-[1-methylethyl(phenylmethyl)amino]pentyl]benzeneacetonitrile;
(±)-3,4-difluoro-α-(1-cyclopentyl)-α-[3-[ethyl(phenylmethyl)amino]butyl]benzeneacetonitrile;
(±)-3,4-difluoro-α-(1-cyclopentyl)-α-[3-[n-propyl(phenylmethyl)amino]butyl]benzeneacetonitrile;
(±)-3,4-difluoro-α-(1-cyclopentyl)-α-[3-[1-methylethyl(phenylmethyl)amino]butyl]benzeneacetonitrile;
(±)-3,4-difluoro-α-(1-cyclopentyl)-α-[3-[ethyl(phenylmethyl)amino]pentyl]benzeneacetonitrile;
(±)-3,4-difluoro-α-(1-cyclopentyl)-α-[3-[n-propyl(phenylmethyl)amino]pentyl]benzeneacetonitrile;
(±)-3,4-difluoro-α-(1-cyclopentyl)-α-[3-[1-methylethyl(phenylmethyl)amino]pentyl]benzeneacetonitrile;
(±)-3,4-difluoro-α-(1-cyclohexyl)-α-[3-[ethyl(phenylmethyl)amino]butyl]benzeneacetonitrile;
(±)-3,4-difluoro-α-(1-cyclohexyl)-α-[3-[n-propyl(phenylmethyl)amino]butyl]benzeneacetonitrile;
(±)-3,4-difluoro-α-(1-cyclohexyl)-α-[3-[1-methylethyl(phenylmethyl)amino]butyl]benzeneacetonitrile;
(±)-3,4-difluoro-α-(1-cyclohexyl)-α-[3-[ethyl(phenylmethyl)amino]pentyl]benzeneacetonitrile;
(±)-3,4-difluoro-α-(1-cyclohexyl)-α-[3-[n-propyl(phenylmethyl)amino]pentyl]benzeneacetonitrile;
(±)-3,4-difluoro-α-(1-cyclohexyl)-α-[3-[1-methylethyl(phenylmethyl)amino]pentyl]benzeneacetonitrile;
(±)-3,4-difluoro-α-(1-cyclopropyl)-α-[3-[methyl(phenylethyl)amino]butyl]benzeneacetonitrile;
(±)-3,4-difluoro-α-(1-cyclopropyl)-α-[3-[methyl(phenylethyl)amino]pentyl]benzeneacetonitrile;
(±)-3,4-difluoro-α-(1-cyclobutyl)-α-[3-[methyl(phenylethyl)amino]butyl]benzeneacetonitrile;
(±)-3,4-difluoro-α-(1-cyclobutyl)-α-[3-[methyl(phenylethyl)amino]pentyl]benezeneacetonitrile;
(±)-3,4-difluoro-α-(1-cyclopentyl)-α-[3-[methyl(phenylethyl)amino]butyl]benzeneacetonitrile;
(±)-3,4-difluoro-α-(1-cyclopentyl)-α-[3-[methyl(phenylethyl)amino]pentyl]benzeneacetonitrile;
(±)-3,4-difluoro-α-(1-cyclohexyl)-α-[3-[methyl(phenylethyl)amino]butyl]benezeneacetonitrile;

(±)-3,4-difluoro-α-(1-cyclohexyl)-α-[3-[methyl(-phenylethyl)amino]pentyl]benzeneacetonitrile;
(±)-3,4-difluoro-α-(1-cyclopropyl)-α-[3-[ethyl(-phenylethyl)amino]propyl]benzeneacetonitrile;
(±)-3,4-difluoro-α-(1-cyclopropyl)-α-[3-[n-propyl(-phenylethyl)amino]propyl]benzeneacetonitrile;
(±)-3,4-difluoro-α-(1-cyclopropyl)-α-[3-[1-methylethyl(phenylethyl)amino]propyl]benzeneacetonitrile;
(±)-3,4-dichloro-α-(1-cyclopropyl)-α-[3-[ethyl(-phenylethyl)amino]propyl]benzeneacetonitrile;
(±)-3,4-dichloro-α-(1-cyclopropyl)-α-[3-[n-propyl(-phenylethyl)amino]propyl]benzeneacetonitrile;
(±)-3,4-dichloro-α-(1-cyclopropyl)-α-[3-[1-methylethyl(phenylethyl)amino]propyl]benzeneacetonitrile;
(±)-3,4-dichloro-α-(1-cyclopropyl)-α-[3-[ethyl(-phenylethyl)amino]propyl]benzeneacetonitrile;
(±)-3,4-dichloro-α-(1-cyclopropyl)-α-[3-[n-propyl(-phenylethyl)amino]propyl]benzeneacetonitrile;
(±)-3,4-dichloro-α-(1-cyclopropyl)-α-[3-[1-methylethyl(phenylethyl)amino]propyl]benzeneacetonitrile;
(±)-3,4-ditrifluoromethyl-α-(1-cyclopropyl)-α-[3-[ethyl(phenylethyl)amino]propyl]benzeneacetonitrile;
(±)-3,4-ditrifluoromethyl-α-(1-cyclopropyl)-α-[3-[n-propyl(phenylethyl)amino]propyl]benzeneacetonitrile;
(±)-3,4-ditrifluoromethyl-α-(1-cyclopropyl)-α-[3-[1-methylethyl(phenylethyl)amino]propyl]-benezeneacetonitrile;
(±)-3,4-difluoro-α-(1-cyclobutyl)-α-[3-[ethyl(phenylethyl)amino]propyl]benzeneacetonitrile;
(±)-3,4-difluoro-α-(1-cyclobutyl)-α-[3-[n-propyl(-phenylethyl)amino]propyl]benzeneacetonitrile;
(±)-3,4-difluoro-α-(1-cyclobutyl)-α-[3-[1-methylethyl(-phenylethyl)amino]propyl]benzeneacetonitrile;
(±)-3,4-dichloro-α-(1-cyclobutyl)-α-[3-[ethyl(phenylethyl)amino]propyl]benzeneacetonitrile;
(±)-3,4-dichloro-α-(1-cyclobutyl)-α-[3-[n-propyl(-phenylethyl)amino]propyl]benzeneacetonitrile;
(±)-3,4-dichloro-α-(1-cyclobutyl)-α-[3-[1-methylethyl(phenylethyl)amino]propyl]benzeneacetonitrile;
(±)-3,4-dichloro-α-(1-cyclobutyl)-α-[3-[ethyl(phenylethyl)amino]propyl]benzeneacetonitrile;
(±)-3,4-dichloro-α-(1-cyclobutyl)-α-[3-[n-propyl(-phenylethyl)amino]propyl]benezeneacetonitrile;
(±)-3,4-dichloro-α-(1-cyclobutyl)-α-[3-[1-methylethyl(phenylethyl)amino]propyl]benzeneacetonitrile;
(±)-3,4-ditrifluoromethyl-α-(1-cyclobutyl)-α-[3-[ethyl(phenylethyl)amino]propyl]benzeneacetonitrile;
(±)-3,4-ditrifluoromethyl-α-(1-cyclobutyl)-α-[3-[n-propyl(phenylethyl)amino]propyl]benzeneacetonitrile;
(±)-3,4-ditrifluoromethyl-α-(1-cyclobutyl)-α-[3-[1-methylethyl(phenylethyl)amino]propyl]benzeneacetonitrile;
(±)-3,4-difluoro-α-(1-cyclopentyl)-α-[3-[ethyl(phenylethyl)amino]propyl]benzeneacetonitrile;
(±)-3,4-difluoro-α-(1-cyclopentyl)-α-[3-[n-propyl(-phenylethyl)amino]propyl]benzeneacetonitrile;
(±)-3,4-difluoro-α- i 1-cyclopentyl)-α-[3-[1-methylethyl(phenylethyl)amino]propyl]benzeneacetonitrile;
(±)-3,4-dichloro-α-(1-cyclopentyl)-α-[3-[ethyl(-phenylethyl)amino]propyl]benzeneacetonitrile;
(±)-3,4-dichloro-α-(1-cyclopentyl)-α-[3-[n-propyl(-phenylethyl)amino]propyl]benzeneacetonitrile;
(±)-3,4-dichloro-α-(1-cyclopentyl)-α-[3-[1-methylethyl(phenylethyl)amino]propyl]benzeneacetonitrile;
(±)-3,4-dichloro-α-(1-cyclopentyl)-α-[3-[ethyl(-phenylethyl)amino]propyl]benzeneacetonitrile;
(±)-3,4-dichloro-α-(1-cyclopentyl)-α-[3-[n-propyl(-phenylethyl)amino]propyl]benzeneacetonitrile;
(±)-3,4-dichloro-α-(1-cyclopentyl)-α-[3-[1-methylethyl(phenylethyl)amino]propyl]benzeneacetonitrile;
(±)-3,4-ditrifluoromethyl-α-(1-cyclopentyl)-α-[3-[ethyl(phenylethyl)amino]propyl]benzeneacetonitrile;
(±)-3,4-ditrifluoromethyl-α-(1-cyclopentyl)-α-[3-[n-propyl(phenylethyl)amino]propyl]benzeneacetonitrile;
(±)-3,4-ditrifluoromethyl-α-(1-cyclopentyl)-α-[3-[1-methylethyl(phenylethyl)amino]propyl]benzeneacetonitrile;
(±)-3,4-difluoro-α-(1-cyclohexyl)-α-[3-[ethyl(phenylethyl)amino]propyl]benzeneacetonitrile;
(±)-3,4-difluoro-α-(1-cyclohexyl)-α-[3-[n-propyl(-phenylethyl)amino]propyl]benzeneacetonitrile;
(±)-3,4-difluoro-α-(1-cyclohexyl)-α-[3-[1-methylethyl(phenylethyl)amino]propyl]benzeneacetonitrile;
(±)-3,4-dichloro-α-(1-cyclohexyl)-α-[3-[ethyl(phenylethyl)amino]propyl]benzeneacetonitrile;
(±)-3,4-dichloro-α-(1-cyclohexyl)-α-[3-[n-propyl(-phenylethyl)amino]propyl]benzeneacetonitrile;
(±)-3,4-dichloro-α-(1-cyclohexyl)-α-[3-[1-methylethyl(phenylethyl)amino]propyl]benzeneacetonitrile;
(±)-3,4-dichloro-α-(1-cyclohexyl)-α-[3-[ethyl(phenylethyl)amino]propyl]benzeneacetonitrile;
(±)-3,4-dichloro-α-(1-cyclohexyl)-α-[3-[n-propyl(-phenylethyl)amino]propyl]benzeneacetonitrile;
(±)-3,4-dichloro-α-(1-cyclohexyl)-α-[3-[1-methylethyl(phenylethyl)amino]propyl]benzeneacetonitrile;
(±)-3,4-ditrifluoromethyl-α-(1-cyclohexyl)-α-[3-[ethyl(phenylethyl)amino]propyl]benzeneacetonitrile;
(±)-3,4-ditrifluoromethyl-α-(1-cyclohexyl)-α-[3-[n-propyl(phenylethyl)amino]propyl]benzeneacetonitrile;
(±)-3,4-ditrifluoromethyl-α-(1-cyclohexyl)-α-[3-[1-methylethyl(phenylethyl)amino]propyl]benzeneacetonitrile;
(±)-3,4-difluoro-α-(1-cyclopropyl)-α-[3-[ethyl(-phenylethyl)amino]butyl]benzeneacetonitrile;
(±)-3,4-difluoro-α-(1-cyclopropyl)-α-[3-[n-propyl(-phenylethyl)amino]butyl]benzeneacetonitrile;
(±)-3,4-difluoro-α-(1-cyclopropyl)-α-[3-[1-methylethyl(phenylethyl)amino]butyl]benzeneacetonitrile;
(±)-3,4-dichloro-α-(1-cyclopropyl)-α-[3-[ethyl(-phenylethyl)amino]butyl]benzeneacetonitrile;
(±)-3,4-dichloro-α-(1-cyclopropyl)-α-[3-[n-propyl(-phenylethyl)amino]butyl]benzeneacetonitrile;
(±)-3,4-dichloro-α-(1-cyclopropyl)-α-[3-[1-methylethyl(phenylethyl)amino]butyl]benzeneacetonitrile;
(±)-3,4-dichloro-α-(1-cyclopropyl)-α-[3-[ethyl(-phenylethyl)amino]butyl]benzeneacetonitrile;
(±)-3,4-dichloro-α-(1-Cyclopropyl)-α-[3-[n-propyl(-phenylethyl)amino]butyl]benzeneacetonitrile;
(±)-3,4-dichloro-α-(1-cyclopropyl)-α-[3-[1-methylethyl(phenylethyl)amino]butyl]benzeneacetonitrile;
(±)-3,4-ditrifluoromethyl-α-(1-cyclopropyl)-α-[3-[ethyl(phenylethyl)amino]butyl]benzeneacetonitrile;
(±)-3,4-ditrifluoromethyl-α-(1-cyclopropyl)-α-[3-[n-propyl(phenylethyl)amino]butyl]benzeneacetonitrile;
(±)-3,4-ditrifluoromethyl-α-(1-cyclopropyl)-α-[3-[1-methylethyl(phenylethyl)amino]butyl]benzeneacetonitrile;

(±)-3,4-difluoro-α-(1-cyclobutyl)-α-[3-[ethyl(phenylethyl)amino]butyl]benzeneacetonitrile;
(±)-3,4-difluoro-α-(1-cyclobutyl)-α-[3-[n-propyl(phenylethyl)amino]butyl]benzeneacetonitrile;
(±)-3,4-difluoro-α-(1-cyclobutyl)-α-[3-[1-methylethyl(phenylethyl)amino]butyl]benzeneacetonitrile;
(±)-3,4-dichloro-α-(1-cyclobutyl)-α-[3-[ethyl(phenylethyl)amino]butyl]benzeneacetonitrile;
(±)-3,4-dichloro-α-(1-cyclobutyl)-α-[3-[n-propyl(phenylethyl)amino]butyl]benzeneacetonitrile;
(±)-3,4-dichloro-α-(1-cyclobutyl)-α-[3-[1-methylethyl(phenylethyl)amino]butyl]benzeneacetonitrile;
(±)-3,4-dichloro-α-(1-cyclobutyl)-α-[3-[ethyl(phenylethyl)amino]butyl]benzeneacetonitrile;
(±)-3,4-dichloro-α-(1-cyclobutyl)-α-[3-[n-propyl(phenylethyl)amino]butyl]benzeneacetonitrile;
(±)-3,4-dichloro-α-(1-cyclobutyl)-α-[3-[1-methylethyl(phenylethyl)amino]butyl]benzeneacetonitrile;
(±)-3,4-ditrifluoromethyl-α-(1-cyclobutyl)-α-[3-[ethyl(phenylethyl)amino]butyl]benzeneacetonitrile;
(±)-3,4-ditrifluoromethyl-α-(1-cyclobutyl)-α-[3-[n-propyl(phenylethyl)amino]butyl]benzeneacetonitrile;
(±)-3,4-ditrifluoromethyl-α-(1-cyclobutyl)-α-[3-[1-methylethyl(phenylethyl)amino]butyl]benzeneacetonitrile;
(±)-3,4-difluoro-α-(1-cyclopentyl)-α-[3-[ethyl(phenylethyl)amino]butyl]benzeneacetonitrile;
(±)-3,4-difluoro-α-(1-cyclopentyl)-α-[3-[n-propyl(phenylethyl)amino]butyl]benzeneacetonitrile;
(±)-3,4-difluoro-α-(1-cyclopentyl)-α-[3-[1-methylethyl(phenylethyl)amino]butyl]benzeneacetonitrile;
(±)-3,4-dichloro-α-(1-cyclopentyl)-α-[3-[ethyl(phenylethyl)amino]butyl]benzeneacetonitrile;
(±)-3,4-dichloro-α-(1-cyclopentyl)-α-[3-[n-propyl(phenylethyl)amino]butyl]benzeneacetonitrile;
(±)-3,4-dichloro-α-(1-cyclopentyl)-α-[3-[1-methylethyl(phenylethyl)amino]butyl]benzeneacetonitrile;
(±)-3,4-dichloro-α-(1-cyclopentyl)-α-[3-[ethyl(phenylethyl)amino]butyl]benzeneacetonitrile;
(±)-3,4-dichloro-α-(1-cyclopentyl)-α-[3-[n-propyl(phenylethyl)amino]butyl]benzeneacetonitrile;
(±)-3,4-dichloro-α-(1-cyclopentyl)-α-[3-[1-methylethyl(phenylethyl)amino]butyl]benzeneacetonitrile;
(±)-3,4-ditrifluoromethyl-α-(1-cyclopentyl)-α-[3-[ethyl(phenylethyl)amino]butyl]benzeneacetonitrile;
(±)-3,4-ditrifluoromethyl-α-(1-cyclopentyl)-α-[3-[n-propyl(phenylethyl)amino]butyl]benzeneacetonitrile;
(±)-3,4-ditrifluoromethyl-α-(1-cyclopentyl)-α-[3-[1-methylethyl(phenylethyl)amino]butyl]benzeneacetonitrile;
(±)-3,4-difluoro-α-(1-cyclohexyl)-α-[3-[ethyl(phenylethyl)amino]butyl]benzeneacetonitrile;
(±)-3,4-difluoro-α-(1-cyclohexyl)-α-[3-[n-propyl(phenylethyl)amino]butyl]benzeneacetonitrile;
(±)-3,4-difluoro-α-(1-cyclohexyl)-α-[3-[1-methylethyl(phenylethyl)amino]butyl]benzeneacetonitrile;
(±)-3,4-dichloro-α-(1-cyclohexyl)-α-[3-[ethyl(phenylethyl)amino]butyl]benzeneacetonitrile;
(±)-3,4-dichloro-α-(1-cyclohexyl)-α-[3-[n-propyl(phenylethyl)amino]butyl]benzeneacetonitrile;
(±)-3,4-dichloro-α-(1-cyclohexyl)-α-[3-[1-methylethyl(phenylethyl)amino]butyl]benzeneacetonitrile;
(±)-3,4-dichloro-α-(1-cyclohexyl)-α-[3-[ethyl(phenylethyl)amino]butyl]benzeneacetonitrile;
(±)-3,4-dichloro-α-(1-cyclohexyl)-α-[3-[n-propyl(phenylethyl)amino]butyl]benzeneacetonitrile;
(±)-3,4-dichloro-α-(1-cyclohexyl)-α-[3-[1-methylethyl(phenylethyl)amino]butyl]benzeneacetonitrile;
(±)-3,4-ditrifluoromethyl-α-(1-cyclohexyl)-α-[3-[ethyl(phenylethyl)amino]butyl]benzeneacetonitrile;
(±)-3,4-ditrifluoromethyl-α-(1-cyclohexyl)-α-[3-[n-propyl(phenylethyl)amino]butyl]benzeneacetonitrile;
(±)-3,4-ditrifluoromethyl-α-(1-cyclohexyl)-α-[3-[1-methylethyl(phenylethyl)amino]butyl]benzeneacetonitrile;
(±)-3,4-difluoro-α-(1-cyclopropyl)-α-[3-[ethyl(phenylethyl)amino]pentyl]benzeneacetonitrile;
(±)-3,4-difluoro-α-(1-cyclopropyl)-α-[3-[n-propyl(phenylethyl)amino]pentyl]benzeneacetonitrile;
(±)-3,4-difluoro-α-(1-cyclopropyl)-α-[3-[1-methylethyl(phenylethyl)amino]pentyl]benzeneacetonitrile;
(±)-3,4-dichloro-α-(1-cyclopropyl)-α-[3-[ethyl(phenylethyl)amino]pentyl]benzeneacetonitrile;
(±)-3,4-dichloro-α-(1-cyclopropyl)-α-[3-[n-propyl(phenylethyl)amino]pentyl]benzeneacetonitrile;
(±)-3,4-dichloro-α-(1-cyclopropyl)-α-[3-[1-methylethyl(phenylethyl)amino]pentyl]benzeneacetonitrile;
(±)-3,4-dichloro-α-(1-cyclopropyl)-α-[3-[ethyl(phenylethyl)amino]pentyl]benzeneacetonitrile;
(±)-3,4-dichloro-α-(1-cyclopropyl)-α-[3-[n-propyl(phenylethyl)amino]pentyl]benzeneacetonitrile;
(±)-3,4-dichloro-α-(1-cyclopropyl)-α-[3-[1-methylethyl(phenylethyl)amino]pentyl]benzeneacetonitrile;
(±)-3,4-ditrifluoromethyl-5-(1-cyclopropyl)-α-[3-[ethyl(phenylethyl)amino]pentyl]benzeneacetonitrile;
(±)-3,4-ditrifluoromethyl-α-(1-cyclopropyl)-α-[3-[n-propyl(phenylethyl)amino]pentyl]benzeneacetonitrile;
(±)-3,4-ditrifluoromethyl-α-(1-cyclopropyl)-α-[3-[1-methylethyl(phenylethyl)amino]pentyl]benzeneacetonitrile;
(±)-3,4-difluoro-α-(1-cyclobutyl)-α-[3-[ethyl(phenylethyl)amino]pentyl]benzeneacetonitrile;
(±)-3,4-difluoro-α-(1-cyclobutyl)-α-[3-[n-propyl(phenylethyl)amino]pentyl]benzeneacetonitrile;
(±)-3,4-difluoro-α-(1-cyclobutyl)-α-[3-[1-methylethyl(phenylethyl)amino]pentyl]benzeneacetonitrile;
(±)-3,4-dichloro-α-(1-cyclobutyl)-α-[3-[ethyl(phenylethyl)amino]pentyl]benzeneacetonitrile;
(±)-3,4-dichloro-α-(1-cyclobutyl)-α-[3-[n-propyl(phenylethyl)amino]pentyl]benzeneacetonitrile;
(±)-3,4-dichloro-α-(1-cyclobutyl)-α-[3-[1-methylethyl(phenylethyl)amino]pentyl]benzeneacetonitrile;
(±)-3,4-dichloro-α-(1-cyclobutyl)-α-[3-[ethyl(phenylethyl)amino]pentyl]benzeneacetonitrile;
(±)-3,4-dichloro-α-(1-cyclobutyl)-α-[3-[n-propyl(phenylethyl)amino]pentyl]benzeneacetonitrile;
(±)-3,4-dichloro-α-(1-cyclobutyl)-α-[3-[1-methylethyl(phenylethyl)amino]pentyl]benzeneacetonitrile;
(±)-3,4-ditrifluoromethyl-α-(1-cyclobutyl)-α-[3-[ethyl(phenylethyl)amino]pentyl]benzeneacetonitrile;
(±)-3,4-ditrifluoromethyl-α-(1-cyclobutyl)-α-[3-[n-propyl(phenylethyl)amino]pentyl]benzeneacetonitrile;
(±)-3,4-ditrifluoromethyl-α-(1-cyclobutyl)-α-[3-[1-methylethyl(phenylethyl)amino]pentyl]benzeneacetonitrile;
(±)-3,4-difluoro-α-(1-cyclopentyl)-α-[3-[ethyl(phenylethyl)amino]pentyl]benezeneacetonitrile;
(±)-3,4-difluoro-α-(1-cyclopentyl)-α-[3-[n-propyl(phenylethyl)amino]pentyl]benzeneacetonitrile;
(±)-3,4-difluoro-α-(1-cyclopentyl)-α-[3-[1-methylethyl(phenylethyl)amino]pentyl]benzeneacetonitrile;

(±)-3,4-dichloro-α-(1-cyclopentyl)-α-[3-[ethyl(-phenylethyl)amino]pentyl]benzeneacetonitrile;
(±)-3,4-dichloro-α-(1-cyclopentyl)-α-[3-[n-propyl(-phenylethyl)amino]pentyl]benzeneacetonitrile;
(±)-3,4-dichloro-α-(1-cyclopentyl)-α-[3-[1-methylethyl(phenylethyl)amino]pentyl]benzeneacetonitrile;
(±)-3,4-dichloro-α-(1-cyclopentyl)-α-[3-[ethyl(-phenylethyl)amino]pentyl]benzeneacetonitrile;
(±)-3,4-dichloro-α-(1-cyclopentyl)-α-[3-[n-propyl(-phenylethyl)amino]pentyl]benzeneacetonitrile;
(±)-3,4-dichloro-α-(1-cyclopentyl)-α-[3-[1-methylethyl(phenylethyl)amino]pentyl]benzeneacetonitrile;
(±)-3,4-ditrifluoromethyl-α-(1-cyclopentyl)-α-[3-[ethyl(phenylethyl)amino]pentyl]benzeneacetonitrile;
(±)-3,4-ditrifluoromethyl-α-(1-cyclopentyl)-α-[3-[n-propyl(phenylethyl)amino]pentyl]benzeneacetonitrile;
(±)-3,4-ditrifluoromethyl-α-(1-cyclopentyl)-α-[3-[1-methylethyl(phenylethyl)amino]pentyl]benzeneacetonitrile;
(±)-3,4-difluoro-α-(1-cyclohexyl)-α-[3-[ethyl(phenylethyl)amino]pentyl]benzeneacetonitrile;
(±)-3,4-difluoro-α-(1-cyclohexyl)-α-[3-[n-propyl(-phenylethyl)amino]pentyl]benzeneacetonitrile;
(±)-3,4-difluoro-α-(1-cyclohexyl)-α-[3-[1-methylethyl(phenylethyl)amino]pentyl]benzeneacetonitrile;
(±)-3,4-dichloro-α-(1-cyclohexyl)-α-[3-[ethyl(phenylethyl)amino]pentyl]benzeneacetonitrile;
(±)-3,4-dichloro-α-(1-cyclohexyl)-α-[3-[n-propyl(-phenylethyl)amino]pentyl]benzeneacetonitrile;
(±)-3,4-dichloro-α-(1-cyclohexyl)-α-[3-[1-methylethyl(phenylethyl)amino]pentyl]benzeneacetonitrile;
(±)-3,4-dichloro-α-(1-cyclohexyl)-α-[3-[ethyl(phenylethyl)amino]pentyl]benzeneacetonitrile;
(±)-3,4-dichloro-α-(1-cyclohexyl)-α-[3-[n-propyl(-phenylethyl)amino]pentyl]benzeneacetonitrile;
(±)-3,4-dichloro-α-(1-cyclohexyl)-α-[3-[1-methylethyl(phenylethyl)amino]pentyl]benzeneacetonitrile;
(±)-3,4-ditrifluoromethyl-α-(1-cyclohexyl)-α-[3-[ethyl(phenylethyl)amino]pentyl]benzeneacetonitrile;
(±)-3,4-ditrifluoromethyl-α-(1-cyclohexyl)-α-[3-[n-propyl(phenylethyl)amino]pentyl]benzeneacetonitrile;
(±)-3,4-ditrifluoromethyl-α-(1-cyclohexyl)-α-[3-[1-methylethyl(phenylethyl)amino]pentyl]benzeneacetonitrile;
(±)-4-fluoro-α-(1-methylethyl)-α-[3-[methyl(phenylmethyl)amino]propyl]benzeneacetonitrile;
(±)-4-chloro-α-(1-methylethyl)-α-[3-[methyl(phenylmethyl)amino]propyl]benzeneacetonitrile;
(±)-4-bromo-α-(1-methylethyl)-α-[3-[methyl(phenylmethyl)amino]propyl]benzeneacetonitrile;
(±)-4-trifluoromethyl-α-(1-methylethyl)-α-[3-[methyl(phenylmethyl)amino]propyl]benzeneacetonitrile;
(±)-4-fluoro-α-(1-cyclopropyl)-α-[3-[methyl(phenylmethyl)amino]propyl]benzeneacetonitrile;
(±)-4-fluoro-α-(1-cyclobutyl)-α-[3-[methyl(phenylmethyl)amino]propyl]benzeneacetonitrile;
(±)-4-fluoro-α-(1-cyclopentyl)-α-[3-[methyl(phenylmethyl)amino]propyl]benzeneacetonitrile;
(±)-4-fluoro-α-(1-cyclohexyl)-α-[3-[methyl(phenylmethyl)amino]propyl]benzeneacetonitrile;
(±)-4-fluoro-α-(1-methylethyl)-α-[3-[ethyl(phenylmethyl)amino]propyl]benzeneacetonitrile;
(±)-4-fluoro-α-(1-methylethyl)-α-[3-[n-propyl(phenylmethyl)amino]propyl]benzeneacetonitrile;

(±)-4-fluoro-α-(1-methylethyl)-α-[3-[1-methylethyl(phenylmethyl)amino]propyl]benzeneacetonitrile;
(±)-4-fluoro-α-(1-methylethyl)-α-[3-[methyl(phenylethyl)amino]propyl]benzeneacetonitrile;
(±)-4-fluoro-α-(1-methylethyl)-α-[3-[methyl(phenylmethyl)amino]butyl]benzeneacetonitrile;
(±)-4-fluoro-α-(1-methylethyl)-α-[3-[methyl(phenylmethyl)amino]pentyl]benzeneacetonitrile;
(±)-4-fluoro-α-(1-cyclopropyl)-α-[3-[methyl(phenylmethyl)amino]propyl]benzeneacetonitrile;
(±)-4-fluoro-α-(1-cyclobutyl)-α-[3-[methyl(phenylmethyl)amino]propyl]benzeneacetonitrile;
(±)-4-fluoro-α-(1-cyclopentyl)-α-[3-[methyl(phenylmethyl)amino]propyl]benzeneacetonitrile;
(±)-4-fluoro-α-(1-cyclohexyl)-α-[3-[methyl(phenylmethyl)amino]propyl]benzeneacetonitrile;
(±)-4-chloro-α-(1-cyclopropyl)[3-[methyl(phenylmethyl)amino]propyl]benzeneacetonitrile;
(±)-4-chloro-α-(1-cyclobutyl)-α-[3-[methyl(phenylmethyl)amino]propyl]benzeneacetonitrile;
(±)-4-chloro-α-(1-cyclopentyl)-α-[3-[methyl(phenylmethyl)amino]propyl]benzeneacetonitrile;
(±)-4-chloro-α-(1-cyclohexyl)-α-[3-[methyl(phenylmethyl)amino]propyl]benzeneacetonitrile;
(±)-4-bromo-α-(1-cyclopropyl)-α-[3-[methyl(phenylmethyl)amino]propyl]benzeneacetonitrile;
(±)-4-bromo-α-(1-cyclobutyl)-α-[3-[methyl(phenylmethyl)amino]propyl]benzeneacetonitrile;
(±)-4-bromo-α-(1-cyclopentyl)-α-[3-[methyl(phenylmethyl)amino]propyl]benzeneacetonitrile;
(±)-4-bromo-α-(1-cyclohexyl)-α-[3-[methyl(phenylmethyl)amino]propyl]benzeneacetonitrile;
(±)-4-trifluoromethyl-α-(1-cyclopropyl)-α-[3-[methyl(phenylmethyl)amino]propyl]benzeneacetonitrile;
(±)-4-trifluoromethyl-α-(1-cyclobutyl)-α-[3-[methyl(phenylmethyl)amino]propyl]benezeneacetonitrile;
(±)-4-trifluoromethyl-α-(1-cyclopentyl)-α-[3-[methyl(phenylmethyl)amino]propyl]benzeneacetonitrile;
(±)-4-trifluoromethyl-α-(1-cyclohexyl)-α-[3-[methyl(phenylmethyl)amino]propyl]benzeneacetonitrile;
(±)-4-fluoro-α-(1-methylethyl)-α-[3-[ethyl(phenylmethyl)amino]propyl]benzeneacetonitrile;
(±)-4-fluoro-α-(1-methylethyl)-α-[3-[n-propryl(-phenylmethyl)amino]propyl]benzeneacetonitrile;
(±)-4-fluoro-α-(1-methylethyl)-α-[3-[1-methylethyl(-phenylmethyl)amino]propyl]benzeneacetonitrile;
(±)-4-chloro-α-(1-methylethyl)-α-[3-[ethyl(phenylmethyl)amino]propyl]benzeneacetonitrile;
(±)-4-chloro-α-(1-methylethyl)-α-[3-[n-propryl(-phenylmethyl)amino]propyl]benzeneacetonitrile;
(±)-4-chloro-α-(1-methylethyl)-α-[3-[1-methylethyl(-phenylmethyl)amino]propyl]benzeneacetonitrile;
(±)-4-bromo-α-(1-methylethyl)-α-[3-[ethyl(phenylmethyl)amino]propyl]benzeneacetonitrile;
(±)-4-bromo-α-(1-methylethyl)-α-[3-[n-propyl(phenylmethyl)amino]propyl]benezeneacetonitrile;
(±)-4-bromo-α-(1-methylethyl)-α-[3-[1-methylethyl(-phenylmethyl)amino]propyl]benzeneacetonitrile;
(±)-4-trifluoromethyl-α-(1-methylethyl)-α-[3-[ethyl(-phenylethyl)amino]propyl]benezeneacetonitrile;
(±)-4-trifluoromethyl-α-(1-methylethyl)-α-[3-[n-propyl(phenylmethyl)amino]propyl]benzeneacetonitrile;
(±)-4-trifluoromethyl-α-(1-methylethyl)-α-[3-[1-methylethyl(phenylmethyl)amino]propyl]benzeneacetonitrile;
(±)-4-fluoro-α-(1-cyclohexyl)-α-[3-[ethyl(phenylethyl)amino]propyl]benzeneacetonitrile;

(±)-4-chloro-α-(1-methylethyl)-α-[3-[methyl(phenylethyl)amino]propyl]benzeneacetonitrile;
(±)-4-bromo-α-(1-methylethyl)-α-[3-[methyl(phenylethyl)amino]propyl]benzeneacetonitrile;
(±)-4- trifluoromethyl-α-(1-methylethyl)-α-[3 -[methyl(phenylethyl)amino]propyl]benzeneacetonitrile;
(±)-4-fluoro-α-(1-cyclohexyl)-α-[3-[ethyl(phenylmethyl)amino]butyl]benzeneacetonitrile;
(±)-4-fluoro-α-(1-cyclohexyl)-α-[3-[ethyl(phenylmethyl)amino]pentyl]benzeneacetonitrile;
(±)-4-chloro-α-(1-methylethyl)-α-[3 -[methyl(phenylmethyl)amino]butyl]benzeneacetonitrile;
(±)-4-chloro-α-(1-methylethyl)-α-[3-[methyl(phenylmethyl)amino]pentyl]benzeneacetonitrile;
(±)-4-bromo-α-(1-methylethyl)-α-[3-[methyl(phenylmethyl)amino]butyl]benzeneacetonitrile;
(±)-4-bromo-α-(1-methylethyl)-α-[3-[methyl(phenylmethyl)amino]pentyl]benzeneacetonitrile;
(±)-4-trifluoromethyl-α-(1-methylethyl)-α-[3-[methyl(phenylmethyl)amino]butyl]benzeneacetonitrile;
(±)-4 -trifluoromethyl-α-(1-methylethyl)-α-[3-[methyl(phenylmethyl)amino]pentyl]benzeneacetonitrile;
(±)-4-fluoro-α-(1-cyclopropyl)-α-[3-[ethyl(phenylmethyl)amino]propyl]benzeneacetonitrile;
(±)-4-fluoro-α-(1-cyclopropyl)-α-[3-[n-propyl(phenylmethyl)amino]propyl]benzeneacetonitrile;
(±)-4-fluoro-α-(1-cyclopropyl)-α-[3-[1-methylethyl(phenylmethyl)amino]propyl]benzeneacetonitrile;
(±)-4-fluoro-α-(1-cyclobutyl)-α-[3-[ethyl(phenylmethyl)amino]propyl]benzeneacetonitrile;
(±)-4-fluoro-α-(1-cyclobutyl)-α-[3-[nn-propyl-propyl(phenylmethyl)amino]propyl]benzeneacetonitrile;
(±)-4-fluoro-α-(1-cyclobutyl)-α-[3-[1-methylethyl(phenylmethyl)amino]propyl]benzeneacetonitrile;
(±)-4-fluoro-α-(1-cyclopentyl)-α-[3-[ethyl(phenylmethyl)amino]propyl]benzeneacetonitrile;
(±)-4-fluoro-α-(1-cyclopentyl)-α-[3-[n-propyl(phenylmethyl)amino]propyl]benzeneacetonitrile;
(±)-4-fluoro-α-(1-cyclopentyl)-α-[3-[1-methylethyl(phenylmethyl)amino]propyl]benzeneacetonitrile;
(±)-4-fluoro-α-(1-cyclohexyl)-α-[3-[1-ethyl(phenylmethyl)amino]propyl]benzeneacetonitrile;
(±)-4-fluoro-α-(1-cyclohexyl)-α-[3-[1-n-propyl(phenylmethyl)amino]propyl]benzeneacetonitrile;
(±)-4-fluoro-α-(1-cyclohexyl)-α-[3-[1-1-methylethyl(phenylmethyl)amino]propyl]benzeneacetonitrile;
(±)-4-fluoro-α-(1-cyclopropyl)-α-[3-[methyl(phenylethyl)amino]propyl]benzeneacetonitrile;
(±)-4-fluoro-α-(1-cyclobutyl)-α-[3-[methyl(phenylethyl)amino]propyl]benzeneacetonitrile;
(±)-4-fluoro-α-(1-cyclopentyl)-α-[3 -[methyl(phenylethyl)amino]propyl]benzeneacetonitrile;
(±)-4-fluoro-α-(1-cyclohexyl)-α-[3-[methyl(phenylethyl)amino]propyl]benzeneacetonitrile;
(±)-4-fluoro-α-(1-cyclopropyl)-α-[3-[methyl(phenylmethyl)amino]propyl]benzeneacetonitrile;
(±)-4-fluoro-α-(1-cyclopropyl)-α-[3-[methyl(phenylmethyl)amino]butyl]benzeneacetonitrile;
(±)-4-fluoro-α-(1-cyclopropyl)-α-[3-[methyl(phenylmethyl)amino]pentyl]benzeneacetonitrile;
(±)-4-fluoro-α-(1-cyclobutyl)-α-[3-[methyl(phenylmethyl)amino]propyl]benzeneacetonitrile;
(±)-4-fluoro-α-(1-cyclobutyl)-α-[3-[methyl(phenylmethyl)amino]butyl]benzeneacetonitrile;
(±)-4-fluoro-α-(1-cyclobutyl)-α-[3-[methyl(phenylmethyl)amino]pentyl]benzeneacetonitrile;
(±)-4-fluoro-α-(1-cyclopentyl)-α-[3-[methyl(phenylmethyl)amino]propyl]benzeneacetonitrile;
(±)-4-fluoro-α-(1-cyclopentyl)-α-[3-[methyl(phenylmethyl)amino]butyl]benzeneacetonitrile;
(±)-4-fluoro-α-(1-cyclopentyl)-α-[3-[methyl(phenylmethyl)amino]pentyl]benzeneacetonitrile;
(±)-4-fluoro-α-(1-cyclohexyl)-α-[3-[methyl(phenylmethyl)amino]propyl]benzeneacetonitrile;
(±)-4-fluoro-α-(1-cyclohexyl)-α-[3-[methyl(phenylmethyl)amino]butyl]benzeneacetonitrile;
(±)-4-fluoro-α-(1-cyclohexyl)-α-[3-[methyl(phenylmethyl)amino]pentyl]benzeneacetonitrile;
(±)-4-fluoro-α-(1-methylethyl)-α-[3-[methyl(phenylethyl)amino]propyl]benzeneacetonitrile;
(±)-4-fluoro-α-(1-methylethyl)-α-[3-[ethyl(phenylethyl)amino]propyl]benzeneacetonitrile;
(±)-4-fluoro-α-(1-methylethyl)-α-[3-[n-propyl(phenylethyl)amino]propyl]benzeneacetonitrile;
(±)-4-fluoro-α-(1-methylethyl)-α-[3-[1-methylethyl(phenylethyl)amino]propyl]benzeneacetonitrile;
(±)-4-fluoro-α-(1-methylethyl)-α-[3-[ethyl(phenylmethyl)amino]propyl]benzeneacetonitrile;
(±)-4-fluoro-α-(1-methylethyl)-α-[3-[ethyl(phenylmethyl)amino]butyl]benzeneacetonitrile;
(±)-4-fluoro-α-(1-methylethyl)-α-[3-[ethyl(phenylmethyl)amino]pentyl]benzeneacetonitrile;
(±)-4-fluoro-α-(1-methylethyl)-α-[n-propyl(phenylmethyl)amino]propyl]benezeneacetonitrile;
(±)-4-fluoro-α-(1-methylethyl)-α-[3-[n-propyl(phenylmethyl)amino]butyl]benzeneacetonitrile;
(±)-4- fluoro-α-(1-methylethyl)-α-[3-[n-propyl(phenylmethyl)amino]pentyl]benzeneacetonitrile;
(±)-4-fluoro-α-(1-methylethyl)-α-[3-[methylethyl(phenylmethyl)amino]propyl]benzeneacetonitrile;
(±)-4-fluoro-α-(1-methylethyl)-α-[3-[1-methylethyl(phenylmethyl)amino]butyl]benzeneacetonitrile;
(±)-4-fluoro-α-(1-methylethyl)-α-[3-[1-methylethyl(phenylmethyl)amino]pentyl]benzeneacetonitrile;
(±)-4-fluoro-α-(1-methylethyl)-α-[3-[methyl(phenylethyl)amino]propyl]benzeneacetonitrile;
(±)-4-fluoro-α-(1-methylethyl)-α-[3-[methyl(phenylethyl)amino]butyl]benzeneacetonitrile;
(±)-4-fluoro-α-(1-methylethyl)-α-[3-[methyl(phenylethyl)amino]pentyl]benzeneacetonitrile;
(±)-4-fluoro-α-(1-cyclopropyl)-α-[3-[ethyl(phenylmethyl)amino]propyl]benzeneacetonitrile;
(±)-4-fluoro-α-(1-cyclopropyl)-α-[3-[n-propyl(phenylmethyl)amino]propyl]benzeneacetonitrile;
(±)-4-fluoro-α-(1-cyclopropyl)-α-[3-[1-methylethyl(phenylmethyl)amino]propyl]benzeneacetonitrile;
(±)-4-fluoro-α-(1-cyclobutyl)-α-[3-[ethyl(phenylmethyl)amino]propyl]benzeneacetonitrile;
(±)-4-fluoro-α-(1-cyclobutyl)-α-[3-[n-propyl(phenylmethyl)amino]propyl]benzeneacetonitrile;
(±)-4-fluoro-α-(1-cyclobutyl)-α-[3-[1-methylethyl(phenylmethyl)amino]propyl]benzeneacetonitrile;
(±)-4-fluoro-α-(1-cyclopentyl)-α-[3-[ethyl(phenylmethyl)amino]propyl]benzeneacetonitrile;
(±)-4-fluoro-α-(1-cyclopentyl)-α-[3-[n-propyl(phenylmethyl)amino]propyl]benezeneacetonitrile;
(±)-4-fluoro-α-(1-cyclopentyl)-α-[3-[1-methylethyl(phenylmethyl)amino]propyl]benzeneacetonitrile;
(±)-4-fluoro-α-(1-cyclohexyl)-α-[3-[ethyl(phenylmethyl)amino]propyl]benzeneacetonitrile;
(±)-4-fluoro-α-(1-cyclohexyl)-α-[3-[n-propyl(phenylmethyl)amino]propyl]benzeneacetonitrile;
(±)-4-fluoro-α-(1-cyclohexyl)-α-[3-[1-methylethyl(phenylmethyl)amino]propyl]benzeneacetonitrile;

(±)-4-chloro-α-(1-cyclopropyl)-α-[3-[ethyl(phenylmethyl)amino]propyl]benzeneacetonitrile;
(±)-4-chloro-α-(1-cyclopropyl)-α-[3-[n-propyl(phenylmethyl)amino]propyl]benzeneacetonitrile;
(±)-4-chloro-α-(1-cyclopropyl)-α-[3-[1-methylethyl(phenylmethyl)amino]propyl]benzeneacetonitrile;
(±)-4-chloro-α-(1-cyclobutyl)-α-[3-[ethyl(phenylmethyl)amino]propyl]benzeneacetonitrile;
(±)-4-chloro-α-(1-cyclobutyl)-α-[3-[n-propyl(phenylmethyl)amino]propyl]benzeneacetonitrile;
(±)-4-chloro-α-(1-cyclobutyl)-α-[3-[1-methylethyl(phenylmethyl)amino]propyl]benzeneacetonitrile;
(±)-4-chloro-α-(1-cyclopentyl)-α-[3-[ethyl(phenylmethyl)amino]propyl]benzeneacetonitrile;
(±)-4-chloro-α-(1-cyclopentyl)-α-[3-[n-propyl(phenylmethyl)amino]propyl]benzeneacetonitrile;
(±)-4-chloro-α-(1-cyclopentyl)-α-[3-[1-methylethyl(phenylmethyl)amino]propyl]benzeneacetonitrile;
(±)-4-chloro-α-(1-cyclohexyl)-α-[3-[ethyl(phenylmethyl)amino]propyl]benzeneacetonitrile;
(±)-4-chloro-α-(1-cyclohexyl)-α-[3-[n-propyl(phenylmethyl)amino]propyl]benzeneacetonitrile;
(±)-4-chloro-α-(1-cyclohexyl)-α-[3-[1-methylethyl(phenylmethyl)amino]propyl]benzeneacetonitrile;
(±)-4-bromo-α-(1-cyclopropyl)-α-[3-[ethyl(phenylmethyl)amino]propyl]benzeneacetonitrile;
(±)-4-bromo-α-(1-cyclopropyl)-α-[3-[n-propyl(phenylmethyl)amino]propyl]benzeneacetonitrile;
(±)-4-bromo-α-(1-cyclopropyl)-α-[3-[1-methylethyl(phenylmethyl)amino]propyl]benzeneacetonitrile;
(±)-4-bromo-α-(1-cyclobutyl)-α-[3-[ethyl(phenylmethyl)amino]propyl]benzeneacetonitrile;
(±)-4-bromo-α-(1-cyclobutyl)-α-[3-[n-propyl(phenylmethyl)amino]propyl]benzeneacetonitrile;
(±)-4-bromo-α-(1-cyclobutyl)-α-[3-[1-methylethyl(phenylmethyl)amino]propyl]benzeneacetonitrile;
(±)-4-bromo-α-(1-cyclopentyl)-α-[3-[ethyl(phenylmethyl)amino]propyl]benzeneacetonitrile;
(±)-4-bromo-α-(1-cyclopentyl)-α-[3-[n-propyl(phenylmethyl)amino]propyl]benzeneacetonitrile;
(±)-4-bromo-α-(1-cyclopentyl)-α-[3-[1-methylethyl(phenylmethyl)amino]propyl]benzeneacetonitrile;
(±)-4-bromo-α-(1-cyclohexyl)-α-[3-[ethyl(phenylmethyl)amino]propyl]benzeneacetonitrile;
(±)-4-bromo-α-(1-cyclohexyl)-α-[3-[n-propyl(phenylmethyl)amino]propyl]benzeneacetonitrile;
(±)-4-bromo-α-(1-cyclohexyl)-α-[3-[1-methylethyl(phenylmethyl)amino]propyl]benzeneacetonitrile;
(±)-4-trifluoromethyl-α-(1-cyclopropyl)-α-[3-[ethyl(phenylmethyl)amino]propyl]benzeneacetonitrile;
(±)-4-trifluoromethyl-α-(1-cyclopropyl)-α-[3-[n-propyl(phenylmethyl)amino]propyl]benzeneacetonitrile;
(±)-4-trifluoromethyl-α-(1-cyclopropyl)-α-[3-[1-methylethyl(phenylmethyl)amino]propyl]benzeneacetonitrile;
(±)-4-trifluoromethyl-α-(1-cyclobutyl)-α-[3-[ethyl(phenylmethyl)amino]propyl]benzeneacetonitrile;
(±)-4-trifluoromethyl-α-(1-cyclobutyl)-α-[3-[n-propyl(phenylmethyl)amino]propyl]benzeneacetonitrile;
(±)-4-trifluoromethyl-α-(1-cyclobutyl)-α-[3-[1-methylethyl(phenylmethyl)amino]propyl]benzeneacetonitrile;
(±)-4-trifluoromethyl-α-(1-cyclopentyl)-α-[3-[ethyl(phenylmethyl)amino]propyl]benzeneacetonitrile;
(±)-4-trifluoromethyl-α-(1-cyclopentyl)-α-[3-[(phenylmethyl)amino]propyl]benzeneacetonitrile;
(±)-4-trifluoromethyl-α-(1-cyclopentyl)-α-[3-[1-methylethyl(phenylmethyl)amino]propyl]benzeneacetonitrile;
(±)-4-trifluoromethyl-α-(1-cyclohexyl)-α-[3-[ethyl(phenylmethyl)amino]propyl]benzeneacetonitrile;
(±)-4-trifluoromethyl-α-(1-cyclohexyl)-α-[3-[n-propyl(phenylmethyl)amino]propyl]benzeneacetonitrile;
(±)-4-trifluoromethyl-α-(1-cyclohexyl)-α-[3-[1-methylethyl(phenylmethyl)amino]propyl]benzeneacetonitrile;
(±)-4-fluoro-α-(1-methylethyl)-α-[3-[ethyl(phenylethyl)amino]propyl]benzeneacetonitrile;
(±)-4-fluoro-α-(1-methylethyl)-α-[3-[n-propyl(phenylethyl)amino]propyl]benzeneacetonitrile;
(±)-4-fluoro-α-(1-methylethyl)-α-[3-[1-methylethyl(phenylmethyl)amino]propyl]benzeneacetonitrile;
(±)-4-chloro-α-(1-methylethyl)-α-[3-[ethyl(phenylethyl)amino]propyl]benzeneacetonitrile;
(±)-4-chloro-α-(1-methylethyl)-α-[3-[n-propyl(phenylethyl)amino]propyl]benzeneacetonitrile;
(±)-4-chloro-α-(1-methylethyl)-α-[3-[1-methylethyl(phenylethyl)amino]propyl]benzeneacetonitrile;
(±)-4-bromo-α-(1-methylethyl)-α-[3-[ethyl(phenylethyl)amino]propyl]benzeneacetonitrile;
(±)-4-bromo-α-(1-methylethyl)-α-[3-[n-propyl(phenylethyl)amino]propyl]benzeneacetonitrile;
(±)-4-bromo-α-(1-methylethyl)-α-[3-[1-methylethyl(phenylethyl)amino]propyl]benzeneacetonitrile;
(±)-4-trifluoromethyl-α-(1-methylethyl)-α-[3-[ethyl(phenylethyl)amino]propyl]benzeneacetonitrile;
(±)-4-trifluoromethyl-α-(1-methylethyl)-α-[3-[n-propyl(phenylethyl)amino]propyl]benzeneacetonitrile;
(±)-4-trifluoromethyl-α-(1-methylethyl)-α-[3-[1-methylethyl(phenylethyl)amino]propyl]benzeneacetonitrile;
(±)-4-fluoro-α-(1-cyclopropyl)-α-[3-[methyl(phenylethyl)amino]propyl]benzeneacetonitrile;
(±)-4-fluoro-α-(1-cyclobutyl)-α-[3-[methyl(phenylethyl)amino]propyl]benzeneacetonitrile;
(±)-4-fluoro-α-(1-cyclopentyl)-α-[3-[methyl(phenylethyl)amino]propyl]benzeneacetonitrile;
(±)-4-fluoro-α-(1-cyclohexyl)-α-[3-[methyl(phenylethyl)amino]propyl]benzeneacetonitrile;
(±)-4-chloro-α-(1-cyclopropyl)-α-[3-[methyl(phenylethyl)amino]propyl]benzeneacetonitrile;
(±)-4-chloro-α-(1-cyclobutyl)-α-[3-[methyl(phenylethyl)amino]propyl]benzeneacetonitrile;
(±)-4-chloro-α-(1-cyclopentyll)-α-[3-[methyl(phenylethyl)amino]propyl]benezeneacetonitrile;
(±)-4-chloro-α-(1-cyclohexyl)-α-[3-[methyl(phenylethyl)amino]propyl]benzeneacetonitrile;
(±)-4-bromo-α-(1-cyclopropyl)[3-[methyl(phenylethyl)amino]propyl]benzeneacetonitrile;
(±)-4-bromo-α-(1-cyclobutyl)-α-[3-[methyl(phenylethyl)amino]propyl]benzeneacetonitrile;
(±)-4-bromo-α-(1-cyclopentyll)-α-[3-[methyl(phenylethyl)amino]propyl]benzeneacetonitrile;
(±)-4-bromo-α-(1-cyclohexyl)-α-[3-[methyl(phenylethyl)amino]propyl]benzeneacetonitrile;
(±)-4-trifluoromethyl-α-(1-cyclopropyl)-α-[3-[methyl(phenylethyl)amino]propyl]benzeneacetonitrile;
(±)-4-trifluoromethyl-α-(1-cyclobutyl)-α-[3-[methyl(phenylethyl)amino]propyl]benzeneacetonitrile;
(±)-4-trifluoromethyl-α-(1-cyclopentyll)-α-[3-[methyl(phenylethyl)amino]propyl]benezeneacetonitrile;

(±)-4-trifluoromethyl-α-(1-cyclohexyl)-α-[3-[methyl(phenylethyl)amino]propyl]benzeneacetonitrile;
(±)-4-fluoro-α-(1-cyclopropyl)-α-[3-[methyl(phenylmethyl)amino]propyl]benzeneacetonitrile;
(±)-4-fluoro-α-(1-cyclopropyl)-α-[3-[methyl(phenylmethyl)amino]butyl]benzeneacetonitrile;
(±)-4-fluoro-α-(1-cyclopropyl)-α-[3-[methyl(phenylmethyl)amino]pentyl]benezeneacetonitrile;
(±)-4-fluoro-α-(1-cyclobutyl)-α-[methyl(phenylmethyl)amino]propyl]benzeneacetonitrile;
(±)-4-fluoro-α-(1-cyclobutyl)-α-[3-[methyl(phenylmethyl)amino]butyl]benzeneacetonitrile;
(±)-4-fluoro-α-(1-cyclobutyl)-α-[3-[methyl(phenylmethyl)amino]pentyl]benzeneacetonitrile;
(±)-4-fluoro-α-(1-cyclopentyl)-α-[3-[methyl(phenylmethyl)amino]propyl]benzeneacetonitrile;
(±)-4-fluoro-α-(1-cyclopentyl)-α-[3-[methyl(phenylmethyl)amino]butyl]benzeneacetonitrile;
(±)-4-fluoro-α-(1-cyclopentyl)-α-[3-[methyl(phenylmethyl)amino]pentyl]benzeneacetonitrile;
(±)-4-fluoro-α-(1-cyclohexyl)-α-[3-[methyl(phenylmethyl)amino]propyl]benzeneacetonitrile;
(±)-4-fluoro-α-(1-cyclohexyl)-α-[3-[methyl(phenylmethyl)amino]butyl]benzeneacetonitrile;
(±)-4-fluoro-α-(1-cyclohexyl)-α-[3-[methyl(phenylmethyl)amino]pentyl]benzeneacetonitrile;
(±)-4-chloro-α-(1-cyclopropyl)-α-[3-[methyl(phenylmethyl)amino]propyl]benzeneacetonitrile;
(±)-4-chloro-α-(1-cyclopropyl)-α-[3-[methyl(phenylmethyl)amino]butyl]benzeneacetonitrile;
(±)-4-chloro-α-(1-cyclopropyl)-α-[3-[methyl(phenylmethyl)amino]pentyl]benzeneacetonitrile;
(±)-4-chloro-α-(1-cyclobutyl)-α-[3-[methyl(phenylmethyl)amino]propyl]benzeneacetonitrile;
(±)-4-chloro-α-(1-cyclobutyl)-α-[3-[methyl(phenylmethyl)amino]butyl]benzeneacetonitrile;
(±)-4-chloro-α-(1-cyclobutyl)-α-[3-[methyl(phenylmethyl)amino]pentyl]benzeneacetonitrile;
(±)-4-chloro-α-(1-cyclopentyl)-α-[3-[methyl(phenylmethyl)amino]propyl]benzeneacetonitrile;
(±)-4-chloro-α-(1-cyclopentyl)-α-[3-[methyl(phenylmethyl)amino]butyl]benzeneacetonitrile;
(±)-4-chloro-α-(1-cyclopentyl)-α-[3-[methyl(phenylmethyl)amino]pentyl]benzeneacetonitrile;
(±)-4-chloro-α-(1-cyclohexyl)-α-[3-[methyl(phenylmethyl)amino]propyl]benzeneacetonitrile;
(±)-4-chloro-α-(1-cyclohexyl)-α-[3-[methyl(phenylmethyl)amino]butyl]benzeneacetonitrile;
(±)-4-chloro-α-(1-cyclohexyl)-α-[3-[methyl(phenylmethyl)amino]pentyl]benzeneacetonitrile;
(±)-4-trifluoromethyl-α-(1-cyclopropyl)-α-[3-[methyl(phenylmethyl)amino]propyl]benzeneacetonitrile;
(±)-4-trifluoromethyl-α-(1-cyclopropyl)-α-[3-[methyl(phenylmethyl)amino]butyl]benzeneacetonitrile;
(±)-4-trifluoromethyl-α-(1-cyclopropyl)-α-[3-[methyl(phenylmethyl)amino]pentyl]benzeneacetonitrile;
(±)-4-trifluoromethyl-α-(1-cyclobutyl)-α-[3-[methyl(phenylmethyl)amino]propyl]benzeneacetonitrile;
(±)-4-trifluoromethyl-α-(1-cyclobutyl)-α-[3-[methyl(phenylmethyl)amino]butyl]benzeneacetonitrile;
(±)-4-trifluoromethyl-α-(1-cyclobutyl)-α-[3-[methyl(phenylmethyl)amino]pentyl]benzeneacetonitrile;
(±)-4-trifluoromethyl-α-(1-cyclopentyl)-α-[3-[methyl(phenylmethyl)amino]propyl]benzeneacetonitrile;
(±)-4-trifluoromethyl-α-(1-cyclopentyl)-α-[3-[methyl(phenylmethyl)amino]butyl]benzeneacetonitrile;
(±)-4-trifluoromethyl-α-(1-cyclopentyl)-α-[3-[methyl(phenylmethyl)amino]pentyl]benzeneacetonitrile;
(±)-4-trifluoromethyl-α-(1-cyclohexyl)-α-[3-[methyl(phenylmethyl)amino]propyl]benzeneacetonitrile;
(±)-4-trifluoromethyl-α-(1-cyclohexyl)-α-[3-[methyl(phenylmethyl)amino]butyl]benzeneacetonitrile;
(±)-4-trifluoromethyl-α-(1-cyclohexyl)-α-[3-[methyl(phenylmethyl)amino]pentyl]benzeneacetonitrile;
(±)-4-fluoro-α-(1-methylethyl)-α-[3-[ethyl(phenylmethyl)amino]propyl]benzeneacetonitrile;
(±)-4-fluoro-α-(1-methylethyl)-α-[3-[n-propyl](phenylmethyl)amino]propyl]benzeneacetonitrile;
(±)-4-fluoro-α-(1-methylethyl)-α-[3-[1-methylethyl(phenylmethyl)amino]propyl]benzeneacetonitrile;
(±)-4-fluoro-α-(1-methylethyl)-α-[3-[ethyl(phenylmethyl)amino]butyl]benzeneacetonitrile;
(±)-4-fluoro-α-(1-methylethyl)-α-[3-[n-propyl](phenylmethyl)amino]butyl]benzeneacetonitrile;
(±)-4-fluoro-α-(1-methylethyl)-α-[3-[1-methylethyl(phenylmethyl)amino]butyl]benzeneacetonitrile;
(±)-4-fluoro-α-(1-methylethyl)-α-[3-[ethyl(phenylmethyl)amino]pentyl]benzeneacetonitrile;
(±)-4-fluoro-α-(1-methylethyl)-α-[3-[n-propyl](phenylmethyl)amino]pentyl]benzeneacetonitrile;
(±)-4-fluoro-α-(1-methylethyl)-α-[3-[1-methylethyl(phenylmethyl)amino]pentyl]benzeneacetonitrile;
(±)-4-chloro-α-(1-methylethyl)-α-[3-[ethyl(phenylmethyl)amino]propyl]benzeneacetonitrile;
(±)-4-chloro-α-(1-methylethyl)-α-[3-[n-propyl](phenylmethyl)amino]propyl]benzeneacetonitrile;
(±)-4-chloro-α-(1-methylethyl)-α-[3-[1-methylethyl(phenylmethyl)amino]propyl]benzeneacetonitrile;
(±)-4-chloro-α-(1-methylethyl)-α-[3-[ethyl(phenylmethyl)amino]butyl]benzeneacetonitrile;
(±)-4-chloro-α-(1-methylethyl)-α-[3-[n-propyl](phenylmethyl)amino]butyl]benzeneacetonitrile;
(±)-4-chloro-α-(1-methylethyl)-α-[3-[1-methylethyl(phenylmethyl)amino]butyl]benzeneacetonitrile;
(±)-4-chloro-α-(1-methylethyl)-α-[3-[ethyl(phenylmethyl)amino]pentyl]benzeneacetonitrile;
(±)-4-chloro-α-(1-methylethyl)-α-[3-[n-propyl](phenylmethyl)amino]pentyl]benzeneacetonitrile;
(±)-4-chloro-α-(1-methylethyl)-α-[3-[1-methylethyl(phenylmethyl)amino]pentyl]benzeneacetonitrile;
(±)-4-bromo-α-(1-methylethyl)-α-[3-[ethyl(phenylmethyl)amino]propyl]benzeneacetonitrile;
(±)-4-bromo-α-(1-methylethyl)-α-[3-[n-propyl](phenylmethyl)amino]propyl]benzeneacetonitrile;
(±)-4-bromo-α-(1-methylethyl)-α-[3-[1-methylethyl(phenylmethyl)amino]propyl]benzeneacetonitrile;
(±)-4-bromo-α-(1-methylethyl)-α-[3-[ethyl(phenylmethyl)amino]butyl]benzeneacetonitrile;
(±)-4-bromo-α-(1-methylethyl)-α-[3-[n-propyl](phenylmethyl)amino]butyl]benezeneacetonitrile;
(±)-4-bromo-α-(1-methylethyl)-α-[3-[1-methylethyl(phenylmethyl)amino]butyl]benzeneacetonitrile;
(±)-4-bromo-α-(1-methylethyl)-α-[3-[ethyl(phenylmethyl)amino]pentyl]benzeneacetonitrile;
(±)-4-bromo-α-(1-methylethyl)-α-[3, -[n-propyl](phenylmethyl)amino]pentyl]benzeneacetonitrile;
(±)-4-bromo-α-(1-methylethyl)-α-[3-[1-methylethyl(phenylmethyl)amino]pentyl]benzeneacetonitrile;
(±)-4-trifluoromethyl-α-(1-methylethyl)-α-[3-[ethyl(phenylmethyl)amino]propyl]benezeneacetonitrile;
(±)-4-trifluoromethyl-α-(1-methylethyl)-α-[3-[n-propyl](phenylmethyl)amino]propyl]benzeneacetonitrile;
(±)-4-trifluoromethyl-α-(1-methylethyl)-α-[3-[1-methylethyl(phenylmethyl)amino]propyl]benzeneacetonitrile;

(±)-4-trifluoromethyl-α-(1-methylethyl)-α-[3-[ethyl(-phenylmethyl)amino]butyl]benzeneacetonitrile;
(±)-4-trifluoromethyl-α-(1-methylethyl)-α-[3-[n-propyl](phenylmethyl)amino]butyl]benzeneacetonitrile;
(±)-4-trifluoromethyl-α-(1-methylethyl)-α-[3-[1-methylethyl(phenylmethyl)amino]butyl]benzeneacetonitrile;
(±)-4-trifluoromethyl-α-(1-methylethyl)-α-[3-[ethyl(-phenylmethyl)amino]pentyl]benzeneacetonitrile;
(±)-4-trifluoromethyl-α-(1-methylethyl)-α-[3-[n-propyl](phenylmethyl)amino]pentyl]benzeneacetonitrile;
(±)-4-trifluoromethyl-α-(1-methylethyl)-α-[3-[1-methylethyl(phenylmethyl)amino]pentyl]benzeneacetonitrile;
(±)-4-fluoro-α-(1-methylethyl)-α-[3-[methyl(phenylethyl)amino]propyl]benzeneacetonitrile;
(±)-4-fluoro-α-(1-methylethyl)-α-[3-[methyl(phenylethyl)amino]butyl]benzeneacetonitrile;
(±)-4-fluoro-α-(1-methylethyl)-α-[3-[methyl(phenylethyl)amino]pentyl]benzeneacetonitrile;
(±)-4-chloro-α-(1-methylethyl)-α-[3-[methyl(phenylethyl)amino]propyl]benzeneacetonitrile;
(±)-4-chloro-α-(1-methylethyl)-α-[3-[methyl(phenylethyl)amino]butyl]benzeneacetonitrile;
(±)-4-chloro-α-(1-methylethyl)-α-[3-[methyl(phenylethyl)amino]pentyl]benezeneacetonitrile;
(±)-4-bromo-α-(1-methylethyl)-α-[3-[methyl(phenylethyl)amino]propyl]benzeneacetonitrile;
(±)-4-bromo-α-(1-methylethyl)-α-[3-[methyl(phenylethyl)amino]butyl]benzeneacetonitrile;
(±)-4-bromo-α-(1-methylethyl)-α-[3 -[methyl(phenylethyl)amino]pentyl]benzeneacetonitrile;
(±)-4-trifluoromethyl-α-(1-methylethyl)-α-[3-[methyl(-phenylethyl)amino]propyl]benezeneacetonitrile;
(±)-4-trifluoromethyl-α-(1-methylethyl)-α-[3-[methyl(-phenylethyl)amino]butyl]benzeneacetonitrile;
(±)-4-trifluoromethyl-α-(1-methylethyl)-α-[3-[methyl(-phenylethyl)amino]pentyl]benzeneacetonitrile;
(±)-4-fluoro-α-(1-cyclopropyl)-α-[3-[ethyl(phenylethyl)amino]propyl]benzeneacetonitrile;
(±)-4-fluoro-α-(1-cyclopropyl )-α-[3 -[n-propyl(-phenylethyl)amino]propyl]benzeneacetonitrile;
(±)-4-fluoro-α-(1-cyclopropyl)-α-[3-[1-methylethyl(-phenylethyl)amino]propyl]benzeneacetonitrile;
(±)-4-fluoro-α-(1-cyclopbutyl)-α-[3-[ethyl(phenylethyl)amino]propyl]benzeneacetonitrile;
(±)-4-fluoro-α-(1-cyclopbutyl )-α-[3 -[n-propyl(-phenylethyl)amino]propyl]benzeneacetonitrile;
(±)-4-fluoro-α-(1-cyclopbutyl )-α-[3-[1-methylethyl(-phenylethyl)amino]propyl]benzeneacetonitrile;
(±)-4-fluoro-α-(1-cyclopentyl)-α-[3-[ethyl(phenylethyl)amino]propyl]benzeneacetonitrile;
(±)-4-fluoro-α-(1-cyclopentyl)-α-[3-[n-propyl(phenylethyl)amino]propyl]benzeneacetonitrile;
(±)-4-fluoro-α-(1-cyclopentyl)-α-[3-[1-methylethyl(-phenylethyl)amino]propyl]benzeneacetonitrile;
(±)-4-fluoro-α-(1-cyclohexyl)-α-[3-[ethyl(phenylethyl)amino]propyl]benzeneacetonitrile;
(±)-4-fluoro-α-(1-cyclohexyl)-α-[3-[n-propyl(phenylethyl)amino]propyl]benzeneacetonitrile;
(±)-4-fluoro-α-(1-cyclohexyl)-α-[3-[1-methylethyl(-phenylethyl)amino]propyl]benzeneacetonitrile;
(±)-4-fluoro-α-(1-cyclopropyl)-α-[3-[ethyl(phenylethyl)amino]propyl]benzeneacetonitrile;
(±)-4-fluoro-α-(1-cyclopropyl)-α-[3-[n-propyl(-phenylethyl)amino]propyl]benzeneacetonitrile;
(±)-4-fluoro-α-(1-cyclopropyl)-α-[3-[1-methylethyl(-phenylethyl)amino]propyl]benzeneacetonitrile;
(±)-4-fluoro-α-(1-cyclobutyl)-α-[3-[ethyl(phenylethyl)amino]propyl]benzeneacetonitrile;
(±)-4-fluoro-α-(1-cyclobutyl)-α-[3-[n-propyl(phenylethyl)amino]propyl]benzeneacetonitrile;
(±)-4-fluoro-α-(1-cyclobutyl)-α-[3-[1-methylethyl(-phenylethyl)amino]propyl]benzeneacetonitrile;
(±)-4-fluoro-α-(1-cyclopentyl)-α-[3-[ethyl(phenylethyl)amino]propyl]benzeneacetonitrile;
(±)-4-fluoro-α-(1-cyclopentyl)-α-[3-[n-propyl(phenylethyl)amino]propyl]benzeneacetonitrile;
(±)-4-fluoro-α-(1-cyclopentyl)-α-[3-[1-methylethyl(-phenylethyl)amino]propyl]benzeneacetonitrile;
(±)-4-fluoro-α-(1-cyclohexyl)-α-[3-[ethyl(phenylethyl)amino]propyl]benzeneacetonitrile;
(±)-4-fluoro-α-(1-cyclohexyl)-α-[3-[n-propyl(phenylethyl)amino]propyl]benzeneacetonitrile;
(±)-4-fluoro-α-(1-cyclohexyl)-α-[3-[1-methylethyl(-phenylethyl)amino]propyl]benzeneacetonitrile;
(±)-4-fluoro-α-(1-cyclopropyl)-α-[3-[ethyl(phenylmethyl)amino]butyl]benzeneacetonitrile;
(±)-4-fluoro-α-(1-cyclopropyl)-α-[3-[n-propyl(phenylmethyl)amino]butyl]benzeneacetonitrile;
(±)-4-fluoro-α-(1-cyclopropyl)-α-[3-[1-methylethyl(-phenylmethyl)amino]butyl]benzeneacetonitrile;
(±)-4-fluoro-α-(1-cyclopropyl)-α-[3-[ethyl(phenylmethyl)amino]pentyl]benzeneacetonitrile;
(±)-4-fluoro-α-(1-cyclopropyl)-α-[3-[n-propyl(phenylmethyl)amino]pentyl]benzeneacetonitrile;
(±)-4-fluoro-α-(1-cyclopropyl)-α-[3-[1-methylethyl(-phenylmethyl)amino]pentyl]benzeneacetonitrile;
(±)-4-fluoro-α-(1-cyclobutyl)-α-[3-[ethyl(phenylmethyl)amino]butyl]benzeneacetonitrile;
(±)-4-fluoro-α-(1-cyclobutyl)-α-[3-[n-propyl(phenylmethyl)amino]butyl]benzeneacetonitrile;
(±)-4-fluoro-α-(1-cyclobutyl)-α-[3-[1-methylethyl(-phenylmethyl)amino]butyl]benzeneacetonitrile;
(±)-4-fluoro-α-(1-cyclobutyl)-α-[3-[ethyl(phenylmethyl)amino]pentyl]benzeneacetonitrile;
(±)-4-fluoro-α-(1-cyclobutyl)-α-[3-[n-propyl(phenylmethyl)amino]pentyl]benzeneacetonitrile;
(±)-4-fluoro-α-(1-cyclobutyl)-α-[3-[1-methylethyl(-phenylmethyl)amino]pentyl]benzeneacetonitrile;
(±)-4-fluoro-α-(1-cyclopentyl)-α-[3-[ethyl(phenylmethyl)amino]butyl]benzeneacetonitrile;
(±)-4-fluoro-α-(1-cyclopentyl)-α-[3-[n-propyl(phenylmethyl)amino]butyl]benzeneacetonitrile;
(±)-4-fluoro-α-(1-cyclopentyl)-α-[3 -[1-methylethyl(-phenylmethyl)amino]butyl]benzeneacetonitrile;
(±)-4-fluoro-α-(1-cyclopentyl)-α-[3-[ethyl(phenylmethyl)amino]pentyl]benzeneacetonitrile;
(±)-4-fluoro-α-(1-cyclopentyl)-α-[3-[n-propyl(phenylmethyl)amino]pentyl]benzeneacetonitrile;
(±)-4-fluoro-α-(1-cyclopentyl)-α-[3-[1-methylethyl(-phenylmethyl)amino]pentyl]benzeneacetonitrile;
(±)-4-fluoro-α-(1-cyclohexyl)-α-[3-[ethyl(phenylmethyl)amino]butyl]benzeneacetonitrile;
(±)-4-fluoro-α-(1-cyclohexyl)-α-[3-[n-propyl(phenylmethyl)amino]butyl]benzeneacetonitrile;
(±)-4-fluoro-α-(1-cyclohexyl)-α-[3-[1-methylethyl(-phenylmethyl)amino]butyl]benzeneacetonitrile;
(±)-4-fluoro-α-(1-cyclohexyl)-α-[3-[ethyl(phenylmethyl)amino]pentyl]benzeneacetonitrile;
(±)-4-fluoro-α-(1-cyclohexyl)-α-[3-[n-propyl(phenylmethyl)amino]pentyl]benzeneacetonitrile;
(±)-4-fluoro-α-(1-cyclohexyl)-α-[3-[1-methylethyl(-phenylmethyl)amino]pentyl]benzeneacetonitrile;

(±)-4-fluoro-α-(1-cyclopropyl)-α-[3-[methyl(phenylethyl)amino]butyl]benzeneacetonitrile;
(±)-4-fluoro-α-(1-cyclopropyl)-α-[3-[methyl(phenylethyl)amino]pentyl]benzeneacetonitrile;
(±)-4-fluoro-α-(1-cyclobutyl)-α-[3-[methyl(phenylethyl)amino]butyl]benzeneacetonitrile;
(±)-4-fluoro-α-(1-cyclobutyl)-α-[3-[methyl(phenylethyl)amino]pentyl]benzeneacetonitrile;
(±)-4-fluoro-α-(1-cyclopentyl)-α-[3-[methyl(phenylethyl)amino]butyl]benzeneacetonitrile;
(±)-4-fluoro-α-(1-cyclopentyl)-α-[3-[methyl(phenylethyl)amino]pentyl]benzeneacetonitrile;
(±)-4-fluoro-α-(1-cyclohexyl)-α-[3-[methyl(phenylethyl)amino]butyl]benzeneacetonitrile;
(±)-4-fluoro-α-(1-cyclohexyl)-α-[3-[methyl(phenylethyl)amino]pentyl]benzeneacetonitrile;
(±)-4-fluoro-α-(1-cyclopropyl)-α-[3-[ethyl(phenylethyl)amino]propyl]benzeneacetonitrile;
(±)-4-fluoro-α-(1-cyclopropyl)-α-[3-[n-propyl(phenylethyl)amino]propyl]benzeneacetonitrile;
(±)-4-fluoro-α-(1-cyclopropyl)-α-[3-[1-methylethyl(phenylethyl)amino]propyl]benzeneacetonitrile;
(±)-4-chloro-α-(1-cyclopropyl)-α-[3-[ethyl(phenylethyl)amino]propyl]benzeneacetonitrile;
(±)-4-chloro-α-(1-cyclopropyl)-α-[3-[n-propyl(phenylethyl)amino]propyl]benzeneacetonitrile;
(±)-4-chloro-α-(1-cyclopropyl)-α-[3-[1methylethyl(phenylethyl)amino]propyl]benzeneacetonitrile;
(±)-4-chloro-α-(1-cyclopropyl)-α-[3-[ethyl(phenylethyl)amino]propyl]benzeneacetonitrile;
(±)-4-chloro-α-(1-cyclopropyl)-α-[3-[n-propyl(phenylethyl)amino]propyl]benzeneacetonitrile;
(±)-4-chloro-α-(1-cyclopropyl)-α-[3-[1-methylethyl(phenylethyl)amino]propyl]benzeneacetonitrile;
(±)-4-trifluoromethyl-α-(1-cyclopropyl)-α-[3-[ethyl(phenyl ethyl)amino]propyl]benzeneacetonitrile;
(±)-4-trifluoromethyl-α-(1-cyclopropyl)-α-[3-[n-propyl(phenylethyl)amino]propyl]benzeneacetonitrile;
(±)-4-trifluoromethyl-α-(1-cyclopropyl)-α-[3-[1-methylethyl(phenylethyl)amino]propyl]benzeneacetonitrile;
(±)-4-fluoro-α-(1-cyclobutyl)-α-[3-[ethyl(phenylethyl)amino]propyl]benzeneacetonitrile;
(±)-4-fluoro-α-(1-cyclobutyl)-α-[3-[n-propyl(phenylethyl)amino]propyl]benzeneacetonitrile;
(±)-4-fluoro-α-(1-cyclobutyl)-α-[3-[1-methylethyl(phenylethyl)amino]propyl]benzeneacetonitrile;
(±)-4-chloro-α-(1-cyclobutyl)-α-[3-[ethyl(phenylethyl)amino]propyl]benzeneacetonitrile;
(±)-4-chloro-α-(1-cyclobutyl)-α-[3-[n-propyl(phenylethyl)amino]propyl]benzeneacetonitrile;
(±)-4-chloro-α-(1-cyclobutyl)-α-[3-[1-methylethyl(phenylethyl)amino]propyl]benzeneacetonitrile;
(±)-4-chloro-α-(1-cyclobutyl)-α-[3-[ethyl(phenylethyl)amino]propyl]benzeneacetonitrile;
(±)-4-chloro-α-(1-cyclobutyl)-α-[3-[n-propyl(phenylethyl)amino]propyl]benzeneacetonitrile;
(±)-4-chloro-α-(1-cyclobutyl)-α-[3-[1-methylethyl(phenylethyl)amino]propyl]benzeneacetonitrile;
(±)-4-trifluoromethyl-α-(1-cyclobutyl)-α-[3-[ethyl(phenylethyl)amino]propyl]benzeneacetonitrile;
(±)-4-trifluoromethyl-α-(1-cyclobutyl)-α-[3-[n-propyl(phenylethyl)amino]propyl]benzeneacetonitrile;
(±)-4-trifluoromethyl-α-(1-cyclobutyl)-α-[3-[1-methylethyl(phenylethyl)amino]propyl]benzeneacetonitrile;
(±)-4-fluoro-α-(1-cyclopentyl)-α-[3-[ethyl(phenylethyl)amino]propyl]benzeneacetonitrile;
(±)-4-fluoro-α-(1-cyclopentyl)-α-[3-[n-propyl(phenylethyl)amino]propyl]benzeneacetonitrile;
(±)-4-fluoro-α-(1-cyclopentyl)-α-[3-[1-methylethyl(phenylethyl)amino]propyl]benzeneacetonitrile;
(±)-4-chloro-α-(1-cyclopentyl)-α-[3-[ethyl(phenylethyl)amino]propyl]benzeneacetonitrile;
(±)-4-chloro-α-(1-cyclopentyl)-α-[3-[n-propyl(phenylethyl)amino]propyl]benzeneacetonitrile;
(±)-4-chloro-α-(1-cyclopentyl)-α-[3 -[1-methylethyl(phenylethyl)amino]propyl]benzeneacetonitrile;
(±)-4-chloro-α-(1-cyclopentyl)-α-[3 -[ethyl(phenylethyl)amino]propyl]benzeneacetonitrile;
(±)-4-chloro-α-(1-cyclopentyl)-α-[3-[n-propyl(phenylethyl)amino]propyl]benzeneacetonitrile;
(±)-4-chloro-α-(1-cyclopentyl)-α-[3 -[1-methylethyl(phenylethyl)amino]propyl]benzeneacetonitrile;
(±)-4-trifluoromethyl-α-(1-cyclopentyl)-α-[3-[ethyl(phenylethyl)amino]propyl]benzeneacetonitrile;
(±)-4-trifluoromethyl-α-(1-cyclopentyl)-α-[3-[n-propyl(phenylethyl)amino]propyl]benzeneacetonitrile;
(±)-4-trifluoromethyl-α-(1-cyclopentyl)-α-[3-[1-methylethyl(phenylethyl)amino]propyl]benzeneacetonitrile;
(±)-4-fluoro-α-(1-cyclohexyl)-α-[3-[ethyl(phenylethyl)amino]propyl]benzeneacetonitrile;
(±)-4-fluoro-α-(1-cyclohexyl)-α-[3 -[n-propyl(phenylethyl)amino]propyl]benzeneacetonitrile;
(±)-4-fluoro-α-(1-cyclohexyl)-α-[3-[1-methylethyl(phenylethyl)amino]propyl]benzeneacetonitrile;
(±)-4-chloro-α-(1-cyclohexyl)-α-[3-[ethyl(phenylethyl)amino]propyl]benzeneacetonitrile;
(±)-4-chloro-α-(1-cyclohexyl)-α-[3-[n-propyl(phenylethyl)amino]propyl]benzeneacetonitrile;
(±)-4-chloro-α-(1-cyclohexyl)-α-[3-[1-methylethyl(phenylethyl)amino]propyl]benzeneacetonitrile;
(±)-4-chloro-α-(1-cyclohexyl)-α-[3-[ethyl(phenylethyl)amino]propyl]benzeneacetonitrile;
(±)-4-chloro-α-(1-cyclohexyl)-α-[3-[n-propyl(phenylethyl)amino]propyl]benzeneacetonitrile;
(±)-4-chloro-α-(1-cyclohexyl)-α-[3-[1-methylethyl(phenylethyl)amino]propyl]benzeneacetonitrile;
(±)-4-trifluoromethyl-α-(1-cyclohexyl)-α-[3-[ethyl(phenylethyl)amino]propyl]benzeneacetonitrile;
(±)-4-trifluoromethyl-α-(1-cyclohexyl)-α-[3-[n-propyl(phenylethyl)amino]propyl]benzeneacetonitrile;
(±)-4-trifluoromethyl-α-(1-cyclohexyl)-α-[3-[1-methylethyl(phenylethyl)amino]propyl]benzeneacetonitrile;
(±)-4-fluoro-α-(1-cyclopropyl)-α-[3-[ethyl(phenylethyl)amino]butyl]benzeneacetonitrile;
(±)-4-fluoro-α-(1-cyclopropyl)-α-[3-[n-propyl(phenylethyl)amino]butyl]benzeneacetonitrile;
(±)-4-fluoro-α-(1-cyclopropyl)-α-[3-[1-methylethyl(phenylethyl)amino]butyl]benzeneacetonitrile;
(±)-4-chloro-α-(1-cyclopropyl)-α-[3-[ethyl(phenylethyl)amino]butyl]benzeneacetonitrile;
(±)-4-chloro-α-(1-cyclopropyl)-α-[3-[n-propyl(phenylethyl)amino]butyl]benzeneacetonitrile;
(±)-4-chloro-α-(1-cyclopropyl)-α-[3-[1-methylethyl(phenylethyl)amino]butyl]benzeneacetonitrile;
(±)-4-chloro-α-(1-cyclopropyl)-α-[3-[ethyl(phenylethyl)amino]butyl]benzeneacetonitrile;
(±)-4-chloro-α-(1-cyclopropyl)-α-[3-[n-propyl(phenylethyl)amino]butyl]benzeneacetonitrile;

(±)-4-chloro-α-(1-cyclopropyl)-α-[3-[1-methylethyl(phenylethyl)amino]butyl]benzeneacetonitrile;
(±)-4-trifluoromethyl-α-(1-cyclopropyl)-α-[3-[ethyl(phenylethyl)amino]butyl]benzeneacetonitrile;
(±)-4-trifluoromethyl-α-(1-cyclopropyl)-α-[3-[n-propyl(phenylethyl)amino]butyl]benzeneacetonitrile;
(±)-4-trifluoromethyl-α-(1-cyclopropyl)-α-[3-[1-methylethyl(phenylethyl)amino]butyl]benzeneacetonitrile;
(±)-4-fluoro-α-(1-cyclobutyl)-α-[3-[ethyl(phenylethyl)amino]butyl]benzeneacetonitrile;
(±)-4-fluoro-α-(1-cyclobutyl)-α-[3-[n-propyl(phenylethyl)amino]butyl]benzeneacetonitrile;
(±)-4-fluoro-α-(1-cyclobutyl)-α-[3-[1-methylethyl(phenylethyl)amino]butyl]benzeneacetonitrile;
(±)-4-chloro-α-(1-cyclobutyl)-α-[3-[ethyl(phenylethyl)amino]butyl]benzeneacetonitrile;
(±)-4-chloro-α-(1-cyclobutyl)-α-[3-[n-propyl(phenylethyl)amino]butyl]benzeneacetonitrile;
(±)-4-chloro-α-(1-cyclobutyl)-α-[3-[1-methylethyl(phenylethyl)amino]butyl]benzeneacetonitrile;
(±)-4-chloro-α-(1-cyclobutyl)-α-[3-[ethyl(phenylethyl)amino]butyl]benzeneacetonitrile;
(±)-4-chloro-α-(1-cyclobutyl)-α-[3-[n-propyl(phenylethyl)amino]butyl]benzeneacetonitrile;
(±)-4-chloro-α-(1-cyclobutyl)-α-[3-[1-methylethyl(phenylethyl)amino]butyl]benzeneacetonitrile;
(±)-4-trifluoromethyl-α-(1-cyclobutyl)-α-[3-[ethyl(phenylethyl)amino]butyl]benzeneacetonitrile;
(±)-4-trifluoromethyl(1-cyclobutyl)-α-[3-[n-propyl(phenylethyl)amino]butyl]benzeneacetonitrile;
(±)-4-trifluoromethyl-α-(1-cyclobutyl)-α-[3-[1-methylethyl(phenylethyl)amino]butyl]-benezeneacetonitrile;
(±)-4-fluoro-α-(1-cyclopentyl)-α-[3-[ethyl(phenylethyl)amino]butyl]benzeneacetonitrile;
(±)-4-fluoro-α-(1-cyclopentyl)-α-[3-[n-propyl(phenylethyl)amino]butyl]benzeneacetonitrile;
(±)-4-fluoro-α-(1-cyclopentyl)-α-[3-[1-methylethyl(phenylethyl)amino]butyl]benzeneacetonitrile;
(±)-4-chloro-α-(1-cyclopentyl)-α-[3-[ethyl(phenylethyl)amino]butyl]benzeneacetonitrile;
(±)-4-chloro-α-(1-cyclopentyl)-α-[3-[n-propyl(phenylethyl)amino]butyl]benzeneacetonitrile;
(±)-4-chloro-α-(1-cyclopentyl)-α-[3-[1-methylethyl(phenylethyl)amino]butyl]benzeneacetonitrile;
(±)-4-chloro-α-(1-cyclopentyl)-α-[3-[ethyl(phenylethyl)amino]butyl]benezeneacetonitrile;
(±)-4-chloro-α-(1-cyclopentyl)-α-[3-[n-propyl(phenylethyl)amino]butyl]benzeneacetonitrile;
(±)-4-chloro-α-(1-cyclopentyl)-α-[3-[1-methylethyl(phenylethyl)amino]butyl]benzeneacetonitrile;
(±)-4-trifluoromethyl-α-(1-cyclopentyl)-α-[3-[ethyl(phenylethyl)amino]butyl]benezeneacetonitrile;
(±)-4-trifluoromethyl-α-(1-cyclopentyl)-α-[3-[n-propyl(phenylethyl)amino]butyl]benzeneacetonitrile;
(±)4-trifluoromethyl-α-(1-cyclopentyl)-α-[3-[1-methylethyl(phenylethyl)amino]butyl]benzeneacetonitrile;
(±)-4-fluoro-α-(1-cyclohexyl)-α-[3-[ethyl(phenylethyl)amino]butyl]benzeneacetonitrile;
(±)-4-fluoro-α-(1-cyclohexyl)-α-[3-[n-propyl(phenylethyl)amino]butyl]benzeneacetonitrile;
(±)-4-fluoro-α-(1-cyclohexyl)-α-[3-[1-methylethyl(phenylethyl)amino]butyl]benzeneacetonitrile;
(±)-4-chloro-α-(1-cyclohexyl)-α-[3-[ethyl(phenylethyl)amino]butyl]benzeneacetonitrile;
(±)-4-chloro-α-(1-cyclohexyl)-α-[3-[n-propyl(phenylethyl)amino]butyl]benzeneacetonitrile;
(±)-4-chloro-α-(1-cyclohexyl)-α-[3-[1-methylethyl(phenylethyl)amino]butyl]benzeneacetonitrile;
(±)-4-chloro-α-(1-cyclohexyl)-α-[3-[ethyl(phenylethyl)amino]butyl]benzeneacetonitrile;
(±)-4-chloro-α-(1-cyclohexyl)-α-[3-[n-propyl(phenylethyl)amino]butyl]benzeneacetonitrile;
(±)-4-chloro-α-(1-cyclohexyl)-α-[3-[1-methylethyl(phenylethyl)amino]butyl]benzeneacetonitrile;
(±)-4-trifluoromethyl-α-(1-cyclohexyl)-α-[3-[ethyl(phenylethyl)amino]butyl]benzeneacetonitrile;
(±)-4-trifluoromethyl-α-(1-cyclohexyl)-α-[3-[n-propyl(phenylethyl)amino]butyl]benzeneacetonitrile;
(±)-4-trifluoromethyl-α-(1-cyclohexyl)-α-[3-[1-methylethyl(phenylethyl)amino]butyl]benzeneacetonitrile;
(±)-4-fluoro-α-(1-cyclopropyl)-α-[3-[ethyl(phenylethyl)amino]pentyl]benzeneacetonitrile;
(±)-4-fluoro-α-(1-cyclopropyl)-α-[3-[n-propyl(phenylethyl)amino]pentyl]benzeneacetonitrile;
(±)-4-fluoro-α-(1-cyclopropyl)-α-[3-[1-methylethyl(phenylethyl)amino]pentyl]benzeneacetonitrile;
(±)-4-chloro-α-(1-cyclopropyl)-α-[3-[ethyl(phenylethyl)amino]pentyl]benzeneacetonitrile;
(±)-4-chloro-α-(1-cyclopropyl)-α-[3-[n-propyl(phenylethyl)amino]pentyl]benzeneacetonitrile;
(±)-4-chloro-α-(1-cyclopropyl)-α-[3-[1-methylethyl(phenylethyl)amino]pentyl]benzeneacetonitrile;
(±)-4-chloro-α-(1-cyclopropyl)-α-[3-[ethyl(phenylethyl)amino]pentyl]benzeneacetonitrile;
(±)-4-chloro-α-(1-cyclopropyl)-α-[3-[n-propyl(phenylethyl)amino]pentyl]benzeneacetonitrile;
(±)-4-chloro-α-(1-cyclopropyl)-α-[3-[1-methylethyl(phenylethyl)amino]pentyl]benzeneacetonitrile;
(±)-4-trifluoromethyl-α-(1-cyclopropyl)-α-[3-[ethyl(phenylethyl)amino]pentyl]benzeneacetonitrile;
(±)-4-trifluoromethyl-α-(1-cyclopropyl)-α-[3-[n-propyl(phenylethyl)amino]pentyl]benzeneacetonitrile;
(±)-4-trifluoromethyl-α-(1-cyclopropyl)-α-[3-[1-methylethyl(phenylethyl)amino]pentyl]benzeneacetonitrile;
(±)-4-fluoro-α-(1-cyclobutyl)-α-[3-[ethyl(phenylethyl)amino]pentyl]benzeneacetonitrile;
(±)-4-fluoro-α-(1-cyclobutyl)-α-[3-[n-propyl(phenylethyl)amino]pentyl]benzeneacetonitrile;
(±)-4-fluoro-α-(1-cyclobutyl)-α-[3-[1-methylethyl(phenylethyl)amino]pentyl]benzeneacetonitrile;
(±)-4-chloro-α-(1-cyclobutyl)-α-[3-[ethyl(phenylethyl)amino]pentyl]benzeneacetonitrile;
(±)-4-chloro-α-(1-cyclobutyl)-α-[3-[n-propyl(phenylethyl)amino]pentyl]benzeneacetonitrile;
(±)-4-chloro-α-(1-cyclobutyl)-α-[3-[1-methylethyl(phenylethyl)amino]pentyl]benzeneacetonitrile;
(±)-4-chloro-α-(1-cyclobutyl)-α-[3-[ethyl(phenylethyl)amino]pentyl]benzeneacetonitrile;
(±)-4-chloro-α-(1-cyclobutyl)-α-[3-[n-propyl(phenylethyl)amino]pentyl]benzeneacetonitrile;
(±)-4-chloro-α-(1-cyclobutyl)-α-[3-[1-methylethyl(phenylethyl)amino]pentyl]benzeneacetonitrile;
(±)-4-trifluoromethyl-α-(1-cyclobutyl)-α-[3-[ethyl(phenylethyl)amino]pentyl]benzeneacetonitrile;
(±)-4-trifluoromethyl-α-(1-cyclobutyl)-α-[3-[n-propyl(phenylethyl)amino]pentyl]benzeneacetonitrile;

(±)-4-trifluoromethyl-α-(1-cyclobutyl)-α-[3-[1-methylethyl(phenylethyl)amino]pentyl]benzeneacetonitrile;
(±)-4-fluoro-α-(1-cyclopentyl)-α-[3-[ethyl(phenylethyl)amino]pentyl]benzeneacetonitrile;
(±)-4-fluoro-α-(1-cyclopentyl)-α-[3-[n-propyl(phenylethyl)amino]pentyl]benzeneacetonitrile;
(±)-4-fluoro-α-(1-cyclopentyl)-α-[3-[1-methylethyl(phenylethyl)amino]pentyl]benzeneacetonitrile;
(±)-4-chloro-α-(1-cyclopentyl)-α-[3-[ethyl(phenylethyl)amino]pentyl]benzeneacetonitrile;
(±)-4-chloro-α-(1-cyclopentyl)-α-[3-[n-propyl(phenylethyl)amino]pentyl]benzeneacetonitrile;
(±)-4-chloro-α-(1-cyclopentyl)-α-[3-[1-methylethyl(phenylethyl)amino]pentyl]benzeneacetonitrile;
(±)-4-chloro-α-(1-cyclopentyl)-α-[3-[ethyl(phenylethyl)amino]pentyl]benzeneacetonitrile;
(±)-4-chloro-α-(1-cyclopentyl)-α-[3-[n-propyl(phenylethyl)amino]pentyl]benzeneacetonitrile;
(±)-4-chloro-α-(1-cyclopentyl)-α-[3-[1-methylethyl(phenylethyl)amino]pentyl]benzeneacetonitrile;
(±)-4-trifluoromethyl-α-(1-cyclopentyl)-α-[3-[ethyl(phenylethyl)amino]pentyl]benzeneacetonitrile;
(±)-4-trifluoromethyl-α-(1-cyclopentyl)-α-[3-[n-propyl(phenylethyl)amino]pentyl]benzeneacetonitrile;
(±)-4-trifluoromethyl-α-(1-cyclopentyl)-α-[3-[1-methylethyl(phenylethyl)amino]pentyl]benzeneacetonitrile;
(±)-4-fluoro-α-(1-cyclohexyl)-α-[3-[ethyl(phenylethyl)amino]pentyl]benzeneacetonitrile;
(±)-4-fluoro-α-(1-cyclohexyl)-α-[3-[n-propyl(phenylethyl)amino]pentyl]benzeneacetonitrile;
(±)-4-fluoro-α-(1-cyclohexyl)-α-[3-[1-methylethyl(phenylethyl)amino]pentyl]benzeneacetonitrile;
(±)-4-chloro-α-(1-cyclohexyl)-α-[3-[ethyl(phenylethyl)amino]pentyl]benzeneacetonitrile;
(±)-4-chloro-α-(1-cyclohexyl)-α-[3-[n-propyl(phenylethyl)amino]pentyl]benzeneacetonitrile;
(±)-4-chloro-α-(1-cyclohexyl)-α-[3-[1-methylethyl(phenylethyl)amino]pentyl]benzeneacetonitrile;
(±)-4-chloro-α-(1-cyclohexyl)-α-[3-[ethyl(phenylethyl)amino]pentyl]benzeneacetonitrile;
(±)-4-chloro-α-(1-cyclohexyl)-α-[3-[n-propyl(phenylethyl)amino]pentyl]benzeneacetonitrile;
(±)-4-chloro-α-(1-cyclohexyl)-α-[3-[1-methylethyl(phenylethyl)amino]pentyl]benzeneacetonitrile;
(±)-4-trifluoromethyl-α-(1-cyclohexyl)-α-[3-[ethyl(phenylethyl)amino]pentyl]benzeneacetonitrile;
(±)-4-trifluoromethyl-α-(1-cyclohexyl)-α-[3-[n-propyl(phenylethyl)amino]pentyl]benzeneacetonitrile;
(±)-4-trifluoromethyl-α-(1-cyclohexyl)-α-[3-[1-methylethyl(phenylethyl)amino]pentyl]benzeneacetonitrile;
(±)-2-fluoro-α-(1-methylethyl)-α-[3-[methyl(phenylmethyl)amino]propyl]benzeneacetonitrile;
(±)-2-chloro-α-(1-methylethyl)-α-[3-[methyl(phenylmethyl)amino]propyl]benzeneacetonitrile;
(±)-2-bromo-α-(1-methylethyl)-α-[3-[methyl(phenylmethyl)amino]propyl]benzeneacetonitrile;
(±)-2-trifluoromethyl-α-(1-methylethyl)-α-[3-[methyl(phenylmethyl)amino]propyl]benzeneacetonitrile;
(±)-2-fluoro-α-(1-cyclopropyl)[3-[methyl(phenylmethyl)amino]propyl]benzeneacetonitrile;
(±)-2-fluoro-α-(1-cyclobutyl)-α-[3-[methyl(phenylmethyl)amino]propyl]benzeneacetonitrile;
(±)-2-fluoro-α-(1-cyclopentyl)-α-[3-[methyl(phenylmethyl)amino]propyl]benzeneacetonitrile;
(±)-2-fluoro-α-(1-cyclohexyl)-α-[3-[methyl(phenylmethyl)amino]propyl]benzeneacetonitrile;
(±)-2-fluoro-α-(1-methylethyl)-α-[3-[ethyl(phenylmethyl)amino]propyl]benzeneacetonitrile;
(±)-2-fluoro-α-(1-methylethyl)-α-[3-[n-propyl(phenylmethyl)amino]propyl]benzeneacetonitrile;
(±)-2-fluoro-α-(1-methylethyl)-α-[3-[1-methylethyl(phenylmethyl)amino]propyl]benzeneacetonitrile;
(±)-2-fluoro-α-(1-methylethyl)-α-[3-[methyl(phenylethyl)amino]propyl]benzeneacetonitrile;
(±)-2-fluoro-α-(1-methylethyl)-α-[3-[methyl(phenylmethyl)amino]butyl]benzeneacetonitrile;
(±)-2-fluoro-α-(1-methylethyl)-α-[3-[methyl(phenylmethyl)amino]pentyl]benezeneacetonitrile;
(±)-2-fluoro-α-(1-cyclopropyl)-α-[3-[methyl(phenylmethyl)amino]propyl]benzeneacetonitrile;
(±)-2-fluoro-α-(1-cyclobutyl)-α-[3-[methyl(phenylmethyl)amino]propyl]benzeneacetonitrile;
(±)-2-fluoro-α-(1-cyclopentyl)-α-[3-[methyl(phenylmethyl)amino]propyl]benzeneacetonitrile;
(±)-2-fluoro-α-(1-cyclohexyl)-α-[3-[methyl(phenylmethyl)amino]propyl]benzeneacetonitrile;
(±)-2-chloro-α-(1-cyclopropyl)-α-[3-[methyl(phenylmethyl)amino]propyl]benzeneacetonitrile;
(±)-2-chloro-α-(1-cyclobutyl)-α-[3-[methyl(phenylmethyl)amino]propyl]benzeneacetonitrile;
(±)-2-chloro-α-(1-cyclopentyl)-α-[3-[methyl(phenylmethyl)amino]propyl]benzeneacetonitrile;
(±)-2-chloro-α-(1-cyclohexyl)-α-[3-[methyl(phenylmethyl)amino]propyl]benzeneacetonitrile;
(±)-2-bromo-α-(1-cyclopropyl)-α-[3-[methyl(phenylmethyl)amino]propyl]benzeneacetonitrile;
(±)-2-bromo-α-(1-cyclobutyl)-α-[3-[methyl(phenylmethyl)amino]propyl]benzeneacetonitrile;
(±)-2-bromo-α-(1-cyclopentyl)-α-[3-[methyl(phenylmethyl)amino]propyl]benzeneacetonitrile;
(±)-2-bromo-α-(1-cyclohexyl)-α-[3-[methyl(phenylmethyl)amino]propyl]benzeneacetonitrile;
(±)-2-trifluoromethyl-α-(1-cyclopropyl)-α-[3-[methyl(phenylmethyl)amino]propyl]benzeneacetonitrile;
(±)-2-trifluoromethyl-α-(1-cyclobutyl)-α-[3-[methyl(phenylmethyl)amino]propyl]benzeneacetonitrile;
(±)-2-trifluoromethyl-α-(1-cyclopentyl)-α-[3-[methyl(phenylmethyl)amino]propyl]benzeneacetonitrile;
(±)-2-trifluoromethyl-α-(1-cyclohexyl)-α-[3-[methyl(phenylmethyl)amino]propyl]benzeneacetonitrile;
(±)-2-fluoro-α-(1-methylethyl)-α-[3-[ethyl(phenylmethyl)amino]propyl]benzeneacetonitrile;
(±)-2-fluoro-α-(1-methylethyl)-α-[3-[n-propyl(phenylmethyl)amino]propyl]benzeneacetonitrile;
(±)-2-fluoro-α-(1-methylethyl)-α-[3-[1-methylethyl(phenylmethyl)amino]propyl]benzeneacetonitrile;
(±)-2-chloro-α-(1-methylethyl)-α-[3-[ethyl(phenylmethyl)amino]propyl]benezeneacetonitrile;
(±)-2-chloro-α-(1-methylethyl)-α-[3-[n-propryl(phenylmethyl)amino]propyl]benzeneacetonitrile;
(±)-2-chloro-α-(1-methylethyl)-α-[3-[1-methylethyl(phenylmethyl)amino]propyl]benzeneacetonitrile;
(±)-2-bromo-α-(1-methylethyl)-α-[3-[ethyl(phenylmethyl)amino]propyl]benezeneacetonitrile;
(±)-2-bromo-α-(1-methylethyl)-α-[3-[n-propyl(phenylmethyl)amino]propyl]benzeneacetonitrile;
(±)-2-bromo-α-(1-methylethyl)-α-[3-[1-methylethyl(phenylmethyl)amino]propyl]benzeneacetonitrile;
(±)-2-trifluoromethyl-α-(1-methylethyl)-α-[3-[ethyl(phenylmethyl)amino]propyl]benzeneacetonitrile;

(±)-2-trifluoromethyl-α-(1-methylethyl)-α-[3-[n-propyl(phenylmethyl)amino]propyl]benzeneacetonitrile;
(±)-2-trifluoromethyl-α-(1-methylethyl)-α-[3-[1-methylethyl(phenylmethyl)amino]propyl]benzeneacetonitrile;
(±)-2-fluoro-α-(1-cyclohexyl)-α-[3-[ethyl(phenylethyl)amino]propyl]benzeneacetonitrile;
(±)-2-chloro-α-(1-methylethyl)-α-[3-[methyl(phenylethyl)amino]propyl]benzeneacetonitrile;
(±)-2-bromo-α-(1-methylethyl)-α-[3-[methyl(phenylethyl)amino]propyl]benzeneacetonitrile;
(±)-2-trifluoromethyl-α-(1-methylethyl)-α-[3-[methyl(phenylethyl)amino]propyl]benzeneacetonitrile;
(±)-2-fluoro-α-(1-cyclohexyl)-α-[3-[ethyl(phenylmethyl)amino]butyl]benzeneacetonitrile;
(±)-2-fluoro-α-(1-cyclohexyl)-α-[3-[ethyl(phenylmethyl)amino]pentyl]benzeneacetonitrile;
(±)-2-chloro-α-(1-methylethyl)-α-[3-[methyl(phenylmethyl)amino]butyl]benzeneacetonitrile;
(±)-2-chloro-α-(1-methylethyl)-α-[3-[methyl(phenylmethyl)amino]pentyl]benzeneacetonitrile;
(±)-2-bromo-α-(1-methylethyl)-α-[3-[methyl(phenylmethyl)amino]butyl]benzeneacetonitrile;
(±)-2-bromo-α-(1-methylethyl)-α-[3-[methyl(phenylmethyl)amino]pentyl]benzeneacetonitrile;
(±)-2-trifluoromethyl-α-(1-methylethyl)-α-[3-[methyl(phenylmethyl)amino]butyl]benzeneacetonitrile;
(±)-2-trifluoromethyl-α-(1-methylethyl)-α-[3-[methyl(phenylmethyl)amino]pentyl]benzeneacetonitrile;
(±)-2-fluoro-α-(1-cyclopropyl)-α-[3-[ethyl(phenylmethyl)amino]propyl]benzeneacetonitrile;
(±)-2-fluoro-α-(1-cyclopropyl)-α-[3-[n-propyl(phenylmethyl)amino]propyl]benzeneacetonitrile;
(±)-2-fluoro-α-(1-cyclopropyl)-α-[3-[1-methylethyl(phenylmethyl)amino]propyl]benzeneacetonitrile;
(±)-2-fluoro-α-(1-cyclobutyl)-α-[3-[ethyl(phenylmethyl)amino]propyl]benzeneacetonitrile;
(±)-2-fluoro-α-(1-cyclobutyl)-α-[3-[nn-propyl(phenylmethyl)amino]propyl]benzeneacetonitrile;
(±)-2-fluoro-α-(1-cyclobutyl)-α-[3-[1-methylethyl(phenylmethyl)amino]propyl]benzeneacetonitrile;
(±)-2-fluoro-α-(1-cyclopentyl)-α-[3-[ethyl(phenylmethyl)amino]propyl]benzeneacetonitrile;
(±)-2-fluoro-α-(1-cyclopentyl)-α-[3-[n-propyl(phenylmethyl)amino]propyl]benzeneacetonitrile;
(±)-2-fluoro-α-(1-cyclopentyl)-α-[3-[1-methylethyl(phenylmethyl)amino]propyl]benzeneacetonitrile;
(±)-2-fluoro-α-(1-cyclohexyl)-α-[3-[1ethyl(phenylmethyl)amino]propyl]benzeneacetonitrile;
(±)-2-fluoro-α-(1-cyclohexyl)-α-[3-[1-n-propyl(phenylmethyl)amino]propyl]benzeneacetonitrile;
(±)-2-fluoro-α-(1-cyclohexyl)-α-[3-[1-1-methylethyl(phenylmethyl)amino]propyl]benzeneacetonitrile;
(±)-2-fluoro-α-(1-cyclopropyl)-α-[3-[methyl(phenylethyl)amino]propyl]benzeneacetonitrile;
(±)-2-fluoro-α-(1-cyclobutyl)-α-[3-[methyl(phenylethyl)amino]propyl]benzeneacetonitrile;
(±)-2-fluoro-α-(1-cyclopentyl)-α-[3-[methyl(phenylethyl)amino]propyl]benzeneacetonitrile;
(±)-2-fluoro-α-(1-cyclohexyl)-α-[3-[methyl(phenylethyl)amino]propyl]benzeneacetonitrile;
(±)-2-fluoro-α-(1-cyclopropyl)-α-[3-[methyl(phenylmethyl)amino]propyl]benzeneacetonitrile;
(±)-2-fluoro-α-(1-cyclopropyl)-α-[3-[methyl(phenylmethyl)amino]butyl]benzeneacetonitrile;
(±)-2-fluoro-α-(1-cyclopropyl)-α-[3-[methyl(phenylmethyl)amino]pentyl]benzeneacetonitrile;
(±)-2-fluoro-α-(1-cyclobutyl)-α-[3-[methyl(phenylmethyl)amino]propyl]benzeneacetonitrile;
(±)-2-fluoro-α-(1-cyclobutyl)-α-[3-[methyl(phenylmethyl)amino]butyl]benzeneacetonitrile;
(±)-2-fluoro-α-(1-cyclobutyl)-α-[3-[methyl(phenylmethyl)amino]pentyl]benzeneacetonitrile;
(±)-2-fluoro-α-(1-cyclopentyl)-α-[3-[methyl(phenylmethyl)amino]propyl]benzeneacetonitrile;
(±)-2-fluoro-α-(1-cyclopentyl)-α-[3-[methyl, (phenylmethyl)amino]butyl]benzeneacetonitrile;
(±)-2-fluoro-α-(1-cyclopentyl)-α-[3-[methyl(phenylmethyl)amino]pentyl]benzeneacetonitrile;
(±)-2-fluoro-α-(1-cyclohexyl)-α-[3-[methyl(phenylmethyl)amino]propyl]benzeneacetonitrile;
(±)-2-fluoro-α-(1-cyclohexyl)-α-[3-[methyl(phenylmethyl)amino]butyl]benzeneacetonitrile;
(±)-2-fluoro-α-(1-cyclohexyl)-α-[3-[methyl(phenylmethyl)amino]pentyl]benzeneacetonitrile;
(±)-2-fluoro-α-(1-methylethyl)-α-[3-[methyl(phenylethyl)amino]propyl]benzeneacetonitrile;
(±)2-fluoro-α-(1-methylethyl)-α-[3-[ethyl(phenylethyl)amino]propyl]benezeneacetonitrile;
(±)-2-fluoro-α-(1-methylethyl)-α-[3-[n-propyl(phenylethyl)amino]propyl]benezeneacetonitrile;
(±)-2-fluoro-α-(1-methylethyl)-α-[3-[1-methylethyl(phenylethyl)amino]propyl]benezeneacetonitrile;
(±)-2-fluoro-α-(1-methylethyl)-α-[3-[ethyl(phenylmethyl)amino]propyl]benzeneacetonitrile;
(±)-2-fluoro-α-(1-methylethyl)-α-[3-[ethyl(phenylmethyl)amino]butyl]benzeneacetonitrile;
(±)-2-fluoro-α-(1-methylethyl)-α-[3-[ethyl(phenylmethyl)amino]pentyl]benzeneacetonitrile;
(±)-2-fluoro-α-(1-methylethyl)-α-[n-propyl(phenylmethyl)amino]propyl]benzeneacetonitrile;
(±)-2-fluoro-α-(1-methylethyl)-α-[3-[n-propyl(phenylmethyl)amino]butyl]benzeneacetonitrile;
(±)-2-fluoro-α-(1-methylethyl)-α-[3-[n-propyl(phenylmethyl)amino]pentyl]benzeneacetonitrile;
(±)-2-fluoro-α-(1-methylethyl)-α-[3-[methylethyl(phenylmethyl)amino]propyl]benzeneacetonitrile;
(±)-2-fluoro-α-(1-methylethyl)-α-[3-[1-methylethyl(phenylmethyl)amino]butyl]benzeneacetonitrile;
(±)-2-fluoro-α-(1-methylethyl)-α-[3-[1-methylethyl(phenylmethyl)amino]pentyl]benzeneacetonitrile;
(±)-2-fluoro-α-(1-methylethyl)-α-[3-[methyl(phenylethyl)amino]propyl]benzeneacetonitrile;
(±)-2-fluoro-α-(1-methylethyl)-α-[3-[methyl(phenylethyl)amino]butyl]benzeneacetonitrile;
(±)-2-fluoro-α-(1-methylethyl)-α-[3-[methyl(phenylethyl)amino]pentyl]benzeneacetonitrile;
(±)-2-fluoro-α-(1-cyclopropyl)-α-[3-[ethyl(phenylmethyl)amino]propyl]benzeneacetonitrile;
(±)-2-fluoro-α-(1-cyclopropyl)-α-[3-[n-propyl(phenylmethyl)amino]propyl]benzeneacetonitrile;
(±)-2-fluoro-α-(1-cyclopropyl)-α-[3-[1-methylethyl(phenylmethyl)amino]propyl]benzeneacetonitrile;
(±)-2-fluoro-α-(1-cyclobutyl)-α-[3-[ethyl(phenylmethyl)amino]propyl]benzeneacetonitrile;
(±)-2-fluoro-α-(1-cyclobutyl)-α-[3-[n-propyl(phenylmethyl)amino]propyl]benzeneacetonitrile;
(±)-2-fluoro-α-(1-cyclobutyl)-α-[3-[1-methylethyl(phenylmethyl)amino]propyl]benzeneacetonitrile;
(±)-2-fluoro-α-(1-cyclopentyl)-α-[3-[ethyl(phenylmethyl)amino]propyl]benzeneacetonitrile;
(±)-2-fluoro-α-(1-cyclopentyl)-α-[3-[n-propyl(phenylmethyl)amino]propyl]benzeneacetonitrile;
(±)-2-fluoro-α-(1-cyclopentyl)-α-[3-[1-methylethyl(phenylmethyl)amino]propyl]benzeneacetonitrile;

(±)-2-fluoro-α-(1-cyclohexyl)-α-[3-[ethyl(phenylmethyl)amino]propyl]benzeneacetonitrile;
(±)-2-fluoro-α-(1-cyclohexyl)-α-[3-[n-propyl(phenylmethyl)amino]propyl]benzeneacetonitrile;
(±)-2-fluoro-α-(1-cyclohexyl)-α-[3-[1-methylethyl(phenylmethyl)amino]propyl]benzeneacetonitrile;
(±)-2-chloro-α-(1-cyclopropyl)-α-[3-[ethyl(phenylmethyl)amino]propyl]benzeneacetonitrile;
(±)-2-chloro-α-(1-cyclopropyl)-α-[3-[n-propyl(phenylmethyl)amino]propyl]benzeneacetonitrile;
(±)-2-chloro-α-(1-cyclopropyl)-α-[3-[1-methylethyl(phenylmethyl)amino]propyl]benzeneacetonitrile;
(±)-2-chloro-α-(1-cyclobutyl)-α-[3-[ethyl(phenylmethyl)amino]propyl]benzeneacetonitrile;
(±)-2-chloro-α-(1-cyclobutyl)-α-[3-[n-propyl(phenylmethyl)amino]propyl]benezeneacetonitrile;
(±)-2-chloro-α-(1-cyclobutyl)-α-[3-[1-methylethyl(phenylmethyl)amino]propyl]benezeneacetonitrile;
(±)-2-chloro-α-(1-cyclopentyl)-α-[3-[ethyl(phenylmethyl)amino]propyl]benzeneacetonitrile;
(±)-2-chloro-α-(1-cyclopentyl)-α-[3-[n-propyl(phenylmethyl)amino]propyl]benezeneacetonitrile;
(±)-2-chloro-α-(1-cyclopentyl)-α-[3-[1-methylethyl(phenylmethyl)amino]propyl]benzeneacetonitrile;
(±)-2-chloro-α-(1-cyclohexyl)-α-[3-[ethyl(phenylmethyl)amino]propyl]benzeneacetonitrile;
(±)-2-chloro-α-(1-cyclohexyl)-α-[3-[n-propyl(phenylmethyl)amino]propyl]benzeneacetonitrile;
(±)-2-chloro-α-(1-cyclohexyl)-α-[3-[1-methylethyl(phenylmethyl)amino]propyl]benzeneacetonitrile;
(±)-2-bromo-α-(1-cyclopropyl)-α-[3-[ethyl(phenylmethyl)amino]propyl]benzeneacetonitrile;
(±)-2-bromo-α-(1-cyclopropyl)-α-[3-[n-propyl(phenylmethyl)amino]propyl]benzeneacetonitrile;
(±)-2-bromo-α-(1-cyclopropyl)-α-[3-[1-methylethyl(phenylmethyl)amino]propyl]benzeneacetonitrile;
(±)-2-bromo-α-(1-cyclobutyl)-α-[3-[ethyl(phenylmethyl)amino]propyl]benzeneacetonitrile;
(±)-2-bromo-α-(1-cyclobutyl)-α-[3-[n-propyl(phenylmethyl)amino]propyl]benzeneacetonitrile;
(±)-2-bromo-α-(1-cyclobutyl)-α-[3-[1-methylethyl(phenylmethyl)amino]propyl]benzeneacetonitrile;
(±)-2-bromo-α-(1-cyclopentyl)-α-[3-[ethyl(phenylmethyl)amino]propyl]benezeneacetonitrile;
(±)-2-bromo-α-(1-cyclopentyl)-α-[3-[n-propyl(phenylmethyl)amino]propyl]benezeneacetonitrile;
(±)-2-bromo-α-(1-cyclopentyl)-α-[3-[1-methylethyl(phenylmethyl)amino]propyl]benzeneacetonitrile;
(±)-2-bromo-α-(1-cyclohexyl)-α-[3-[ethyl(phenylmethyl)amino]propyl]benzeneacetonitrile;
(±)-2-bromo-α-(1-cyclohexyl)-α-[3-[n-propyl(phenylmethyl)amino]propyl]benzeneacetonitrile;
(±)-2-bromo-α-(1-cyclohexyl)-α-[3-[1-methylethyl(phenylmethyl)amino]propyl]benzeneacetonitrile;
(±)-2-trifluoromethyl-α-(1-cyclopropyl)-α-[3-[ethyl(phenylmethyl)amino]propyl]benzeneacetonitrile;
(±)-2-trifluoromethyl-α-(1-cyclopropyl)-α-[3-[n-propyl(phenylmethyl)amino]propyl]benzeneacetonitrile;
(±)-2-trifluoromethyl-α-(1-cyclopropyl)-α-[3-[1-methylethyl(phenylmethyl)amino]propyl]benzeneacetonitrile;
(±)-2-trifluoromethyl-α-(1-cyclobutyl)-α-[3-[ethyl(phenylmethyl)amino]propyl]benzeneacetonitrile;
(±)-2-trifluoromethyl-α-(1-cyclobutyl)-α-[3-[n-propyl(phenylmethyl)amino]propyl]benzeneacetonitrile;
(±)-2-trifluoromethyl-α-(1-cyclobutyl)-α-[3-[1-methylethyl(phenylmethyl)amino]propyl]benzeneacetonitrile;
(±)-2-trifluoromethyl-α-(1-cyclopentyl)-α-[3-[ethyl(phenylmethyl)amino]propyl]benzeneacetonitrile;
(±)-2-trifluoromethyl-α-(1-cyclopentyl)-α-[3-[n-propyl(phenylmethyl)amino]propyl]benzeneacetonitrile;
(±)-2-trifluoromethyl-α-(1-cyclopentyl)-α-[3-[1-methylethyl(phenylmethyl)amino]propyl]benzeneacetonitrile;
(±)-2-trifluoromethyl-α-(1-cyclohexyl)-α-[3-[ethyl(phenylmethyl)amino]propyl]benzeneacetonitrile;
(±)-2-trifluoromethyl-α-(1-cyclohexyl)-α-[3-[n-propyl(phenylmethyl)amino]propyl]benzeneacetonitrile;
(±)-2-trifluoromethyl-α-(1-cyclohexyl)-α-[3-[1-methylethyl(phenylmethyl)amino]propyl]benzeneacetonitrile;
(±)-2-fluoro-α-(1-methylethyl)-α-[3-[ethyl(phenylethyl)amino]propyl]benzeneacetonitrile;
(±)-2-fluoro-α-(1-methylethyl)-α-[3-[n-propyl(phenylethyl)amino]propyl]benzeneacetonitrile;
(±)-2-fluoro-α-(1-methylethyl)-α-[3-[1-methylethyl(phenylethyl)amino]propyl]benzeneacetonitrile;
(±)-2-chloro-α-(1-methylethyl)-α-[3-[ethyl(phenylethyl)amino]propyl]benzeneacetonitrile;
(±)-2-chloro-α-(1-methylethyl)-α-[3-[n-propyl(phenylethyl)amino]propyl]benzeneacetonitrile;
(±)-2-chloro-α-(1-methylethyl)-α-[3-[1-methylethyl(phenylethyl)amino]propyl]benzeneacetonitrile;
(±)-2-bromo-α-(1-methylethyl)-α-[3-[ethyl(phenylethyl)amino]propyl]benzeneacetonitrile;
(±)-2-bromo-α-(1-methylethyl)-α-[3-[n-propyl(phenylethyl)amino]propyl]benzeneacetonitrile;
(±)-2-bromo-α-(1-methylethyl)-α-[3-[1-methylethyl(phenylethyl)amino]propyl]benzeneacetonitrile;
(±)-2-trifluoromethyl-α-(1-methylethyl)-α-[3-[ethyl(phenylethyl)amino]propyl]benzeneacetonitrile;
(±)-2-trifluoromethyl-α-(1-methylethyl)-α-[3-[n-propyl(phenylethyl)amino]propyl]benzeneacetonitrile;
(±)-2-trifluoromethyl-α-(1-methylethyl)-α-[3-[1-methylethyl(phenylethyl)amino]propyl]benzeneacetonitrile;
(±)-2-fluoro-α-(1-cyclopropyl)-α-[3-[methyl(phenylethyl)amino]propyl]benzeneacetonitrile;
(±)-2-fluoro-α-(1-cyclobutyl)-α-[3-[methyl(phenylethyl)amino]propyl]benzeneacetonitrile;
(±)-2-fluoro-α-(1-cyclopentyl)-α-[3-[methyl(phenylethyl)amino]propyl]benzeneacetonitrile;
(±)-2-fluoro-α-(1-cyclohexyl)-α-[3-[methyl(phenylethyl)amino]propyl]benezeneacetonitrile;
(±)-2-chloro-α-(1-cyclopropyl)-α-[3-[methyl(phenylethyl)amino]propyl]benzeneacetonitrile;
(±)-2-chloro-α-(1-cyclobutyl)-α-[3-[methyl(phenylethyl)amino]propyl]benzeneacetonitrile;
(±)-2-chloro-α-(1-cyclopentyll)-α-[3-[methyl(phenylethyl)amino]propyl]benzeneacetonitrile;
(±)-2-chloro-α-(1-cyclohexyl)-α-[3-[methyl(phenylethyl)amino]propyl]benzeneacetonitrile;
(±)-2-bromo-α-(1-cyclopropyl)-α-[3-[methyl(phenylethyl)amino]propyl]benezeneacetonitrile;
(±)-2-bromo-α-(1-cyclobutyl)-α-[3-[methyl(phenylethyl)amino]propyl]benezeneacetonitrile;
(±)-2-bromo-α-(1-cyclopentyll)-α-[3-[methyl(phenylethyl)amino]propyl]benezeneacetonitrile;

(±)-2-bromo-α-(1-cyclohexyl)-α-[3-[methyl(phenylethyl)amino]propyl]benzeneacetonitrile;
(±)-2-trifluoromethyl-α-(1-cyclopropyl)-α-[3-[methyl(phenylethyl)amino]propyl]benzeneacetonitrile;
(±)-2-trifluoromethyl-α-(1-cyclobutyl)-α-[3-[methyl(phenylethyl)amino]propyl]benzeneacetonitrile;
(±)-2-trifluoromethyl-α-(1-cyclopentyl)-α-[3-[methyl(phenylethyl)amino]propyl]benzeneacetonitrile;
(±)-2-trifluoromethyl-α-(1-cyclohexyl)-α-[3-[methyl(phenylethyl)amino]propyl]benezeneacetonitrile;
(±)-2-fluoro-α-(1-cyclopropyl)-α-[3-[methyl(phenylmethyl)amino]propyl]benzeneacetonitrile;
(±)-2-fluoro-α-(1-cyclopropyl)-α-[3-[methyl(phenylmethyl)amino]butyl]benzeneacetonitrile;
(±)-2-fluoro-α-(1-cyclopropyl)-α-[3-[methyl(phenylmethyl)amino]pentyl]benzeneacetonitrile;
(±)-2-fluoro-α-(1-cyclobutyl)-α-[3-[methyl(phenylmethyl)amino]propyl]benzeneacetonitrile;
(±)-2-fluoro-α-(1-cyclobutyl)-α-[3-[methyl(phenylmethyl)amino]butyl]benzeneacetonitrile;
(±)-2-fluoro-α-(1-cyclobutyl)-α-[3-[methyl(phenylmethyl)amino]pentyl]benzeneacetonitrile;
(±)-2-fluoro-α-(1-cyclopentyl)[3-[methyl(phenylmethyl)amino]propyl]benzeneacetonitrile;
(±)-2-fluoro-α-(1-cyclopentyl)-α-[3-[methyl(phenylmethyl)amino]butyl]benzeneacetonitrile;
(±)-2-fluoro-α-(1-cyclopentyl)-α-[3-[methyl(phenylmethyl)amino]pentyl]benzeneacetonitrile;
(±)-2-fluoro-α-(1-cyclohexyl)-α-[3-[methyl(phenylmethyl)amino]propyl]benzeneacetonitrile;
(±)-2-fluoro-α-(1-cyclohexyl)-α-[3-[methyl(phenylmethyl)amino]butyl]benzeneacetonitrile;
(±)-2-fluoro-α-(1-cyclohexyl)-α-[3-[methyl(phenylmethyl)amino]pentyl]benzeneacetonitrile;
(±)-2-chloro-α-(1-cyclopropyl)-α-[3-[methyl(phenylmethyl)amino]propyl]benzeneacetonitrile;
(±)-2-chloro-α-(1-cyclopropyl)-α-[3-[methyl(phenylmethyl)amino]butyl]benzeneacetonitrile;
(±)-2-chloro-α-(1-cyclopropyl)-α-[3-[methyl(phenylmethyl)amino]pentyl]benzeneacetonitrile;
(±)-2-chloro-α-(1-cyclobutyl)-α-[3-[methyl(phenylmethyl)amino]propyl]benzeneacetonitrile;
(±)-2-chloro-α-(1-cyclobutyl)-α-[3-[methyl(phenylmethyl)amino]butyl]benzeneacetonitrile;
(±)-2-chloro-α-(1-cyclobutyl)-α-[3-[methyl(phenylmethyl)amino]pentyl]benzeneacetonitrile;
(±)-2-chloro-α-(1-cyclopentyl)-α-[3-[methyl(phenylmethyl)amino]propyl]benzeneacetonitrile;
(±)-2-chloro-α-(1-cyclopentyl)-α-[3-[methyl(phenylmethyl)amino]butyl]benzeneacetonitrile;
(±)-2-chloro-α-(1-cyclopentyl)-α-[3-[methyl(phenylmethyl)amino]pentyl]benzeneacetonitrile;
(±)-2-chloro-α-(1-cyclohexyl)-α-[3-[methyl(phenylmethyl)amino]propyl]benezeneacetonitrile;
(±)-2-chloro-α-(1-cyclohexyl)-α-[3-[methyl(phenylmethyl)amino]butyl]benzeneacetonitrile;
(±)-2-chloro-α-(1-cyclohexyl)-α-[3-[methyl(phenylmethyl)amino]pentyl]benzeneacetonitrile;
(±)-2-trifluoromethyl-α-(1-cyclopropyl)-α-[3-[methyl(phenylmethyl)amino]propyl]benzeneacetonitrile;
(±)-2-trifluoromethyl-α-(1-cyclopropyl)-α-[3-[methyl(phenylmethyl)amino]butyl]benzeneacetonitrile;
(±)-2-trifluoromethyl-α-(1-cyclopropyl)-α-[3-[methyl(phenylmethyl)amino]pentyl]benzeneacetonitrile;
(±)-2-trifluoromethyl-α-(1-cyclobutyl)-α-[3-[methyl(phenylmethyl)amino]propyl]benzeneacetonitrile;
(±)-2-trifluoromethyl-α-(1-cyclobutyl)-α-[3-[methyl(phenylmethyl)amino]butyl]benzeneacetonitrile;
(±)-2-trifluoromethyl-α-(1-cyclobutyl)-α-[3-[methyl(phenylmethyl)amino]pentyl]benezeneacetonitrile;
(±)-2-trifluoromethyl-α-(1-cyclopentyl)-α-[3-[methyl(phenylmethyl)amino]propyl]benzeneacetonitrile;
(±)-2-trifluoromethyl-α-(1-cyclopentyl)-α-[3-[methyl(phenylmethyl)amino]butyl]benzeneacetonitrile;
(±)-2-trifluoromethyl-α-(1-cyclopentyl)-α-[3-[methyl(phenylmethyl)amino]pentyl]benzeneacetonitrile;
(±)-2-trifluoromethyl-α-(1-cyclohexyl)-α-[3-[methyl(phenylmethyl)amino]propyl]benzeneacetonitrile;
(±)-2-trifluoromethyl-α-(1-cyclohexyl)-α-[3-[methyl(phenylmethyl)amino]butyl]benzeneacetonitrile;
(±)-2-trifluoromethyl-α-(1-cyclohexyl)-α-[3-[methyl(phenylmethyl)amino]pentyl]benzeneacetonitrile;
(±)-2-fluoro-α-(1-methylethyl)-α-[3-[ethyl(phenylmethyl)amino]propyl]benzeneacetonitrile;
(±)-2-fluoro-α-(1-methylethyl)-α-[3-[n-propyll(phenylmethyl)amino]propyl]benzeneacetonitrile;
(±)-2-fluoro-α-(1-methylethyl)-α-[3-[1-methylethyl(phenylmethyl)amino]propyl]benzeneacetonitrile;
(±)-2-fluoro-α-(1-methylethyl)-α-[3-[ethyl(phenylmethyl)amino]butyl]benzeneacetonitrile;
(±)-2-fluoro-α-(1-methylethyl)-α-[3-[n-propyll(phenylmethyl)amino]butyl]benzeneacetonitrile;
(±)-2-fluoro-α-(1-methylethyl)-α-[3-[1-methylethyl(phenylmethyl)amino]butyl]benzeneacetonitrile;
(±)-2-fluoro-α-(1-methylethyl)-α-[3-[ethyl(phenylmethyl)amino]pentyl]benzeneacetonitrile;
(±)-2-fluoro-α-(1-methylethyl)-α-[3-[n-propyll(phenylmethyl)amino]pentyl]benzeneacetonitrile;
(±)-2-fluoro-α-(1-methylethyl)-α-[3-[1-methylethyl(phenylmethyl)amino]pentyl]benzeneacetonitrile;
(±)-2-chloro-α-(1-methylethyl)-α-[3-[ethyl(phenylmethyl)amino]propyl]benzeneacetonitrile;
(±)-2-chloro-α-(1-methylethyl)-α-[3-[n-propyll(phenylmethyl)amino]propyl]benzeneacetonitrile;
(±)-2-chloro-α-(1-methylethyl)-α-[3-[1-methylethyl(phenylmethyl)amino]propyl]benzeneacetonitrile;
(±)-2-chloro-α-(1-methylethyl)-α-[3-[ethyl(phenylmethyl)amino]butyl]benzeneacetonitrile;
(±)-2-chloro-α-(1-methylethyl)-α-[3-[n-propyll(phenylmethyl)amino]butyl]benzeneacetonitrile;
(±)-2-chloro-α-(1-methylethyl)-α-[3-[1-methylethyl(phenylmethyl)amino]butyl]benzeneacetonitrile;
(±)-2-chloro-α-(1-methylethyl)-α-[3-[ethyl(phenylmethyl)amino]pentyl]benzeneacetonitrile;
(±)-2-chloro-α-(1-methylethyl)-α-[3-[n-propyll(phenylmethyl)amino]pentyl]benzeneacetonitrile;
(±)-2-chloro-α-(1-methylethyl)-α-[3-[1-methylethyl(phenylmethyl)amino]pentyl]benzeneacetonitrile;
(±)-2-bromo-α-(1-methylethyl)-α-[3-[ethyl(phenylmethyl)amino]propyl]benzeneacetonitrile;
(±)-2-bromo-α-(1-methylethyl)-α-[3-[n-propyll(phenylmethyl)amino]propyl]benzeneacetonitrile;
(±)-2-bromo-α-(1-methylethyl)-α-[3-[1-methylethyl(phenylmethyl)amino]propyl]benzeneacetonitrile;
(±)-2-bromo-α-(1-methylethyl)-α-[3-[ethyl(phenylmethyl)amino]butyl]benzeneacetonitrile;
(±)-2-bromo-α-(1-methylethyl)-α-[3-[n-propyll(phenylmethyl)amino]butyl]benzeneacetonitrile;
(±)-2-bromo-α-(1-methylethyl)-α-[3-[1-methylethyl(phenylmethyl)amino]butyl]benzeneacetonitrile;
(±)-2-bromo-α-(1-methylethyl)-α-[3-[ethyl(phenylmethyl)amino]pentyl]benzeneacetonitrile;
(±)-2-bromo-α-(1-methylethyl)-α-[3-[n-propyll(phenylmethyl)amino]pentyl]benzeneacetonitrile;
(±)-2-bromo-α-(1-methylethyl)-α-[3-[1-methylethyl(phenylmethyl)amino]pentyl]benzeneacetonitrile;

(±)-2-trifluoromethyl-α-(1-methylethyl)-α-[3-[ethyl(-phenylmethyl)amino]propyl]benzeneacetonitrile;
(±)-2-trifluoromethyl-α-(1-methylethyl)-α-[3-[n-propyll(phenylmethyl)amino]propyl]-benezeneacetonitrile;
(±)-2-trifluoromethyl-α-(1-methylethyl)-α-[3-[1-methylethyl(phenylmethyl)amino]propyl]benzeneacetonitrile;
(±)-2-trifluoromethyl-α-(1-methylethyl)-α-[3-[ethyl(-phenylmethyl)amino]butyl]benzeneacetonitrile;
(±)-2-trifluoromethyl-α-(1-methylethyl)-α-[3-[n-propyll(phenylmethyl)amino]butyl]benzeneacetonitrile;
(±)-2-trifluoromethyl-α-(1-methylethyl)-α-[3-[1-methylethyl(phenylmethyl)amino]butyl]benzeneacetonitrile;
(±)-2-trifluoromethyl-α-(1-methylethyl)-α-[3-[ethyl(-phenylmethyl)amino]pentyl]benzeneacetonitrile;
(±)-2-trifluoromethyl-α-(1-methylethyl)-α-[3-[n-propyll(phenylmethyl)amino]pentyl]benzeneacetonitrile;
(±)-2-trifluoromethyl-α-(1-methylethyl)-α-[3-[1-methylethyl(phenylmethyl)amino]pentyl]benzeneacetonitrile;
(±)-2-fluoro-α-(1-methylethyl)-α-[3-[methyl(phenylethyl)amino]propyl]benzeneacetonitrile;
(±)-2-fluoro-α-(1-methylethyl)-α-[3-[methyl(phenylethyl)amino]butyl]benzeneacetonitrile;
(±)-2-fluoro-α-(1-methylethyl)-α-[3-[methyl(phenylethyl)amino]pentyl]benzeneacetonitrile;
(±)-2-chloro-α-(1-methylethyl)-α-[3-[methyl(phenylethyl)amino]propyl]benezeneacetonitrile;
(±)-2-chloro-α-(1-methylethyl)-α-[3-[methyl(phenylethyl)amino]butyl]benzeneacetonitrile;
(±)-2-chloro-α-(1-methylethyl)-α-[3-[methyl(phenylethyl)amino]pentyl]benzeneacetonitrile;
(±)-2-bromo-α-(1-methylethyl)-α-[3-[methyl(phenylethyl)amino]propyl]benzeneacetonitrile;
(±)-2-bromo-α-(1-methylethyl)-α-[3-[methyl(phenylethyl)amino]butyl]benzeneacetonitrile;
(±)-2-bromo-α-(1-methylethyl)-α-[3-[methyl(phenylethyl)amino]pentyl]benzeneacetonitrile;
(±)-2-trifluoromethyl-α-(1-methylethyl)-α-[3-[methyl(-phenylethyl)amino]propyl]benzeneacetonitrile;
(±)-2-trifluoromethyl-α-(1-methylethyl)-α-[3-[methyl(-phenylethyl)amino]butyl]benzeneacetonitrile;
(±)-2-trifluoromethyl-α-(1-methylethyl)-α-[3-[ethyl(-phenylethyl)amino]pentyl]benezeneacetonitrile;
(±)-2-fluoro-α-(1-cyclopropyl)-α-[3-[ethyl(phenylethyl)amino]propyl]benzeneacetonitrile;
(±)-2-fluoro-α-(1-cyclopropyl)-α-[3-[n-propyl(-phenylethyl)amino]propyl]benzeneacetonitrile;
(±)-2-fluoro-α-(1-cyclopropyl)-α-[3-[1-methylethyl(-phenylethyl)amino]propyl]benzeneacetonitrile;
(±)-2-fluoro-α-(1-cyclopbutyl)-α-[3-[ethyl(phenylethyl)amino]propyl]benzeneacetonitrile;
(±)-2-fluoro-α-(1-cyclopbutyl)-α-[3-[n-propyl(-phenylethyl)amino]propyl]benzeneacetonitrile;
(±)-2-fluoro-α-(1-cyclopbutyl)-α-[3-[1-methylethyl(-phenylethyl)amino]propyl]benzeneacetonitrile;
(±)-2-fluoro-α-(1-cyclopentyl)-α-[3-[ethyl(phenylethyl)amino]propyl]benzeneacetonitrile;
(±)-2-fluoro-α-(1-cyclopentyl)-α-[3-[n-propyl(phenylethyl)amino]propyl]benzeneacetonitrile;
(±)-2-fluoro-α-(1-cyclopentyl)-α-[3-[1-methylethyl(-phenylethyl)amino]propyl]benzeneacetonitrile;
(±)-2-fluoro-α-(1-cyclohexyl)-α-[3-[ethyl(phenylethyl)amino]propyl]benzeneacetonitrile;
(±)-2-fluoro-α-(1-cyclohexyl)-α-[3-[n-propyl(phenylethyl)amino]propyl]benzeneacetonitrile;
(±)-2-fluoro-α-(1-cyclohexyl)-α-[3-[1-methylethyl(-phenylethyl)amino]propyl]benzeneacetonitrile;
(±)-2-fluoro-α-(1-cyclopropyl)-α-[3-[ethyl(phenylethyl)amino]propyl]benzeneacetonitrile;
(±)-2-fluoro-α-(1-cyclopropyl)-α-[3-[n-propyl(-phenylethyl)amino]propyl]benzeneacetonitrile;
(±)-2-fluoro-α-(1-cyclopropyl)-α-[3-[1-methylethyl(-phenylethyl)amino]propyl]benzeneacetonitrile;
(±)-2-fluoro-α-(1-cyclobutyl)-α-[3-[ethyl(phenylethyl)amino]propyl]benzeneacetonitrile;
(±)-2-fluoro-α-(1-cyclobutyl)-α-[3-[n-propyl(phenylethyl)amino]propyl]benzeneacetonitrile;
(±)-2-fluoro-α-(1-cyclobutyl)-α-[3-[1-methylethyl(-phenylethyl)amino]propyl]benzeneacetonitrile;
(±)-2-fluoro-α-(1-cyclopentyl)-α-[3-[ethyl(phenylethyl)amino]propyl]benezeneacetonitrile;
(±)-2-fluoro-α-(1-cyclopentyl)-α-[3-[n-propyl(phenylethyl)amino]propyl]benzeneacetonitrile;
(±)-2-fluoro-α-(1-cyclopentyl)-α-[3-[1-methylethyl(-phenylethyl)amino]propyl]benzeneacetonitrile;
(±)-2-fluoro-α-(1-cyclohexyl)-α-[3-[ethyl(phenylethyl)amino]propyl]benzeneacetonitrile;
(±)-2-fluoro-α-(1-cyclohexyl)-α-[3-[n-propyl(phenylethyl)amino]propyl]benzeneacetonitrile;
(±)-2-fluoro-α-(1-cyclohexyl)-α-[3-[1-methylethyl(-phenylethyl)amino]propyl]benzeneacetonitrile;
(±)-2-fluoro-α-(1-cyclopropyl)-α-[3-[ethyl(phenylmethyl)amino]butyl]benzeneacetonitrile;
(±)-2-fluoro-α-(1-cyclopropyl)-α-[3-[n-propyl(phenylmethyl)amino]butyl]benzeneacetonitrile;
(±)-2-fluoro-α-(1-cyclopropyl)-α-[3-[1-methylethyl(-phenylmethyl)amino]butyl]benzeneacetonitrile;
(±)-2-fluoro-α-(1-cyclopropyl)-α-[3-[ethyl(phenylmethyl)amino]pentyl]benzeneacetonitrile;
(±)-2-fluoro-α-(1-cyclopropyl)-α-[3-[n-propyl(phenylmethyl)amino]pentyl]benzeneacetonitrile;
(±)-2-fluoro-α-(1-cyclopropyl)-α-[3-[1-methylethyl(-phenylmethyl)amino]pentyl]benzeneacetonitrile;
(±)-2-fluoro-α-(1-cyclobutyl)-α-[3-[ethyl(phenylmethyl)amino]butyl]benzeneacetonitrile;
(±)-2-fluoro-α-(1-cyclobutyl)-α-[3-[n-propyl(phenylmethyl)amino]butyl]benzeneacetonitrile;
(±)-2-fluoro-α-(1-cyclobutyl)-α-[3-[1-methylethyl(-phenylmethyl)amino]butyl]benzeneacetonitrile;
(±)-2-fluoro-α-(1-cyclobutyl)-α-[3-[ethyl(phenylmethyl)amino]pentyl]benzeneacetonitrile;
(±)-2-fluoro-α-(1-cyclobutyl)-α-[3-[n-propyl(phenylmethyl)amino]pentyl]benzeneacetonitrile;
(±)-2-fluoro-α-(1-cyclobutyl)-α-[3-[1-methylethyl(-phenylmethyl)amino]pentyl]benzeneacetonitrile;
(±)-2-fluoro-α-(1-cyclopentyl)-α-[3-[ethyl(phenylmethyl)amino]butyl]benzeneacetonitrile;
(±)-2-fluoro-α-(1-cyclopentyl)-α-[3-[n-propyl(phenylmethyl)amino]butyl]benzeneacetonitrile;
(±)-2-fluoro-α-(1-cyclopentyl)-α-[3-[1-methylethyl(-phenylmethyl)amino]butyl]benzeneacetonitrile;
(±)-2-fluoro-α-(1-cyclopentyl)-α-[3-[ethyl(phenylmethyl)amino]pentyl]benzeneacetonitrile;
(±)-2-fluoro-α-(1-cyclopentyl)-α-[3-[n-propyl(phenylmethyl)amino]pentyl]benzeneacetonitrile;
(±)-2-fluoro-α-(1-cyclopentyl)-α-[3-[1-methylethyl(-phenylmethyl)amino]pentyl]benzeneacetonitrile;
(±)-2-fluoro-α-(1-cyclohexyl)-α-[3-[ethyl(phenylmethyl)amino]butyl]benzeneacetonitrile;
(±)-2-fluoro-α-(1-cyclohexyl)-α-[3-[n-propyl(phenylmethyl)amino]butyl]benzeneacetonitrile;

(±)-2-fluoro-α-(1-cyclohexyl)-α-[3-[1-methylethyl(-phenylmethyl)amino]butyl]benzeneacetonitrile;
(±)-2-fluoro-α-(1-cyclohexyl)-α-[3-[ethyl(phenylmethyl)amino]pentyl]benzeneacetonitrile;
(±)-2-fluoro-α-(1-cyclohexyl)-α-[3-[n-propyl(phenylmethyl)amino]pentyl]benzeneacetonitrile;
(±)-2-fluoro-α-(1-cyclohexyl)-α-[3-[1-methylethyl(-phenylmethyl)amino]pentyl]benzeneacetonitrile;
(±)-2-fluoro-α-(1-cyclopropyl)-α-[3-[methyl(phenylethyl)amino]butyl]benzeneacetonitrile;
(±)-2-fluoro-α-(1-cyclopropyl)-α-[3-[methyl(phenylethyl)amino]pentyl]benzeneacetonitrile;
(±)-2-fluoro-α-(1-cyclobutyl)-α-[3-[methyl(phenylethyl)amino]butyl]benzeneacetonitrile;
(±)-2-fluoro-α-(1-cyclobutyl)-α-[3-[methyl(phenylethyl)amino]pentyl]benzeneacetonitrile;
(±)-2-fluoro-α-(1-cyclopentyl)-α-[3-[methyl(phenylethyl)amino]butyl]benzeneacetonitrile;
(±)-2-fluoro-α-(1-cyclopentyl)-α-[3-[methyl(phenylethyl)amino]pentyl]benzeneacetonitrile;
(±)-2-fluoro-α-(1-cyclohexyl)-α-[3-[methyl(phenylethyl)amino]butyl]benzeneacetonitrile;
(±)-2-fluoro-α-(1-cyclohexyl)-α-[3-[methyl(phenylethyl)amino]pentyl]benzeneacetonitrile;
(±)-2-fluoro-α-(1-cyclopropyl)-α-[3-[ethyl(phenylethyl)amino]propyl]benzeneacetonitrile;
(±)-2-fluoro-α-(1-cyclopropyl)-α-[3-[n-propyl(phenylethyl)amino]propyl]benzeneacetonitrile;
(±)-2-fluoro-α-(1-cyclopropyl)-α-[3-[1-methylethyl(-phenylethyl)amino]propyl]benzeneacetonitrile;
(±)-2-chloro-α-(1-cyclopropyl)-α-[3-[ethyl(phenylethyl)amino]propyl]benzeneacetonitrile;
(±)-2-chloro-α-(1-cyclopropyl)-α-[3-[n-propyl(-phenylethyl)amino]propyl]benzeneacetonitrile;
(±)-2-chloro-α-(1-cyclopropyl)-α-[3-[1-methylethyl(-phenylethyl)amino]propyl]benzeneacetonitrile;
(±)-2-chloro-α-(1-cyclopropyl)-α-[3-[ethyl(phenylethyl)amino]propyl]benzeneacetonitrile;
(±)-2-chloro-α-(1-cyclopropyl)-α-[3-[n-propyl(-phenylethyl)amino]propyl]benzeneacetonitrile;
(±)-2-chloro-α-(1-cyclopropyl)-α-[3-[1-methylethyl(-phenylethyl)amino]propyl]benzeneacetonitrile;
(±)-2-trifluoromethyl-α-(1-cyclopropyl)-α-[3-[ethyl(-phenylethyl)amino]propyl]benzeneacetonitrile;
(±)-2-trifluoromethyl-α-(1-cyclopropyl)-α-[3-[n-propyl(phenylethyl)amino]propyl]benzeneacetonitrile;
(±)-2-trifluoromethyl-α-(1-cyclopropyl)-α-[3-[1-methylethyl(phenylethyl)amino]propyl]benzeneacetonitrile;
(±)-2-fluoro-α-(1-cyclobutyl)-α-[3-[ethyl(phenylethyl)amino]propyl]benzeneacetonitrile;
(±)-2-fluoro-α-(1-cyclobutyl)-α-[3-[n-propyl(phenylethyl)amino]propyl]benzeneacetonitrile;
(±)-2-fluoro-α-(1-cyclobutyl)-α-[3-[1-methylethyl(-phenylethyl)amino]propyl]benzeneacetonitrile;
(±)-2-chloro-α-(1-cyclobutyl)-α-[3-[ethyl(phenylethyl)amino]propyl]benzeneacetonitrile;
(±)-2-chloro-α-(1-cyclobutyl)-α-[3-[n-propyl(phenylethyl)amino]propyl]benzeneacetonitrile;
(±)-2-chloro-α-(1-cyclobutyl)-α-[3-[1-methylethyl(-phenylethyl)amino]propyl]benzeneacetonitrile;
(±)-2-chloro-α-(1-cyclobutyl)-α-[3-[ethyl(phenylethyl)amino]propyl]benzeneacetonitrile;
(±)-2-chloro-α-(1-cyclobutyl)-α-[3-[n-propyl(phenylethyl)amino]propyl]benzeneacetonitrile;
(±)-2-chloro-α-(1-cyclobutyl)-α-[3-[1-methylethyl(-phenylethyl)amino]propyl]benzeneacetonitrile;
(±)-2-trifluoromethyl-α-(1-cyclobutyl)-α-[3-[ethyl(-phenylethyl)amino]propyl]benzeneacetonitrile;
(±)-2-trifluoromethyl-α-(1-cyclobutyl)-α-[3-[n-propyl(phenylethyl)amino]propyl]benzeneacetonitrile;
(±)-2-trifluoromethyl-α-(1-cyclobutyl)-α-[3-[1-methylethyl(phenylethyl)amino]propyl]benzeneacetonitrile;
(±)-2-fluoro-α-(1-cyclopentyl)-α-[3-[ethyl(phenylethyl)amino]propyl]benzeneacetonitrile;
(±)-2-fluoro-α-(1-cyclopentyl)-α-[3-[n-propyl(phenylethyl)amino]propyl]benzeneacetonitrile;
(±)-2-fluoro-α-(1-cyclopentyl)-α-[3-[1-methylethyl(-phenylethyl)amino]propyl]benzeneacetonitrile;
(±)-2-chloro-α-(1-cyclopentyl)-α-[3-[ethyl(phenylethyl)amino]propyl]benzeneacetonitrile;
(±)-2-chloro-α-(1-cyclopentyl)-α-[3-[n-propyl(-phenylethyl)amino]propyl]benzeneacetonitrile;
(±)-2-chloro-α-(1-cyclopentyl)-α-[3-[1-methylethyl(-phenylethyl)amino]propyl]benzeneacetonitrile;
(±)-2-chloro-α-(1-cyclopentyl)-α-[3-[ethyl(phenylethyl)amino]propyl]benzeneacetonitrile;
(±)-2-chloro-α-(1-cyclopentyl)-α-[3-[n-propyl(-phenylethyl)amino]propyl]benzeneacetonitrile;
(±)-2-chloro-α-(1-cyclopentyl)-α-[3-[1-methylethyl(-phenylethyl)amino]propyl]benzeneacetonitrile;
(±)-2-trifluoromethyl-α-(1-cyclopentyl)-α-[3-[ethyl(-phenylethyl)amino]propyl]benzeneacetonitrile;
(±)-2-trifluoromethyl-α-(1-cyclopentyl)-α-[3-[n-propyl(phenylethyl)amino]propyl]benzeneacetonitrile;
(±)-2-trifluoromethyl-α-(1-cyclopentyl)-α-[3-[1-methylethyl(phenylethyl)amino]propyl]benzeneacetonitrile;
(±)-2-fluoro-α-(1-cyclohexyl)-α-[3-[ethyl(phenylethyl)amino]propyl]benzeneacetonitrile;
(±)-2-fluoro-α-(1-cyclohexyl)-α-[3-[n-propyl(phenylethyl)amino]propyl]benzeneacetonitrile;
(±)-2-fluoro-α-(1-cyclohexyl)-α-[3-[1-methylethyl(-phenylethyl)amino]propyl]benzeneacetonitrile;
(±)-2-chloro-α-(1-cyclohexyl)-α-[3-[ethyl(phenylethyl)amino]propyl]benzeneacetonitrile;
(±)-2-chloro-α-(1-cyclohexyl)-α-[3-[n-propyl(phenylethyl)amino]propyl]benzeneacetonitrile;
(±)-2-chloro-α-(1-cyclohexyl)-α-[3-[1-methylethyl(-phenylethyl)amino]propyl]benzeneacetonitrile;
(±)-2-chloro-α-(1-cyclohexyl)-α-[3-[ethyl(phenylethyl)amino]propyl]benzeneacetonitrile;
(±)-2-chloro-α-(1-cyclohexyl)-α-[3-[n-propyl(phenylethyl)amino]propyl]benzeneacetonitrile;
(±)-2-chloro-α-(1-cyclohexyl)-α-[3-[1-methylethyl(-phenylethyl)amino]propyl]benzeneacetonitrile;
(±)-2-trifluoromethyl-α-(1-cyclohexyl)-α-[3-[ethyl(-phenylethyl)amino]propyl]benzeneacetonitrile;
(±)-2-trifluoromethyl-α-(1-cyclohexyl)-α-[3-[n-propyl(phenylethyl)amino]propyl]benzeneacetonitrile;
(±)-2-trifluoromethyl-α-(1-cyclohexyl)-α-[3-[1-methylethyl(phenylethyl)amino]propyl]benzeneacetonitrile;
(±)-2-fluoro-α-(1-cyclopropyl)-α-[3-[ethyl(phenylethyl)amino]butyl]benzeneacetonitrile;
(±)-2-fluoro-α-(1-cyclopropyl)-α-[3-[n-propyl(-phenylethyl)amino]butyl]benzeneacetonitrile;
(±)-2-fluoro-α-(1-cyclopropyl)-α-[3-[1-methylethyl(-phenylethyl)amino]butyl]benzeneacetonitrile;
(±)-2-chloro-α-(1-cyclopropyl)-α-[3-[ethyl(phenylethyl)amino]butyl]benzeneacetonitrile;

(±)-2-chloro-α-(1-cyclopropyl)-α-[3-[n-propyl(phenylethyl)amino]butyl]benzeneacetonitrile;
(±)-2-chloro-α-(1-cyclopropyl)-α-[3-[1-methylethyl(phenylethyl)amino]butyl]benzeneacetonitrile;
(±)-2-chloro-α-(1-cyclopropyl)-α-[3-[ethyl(phenylethyl)amino]butyl]benzeneacetonitrile;
(±)-2-chloro-α-(1-cyclopropyl)-α-[3-[n-propyl(phenylethyl)amino]butyl]benzeneacetonitrile;
(±)-2-chloro-α-(1-cyclopropyl)-α-[3-[1-methylethyl(phenylethyl)amino]butyl]benzeneacetonitrile;
(±)-2-trifluoromethyl-α-(1-cyclopropyl)-α-[3-[ethyl(phenylethyl)amino]butyl]benzeneacetonitrile;
(±)-2-trifluoromethyl-α-(1-cyclopropyl)-α-[3-[n-propyl(phenylethyl)amino]butyl]benzeneacetonitrile;
(±)-2-trifluoromethyl-α-(1-cyclopropyl)-α-[3-[1-methylethyl(phenylethyl)amino]butyl]benzeneacetonitrile;
(±)-2-fluoro-α-(1-cyclobutyl)-α-[3-[ethyl(phenylethyl)amino]butyl]benzeneacetonitrile;
(±)-2-fluoro-α-(1-cyclobutyl)-α-[3-[n-propyl(phenylethyl)amino]butyl]benezeneacetonitrile;
(±)-2-fluoro-α-(1-cyclobutyl)-α-[3-[1-methylethyl(phenylethyl)amino]butyl]benzeneacetonitrile;
(±)-2-chloro-α-(1-cyclobutyl)-α-[3-[ethyl(phenylethyl)amino]butyl]benzeneacetonitrile;
(±)-2-chloro-α-(1-cyclobutyl)-α-[3-[n-propyl(phenylethyl)amino]butyl]benzeneacetonitrile;
(±)-2-chloro-α-(1-cyclobutyl)-α-[3-[1-methylethyl(phenylethyl)amino]butyl]benzeneacetonitrile;
(±)-2-chloro-α-(1-cyclobutyl)-α-[3-[ethyl(phenylethyl)amino]butyl]benzeneacetonitrile;
(±)-2-chloro-α-(1-cyclobutyl)-α-[3-[n-propyl(phenylethyl)amino]butyl]benzeneacetonitrile;
(±)-2-chloro-α-(1-cyclobutyl)-α-[3-[1-methylethyl(phenylethyl)amino]butyl]benzeneacetonitrile;
(±)-2-trifluoromethyl-α-(1-cyclobutyl)-α-[3-[ethyl(phenylethyl)amino]butyl]benzeneacetonitrile;
(±)-2-trifluoromethyl-α-(1-cyclobutyl)-α-[3-[n-propyl(phenylethyl)amino]butyl]benzeneacetonitrile;
(±)-2-trifluoromethyl-α-(1-cyclobutyl)-α-[3-[1-methylethyl(phenylethyl)amino]butyl]benzeneacetonitrile;
(±)-2-fluoro-α-(1-cyclopentyl)-α-[3-[ethyl(phenylethyl)amino]butyl]benzeneacetonitrile;
(±)-2-fluoro-α-(1-cyclopentyl)-α-[3-[n-propyl(phenylethyl)amino]butyl]benzeneacetonitrile;
(±)-2-fluoro-α-(1-cyclopentyl)-α-[3-[1-methylethyl(phenylethyl)amino]butyl]benzeneacetonitrile;
(±)-2-chloro-α-(1-cyclopentyl)-α-[3-[ethyl(phenylethyl)amino]butyl]benzeneacetonitrile;
(±)-2-chloro-α-(1-cyclopentyl)-α-[3-[n-propyl(phenylethyl)amino]butyl]benzeneacetonitrile;
(±)-2-chloro-α-(1-cyclopentyl)-α-[3-[1-methylethyl(phenylethyl)amino]butyl]benzeneacetonitrile;
(±)-2-chloro-α-(1-cyclopentyl)-α-[3-[ethyl(phenylethyl)amino]butyl]benzeneacetonitrile;
(±)-2-chloro-α-(1-cyclopentyl)-α-[3-[n-propyl(phenylethyl)amino]butyl]benzeneacetonitrile;
(±)-2-chloro-α-(1-cyclopentyl)-α-[3-[1-methylethyl(phenylethyl)amino]butyl]benzeneacetonitrile;
(±)-2-trifluoromethyl-α-(1-cyclopentyl)-α-[3-[ethyl(phenylethyl)amino]butyl]benzeneacetonitrile;
(±)-2-trifluoromethyl-α-(1-cyclopentyl)-α-[3-[n-propyl(phenylethyl)amino]butyl]benzeneacetonitrile;
(±)-2-trifluoromethyl-α-(1-cyclopentyl)-α-[3-[1-methylethyl(phenylethyl)amino]butyl]benzeneacetonitrile;
(±)-2-fluoro-α-(1-cyclohexyl)-α-[3-[ethyl(phenylethyl)amino]butyl]benzeneacetonitrile;
(±)-2-fluoro-α-(1-cyclohexyl)-α-[3-[n-propyl(phenylethyl)amino]butyl]benzeneacetonitrile;
(±)-2-fluoro-α-(1-cyclohexyl)-α-[3-[1-methylethyl(phenylethyl)amino]butyl]benzeneacetonitrile;
(±)-2-chloro-α-(1-cyclohexyl)-α-[3-[ethyl(phenylethyl)amino]butyl]benzeneacetonitrile;
(±)-2-chloro-α-(1-cyclohexyl)-α-[3-[n-propyl(phenylethyl)amino]butyl]benzeneacetonitrile;
(±)-2-chloro-α-(1-cyclohexyl)-α-[3-[1-methylethyl(phenylethyl)amino]butyl]benzeneacetonitrile;
(±)-2-chloro-α-(1-cyclohexyl)-α-[3-[ethyl(phenylethyl)amino]butyl]benzeneacetonitrile;
(±)-2-chloro-α-(1-cyclohexyl)-α-[3-[n-propyl(phenylethyl)amino]butyl]benzeneacetonitrile;
(±)-2-chloro-α-(1-cyclohexyl)-α-[3-[1-methylethyl(phenylethyl)amino]butyl]benzeneacetonitrile;
(±)-2-trifluoromethyl-α-(1-cyclohexyl)-α-[3-[ethyl(phenylethyl)amino]butyl]benzeneacetonitrile;
(±)-2-trifluoromethyl-α-(1-cyclohexyl)-α-[3-[n-propyl(phenylethyl)amino]butyl]benzeneacetonitrile;
(±)-2-trifluoromethyl-α-(1-cyclohexyl)-α-[3-[1-methylethyl(phenylethyl)amino]butyl]benzeneacetonitrile;
(±)-2-fluoro-α-(1-cyclopropyl)-α-[3-[ethyl(phenylethyl)amino]pentyl]benzeneacetonitrile;
(±)-2-fluoro-α-(1-cyclopropyl)-α-[3-[n-propyl(phenylethyl)amino]pentyl]benzeneacetonitrile;
(±)-2-fluoro-α-(1-cyclopropyl)-α-[3-[1-methylethyl(phenylethyl)amino]pentyl]benzeneacetonitrile;
(±)-2-chloro-α-(1-cyclopropyl)-α-[3-[ethyl(phenylethyl)amino]pentyl]benezeneacetonitrile;
(±)-2-chloro-α-(1-cyclopropyl)-α-[3-[n-propyl(phenylethyl)amino]pentyl]benzeneacetonitrile;
(±)-2-chloro-α-(1-cyclopropyl)-α-[3-[1-methylethyl(phenylethyl)amino]pentyl]benzeneacetonitrile;
(±)-2-chloro-α-(1-cyclopropyl)-α-[3-[ethyl(phenylethyl)amino]pentyl]benzeneacetonitrile;
(±)-2-chloro-α-(1-cyclopropyl)-α-[3-[n-propyl(phenylethyl)amino]pentyl]benzeneacetonitrile;
(±)-2-chloro-α-(1-cyclopropyl)-α-[3-[1-methylethyl(phenylethyl)amino]pentyl]benzeneacetonitrile;
(±)-2-trifluoromethyl-α-(1-cyclopropyl)-α-[3-[ethyl(phenylethyl)amino]pentyl]benzeneacetonitrile;
(±)-2-trifluoromethyl-α-(1-cyclopropyl)-α-[3-[n-propyl(phenylethyl)amino]pentyl]benzeneacetonitrile;
(±)-2-trifluoromethyl-α-(1-cyclopropyl)-α-[3-[1-methylethyl(phenylethyl)amino]pentyl]benzeneacetonitrile;
(±)-2-fluoro-α-(1-cyclobutyl)-α-[3-[ethyl(phenylethyl)amino]pentyl]benzeneacetonitrile;
(±)-2-fluoro-α-(1-cyclobutyl)-α-[3-[n-propyl(phenylethyl)amino]pentyl]benzeneacetonitrile;
(±)-2-fluoro-α-(1-cyclobutyl)-α-[3-[1-methylethyl(phenylethyl)amino]pentyl]benzeneacetonitrile;
(±)-2-chloro-α-(1-cyclobutyl)-α-[3-[ethyl(phenylethyl)amino]pentyl]benzeneacetonitrile;
(±)-2-chloro-α-(1-cyclobutyl)-α-[3-[n-propyl(phenylethyl)amino]pentyl]benzeneacetonitrile;
(±)-2-chloro-α-(1-cyclobutyl)-α-[3-[1-methylethyl(phenylethyl)amino]pentyl]benzeneacetonitrile;
(±)-2-chloro-α-(1-cyclobutyl )-α-[3-[ethyl(phenylethyl)amino]pentyl]benzeneacetonitrile;
(±)-2-chloro-α-(1-cyclobutyl)-α-[3-[n-propyl(phenylethyl)amino]pentyl]benzeneacetonitrile;

(±)-2-chloro-α-(1-cyclobutyl)-α-[3-[1-methylethyl(-phenylethyl)amino]pentyl]benzeneacetonitrile;
(±)-2-trifluoromethyl-α-(1-cyclobutyl)-α-[3-[ethyl(-phenylethyl)amino]pentyl]benzeneacetonitrile;
(±)-2-trifluoromethyl-α-(1-cyclobutyl)-α-[3-[n-propyl(phenylethyl)amino]pentyl]benzeneacetonitrile;
(±)-2-trifluoromethyl-α-(1-cyclobutyl)-α-[3-[1-methylethyl(phenylethyl)amino]pentyl]benzeneacetonitrile;
(±)-2-fluoro-α-(1-cyclopentyl)-α-[3-[ethyl(phenylethyl)amino]pentyl]benzeneacetonitrile;
(±)-2-fluoro-α-(1-cyclopentyl)-α-[3-[n-propyl(phenylethyl)amino]pentyl]benzeneacetonitrile;
(±)-2-fluoro-α-(1-cyclopentyl)-α-[3-[1-methylethyl(-phenylethyl)amino]pentyl]benzeneacetonitrile;
(±)-2-chloro-α-(1-cyclopentyl)-α-[3-[ethyl(phenylethyl)amino]pentyl]benzeneacetonitrile;
(±)-2-chloro-α-(1-cyclopentyl)-α-[3-[n-propyl(-phenylethyl)amino]pentyl]benzeneacetonitrile;
(±)-2-chloro-α-(1-cyclopentyl)-α-[3-[1-methylethyl(-phenylethyl)amino]pentyl]benzeneacetonitrile;
(±)-2-chloro-α-(1-cyclopentyl)-α-[3-[ethyl(phenylethyl)amino]pentyl]benzeneacetonitrile;
(±)-2-chloro-α-(1-cyclopentyl)-α-[3-[n-propyl(-phenylethyl)amino]pentyl]benzeneacetonitrile;
(±)-2-chloro-α-(1-cyclopentyl)-α-[3-[1-methylethyl(-phenylethyl)amino]pentyl]benzeneacetonitrile;
(±)-2-trifluoromethyl-α-(1-cyclopentyl)-α-[3-[ethyl(-phenylethyl)amino]pentyl]benzeneacetonitrile;
(±)-2-trifluoromethyl-α-(1-cyclopentyl)-α-[3-[n-propyl(phenylethyl)amino]pentyl]benzeneacetonitrile;
(±)-2-trifluoromethyl-α-(1-cyclopentyl)-α-[3-[1-methylethyl(phenylethyl)amino]pentyl]benzeneacetonitrile;
(±)-2-fluoro-α-(1-cyclohexyl)-α-[3-[ethyl(phenylethyl)amino]pentyl]benzeneacetonitrile;
(±)-2-fluoro-α-(1-cyclohexyl)-α-[3-[n-propyl(phenylethyl)amino]pentyl]benzeneacetonitrile;
(±)-2-fluoro-α-(1-cyclohexyl)-α-[3-[1-methylethyl(-phenylethyl)amino]pentyl]benzeneacetonitrile;
(±)-2-chloro-α-(1-cyclohexyl)-α-[3-[ethyl(phenylethyl)amino]pentyl]benzeneacetonitrile;
(±)-2-chloro-α-(1-cyclohexyl)-α-[3-[n-propyl(phenylethyl)amino]pentyl]benzeneacetonitrile;
(±)-2-chloro-α-(1-cyclohexyl)-α-[3-[1-methylethyl(-phenylethyl)amino]pentyl]benzeneacetonitrile;
(±)-2-chloro-α-(1-cyclohexyl)-α-[3-[ethyl(phenylethyl)amino]pentyl]benzeneacetonitrile;
(±)-2-chloro-α-(1-cyclohexyl)-α-[3-[n-propyl(phenylethyl)amino]pentyl]benzeneacetonitrile;
(±)-2-chloro-α-(1-cyclohexyl)-α-[3-[1-methylethyl(-phenylethyl)amino]pentyl]benzeneacetonitrile;
(±)-2-trifluoromethyl-α-(1-cyclohexyl)-α-[3-[ethyl(-phenylethyl)amino]pentyl]benzeneacetonitrile;
(±)-2-trifluoromethyl-α-(1-cyclohexyl)-α-[3-[n-propyl(phenylethyl)amino]pentyl]benzeneacetonitrile;
(±)-2-trifluoromethyl-α-(1-cyclohexyl)-α-[3-[1-methylethyl(phenylethyl)amino]pentyl]benzeneacetonitrile;
(±)-2,6-difluoro-α-(1-methylethyl)-α-[3-[methyl(-phenylmethyl)amino]propyl]benzeneacetonitrile;
(±)-2,6-dichloro-α-(1-methylethyl)-α-[3-[methyl(-phenylmethyl)amino]propyl]benezeneacetonitrile;
(±)-2,6-dibromo-α-(1-methylethyl)-α-[3-[methyl(-phenylmethyl)amino]propyl]benzeneacetonitrile;
(±)-2,6-ditrifluoromethyl-α-(1-methylethyl)-α-[3-[methyl(phenylmethyl)amino]propyl]benzeneacetonitrile;
(±)-2,6-difluoro-α-(1-cyclopropyl)-α-[3-[methyl(-phenylmethyl)amino]propyl]benzeneacetonitrile;
(±)-2,6-difluoro-α-(1-cyclobutyl)-α-[3-[methyl(phenylmethyl)amino]propyl]benzeneacetonitrile;
(±)-2,6-difluoro-α-(1-cyclopentyl)-α-[3-[methyl(-phenylmethyl)amino]propyl]benzeneacetonitrile;
(±)-2,6-difluoro-α-(1-cyclohexyl)-α-[3-[methyl(-phenylmethyl)amino]propyl]benezeneacetonitrile;
(±)-2,6-difluoro-α-(1-methylethyl)-α-[3-[ethyl(phenylmethyl)amino]propyl]benezeneacetonitrile;
(±)-2,6-difluoro-α-(1-methylethyl)-α-[3-[n-propyl(-phenylmethyl)amino]propyl]benezeneacetonitrile;
(±)-2,6-difluoro-α-(1-methylethyl)-α-[3-[1-methylethyl(phenylmethyl)amino]propyl]benzeneacetonitrile;
(±)-2,6-difluoro-α-(1-methylethyl)-α-[3-[methyl(-phenylethyl)amino]propyl]benzeneacetonitrile;
(±)-2,6-difluoro-α-(1-methylethyl)-α-[3-[methyl(-phenylmethyl)amino]butyl]benzeneacetonitrile;
(±)-2,6-difluoro-α-(1-methylethyl)-α-[3-[methyl(-phenylmethyl)amino]pentyl]benzeneacetonitrile;
(±)-2,6-difluoro-α-(1-cyclopropyl)-α-[3-[methyl(-phenylmethyl)amino]propyl]benzeneacetonitrile;
(±)-2,6-difluoro-α-(1-cyclobutyl)-α-[3-[methyl(phenylmethyl)amino]propyl]benzeneacetonitrile;
(±)-2,6-difluoro-α-(1-cyclopentyl)-α-[3-[methyl(-phenylmethyl)amino]propyl]benzeneacetonitrile;
(±)-2,6-difluoro-α-(1-cyclohexyl)-α-[3-[methyl(-phenylmethyl)amino]propyl]benzeneacetonitrile;
(±)-2,6-dichloro-α-(1-cyclopropyl)-α-[3-[methyl(-phenylmethyl)amino]propyl]benzeneacetonitrile;
(±)-2,6-dichloro-α-(1-cyclobutyl)-α-[3-[methyl(-phenylmethyl)amino]propyl]benzeneacetonitrile;
(±)-2,6-dichloro-α-(1-cyclopentyl)-α-[3-[methyl(-phenylmethyl)amino]propyl]benzeneacetonitrile;
(±)-2,6-dichloro-α-(1-cyclohexyl)-α-[3-[methyl(-phenylmethyl)amino]propyl]benzeneacetonitrile;
(±)-2,6-dibromo-α-(1-cyclopropyl)-α-[3-[methyl(-phenylmethyl)amino]propyl]benzeneacetonitrile;
(±)-2,6-dibromo-α-(1-cyclobutyl)-α-[3-[methyl(-phenylmethyl)amino]propyl]benzeneacetonitrile;
(±)-2,6-dibromo-α-(1-cyclopentyl)-α-[3-[methyl(-phenylmethyl)amino]propyl]benzeneacetonitrile;
(±)-2,6-dibromo-α-(1-cyclohexyl)-α-[3-[methyl(-phenylmethyl)amino]propyl]benzeneacetonitrile;
(±)-2,6-ditrifluoromethyl-α-(1-cyclopropyl)-α-[3-[methyl(phenylmethyl)amino]propyl]benzeneacetonitrile;
(±)-2,6-ditrifluoromethyl-α-(1-cyclobutyl)-α-[3-[methyl(phenylmethyl)amino]propyl]benzeneacetonitrile;
(±)-2,6-ditrifluoromethyl-α-(1-cyclopentyl)-α-[3-[methyl(phenylmethyl)amino]propyl]benzeneacetonitrile;
(±)-2,6-ditrifluoromethyl-α-(1-cyclohexyl)-α-[3-[methyl(phenylmethyl)amino]propyl]benzeneacetonitrile;
(±)-2,6-difluoro-α-(1-methylethyl)-α-[3-[ethyl(phenylmethyl)amino]propyl]benzeneacetonitrile;
(±)-2,6-difluoro-α-(1-methylethyl)-α-[3-[n-propryl(-phenylmethyl)amino]propyl]benzeneacetonitrile;
(±)-2,6-difluoro-α-(1-methylethyl)-α-[3-[1-methylethyl(phenylmethyl)amino]propyl]benzeneacetonitrile;

(±)-2,6-dichloro-α-(1-methylethyl)-α-[3-[ethyl(phenylmethyl)amino]propyl]benzeneacetonitrile;
(±)-2,6-dichloro-α-(1-methylethyl)-α-[3-[n-propyl(phenylmethyl)amino]propyl]benzeneacetonitrile;
(±)-2,6-dichloro-α-(1-methylethyl)-α-[3-[1-methylethyl(phenylmethyl)amino]propyl]benzeneacetonitrile;
(±)-2,6-dibromo-α-(1-methylethyl)-α-[3-[ethyl(phenylmethyl)amino]propyl]benzeneacetonitrile;
(±)-2,6-dibromo-α-(1-methylethyl)-α-[3-[n-propyl(phenylmethyl)amino]propyl]benzeneacetonitrile;
(±)-2,6-dibromo-α-(1-methylethyl)-α-[3-[1-methylethyl(phenylmethyl)amino]propyl]benzeneacetonitrile;
(±)-2,6-ditrifluoromethyl-α-(1-methylethyl)-α-[3-[ethyl(phenylmethyl)amino]propyl]benzeneacetonitrile;
(±)-2,6-ditrifluoromethyl-α-(1-methylethyl)-α-[3-[n-propyl(phenylmethyl)amino]propyl]benzeneacetonitrile;
(±)-2,6-ditrifluoromethyl-α-(1-methylethyl)-α-[3-[1-methylethyl(phenylmethyl)amino]propyl]benzeneacetonitrile;
(±)-2,6-difluoro-α-(1-cyclohexyl)-α-[3-[ethyl(phenylethyl)amino]propyl]benzeneacetonitrile;
(±)-2,6-dichloro-α-(1-methylethyl)-α-[3-[methyl(phenylethyl)amino]propyl]benzeneacetonitrile;
(±)-2,6-dibromo-α-(1-methylethyl)-α-[3-[methyl(phenylethyl)amino]propyl]benzeneacetonitrile;
(±)-2,6-ditrifluoromethyl-α-(1-methylethyl)-α-[3-[methyl(phenylethyl)amino]propyl]benzeneacetonitrile;
(±)-2,6-difluoro-α-(1-cyclohexyl)-α-[3-[ethyl(phenylmethyl)amino]butyl]benzeneacetonitrile;
(±)-2,6-difluoro-α-(1-cyclohexyl)-α-[3-[ethyl(phenylmethyl)amino]pentyl]benzeneacetonitrile;
(±)-2,6-dichloro-α-(1-methylethyl)-α-[3-[methyl(phenylmethyl)amino]butyl]benzeneacetonitrile;
(±)-2,6-dichloro-α-(1-methylethyl)-α-[3-[methyl(phenylmethyl)amino]pentyl]benzeneacetonitrile;
(±)-2,6-dibromo-α-(1-methylethyl)-α-[3-[methyl(phenylmethyl)amino]butyl]benzeneacetonitrile;
(±)-2,6-dibromo-α-(1-methylethyl)-α-[3-[methyl(phenylmethyl)amino]pentyl]benzeneacetonitrile;
(±)-2,6-ditrifluoromethyl-α-(1-methylethyl)-α-[3-[methyl(phenylmethyl)amino]butyl]benzeneacetonitrile;
(±)-2,6-ditrifluoromethyl-α-(1-methylethyl)-α-[3-[methyl(phenylmethyl)amino]pentyl]benzeneacetonitrile;
(±)-2,6-difluoro-α-(1-cyclopropyl)-α-[3-[ethyl(phenylmethyl)amino]propyl]benzeneacetonitrile;
(±)-2,6-difluoro-α-(1-cyclopropyl)-α-[3-[n-propyl(phenylmethyl)amino]propyl]benzeneacetonitrile;
(±)-2,6-difluoro-α-(1-cyclopropyl)-α-[3-[1-methylethyl(phenylmethyl)amino]propyl]benzeneacetonitrile
(±)-2,6-difluoro-α-(1-cyclobutyl)-α-[3-[ethyl(phenylmethyl)amino]propyl]benzeneacetonitrile;
(±)-2,6-difluoro-α-(1-cyclobutyl)-α-[3-[n-propyl(phenylmethyl)amino]propyl]benezeneacetonitrile;
(±)-2,6-difluoro-α-(1-cyclobutyl)-α-[3-[1-methylethyl(phenylmethyl)amino]propyl]benzeneacetonitrile
(±)-2,6-difluoro-α-(1-cyclopentyl)-α-[3-[ethyl(phenylmethyl)amino]propyl]benzeneacetonitrile;
(±)-2,6-difluoro-α-(1-cyclopentyl)-α-[3-[n-propyl(phenylmethyl)amino]propyl]benzeneacetonitrile;
(±)-2,6-difluoro-α-(1-cyclopentyl)-α-[3-[1-methylethyl(phenylmethyl)amino]propyl]benzeneacetonitrile;
(±)-2,6-difluoro-α-(1-cyclohexyl)-α-[3-[1ethyl(phenylmethyl)amino]propyl]benzeneacetonitrile;
(±)-2,6-difluoro-α-(1-cyclohexyl)-α-[3-[1-n-propyl(phenylmethyl)amino]propyl]benzeneacetonitrile;
(±)-2,6-difluoro-α-(1-cyclohexyl)-α-[3-[1-1-methylethyl(phenylmethyl)amino]propyl]benzeneacetonitrile;
(±)-2,6-difluoro-α-(1-cyclopropyl)-α-[3-[methyl(phenylethyl)amino]propyl]benzeneacetonitrile;
(±)-2,6-difluoro-α-(1-cyclobutyl)-α-[3-[methyl(phenylethyl)amino]propyl]benzeneacetonitrile;
(±)-2,6-difluoro-α-(1-cyclopentyl)-α-[3-[methyl(phenylethyl)amino]propyl]benzeneacetonitrile;
(±)-2,6-difluoro-α-(1-cyclohexyl)-α-[3-[methyl(phenylethyl)amino]propyl]benzeneacetonitrile;
(±)-2,6-difluoro-α-(1-cyclopropyl)-α-[3-[methyl(phenylmethyl)amino]propyl]benzeneacetonitrile;
(±)-2,6-difluoro-α-(1-cyclopropyl)-α-[3-[methyl(phenylmethyl)amino]butyl]benzeneacetonitrile;
(±)-2,6-difluoro-α-(1-cyclopropyl)-α-[3-[methyl(phenylmethyl)amino]pentyl]benzeneacetonitrile;
(±)-2,6-difluoro-α-(1-cyclobutyl)-α-[3methyl(phenylmethyl)amino]propyl]benzeneacetonitrile;
(±)-2,6-difluoro-α-(1-cyclobutyl)-α-[3 methyl(phenylmethyl)amino]butyl]benzeneacetonitrile;
(±)-2,6-difluoro-α-(1-cyclobutyl)-α-[3-[methyl(phenylmethyl)amino]pentyl]benzeneacetonitrile;
(±)-2,6-difluoro-α-(1-cyclopentyl)α-[3-[methyl(phenylmethyl)amino]propyl]benzeneacetonitrile;
(±)-2,6-difluoro-α-(1-cyclopentyl)-α-[3-[methyl(phenylmethyl)amino]butyl]benzeneacetonitrile;
(±)-2,6-difluoro-α-(1-cyclopentyl)-α-[3-[methyl(phenylmethyl)amino]pentyl]benzeneacetonitrile;
(±)-2,6-difluoro-α-(1-cyclohexyl)-α-[3-[methyl(phenylmethyl)amino]propyl]benzeneacetonitrile;
(±)-2,6-difluoro-α-(1-cyclohexyl)-α-[3-[methyl(phenylmethyl)amino]butyl]benzeneacetonitrile;
(±)-2,6-difluoro-α-(1-cyclohexyl)-α-[3-[methyl(phenylmethyl)amino]pentyl]benzeneacetonitrile;
(±)-2,6-difluoro-α-(1-methylethyl)-α-[3-[methyl(phenylethyl)amino]propyl]benzeneacetonitrile;
(±)-2,6-difluoro-α-(1-methylethyl)-α-[3-[ethyl(phenylmethyl)amino]propyl]benzeneacetonitrile;
(±)-2,6-difluoro-α-(1-methylethyl)-α-[3-[n-propyl(phenylmethyl)amino]propyl]benzeneacetonitrile;
(±)-2,6-difluoro-α-(1-methylethyl)-α-[3-[1-methylethyl(phenylethyl)amino]propyl]benzeneacetonitrile;
(±)-2,6-difluoro-α-(1-methylethyl)-α-[3-[ethyl(phenylmethyl)amino]propyl]benzeneacetonitrile;
(±)-2,6-difluoro-α-(1-methylethyl)-α-[3-[ethyl(phenylmethyl)amino]butyl]benzeneacetonitrile;
(±)-2,6-difluoro-α-(1-methylethyl)-α-[3-[ethyl(phenylmethyl)amino]pentyl]benzeneacetonitrile;
(±)-2,6-difluoro-α-(1-methylethyl)-α-[n-propyl(phenylmethyl)amino]propyl]benzeneacetonitrile;
(±)-2,6-difluoro-α-(1-methylethyl)-α-[3-[n-propyl(phenylmethyl)amino]butyl]benzeneacetonitrile;
(±)-2,6-difluoro-α-(1-methylethyl)-α-[3-[n-propyl(phenylmethyl)amino]pentyl]benzeneacetonitrile;
(±)-2,6-difluoro-α-(1-methylethyl)-α-[3-[methylethyl(phenylmethyl)amino]propyl]benzeneacetonitrile;
(±)-2,6-difluoro-α-(1-methylethyl)-α-[3-[1-methylethyl(phenylmethyl)amino]butyl]benzeneacetonitrile;
(±)-2,6-difluoro-α-(1-methylethyl)-α-[3-[1-methylethyl(phenylmethyl)amino]pentyl]benzeneacetonitrile;
(±)-2,6-difluoro-α-(1-methylethyl)-α-[3-[methyl(phenylethyl)amino]propyl]benzeneacetonitrile;

(±)-2,6-difluoro-α-(1-methylethyl)-α-[3-[methyl(-phenylethyl)amino]butyl]benzeneacetonitrile;
(±)-2,6-difluoro-α-(1-methylethyl)-α-[3-[methyl(-phenylethyl)amino]pentyl]benzeneacetonitrile;
(±)-2,6-difluoro-α-(1-cyclopropyl)-α-[3-[ethyl(phenylmethyl)amino]propyl]benzeneacetonitrile;
(±)-2,6-difluoro-α-(1-cyclopropyl)-α-[3-[n-propyl(-phenylmethyl)amino]propyl]benzeneacetonitrile;
(±)-2,6-difluoro-α-(1-cyclopropyl)-α-[3-[1-methylethyl(phenylmethyl)amino]propyl]benzeneacetonitrile;
(±)-2,6-difluoro-α-(1-cyclobutyl)-α-[3-[ethyl(phenylmethyl)amino]propyl]benzeneacetonitrile;
(±)-2,6-difluoro-α-(1-cyclobutyl)-α-[3-[n-propyl(-phenylmethyl)amino]propyl]benzeneacetonitrile;
(±)-2,6-difluoro-α-(1-cyclobutyl)-α-[3-[1-methylethyl(phenylmethyl)amino]propyl]benzeneacetonitrile;
(±)-2,6-difluoro-α-(1-cyclopentyl)-α-[3-[ethyl(phenylmethyl)amino]propyl]benzeneacetonitrile;
(±)-2,6-difluoro-α-(1-cyclopentyl)-α-[3-[n-propyl(-phenylmethyl)amino]propyl]benzeneacetonitrile;
(±)-2,6-difluoro-α-(1-cyclopentyl)-α-[3-[1-methylethyl(phenylmethyl)amino]propyl]benzeneacetonitrile;
(±)-2,6-difluoro-α-(1-cyclohexyl)-α-[3-[ethyl(phenylmethyl)amino]propyl]benzeneacetonitrile;
(±)-2,6-difluoro-α-(1-cyclohexyl)-α-[3-[n-propyl(-phenylmethyl)amino]propyl]benzeneacetonitrile;
(±)-2,6-difluoro-α-(1-cyclohexyl)-α-[3-[1-methylethyl(phenylmethyl)amino]propyl]benzeneacetonitrile;
(±)-2,6-dichloro-α-(1-cyclopropyl)-α-[3-[ethyl(phenylmethyl)amino]propyl]benezeneacetonitrile;
(±)-2,6-dichloro-α-(1-cyclopropyl)-α-[3-[n-propyl(-phenylmethyl)amino]propyl]benzeneacetonitrile;
(±)-2, 6-dichloro-α-(1-cyclopropyl)-α-[3-[1-methylethyl(phenylmethyl)amino]propyl]benzeneacetonitrile;
(±)-2,6-dichloro-α-(1-cyclobutyl)-α-[3-[ethyl(phenylmethyl)amino]propyl]benezeneacetonitrile;
(±)-2,6-dichloro-α-(1-cyclobutyl)-α-[3-[n-propyl(-phenylmethyl)amino]propyl]benezeneacetonitrile;
(±)-2,6-dichloro-α-(1-cyclobutyl)-α-[3-[1-methylethyl(phenylmethyl)amino]propyl]benzeneacetonitrile;
(±)-2,6-dichloro-α-(1-cyclopentyl)-α-[3-[ethyl(phenylmethyl)amino]propyl]benzeneacetonitrile;
(±)-2,6-dichloro-α-(1-cyclopentyl)-α-[3-[n-propyl(-phenylmethyl)amino]propyl]benzeneacetonitrile;
(±)-2,6-dichloro-α-(1-cyclopentyl)-α-[3-[1-methylethyl(phenylmethyl)amino]propyl]benzeneacetonitrile;
(±)-2,6-dichloro-α-(1-cyclohexyl)-α-[3-[ethyl(phenylmethyl)amino]propyl]benzeneacetonitrile;
(±)-2,6-dichloro-α-(1-cyclohexyl)-α-[3-[n-propyl(-phenylmethyl)amino]propyl]benzeneacetonitrile;
(±)-2,6-dichloro-α-(1-cyclohexyl)-α-[3-[1-methylethyl(phenylmethyl)amino]propyl]benzeneacetonitrile;
(±)-2,6-dibromo-α-(1-cyclopropyl)-α-[3-[ethyl(phenylmethyl)amino]propyl]benezeneacetonitrile;
(±)-2,6-dibromo-α-(1-cyclopropyl)-α-[3-[n-propyl(-phenylmethyl)amino]propyl]benzeneacetonitrile;
(±)-2,6-dibromo-α-(1-cyclopropyl)-α-[3-[1-methylethyl(phenylmethyl)amino]propyl]benzeneacetonitrile;
(±)-2,6-dibromo-α-(1-cyclobutyl)-α-[3-[ethyl(phenylmethyl)amino]propyl]benzeneacetonitrile;
(±)-2,6-dibromo-α-(1-cyclobutyl)-α-[3-[n-propyl(-phenylmethyl)amino]propyl]benzeneacetonitrile;
(±)-2,6-dibromo-α-(1-cyclobutyl)-α-[3-[1-methylethyl(phenylmethyl)amino]propyl]benzeneacetonitrile;
(±)-2,6-dibromo-α-(1-cyclopentyl)-α-[3-[ethyl(phenylmethyl)amino]propyl]benzeneacetonitrile;
(±)-2,6-dibromo-α-(1-cyclopentyl)-α-[3-[n-propyl(-phenylmethyl)amino]propyl]benezeneacetonitrile;
(±)-2,6-dibromo-α-(1-cyclopentyl)-α-[3-[1-methylethyl(phenylmethyl)amino]propyl]benzeneacetonitrile;
(±)-2,6-dibromo-α-(1-cyclohexyl)-α-[3-[ethyl(phenylmethyl)amino]propyl]benzeneacetonitrile;
(±)-2,6-dibromo-α-(1-cyclohexyl)-α-[3-[n-propyl(-phenylmethyl)amino]propyl]benzeneacetonitrile;
(±)-2,6-dibromo-α-(1-cyclohexyl)-α-[3-[1-methylethyl(phenylmethyl)amino]propyl]benzeneacetonitrile;
(±)-2,6-ditrifluoromethyl-α-(1-cyclopropyl)-α-[3-[ethyl(phenylmethyl)amino]propyl]benzeneacetonitrile;
(±)-2,6-ditrifluoromethyl-α-(1-cyclopropyl)-α-[3-[n-propyl(phenylmethyl)amino]propyl]benzeneacetonitrile;
(±)-2,6-ditrifluoromethyl-α-(1-cyclopropyl)-α-[3-[1-methylethyl(phenylmethyl)amino]propyl]benzeneacetonitrile;
(±)-2,6-ditrifluoromethyl-α-(1-cyclobutyl)-α-[3-[ethyl(phenylmethyl)amino]propyl]benzeneacetonitrile;
(±)-2,6-ditrifluoromethyl-α-(1-cyclobutyl)-α-[3-[n-propyl(phenylmethyl)amino]propyl]benzeneacetonitrile;
(±)-2,6-ditrifluoromethyl-α-(1-cyclobutyl)-α-[3-[1-methylethyl(phenylmethyl)amino]propyl]benzeneacetonitrile;
(±)-2,6-ditrifluoromethyl-α-(1-cyclopentyl)-α-[3-[ethyl(phenylmethyl)amino]propyl]benzeneacetonitrile;
(±)-2,6-ditrifluoromethyl-α-(1-cyclopentyl)-α-[3-[n-propyl(phenylmethyl)amino]propyl]benzeneacetonitrile;
(±)-2,6-ditrifluoromethyl-α-(1-cyclopentyl)-α-[3-[1-methylethyl(phenylmethyl)amino]propyl]benzeneacetonitrile;
(±)-2,6-ditrifluoromethyl-α-(1-cyclohexyl)-α-[3-[ethyl(phenylmethyl)amino]propyl]benzeneacetonitrile;
(±)-2,6-ditrifluoromethyl-α-(1-cyclohexyl)-α-[3-[n-propyl(phenylmethyl)amino]propyl]benzeneacetonitrile;
(±)-2,6-ditrifluoromethyl-α-(1-cyclohexyl)-α-[3-[1-methylethyl(phenylmethyl)amino]propyl]benzeneacetonitrile;
(±)-2,6-difluoro-α-(1-methylethyl)-α-[3-[ethyl(-phenylethyl)amino]propyl]benzeneacetonitrile;
(±)-2,6-difluoro-α-(1-methylethyl)-α-[3-[n-propyl(-phenylethyl)amino]propyl]benzeneacetonitrile;
(±)-2,6-difluoro-α-(1-methylethyl)-α-[3-[1-methylethyl(phenylethyl)amino]propyl]benzeneacetonitrile;
(±)-2,6-dichloro-α-(1-methylethyl)-α-[3-[ethyl(-phenylethyl)amino]propyl]benzeneacetonitrile;
(±)-2,6-dichloro-α-(1-methylethyl)-α-[3-[n-propyl(-phenylethyl)amino]propyl]benzeneacetonitrile;
(±)-2,6-dichloro-α-(1-methylethyl)-α-[3-[1-methylethyl(phenylethyl)amino]propyl]benzeneacetonitrile;

(±)-2,6-dibromo-α-(1-methylethyl)-α-[3-[ethyl(-phenylethyl)amino]propyl]benzeneacetonitrile;
(±)-2,6-dibromo-α-(1-methylethyl)-α-[3-[n-propyl(-phenylethyl)amino]propyl]benzeneacetonitrile;
(±)-2,6-dibromo-α-(1-methylethyl)-α-[3-[1-methylethyl(phenylethyl)amino]propyl]benzeneacetonitrile;
(±)-2,6-ditrifluoromethyl-α-(1-methylethyl)-α-[3-[ethyl(phenylethyl)amino]propyl]benzeneacetonitrile;
(±)-2,6-ditrifluoromethyl-α-(1-methylethyl)-α-[3-[n-propyl(phenylethyl)amino]propyl]benzeneacetonitrile;
(±)-2,6-ditrifluoromethyl-α-(1-methylethyl)-α-[3-[1-methylethyl(phenylethyl)amino]propyl]-benezeneacetonitrile;
(±)-2,6-difluoro-α-(1-cyclopropyl)-α-[3-[methyl(-phenylethyl)amino]propyl]benzeneacetonitrile;
(±)-2,6-difluoro-α-(1-cyclobutyl)-α-[3-[methyl(-phenylethyl)amino]propyl]benzeneacetonitrile;
(±)-2,6-difluoro-α-(1-cyclopentyl)-α-[3-[methyl(-phenylethyl)amino]propyl]benzeneacetonitrile;
(±)-2,6-difluoro-α-(1-cyclohexyl)-α-[3-[methyl(-phenylethyl)amino]propyl]benzeneacetonitrile;
(±)-2,6-dichloro-α-(1-cyclopropyl)-α-[3-[methyl(-phenylethyl)amino]propyl]benzeneacetonitrile;
(±)-2,6-dichloro-α-(1-cyclobutyl)-α-[3-[methyl(-phenylethyl)amino]propyl]benzeneacetonitrile;
(±)-2,6-dichloro-α-(1-cyclopentyl)-α-[3-[methyl(-phenylethyl)amino]propyl]benzeneacetonitrile;
(±)-2,6-dichloro-α-(1-cyclohexyl)-α-[3-[methyl(-phenylethyl)amino]propyl]benzeneacetonitrile;
(±)-2,6-dibromo-α-(1-cyclopropyl)-α-[3-[methyl(-phenylethyl)amino]propyl]benzeneacetonitrile;
(±)-2,6-dibromo-α-(1-cyclobutyl)-α-[3-[methyl(-phenylethyl)amino]propyl]benzeneacetonitrile;
(±)-2,6-dibromo-α-(1-cyclopentyl)-α-[3-[methyl(-phenylethyl)amino]propyl]benezeneacetonitrile;
(±)-2,6-dibromo-α-(1-cyclohexyl)-α-[3-[methyl(-phenylethyl)amino]propyl]benzeneacetonitrile;
(±)-2,6-ditrifluoromethyl-α-(1-cyclopropyl)-α-[3-[methyl(phenylethyl)amino]propyl]benzeneacetonitrile;
(±)-2,6-ditrifluoromethyl-α-(1-cyclobutyl)-α-[3-[methyl(phenylethyl)amino]propyl]benzeneacetonitrile;
(±)-2,6-ditrifluoromethyl-α-(1-cyclopentyl)-α-[3-[methyl(phenylethyl)amino]propyl]benzeneacetonitrile;
(±)-2,6-ditrifluoromethyl-α-(1-cyclohexyl)-α-[3-[methyl(phenylethyl)amino]propyl]benzeneacetonitrile;
(±)-2,6-difluoro-α-(1-cyclopropyl)-α-[3-[methyl(-phenylmethyl)amino]propyl]benzeneacetonitrile;
(±)-2,6-difluoro-α-(1-cyclopropyl)-α-[3-[methyl(-phenylmethyl)amino]butyl]benzeneacetonitrile;
(±)-2,6-difluoro-α-(1-cyclopropyl)-α-[3-[methyl(-phenylmethyl)amino]pentyl]benzeneacetonitrile;
(±)-2,6-difluoro-α-(1-cyclobutyl)-α-[3-[methyl(phenylmethyl)amino]propyl]benezeneacetonitrile;
(±)-2,6-difluoro-α-(1-cyclobutyl)-α-[3-[methyl(phenylmethyl)amino]butyl]benezeneacetonitrile;
(±)-2,6-difluoro-α-(1-cyclobutyl)-α-[3-[methyl(phenylmethyl)amino]pentyl]benezeneacetonitrile;
(±)-2,6-difluoro-α-(1-cyclopentyl)-α-[3-[methyl(-phenylmethyl)amino]propyl]benezeneacetonitrile;
(±)-2,6-difluoro-α-(1-cyclopentyl)-α-[3-[methyl(-phenylmethyl)amino]butyl]benezeneacetonitrile;
(±)-2,6-difluoro-α-(1-cyclopentyl)-α-[3-[methyl(-phenylmethyl)amino]pentyl]benezeneacetonitrile;
(±)-2,6-difluoro-α-(1-cyclohexyl)-α-[3-[methyl(-phenylmethyl)amino]propyl]benezeneacetonitrile;
(±)-2,6-difluoro-α-(1-cyclohexyl)-α-[3-[methyl(-phenylmethyl)amino]butyl]benzeneacetonitrile;
(±)-2,6-difluoro-α-(1-cyclohexyl)-α-[3-[methyl(-phenylmethyl)amino]pentyl]benzeneacetonitrile;
(±)-2,6-dichloro-α-(1-cyclopropyl) [methyl(phenylmethyl)amino]propyl]benzeneacetonitrile;
(±)-2,6-dichloro-α-(1-cyclopropyl)-α-[3-[methyl(-phenylmethyl)amino]butyl]benzeneacetonitrile;
(±)-2,6-dichloro-α-(1-cyclopropyl)-α-[3-[methyl(-phenylmethyl)amino]pentyl]benzeneacetonitrile;
(±)-2,6-dichloro-α-(1-cyclobutyl)-α-[3-[methyl(-phenylmethyl)amino]propyl]benzeneacetonitrile;
(±)-2,6-dichloro-α-(1-cyclobutyl)-α-[3-[methyl(-phenylmethyl)amino]butyl]benezeneacetonitrile;
(±)-2,6-dichloro-α-(1-cyclobutyl)-α-[3-[methyl(-phenylmethyl)amino]pentyl]benzeneacetonitrile;
(±)-2,6-dichloro-α-(1-cyclopentyl)-α-[3-[methyl(-phenylmethyl)amino]propyl]benzeneacetonitrile;
(±)-2,6-dichloro-α-(1-cyclopentyl)-α-[3-[methyl(-phenylmethyl)amino]butyl]benzeneacetonitrile;
(±)-2,6-dichloro-α-(1-cyclopentyl)-α-[3-[methyl(-phenylmethyl)amino]pentyl]benzeneacetonitrile;
(±)-2,6-dichloro-α-(1-cyclohexyl)-α-[3-[methyl(-phenylmethyl)amino]propyl]benzeneacetonitrile;
(±)-2,6-dichloro-α-(1-cyclohexyl)-α-J3-[methyl(-phenylmethyl)amino]butyl]benzeneacetonitrile;
(±)-2,6-dichloro-α-(1-cyclohexyl)-α-[3-[methyl(-phenylmethyl)amino]pentyl]benzeneacetonitrile;
(±)-2,6-ditrifluoromethyl-α-(1-cyclopropyl)-α-[3-[methyl(phenylmethyl)amino]propyl]benezeneacetonitrile;
(±)-2,6-ditrifluoromethyl-α-(1-cyclopropyl)-α-[3-[methyl(phenylmethyl)amino]butyl]benzeneacetonitrile;
(±)-2,6-ditrifluoromethyl-α-(1-cyclopropyl)-α-[3-[methyl(phenylmethyl)amino]pentyl]benzeneacetonitrile;
(±)-2,6-ditrifluoromethyl-α-(1-cyclobutyl)-α-[3-[methyl(phenylmethyl)amino]propyl]benzeneacetonitrile;
(±)-2,6-ditrifluoromethyl-α-(1-cyclobutyl)-α-[3-[methyl(phenylmethyl)amino]butyl]benzeneacetonitrile;
(±)-2,6-ditrifluoromethyl-α-(1-cyclobutyl)-α-[3-[methyl(phenylmethyl)amino]pentyl]benzeneacetonitrile;
(±)-2,6-ditrifluoromethyl-α-(1-cyclopentyl)-α-[3-[methyl(phenylmethyl)amino]propyl]benzeneacetonitrile;
(±)-2,6-ditrifluoromethyl-α-(1-cyclopentyl)-α-[3-[methyl(phenylmethyl)amino]butyl]benzeneacetonitrile;
(±)-2,6-ditrifluoromethyl-α-(1-cyclopentyl)-α-[3-[methyl(phenylmethyl)amino]pentyl]benzeneacetonitrile;
(±)-2,6-ditrifluoromethyl-α-(1-cyclohexyl)-α-[3-[methyl(phenylmethyl)amino]propyl]benzeneacetonitrile;
(±)-2,6-ditrifluoromethyl-α-(1-cyclohexyl)-α-[3-[methyl(phenylmethyl)amino]butyl]benzeneacetonitrile;
(±)-2,6-ditrifluoromethyl-α-(1-cyclohexyl)-α-[3-[methyl(phenylmethyl)amino]pentyl]benzeneacetonitrile;
(±)-2,6-difluoro-α-(1-methylethyl)-α-[3-[ethyl(phenylmethyl)amino]propyl]benzeneacetonitrile;
(±)-2,6-difluoro-α-(1-methylethyl)-α-[3-[n-propyll(-phenylmethyl)amino]propyl]benzeneacetonitrile;
(±)-2,6-difluoro-α-(1-methylethyl)-α-[3-[1-methylethyl(phenylmethyl)amino]propyl]benzeneacetonitrile;

(±)-2,6-difluoro-α-(1-methylethyl)-α-[3-[ethyl(phenylmethyl)amino]butyl]benzeneacetonitrile;
(±)-2,6-difluoro-α-(1-methylethyl)-α-[3-[n-propyll(phenylmethyl)amino]butyl]benzeneacetonitrile;
(±)-2,6-difluoro-α-(1-methylethyl)-α-[3-[1-methylethyl(phenylmethyl)amino]butyl]benzeneacetonitrile;
(±)-2,6-difluoro-α-(1-methylethyl)-α-[3-[ethyl(phenylmethyl)amino]pentyl]benzeneacetonitrile;
(±)-2,6-difluoro-α-(1-methylethyl)-α-[3-[n-propyll(phenylmethyl)amino]pentyl]benzeneacetonitrile;
(±)-2,6-difluoro-α-(1-methylethyl)-α-[3-[1-methylethyl(phenylmethyl)amino]pentyl]benzeneacetonitrile;
(±)-2,6-dichloro-α-(1-methylethyl)-α-[3-[ethyl(phenylmethyl)amino]propyl]benzeneacetonitrile;
(±)-2,6-dichloro-α-(1-methylethyl)-α-[3-[n-propyll(phenylmethyl)amino]propyl]benzeneacetonitrile;
(±)-2,6-dichloro-α-(1-methylethyl)-α-[3-[1-methylethyl(phenylmethyl)amino]propyl]benzeneacetonitrile;
(±)-2,6-dichloro-α-(1-methylethyl)-α-[3-[ethyl(phenylmethyl)amino]butyl]benezeneacetonitrile;
(±)-2,6-dichloro-α-(1-methylethyl)-α-[3-[n-propyll(phenylmethyl)amino]butyl]benzeneacetonitrile;
(±)-2,6-dichloro-α-(1-methylethyl)-α-[3-[1-methylethyl(phenylmethyl)amino]butyl]benzeneacetonitrile;
(±)-2,6-dichloro-α-(1-methylethyl)-α-[3-[ethyl(phenylmethyl)amino]pentyl]benzeneacetonitrile;
(±)-2,6-dichloro-α-(1-methylethyl)-α-[3-[n-propyll(phenylmethyl)amino]pentyl]benzeneacetonitrile;
(±)-2,6-dichloro-α-(1-methylethyl)-α-[3-[1-methylethyl(phenylmethyl)amino]pentyl]benzeneacetonitrile;
(±)-2,6-dibromo-α-(1-methylethyl)-α-[3-[ethyl(phenylmethyl)amino]propyl]benezeneacetonitrile;
(±)-2,6-dibromo-α-(1-methylethyl)-α-[3-[n-propyll(phenylmethyl)amino]propyl]benzeneacetonitrile;
(±)-2,6-dibromo-α-(1-methylethyl)-α-[3-[1-methylethyl(phenylmethyl)amino]propyl]benzeneacetonitrile;
(±)-2,6-dibromo-α-(1-methylethyl)-α-[3-[ethyl(phenylmethyl)amino]butyl]benzeneacetonitrile;
(±)-2,6-dibromo-α-(1-methylethyl)-α-[3-[n-propyll(phenylmethyl)amino]butyl]benzeneacetonitrile;
(±)-2,6-dibromo-α-(1-methylethyl)-α-[3-[1-methylethyl(phenylmethyl)amino]butyl]benzeneacetonitrile;
(±)-2,6-dibromo-α-(1-methylethyl)-α-[3-[ethyl(phenylmethyl)amino]pentyl]benzeneacetonitrile;
(±)-2,6-dibromo-α-(1-methylethyl)-α-[3-[n-propyll(phenylmethyl)amino]pentyl]benzeneacetonitrile;
(±)-2,6-dibromo-α-(1-methylethyl)-α-[3-[1-methylethyl(phenylmethyl)amino]pentyl]benzeneacetonitrile;
(±)-2,6-ditrifluoromethyl-α-(1-methylethyl)-α-[3-[ethyl(phenylmethyl)amino]propyl]benzeneacetonitrile;
(±)-2,6-ditrifluoromethyl-α-(1-methylethyl)-α-[3-[n-propyll(phenylmethyl)amino]propyl]benzeneacetonitrile;
(±)-2,6-ditrifluoromethyl-α-(1-methylethyl)-α-[3-[1-methylethyl(phenylmethyl)amino]propyl]benzeneacetonitrile;
(±)-2,6-ditrifluoromethyl-α-(1-methylethyl)-α-[3-[ethyl(phenylmethyl)amino]butyl]benzeneacetonitrile;
(±)-2,6-ditrifluoromethyl-α-(1-methylethyl)-α-[3-[n-propyll(phenylmethyl)amino]butyl]benzeneacetonitrile;
(±)-2,6-ditrifluoromethyl-α-(1-methylethyl)-α-[3-[1-methylethyl(phenylmethyl)amino]butyl]benzeneacetonitrile;
(±)-2,6-ditrifluoromethyl-α-(1-methylethyl)-α-[3-[ethyl(phenylmethyl)amino]pentyl]benzeneacetonitrile;
(±)-2,6-ditrifluoromethyl-α-(1-methylethyl)-α-[3-[n-propyll(phenylmethyl)amino]pentyl]benzeneacetonitrile;
(±)-2,6-ditrifluoromethyl-α-(1-methylethyl)-α-[3-[1-methylethyl(phenylmethyl)amino]pentyl]benzeneacetonitrile;
(±)-2,6-difluoro-α-(1-methylethyl)-α-[3-[methyl(phenylethyl)amino]propyl]benzeneacetonitrile;
(±)-2,6-difluoro-α-(1-methylethyl)-α-[3-[methyl(phenylethyl)amino]butyl]benzeneacetonitrile;
(±)-2,6-difluoro-α-(1-methylethyl)-α-[3-[methyl(phenylethyl)amino]pentyl]benzeneacetonitrile;
(±)-2,6-dichloro-α-(1-methylethyl)-α-[3-[methyl(phenylethyl)amino]propyl]benezeneacetonitrile;
(±)-2,6-dichloro-α-(1-methylethyl)-α-[3-[methyl(phenylethyl)amino]butyl]benzeneacetonitrile;
(±)-2,6-dichloro-α-(1-methylethyl)-α-[3-[methyl(phenylethyl)amino]pentyl]benzeneacetonitrile;
(±)-2,6-dibromo-α-(1-methylethyl)-α-[3-[methyl(phenylethyl)amino]propyl]benzeneacetonitrile;
(±)-2,6-dibromo-α-(1-methylethyl)-α-[3-[methyl(phenylethyl)amino]butyl]benzeneacetonitrile;
(±)-2,6-dibromo-α-(1-methylethyl)-α-[3-[methyl(phenylethyl)amino]pentyl]benzeneacetonitrile;
(±)-2,6-ditrifluoromethyl-α-(1-methylethyl)-α-[3-[methyl(phenylethyl)amino]propyl]benezeneacetonitrile;
(±)-2,6-ditrifluoromethyl-α-(1-methylethyl)-α-[3-[methyl(phenylethyl)amino]butyl]benzeneacetonitrile;
(±)-2,6-ditrifluoromethyl-α-(1-methylethyl)-α-[3-[methyl(phenylethyl)amino]pentyl]benzeneacetonitrile;
(±)-2,6-difluoro-α-(1-cyclopropyl)-α-[3-[ethyl(phenylethyl)amino]propyl]benzeneacetonitrile;
(±)-2,6-difluoro-α-(1-cyclopropyl)-α-[3-[n-propyl(phenylethyl)amino]propyl]benzeneacetonitrile;
(±)-2,6-difluoro-α-(1-cyclopropyl)-α-[3-[1-methylethyl(phenylethyl)amino]propyl]benzeneacetonitrile;
(±)-2,6-difluoro-α-(1-cyclopbutyl)-α-[3-[ethyl(phenylethyl)amino]propyl]benzeneacetonitrile;
(±)-2,6-difluoro-α-(1-cyclopbutyl )-α-[3-[n-propyl(phenylethyl)amino]propyl]benzeneacetonitrile;
(±)-2,6-difluoro-α-(1-cyclopbutyl )-α-[3-[1-methylethyl(phenylethyl)amino]propyl]benzeneacetonitrile;
(±)-2,6-difluoro-α-(1-cyclopentyl)-α-[3-[ethyl(phenylethyl)amino]propyl]benzeneacetonitrile;
(±)-2,6-difluoro-α-(1-cyclopentyl)-α-[3-[n-propyl(phenylethyl)amino]propyl]benzeneacetonitrile;
(±)-2,6-difluoro-α-(1-cyclopentyl)-α-[3-[1-methylethyl(phenylethyl)amino]propyl]benzeneacetonitrile;
(±)-2,6-difluoro-α-(1-cyclohexyl)-α-[3-[ethyl(phenylethyl)amino]propyl]benzeneacetonitrile;
(±)-2,6-difluoro-α-(1-cyclohexyl)-α-[3-[n-propyl(phenylethyl)amino]propyl]benzeneacetonitrile;
(±)-2,6-difluoro-α-(1-cyclohexyl)-α-[3-[1-methylethyl(phenylethyl)amino]propyl]benzeneacetonitrile;
(±)-2,6-difluoro-α-(1-cyclopropyl)-α-[3-[ethyl(phenylethyl)amino]propyl]benzeneacetonitrile;
(±)-2,6-difluoro-α-(1-cyclopropyl)-α-[3-[n-propyl(phenylethyl)amino]propyl]benzeneacetonitrile;
(±)-2,6-difluoro-α-(1-cyclopropyl)-α-[3-[1-methylethyl(phenylethyl)amino]propyl]benzeneacetonitrile;
(±)-2,6-difluoro-α-(1-cyclobutyl)-α-[3-[ethyl(phenylethyl)amino]propyl]benzeneacetonitrile;

(±)-2,6-difluoro-α-(1-cyclobutyl)-α-[3-[n-propyl(-phenylethyl)amino]propyl]benzeneacetonitrile;
(±)-2,6-difluoro-α-(1-cyclobutyl)-α-[3-[1-methylethyl(-phenylethyl)amino]propyl]benzeneacetonitrile;
(±)-2,6-difluoro-α-(1-cyclopentyl)-α-[3-[ethyl(-phenylethyl)amino]propyl]benzeneacetonitrile;
(±)-2,6-difluoro-α-(1-cyclopentyl)-α-[3-[n-propyl(-phenylethyl)amino]propyl]benzeneacetonitrile;
(±)-2,6-difluoro-α-(1-cyclopentyl)-α-[3-[1-methylethyl(phenylethyl)amino]propyl]benezeneacetonitrile;
(±)-2,6-difluoro-α-(1-cyclohexyl)-α-[3-[ethyl(phenylethyl)amino]propyl]benzeneacetonitrile;
(±)-2,6-difluoro-α-(1-cyclohexyl)-α-[3-[n-propyl(-phenylethyl)amino]propyl]benzeneacetonitrile;
(±)-2,6-difluoro-α-(1-cyclohexyl)-α-[3-[1-methylethyl(phenylethyl)amino]propyl]benzeneacetonitrile;
(±)-2,6-difluoro-α-(1-cyclopropyl)-α-[3-[ethyl(phenylmethyl)amino]butyl]benzeneacetonitrile;
(±)-2,6-difluoro-α-(1-cyclopropyl)-α-[3-[n-propyl(-phenylmethyl)amino]butyl]benezeneacetonitrile;
(±)-2,6-difluoro-α-(1-cyclopropyl)-α-[3-[1-methylethyl(phenylmethyl)amino]butyl]benzeneacetonitrile;
(±)-2,6-difluoro-α-(1-cyclopropyl)-α-[3-[ethyl(phenylmethyl)amino]pentyl]benezeneacetonitrile;
(±)-2, 6-difluoro-α-(1-cyclopropyl)-α-[3-[n-propyl(-phenylmethyl)amino]pentyl]benezeneacetonitrile;
(±)-2, 6-difluoro-α-(1-cyclopropyl)-α-[3-[1-methylethyl(phenylmethyl)amino]pentyl]benzeneacetonitrile;
(±)-2,6-difluoro-α-(1-cyclobutyl)-α-[3-[ethyl(phenylmethyl)amino]butyl]benzeneacetonitrile;
(±)-2,6-difluoro-α-(1-cyclobutyl)-α-[3-[n-propyl(-phenylmethyl)amino]butyl]benzeneacetonitrile;
(±)-2,6-difluoro-α-(1-cyclobutyl)-α-[3-[1-methylethyl(-phenylmethyl)amino]butyl]benzeneacetonitrile;
(±)-2,6-difluoro-α-(1-cyclobutyl)-α-[3-[ethyl(phenylmethyl)amino]pentyl]benzeneacetonitrile;
(±)-2,6-difluoro-α-(1-cyclobutyl)-α-[3-[n-propyl(-phenylmethyl)amino]pentyl]benzeneacetonitrile;
(±)-2,6-difluoro-α-(1-cyclobutyl)-α-[3-[1-methylethyl(-phenylmethyl)amino]pentyl]benzeneacetonitrile;
(±)-2,6-difluoro-α-(1-cyclopentyl)-α-[3-[ethyl(phenylmethyl)amino]butyl]benezeneacetonitrile;
(±)-2,6-difluoro-α-(1-cyclopentyl)-α-[3-[n-propyl(-phenylmethyl)amino]butyl]benezeneacetonitrile;
(±)-2,6-difluoro-α-(1-cyclopentyl)-α-[3-[1-methylethyl(phenylmethyl)amino]butyl]benezeneacetonitrile;
(±)-2,6-difluoro-α-(1-cyclopentyl)-α-[3-[ethyl(phenylmethyl)amino]pentyl]benzeneacetonitrile;
(±)-2,6-difluoro-α-(1-cyclopentyl)-α-[3-[n-propyl(-phenylmethyl)amino]pentyl]benezeneacetonitrile;
(±)-2,6-difluoro-α-(1-cyclopentyl)-α-[3-[1-methylethyl(phenylmethyl)amino]pentyl]benzeneacetonitrile;
(±)-2,6-difluoro-α-(1-cyclohexyl)-α-[3-[ethyl(phenylmethyl)amino]butyl]benzeneacetonitrile;
(±)-2,6-difluoro-α-(1-cyclohexyl)-α-[3-[n-propyl(-phenylmethyl)amino]butyl]benzeneacetonitrile;
(±)-2,6-difluoro-α-(1-cyclohexyl)-α-[3-[1-methylethyl(phenylmethyl)amino]butyl]benzeneacetonitrile;
(±)-2,6-difluoro-α-(1-cyclohexyl)-α-[3-[ethyl(phenylmethyl)amino]pentyl]benzeneacetonitrile;
(±)-2,6-difluoro-α-(1-cyclohexyl)-α-[3-[n-propyl(-phenylmethyl)amino]pentyl]benzeneacetonitrile;
(±)-2,6-difluoro-α-(1-cyclohexyl)-α-[3-[1-methylethyl(phenylmethyl)amino]pentyl]benzeneacetonitrile;

(±)-2, 6-difluoro-α-(1-cyclopropyl)-α-[3-[methyl(-phenylethyl)amino]butyl]benzeneacetonitrile;
(±)-2,6-difluoro-α-(1-cyclopropyl)-α-[3-[methyl(-phenylethyl)amino]pentyl]benezeneacetonitrile;
(±)-2,6-difluoro-α-(1-cyclobutyl)-α-[3-[methyl(-phenylethyl)amino]butyl]benzeneacetonitrile;
(±)-2,6-difluoro-α-(1-cyclobutyl)-α-[3-[methyl(-phenylethyl)amino]pentyl]benzeneacetonitrile;
(±)-2,6-difluoro-α-(1-cyclopentyl)-α-[3-[methyl(-phenylethyl)amino]butyl]benzeneacetonitrile;
(±)-2,6-difluoro-α-(1-cyclopentyl)-α-[3-[methyl(-phenylethyl)amino]pentyl]benzeneacetonitrile;
(±)-2,6-difluoro-α-(1-cyclohexyl)-α-[3-[methyl(-phenylethyl)amino]butyl]benezeneacetonitrile;
(±)-2,6-difluoro-α-(1-cyclohexyl)-α-[3-[methyl(-phenylethyl)amino]pentyl]benzeneacetonitrile;
(±)-2,6-difluoro-α-(1-cyclopropyl)-α-[3-[ethyl(-phenylethyl)amino]propyl]benzeneacetonitrile;
(±)-2,6-difluoro-α-(1-cyclopropyl)-α-[3-[n-propyl(-phenylethyl)amino]propyl]benzeneacetonitrile;
(±)-2,6-difluoro-α-(1-cyclopropyl)-α-[3-[1-methylethyl(phenylethyl)amino]propyl]benzeneacetonitrile;
(±)-2,6-dichloro-α-(1-cyclopropyl)-α-[3-[ethyl(-phenylethyl)amino]propyl]benzeneacetonitrile;
(±)-2,6-dichloro-α-(1-cyclopropyl)-α-[3-[n-propyl(-phenylethyl)amino]propyl]benzeneacetonitrile;
(±)-2,6-dichloro-α-(1-cyclopropyl)-α-[3-[1-methylethyl(phenylethyl)amino]propyl]benzeneacetonitrile;
(±)-2,6-dichloro-α-(1-cyclopropyl)-α-[3-[ethyl(-phenylethyl)amino]propyl]benzeneacetonitrile;
(±)-2,6,dichloro-α-(1-cyclopropyl)-α-[3-[n-propyl(-phenylethyl)amino]propyl]benzeneacetonitrile;
(±)-2,6-dichloro-α-(1-cyclopropyl)-α-[3-[1-methylethyl(phenylethyl)amino]propyl]benzeneacetonitrile;
(±)-2,6-ditrifluoromethyl-α-(1-cyclopropyl)-α-[3-[ethyl(phenylethyl)amino]propyl]benzeneacetonitrile;
(±)-2,6-ditrifluoromethyl-α-(1-cyclopropyl)-α-[3-[n-propyl(phenylethyl)amino]propyl]benzeneacetonitrile;
(±)-2,6-ditrifluoromethyl-α-(1-cyclopropyl)-α-[3-[1-methylethyl(phenylethyl)amino]propyl]benzeneacetonitrile;
(±)-2,6-difluoro-α-(1-cyclobutyl)-α-[3-[ethyl(phenylethyl)amino]propyl]benzeneacetonitrile;
(±)-2,6-difluoro-α-(1-cyclobutyl)-α-[3-[n-propyl(-phenylethyl)amino]propyl]benzeneacetonitrile;
(±)-2,6-difluoro-α-(1-cyclobutyl)-α-[3-[1-methylethyl(-phenylethyl)amino]propyl]benzeneacetonitrile;
(±)-2,6-dichloro-α-(1-cyclobutyl)-α-[3-[ethyl(phenylethyl)amino]propyl]benzeneacetonitrile;
(±)-2,6-dichloro-α-(1-cyclobutyl)-α-[3-[n-propyl(-phenylethyl)amino]propyl]benzeneacetonitrile;
(±)-2,6-dichloro-α-(1-cyclobutyl)-α-[3-[1-methylethyl(phenylethyl)amino]propyl]benzeneacetonitrile;
(±)-2,6-dichloro-α-(1-cyclobutyl)-α-[3-[ethyl(phenylethyl)amino]propyl]benzeneacetonitrile;
(±)-2,6-dichloro-α-(1-cyclobutyl)-α-[3-[n-propyl(-phenylethyl)amino]propyl]benzeneacetonitrile;
(±)-2,6-dichloro-α-(1-cyclobutyl)-α-[3-[1-methylethyl(phenylethyl)amino]propyl]benzeneacetonitrile;
(±)-2,6-ditrifluoromethyl-α-(1-cyclobutyl)-α-[3-[ethyl(phenylethyl)amino]propyl]benzeneacetonitrile;
(±)-2,6-ditrifluoromethyl-α-(1-cyclobutyl)-α-[3-[n-propyl(phenylethyl)amino]propyl]benzeneacetonitrile;

(±)-2,6-ditrifluoromethyl-α-(1-cyclobutyl)-α-[3-[1-methylethyl(phenylethyl)amino]propyl]benzeneacetonitrile;

(±)-2,6-difluoro-α-(1-cyclopentyl)-α-[3-[ethyl(phenylethyl)amino]propyl]benzeneacetonitrile;

(±)-2,6-difluoro-α-(1-cyclopentyl)-α-[3-[n-propyl(phenylethyl)amino]propyl]benzeneacetonitrile;

(±)-2,6-difluoro-α-(1-cyclopentyl)-α-[3-[1-methylethyl(phenylethyl)amino]propyl]benzeneacetonitrile;

(±)-2,6-dichloro-α-(1-cyclopentyl)-α-[3-[ethyl(phenylethyl)amino]propyl]benzeneacetonitrile;

(±)-2,6-dichloro-α-(1-cyclopentyl)-α-[3-[n-propyl(phenylethyl)amino]propyl]benzeneacetonitrile;

(±)-2,6-dichloro-α-(1-cyclopentyl)-α-[3-[1-methylethyl(phenylethyl)amino]propyl]benzeneacetonitrile;

(±)-2,6-dichloro-α-(1-cyclopentyl)-α-[3-[ethyl(phenylethyl)amino]propyl]benzeneacetonitrile;

(±)-2,6-dichloro-α-(1-cyclopentyl)-α-[3-[n-propyl(phenylethyl)amino]propyl]benzeneacetonitrile;

(±)-2,6-dichloro-α-(1-cyclopentyl)-α-[3-[1-methylethyl(phenylethyl)amino]propyl]benzeneacetonitrile;

(±)-2,6-ditrifluoromethyl-α-(1-cyclopentyl)-α-[3-[ethyl(phenylethyl)amino]propyl]benzeneacetonitrile;

(±)-2,6-ditrifluoromethyl-α-(1-cyclopentyl)-α-[3-[n-propyl(phenylethyl)amino]propyl]benzeneacetonitrile;

(±)-2,6-ditrifluoromethyl-α-(1-cyclopentyl)-α-[3-[1-methylethyl(phenylethyl)amino]propyl]benezeneacetonitrile;

(±)-2,6-difluoro-α-(1-cyclohexyl)-α-[3-[ethyl(phenylethyl)amino]propyl]benzeneacetonitrile;

(±)-2,6-difluoro-α-(1-cyclohexyl)-α-[3-[n-propyl(phenylethyl)amino]propyl]benzeneacetonitrile;

(±)-2,6-difluoro-α-(1-cyclohexyl)-α-[3-[1-methylethyl(phenylethyl)amino]propyl]benzeneacetonitrile;

(±)-2,6-dichloro-α-(1-cyclohexyl)-α-[3-[ethyl(phenylethyl)amino]propyl]benzeneacetonitrile;

(±)-2,6-dichloro-α-(1-cyclohexyl)-α-[3-[n-propyl(phenylethyl)amino]propyl]benzeneacetonitrile;

(±)-2,6-dichloro-α-(1-cyclohexyl)-α-[3-[1-methylethyl(phenylethyl)amino]propyl]benzeneacetonitrile;

(±)-2,6-dichloro-α-(1-cyclohexyl)-α-[3-[ethyl(phenylethyl)amino]propyl]benzeneacetonitrile;

(±)-2,6-dichloro-α-(1-cyclohexyl)-α-[3-[n-propyl(phenylethyl)amino]propyl]benzeneacetonitrile;

(±)-2,6-dichloro-α-(1-cyclohexyl)-α-[3-[1-methylethyl(phenylethyl)amino]propyl]benzeneacetonitrile;

(±)-2,6-ditrifluoromethyl-α-(1-cyclohexyl)-α-[3-[ethyl(phenylethyl)amino]propyl]benzeneacetonitrile;

(±)-2,6-ditrifluoromethyl-α-(1-cyclohexyl)-α-[3-[n-propyl(phenylethyl)amino]propyl]benzeneacetonitrile;

(±)-2,6-ditrifluoromethyl-α-(1-cyclohexyl)-α-[3-[1-methylethyl(phenylethyl)amino]propyl]benzeneacetonitrile;

(±)-2,6-difluoro-α-(1-cyclopropyl)-α-[3-[ethyl(phenylethyl)amino]butyl]benzeneacetonitrile;

(±)-2,6-difluoro-α-(1-cyclopropyl)-α-[3-[n-propyl(phenylethyl)amino]butyl]benzeneacetonitrile;

(±)-2,6-difluoro-α-(1-cyclopropyl)-α-[3-[1-methylethyl(phenylethyl)amino]butyl]benzeneacetonitrile;

(±)-2,6-dichloro-α-(1-cyclopropyl)-α-[3-[ethyl(phenylethyl)amino]butyl]benzeneacetonitrile;

(±)-2,6-dichloro-α-(1-cyclopropyl)-α-[3-[n-propyl(phenylethyl)amino]butyl]benzeneacetonitrile;

(±)-2,6-dichloro-α-(1-cyclopropyl)-α-[3-[1-methylethyl(phenylethyl)amino]butyl]benzeneacetonitrile;

(±)-2,6-dichloro-α-(1-cyclopropyl)-α-[3-[ethyl(phenylethyl)amino]butyl]benzeneacetonitrile;

(±)-2,6-dichloro-α-(1-cyclopropyl)-α-[3-[n-propyl(phenylethyl)amino]butyl]benzeneacetonitrile;

(±)-2,6-dichloro-α-(1-cyclopropyl)-α-[3-[1-methylethyl(phenylethyl)amino]butyl]benzeneacetonitrile;

(±)-2,6-ditrifluoromethyl-α-(1-cyclopropyl)-α-[3-[ethyl(phenylethyl)amino]butyl]benzeneacetonitrile;

(±)-2,6-ditrifluoromethyl-α-(1-cyclopropyl)-α-[3-[n-propyl(phenylethyl)amino]butyl]benzeneacetonitrile;

(±)-2,6-ditrifluoromethyl-α-(1-cyclopropyl)-α-[3-[1-methylethyl(phenylethyl)amino]butyl]benzeneacetonitrile;

(±)-2,6-difluoro-α-(1-cyclobutyl)-α-[3-[ethyl(phenylethyl)amino]butyl]benzeneacetonitrile;

(±)-2,6-difluoro-α-(1-cyclobutyl)-α-[3-[n-propyl(phenylethyl)amino]butyl]benzeneacetonitrile;

(±)-2,6-difluoro-α-(1-cyclobutyl)-α-[3-[1-methylethyl(phenylethyl)amino]butyl]benzeneacetonitrile;

(±)-2,6-dichloro-α-(1-cyclobutyl)-α-[3-[ethyl(phenylethyl)amino]butyl]benzeneacetonitrile;

(±)-2,6-dichloro-α-(1-cyclobutyl)-α-[3-[n-propyl(phenylethyl)amino]butyl]benzeneacetonitrile;

(±)-2,6-dichloro-α-(1-cyclobutyl)-α-[3-[1-methylethyl(phenylethyl)amino]butyl]benzeneacetonitrile;

(±)-2,6-dichloro-α-(1-cyclobutyl)-α-[3-[ethyl(phenylethyl)amino]butyl]benzeneacetonitrile;

(±)-2,6-dichloro-α-(1-cyclobutyl)-α-[3-[n-propyl(phenylethyl)amino]butyl]benzeneacetonitrile;

(±)-2,6-dichloro-α-(1-cyclobutyl)-α-[3-[1-methylethyl(phenylethyl)amino]butyl]benzeneacetonitrile;

(±)-2,6-ditrifluoromethyl-α-(1-cyclobutyl)-α-[3-[ethyl(phenylethyl)amino]butyl]benzeneacetonitrile;

(±)-2,6-ditrifluoromethyl-α-(1-cyclobutyl)-α-[3-[n-propyl(phenylethyl)amino]butyl]benzeneacetonitrile;

(±)-2,6-ditrifluoromethyl-α-(1-cyclobutyl)-α-[3-[1-methylethyl(phenylethyl)amino]butyl]benzeneacetonitrile;

(±)-2,6-difluoro-α-(1-cyclopentyl)-α-[3-[ethyl(phenylethyl)amino]butyl]benzeneacetonitrile;

(±)-2,6-difluoro-α-(1-cyclopentyl)-α-[3-[n-propyl(phenylethyl)amino]butyl]benzeneacetonitrile;

(±)-2,6-difluoro-α-(1-cyclopentyl)-α-[3-[1-methylethyl(phenylethyl)amino]butyl]benzeneacetonitrile;

(±)-2,6-dichloro-α-(1-cyclopentyl)-α-[3-[ethyl(phenylethyl)amino]butyl]benzeneacetonitrile;

(±)-2,6-dichloro-α-(1-cyclopentyl)-α-[3-[n-propyl(phenylethyl)amino]butyl]benzeneacetonitrile;

(±)-2,6-dichloro-α-(1-cyclopentyl)-α-[3-[1-methylethyl(phenylethyl)amino]butyl]benzeneacetonitrile;

(±)-2,6-dichloro-α-(1-cyclopentyl)-α-[3-[ethyl(phenylethyl)amino]butyl]benzeneacetonitrile;

(±)-2,6-dichloro-α-(1-cyclopentyl)-α-[3-[n-propyl(phenylethyl)amino]butyl]benzeneacetonitrile;

(±)-2,6-dichloro-α-(1-cyclopentyl)-α-[3-[1-methylethyl(phenylethyl)amino]butyl]benzeneacetonitrile;

(±)-2,6-ditrifluoromethyl-α-(1-cyclopentyl)-α-[3-[ethyl(phenylethyl)amino]butyl]benzeneacetonitrile;

(±)-2,6-ditrifluoromethyl-α-(1-cyclopentyl)-α-[3-[n-propyl(phenylethyl)amino]butyl]benzeneacetonitrile;

(±)-2,6-ditrifluoromethyl-α-(1-cyclopentyl)-α-[3-[1-methylethyl(phenylethyl)amino]butyl]benzeneacetonitrile;

(±)-2,6-difluoro-α-(1-cyclohexyl)-α-[3-[ethyl(phenylethyl)amino]butyl]benzeneacetonitrile;

(±)-2,6-difluoro-α-(1-cyclohexyl)-α-[3-[n-propyl(-phenylethyl)amino]butyl]benzeneacetonitrile;
(±)-2,6-difluoro-α-(1-cyclohexyl)-α-[3-[1-methylethyl(phenylethyl)amino]butyl]benzeneacetonitrile;
(±)-2,6-dichloro-α-(1-cyclohexyl)-α-[3-[ethyl(phenylethyl)amino]butyl]benzeneacetonitrile;
(±)-2,6-dichloro-α-(1-cyclohexyl)-α-[3-[n-propyl(-phenylethyl)amino]butyl]benzeneacetonitrile;
(±)-2,6-dichloro-α-(1-cyclohexyl)-α-[3-[1-methylethyl(phenylethyl)amino]butyl]benzeneacetonitrile;
(±)-2,6-dichloro-α-(1-cyclohexyl)-α-[3-[ethyl(phenylethyl)amino]butyl]benzeneacetonitrile;
(±)-2,6-dichloro-α-(1-cyclohexyl)-α-[3-[n-propyl(-phenylethyl)amino]butyl]benzeneacetonitrile;
(±)-2,6-dichloro-α-(1-cyclohexyl)-α-[3-[1-methylethyl(phenylethyl)amino]butyl]benzeneacetonitrile;
(±)-2,6-ditrifluoromethyl-α-(1-cyclohexyl)-α-[3-[ethyl(phenylethyl)amino]butyl]benzeneacetonitrile;
(±)-2,6-ditrifluoromethyl-α-(1-cyclohexyl)-α-[3-[n-propyl(phenylethyl)amino]butyl]benzeneacetonitrile;
(±)-2,6-ditrifluoromethyl-α-(1-cyclohexyl)-α-[3-[1-methylethyl(phenylethyl)amino]butyl]benzeneacetonitrile;
(±)-2,6-difluoro-α-(1-cyclopropyl)-α-[3-[ethyl(-phenylethyl)amino]pentyl]benzeneacetonitrile;
(±)-2,6-difluoro-α-(1-cyclopropyl)-α-[3-[n-propyl(-phenylethyl)amino]pentyl]benzeneacetonitrile;
(±)-2,6-difluoro-α-(1-cyclopropyl)-α-[3-[1-methylethyl(phenylethyl)amino]pentyl]benzeneacetonitrile;
(±)-2,6-dichloro-α-(1-cyclopropyl)-α-[3-[ethyl(-phenylethyl)amino]pentyl]benzeneacetonitrile;
(±)-2,6-dichloro-α-(1-cyclopropyl)-α-[3-[n-propyl(-phenylethyl)amino]pentyl]benzeneacetonitrile;
(±)-2,6-dichloro-α-(1-cyclopropyl)-α-[3-[1-methylethyl(phenylethyl)amino]pentyl]benezeneacetonitrile;
(±)-2,6-dichloro-α-(1-cyclopropyl)-α-[3-[ethyl(-phenylethyl)amino]pentyl]benzeneacetonitrile;
(±)-2,6-dichloro-α-(1-cyclopropyl)-α-[3-[n-propyl(-phenylethyl)amino]pentyl]benzeneacetonitrile;
(±)-2,6-dichloro-α-(1-cyclopropyl)-α-[3-[1-methylethyl(phenylethyl)amino]pentyl]benzeneacetonitrile;
(±)-2,6-ditrifluoromethyl-α-(1-cyclopropyl)-α-[3-[ethyl(phenylethyl)amino]pentyl]benzeneacetonitrile;
(±)-2,6-ditrifluoromethyl-α-(1-cyclopropyl)-α-[3-[n-propyl(phenylethyl)amino]pentyl]benzeneacetonitrile;
(±)-2,6-ditrifluoromethyl-α-(1-cyclopropyl)-α-[3-[1-methylethyl(phenylethyl)amino]pentyl]benzeneacetonitrile;
(±)-2,6-difluoro-α-(1-cyclobutyl)-α-[3-[ethyl(phenylethyl)amino]pentyl]benzeneacetonitrile;
(±)-2,6-difluoro-α-(1-cyclobutyl)-α-[3-[n-propyl(-phenylethyl)amino]pentyl]benzeneacetonitrile;
(±)-2,6-difluoro-α-(1-cyclobutyl)-α-[3-[1-methylethyl(-phenylethyl)amino]pentyl]benzeneacetonitrile;
(±)-2,6-dichloro-α-(1-cyclobutyl)-α-[3-[ethyl(phenylethyl)amino]pentyl]benzeneacetonitrile;
(±)-2,6-dichloro-α-(1-cyclobutyl)-α-[3-[n-propyl(-phenylethyl)amino]pentyl]benzeneacetonitrile;
(±)-2,6-dichloro-α-(1-cyclobutyl)-α-[3-[1-methylethyl(phenylethyl)amino]pentyl]benzeneacetonitrile;
(±)-2,6-dichloro-α-(1-cyclobutyl)-α-[3-[ethyl(phenylethyl)amino]pentyl]benzeneacetonitrile;
(±)-2,6-dichloro-α-(1-cyclobutyl)-α-[3-[n-propyl(-phenylethyl)amino]pentyl]benzeneacetonitrile;
(±)-2,6-dichloro-α-(1-cyclobutyl)-α-[3-[1-methylethyl(phenylethyl)amino]pentyl]benzeneacetonitrile;
(±)-2,6-ditrifluoromethyl-α-(1-cyclobutyl)-α-[3-[ethyl(phenylethyl)amino]pentyl]benzeneacetonitrile;
(±)-2,6-ditrifluoromethyl-α-(1-cyclobutyl)-α-[3-[n-propyl(phenylethyl)amino]pentyl]benzeneacetonitrile;
(±)-2,6-ditrifluoromethyl-α-(1-cyclobutyl)-α-[3-[1-methylethyl(phenylethyl)amino]pentyl]benzeneacetonitrile;
(±)-2,6-difluoro-α-(1-cyclopentyl)-α-[3-[ethyl(-phenylethyl)amino]pentyl]benzeneacetonitrile;
(±)-2,6-difluoro-α-(1-cyclopentyl)-α-[3-[n-propyl(-phenylethyl)amino]pentyl]benzeneacetonitrile;
(±)-2,6-difluoro-α-(1-cyclopentyl)-α-[3-[1-methylethyl(phenylethyl)amino]pentyl]benzeneacetonitrile;
(±)-2,6-dichloro-α-(1-cyclopentyl)-α-[3-[ethyl(-phenylethyl)amino]pentyl]benezeneacetonitrile;
(±)-2,6-dichloro-α-(1-cyclopentyl)-α-[3-[n-propyl(-phenylethyl)amino]pentyl]benezeneacetonitrile;
(±)-2,6-dichloro-α-(1-cyclopentyl)-α-[3-[1-methylethyl(phenylethyl)amino]pentyl]benzeneacetonitrile;
(±)-2,6-dichloro-α-(1-cyclopentyl)-α-[3-[ethyl(-phenylethyl)amino]pentyl]benzeneacetonitrile;
(±)-2,6-dichloro-α-(1-cyclopentyl)-α-[3-[n-propyl(-phenylethyl)amino]pentyl]benzeneacetonitrile;
(±)-2,6-dichloro-α-(1-cyclopentyl)-α-[3-[1-methylethyl(phenylethyl)amino]pentyl]benezeneacetonitrile;
(±)-2,6-ditrifluoromethyl-α-(1-cyclopentyl)-α-[3-[ethyl(phenylethyl)amino]pentyl]benzeneacetonitrile;
(±)-2,6-ditrifluoromethyl-α-(1-cyclopentyl)-α-[3-[n-propyl(phenylethyl)amino]pentyl]benzeneacetonitrile;
(±)-2,6-ditrifluoromethyl-α-(1-cyclopentyl)-α-[3-[1-methylethyl(phenylethyl)amino]pentyl]benzeneacetonitrile;
(±)-2,6-difluoro-α-(1-cyclohexyl)-α-[3-[ethyl(phenylethyl)amino]pentyl]benzeneacetonitrile;
(±)-2,6-difluoro-α-(1-cyclohexyl)-α-[3-[n-propyl(-phenylethyl)amino]pentyl]benezeneacetonitrile;
(±)-2,6-difluoro-α-(1-cyclohexyl)-α-[3-[1-methylethyl(phenylethyl)amino]pentyl]benzeneacetonitrile;
(±)-2,6-dichloro-α-(1-cyclohexyl)-α-[3-[ethyl(phenylethyl)amino]pentyl]benezeneacetonitrile;
(±)-2,6-dichloro-α-(1-cyclohexyl)-α-[3-[n-propyl(-phenylethyl)amino]pentyl]benzeneacetonitrile;
(±)-2,6-dichloro-α-(1-cyclohexyl)-α-[3-[1-methylethyl(phenylethyl)amino]pentyl]benzeneacetonitrile;
(±)-2,6-dichloro-α-(1-cyclohexyl)-α-[3-[ethyl(phenylethyl)amino]pentyl]benzeneacetonitrile;
(±)-2,6-dichloro-α-(1-cyclohexyl)-α-[3-[n-propyl(-phenylethyl)amino]pentyl]benzeneacetonitrile;
(±)-2,6-dichloro-α-(1-cyclohexyl)-α-[3-[1-methylethyl(phenylethyl)amino]pentyl]benzeneacetonitrile;
(±)-2,6-ditrifluoromethyl-α-(1-cyclohexyl)-α-[3-[ethyl(phenylethyl)amino]pentyl]benzeneacetonitrile;
(±)-2,6-ditrifluoromethyl-α-(1-cyclohexyl)-α-[3-[n-propyl(phenylethyl)amino]pentyl]benzeneacetonitrile;
(±)-2,6-ditrifluoromethyl-α-(1-cyclohexyl)-α-[3-[1-methylethyl(phenylethyl)amino]pentyl]benzeneacetonitrile;
(+)-α-[3-[bis(phenylmethyl)amino]propyl]-4-fluoro-α-(1-methylethyl)benezeneacetonitrile;
(+)-α-[3-[bis(phenylmethyl)amino]propyl]-4-chloro-α-(1-methylethyl)benzeneacetonitrile;

(+)-α-[3-[bis(phenylmethyl)amino]propyl]-4-bromo-α-(1-methylethyl)benzeneacetonitrile;
(±)-α-[3-[bis(phenylmethyl)amino]propyl]-4-trifluoromethyl-α-(1-methylethyl)benzeneacetonitrile;
(+)-α-[3-[bis(phenylmethyl)amino]propyl]-4-fluoro-α-(1cyclopropyl)benzeneacetonitrile;
(+)-α-[3-[bis(phenylmethyl)amino]propyl]-4-fluoro-α-(1-cyclobutyl)benzeneacetonitrile;
(+)-α-[3-[bis(phenylmethyl)amino]propyl]-4-fluoro-α-(1-cyclopentyl)benzeneacetonitrile;
(+)-α-[3-[bis(phenylmethyl)amino]propyl]-4-fluoro-α-(1-cyclohexyl)benzeneacetonitrile;
(+)-α-[3-[bis(phenylethyl)amino]propyl]-4-fluoro-α-(1-methylethyl)benzeneacetonitrile;
(+)-α-[3-[bis(phenylmethyl)amino]butyl]-4-fluoro-α-(1-methylethyl)benzeneacetonitrile;
(+)-α-[3-[bis(phenylmethyl)amino]pentyl]-4-fluoro-α-(1-methylethyl)benezeneacetonitrile;
(+)-α-[3-[bis(phenylmethyl)amino]propyl]-4-fluoro-α-(1-cyclopropyl)benzeneacetonitrile;
(+)-α-[3-[bis(phenylmethyl)amino]propyl]-4-fluoro-α-(1-cyclobutyl)benzeneacetonitrile;
(+)-α-[3-[bis(phenylmethyl)amino]propyl]-4-fluoro-α-(1-cyclopentyl)benzeneacetonitrile;
(+)-α-[3-[bis(phenylmethyl)amino]propyl]-4-fluoro-α-(1-cyclohexyl)benzeneacetonitrile;
(+)-α-[3-[bis(phenylmethyl)amino]propyl]-4-chloro-α-(1-cyclopropyl)benzeneacetonitrile;
(+)-α-[3-[bis(phenylmethyl)amino]propyl]-4-chloro-α-(1-cyclobutyl)benzeneacetonitrile;
(+)-α-[3-[bis(phenylmethyl)amino]propyl]-4-chloro-α-(1-cyclopentyl)benzeneacetonitrile;
(+)-α-[3-[bis(phenylmethyl)amino]propyl]-4-chloro-α-(1-cyclohexyl)benzeneacetonitrile;
(+)-α-[3-[bis(phenylmethyl)amino]propyl]-4-bromo-α-(1-cyclopropyl)benzeneacetonitrile;
(+)-α-[3-[bis(phenylmethyl)amino]propyl]-4-bromo-α-(1-cyclobutyl)benzeneacetonitrile;
(+)-α-[3-[bis(phenylmethyl)amino]propyl]-4-bromo-α-(1-cyclopentyl)benzeneacetonitrile;
(+)-α-[3-[bis(phenylmethyl)amino]propyl]-4-bromo-α-(1-cyclohexyl)benzeneacetonitrile;
(+)-α-[3-[bis(phenylmethyl)amino]propyl]-4-trifluoromethyl-α-(1-cyclopropyl)benzeneacetonitrile;
(+)-α-[3-[bis(phenylmethyl)amino]propyl]-4-trifluoromethyl-α-(1-cyclobutyl)benzeneacetonitrile;
(+)-α-[3-[bis(phenylmethyl)amino]propyl]-4-trifluoromethyl-α-(1-cyclopentyl)benzeneacetonitrile;
(+)-α-[3-[bis(phenylmethyl)amino]propyl]-4-trifluoromethyl-α-(1-cyclohexyl)benzeneacetonitrile;
(+)-α-[3-[bis(phenylethyl)amino]propyl]-4-fluoro-α-(1-methylethyl)benzeneacetonitrile;
(+)-α-[3-[bis(phenylethyl)amino]propyl]-4-chloro-α-(1-methylethyl)benzeneacetonitrile;
(+)-α-[3-[bis(phenylethyl)amino]propyl]-4-bromo-α-(1-methylethyl)benzeneacetonitrile;
(+)-α-[3-[bis(phenylethyl)amino]propyl]-4-trifluoromethyl-α-(1-methylethyl)benezeneacetonitrile;
(+)-α-[3-[bis(phenylmethyl)amino]butyl]-4-fluoro-α-(1-methylethyl)benezeneacetonitrile;
(+)-α-[3-[bis(phenylmethyl)amino]pentyl]-4-fluoro-α-(1-methylethyl)benezeneacetonitrile;
(+)-α-[3-[bis(phenylmethyl)amino]butyl]-4-chloro-α-(1-methylethyl)benezeneacetonitrile;
(+)-α-[3-[bis(phenylmethyl)amino]pentyl]-4-chloro-α-(1-methylethyl)benezeneacetonitrile;
(+)-α-[3-[bis(phenylmethyl)amino]butyl]-4-bromo-α-(1-methylethyl)benezeneacetonitrile;
(+)-α-[3-[bis(phenylmethyl)amino]pentyl]-4-bromo-α-(1-methylethyl)benzeneacetonitrile;
(+)-α-[3-[bis(phenylmethyl)amino]butyl]-4-trifluoromethyl-α-(1-methylethyl)benzeneacetonitrile;
(+)-α-[3-[bis(phenylmethyl)amino]pentyl]-4-trifluoromethyl-α-(1-methylethyl)benzeneacetonitrile;
(+)-α-[3-[bis(phenylethyl)amino]propyl]-4-fluoro-α-(1-cyclopropyl)benzeneacetonitrile;
(+)-α-[3-[bis(phenylethyl)amino]propyl]-4-fluoro-α-(1-cyclobutyl)benzeneacetonitrile;
(+)-α-[3-[bis(phenylethyl)amino]propyl]-4-fluoro-α-(1-cyclopentyl)benzeneacetonitrile
(+)-α-[3-[bis(phenylethyl)amino]propyl]-4-fluoro-α-(1-cyclohexyl)benzeneacetonitrile;
(+)-α-[3-[bis(phenylmethyl)amino]butyl]-4-fluoro-α-(1-cyclopropyl)benzeneacetonitrile;
(+)-α-[3-[bis(phenylmethyl)amino]pentyl]-4-fluoro-α-(1-cyclopropyl)benzeneacetonitrile;
(+)-α-[3-[bis(phenylmethyl)amino]butyl]-4-fluoro-α-(1-cyclobutyl)benzeneacetonitrile;
(+)-α-[3-[bis(phenylmethyl)amino]pentyl]-4-fluoro-α-(1-cyclobutyl)benzeneacetonitrile;
(+)-α-[3-[bis(phenylmethyl)amino]butyl]-4-fluoro-α-(1-cyclopentyl)benzeneacetonitrile;
(+)-α-[3-[bis(phenylmethyl)amino]pentyl]-4-fluoro-α-(1-cyclopentyl)benzeneacetonitrile;
(+)-α-[3-[bis(phenylmethyl)amino]butyl]-4-fluoro-α-(1-cyclohexyl)benzeneacetonitrile;
(+)-α-[3-[bis(phenylmethyl)amino]pentyl]-4-fluoro-α-(1-cyclohexyl)benzeneacetonitrile;
(+)-α-[3-[bis(phenylethyl)amino]butyl]-4-fluoro-α-(1-methylethyl)benzeneacetonitrile;
(+)-α-[3-[bis(phenylmethyl)amino]pentyl]-4-fluoro-α-(1-methylethyl)benzeneacetonitrile;
(+)-α-[3-[bis(phenylethyl)amino]propyl]-4-fluoro-α-(1-cyclopropyl)benzeneacetonitrile;
(+)-α-[3-[bis(phenylethyl)amino]propyl]-4-fluoro-α-(1-cyclobutyl)benzeneacetonitrile;
(+)-α-[3-[bis(phenylethyl)amino]propyl]-4-fluoro-α-(1-cyclopentyl)benzeneacetonitrile;
(+)-α-[3-[bis(phenylethyl)amino]propyl]-4-fluoro-α-(1-cyclohexyl)benzeneacetonitrile;
(+)-α-[3-[bis(phenylethyl)amino]propyl]-4-chloro-α-(1-cyclopropyl)benzeneacetonitrile
(+)-α-[3-[bis(phenylethyl)amino]propyl]-4-chloro-α-(1-cyclobutyl)benzeneacetonitrile;
(+)-α-[3-[bis(phenylethyl)amino]propyl]-4-chloro-α-(1-cyclopentyl)benzeneacetonitrile
(+)-α-[3-[bis(phenylethyl)amino]propyl]-4-chloro-α-(1-cyclohexyl)benzeneacetonitrile;
(+)-α-[3-[bis(phenylethyl)amino]propyl]-4-bromo-α-(1-cyclopropyl)benzeneacetonitrile;
(+)-α-[3-[bis(phenylethyl)amino]propyl]-4-bromo-α-(1-cyclobutyl)benzeneacetonitrile;
(+)-α-[3-[bis(phenylethyl)amino]propyl]-4-bromo-α-(1-cyclopentyl)benzeneacetonitrile;
(+)-α-[3-[bis(phenylethyl)amino]propyl]-4-bromo-α-(1-cyclohexyl)benzeneacetonitrile;
(+)-α-[3-[bis(phenylethyl)amino]propyl]-4-trifluoromethyl-α-(1-cyclopropyl)benzeneacetonitrile;
(+)-α-[3-[bis(phenylethyl)amino]propyl]-4-trifluoromethyl-α-(1-cyclobutyl)benzeneacetonitrile;
(+)-α-[3-[bis(phenylethyl)amino]propyl]-4-trifluoromethyl-α-(1-cyclopentyl)benzeneacetonitrile;
(+)-α-[3-[bis(phenylethyl)amino]propyl]-4-trifluoromethyl-α-(1-cyclohexyl)benzeneacetonitrile;
(+)-α-[3-[bis(phenylmethyl)amino]butyl]-4-fluoro-α-(1-cyclopropyl)benzeneacetonitrile;

(+)-α-[3-[bis(phenylmethyl)amino]butyl]-4-fluoro-α-(1-cyclobutyl)benzeneacetonitrile;
(+)-α-[3-[bis(phenylmethyl)amino]butyl]-4-fluoro-α-(1-cyclopentyl)benzeneacetonitrile;
(+)-α-[3-[bis(phenylmethyl)amino]butyl]-4-fluoro-α-(1-cyclohexyl)benzeneacetonitrile;
(+)-α-[3-[bis(phenylmethyl)amino]pentyl]-4-fluoro-α-(1-cyclopropyl)benzeneacetonitrile;
(+)-α-[3-[bis(phenylmethyl)amino]pentyl]-4-fluoro-α-(1-cyclobutyl)benzeneacetonitrile;
(+)-α-[3-[bis(phenylmethyl)amino]pentyl]-4-fluoro-α-(1-cyclopentyl)benzeneacetonitrile;
(+)-α-[3-[bis(phenylmethyl)amino]pentyl]-4-fluoro-α-(1-cyclohexyl)benzeneacetonitrile;
(+)-α-[3-[bis(phenylmethyl)amino]butyl]-4-chloro-α-(1-cyclopropyl)benzeneacetonitrile;
(+)-α-[3-[bis(phenylmethyl)amino]butyl]-4-chloro-α-(1-cyclobutyl)benzeneacetonitrile;
(+)-α-[3-[bis(phenylmethyl)amino]butyl]-4-chloro-α-(1-cyclopentyl)benzeneacetonitrile;
(+)-α-[3- Ibis (phenylmethyl)amino]butyl]-4-chloro-α-(1-cyclohexyl)benzeneacetonitrile;
(+)-α-[3-[bis(phenylmethyl)amino]pentyl]-4-chloro-α-(1-cyclopropyl)benezeneacetonitrile;
(+)-α-[3-[bis(phenylmethyl)amino]pentyl]-4-chloro-α-(1-cyclobutyl)benzeneacetonitrile;
(+)-α-[3-[bis(phenylmethyl)amino]pentyl]-4-chloro-α-(1-cyclopentyl)benzeneacetonitrile;
(+)-α-[3-[bis(phenylmethyl)amino]pentyl]-4-chloro-α-(1-cyclohexyl)benzeneacetonitrile;
(+)-α-[3-[bis(phenylmethyl)amino]butyl]-4-bromo-α-(1-cyclopropyl)benzeneacetonitrile;
(+)-α-[3-[bis(phenylmethyl)amino]butyl]-4-bromo-α-(1-cyclobutyl)benzeneacetonitrile;
(+)-α-[3-[bis(phenylmethyl)amino]butyl]-4-bromo-α-(1-cyclopentyl)benzeneacetonitrile;
(+)-α-[3-[bis(phenylmethyl)amino]butyl]-4-bromo-α-(1-cyclohexyl)benzeneacetonitrile;
(+)-α-[3-[bis(phenylmethyl)amino]pentyl]-4-bromo-α-(1-cyclopropyl)benzeneacetonitrile;
(+)-α-[3-[bis(phenylmethyl)amino]pentyl]-4-bromo-α-(1-cyclobutyl)benzeneacetonitrile;
(+)-α-[3- Ibis (phenylmethyl)amino]pentyl]-4-bromo-α-(1-cyclopentyl)benzeneacetonitrile;
(+)-α-[3-[bis(phenylmethyl)amino]pentyl]-4-bromo-α-(1-cyclohexyl)benzeneacetonitrile;
(+)-α-[3-[bis(phenylmethyl)amino]butyl]-4-trifluoromethyl-α-(1-cyclopropyl)benzeneacetonitrile;
(+)-α-[3-[bis(phenylmethyl)amino]butyl]-4-trifluoromethyl-α-(1-cyclobutyl)benzeneacetonitrile;
(+)-α-[3-[bis(phenylmethyl)amino]butyl]-4-trifluoromethyl-α-(1-cyclopentyl)benzeneacetonitrile;
(+)-α-[3-[bis(phenylmethyl)amino]butyl]-4-trifluoromethyl-α-(1-cyclohexyl)benzeneacetonitrile;
(+)-α-[3-[bis(phenylmethyl)amino]pentyl]-4-trifluoromethyl-α-(1-cyclopropyl)benzeneacetonitrile;
(+)-α-[3-[bis(phenylmethyl)amino]pentyl]-4-trifluoromethyl-α-(1-cyclobutyl)benzeneacetonitrile;
(+)-α-[3-[bis(phenylmethyl)amino]pentyl]-4-trifluoromethyl-α-(1-cyclopentyl)benzeneacetonitrile;
(+)-α-[3-[bis(phenylmethyl)amino]pentyl]-4-trifluoromethyl-α-(1-cyclohexyl)benzeneacetonitrile;
(+)-α-[3-[bis(phenylethyl)amino]butyl]-4-fluoro-α-(1-methylethyl)benezeneacetonitrile;
(+)-α-[3-[bis(phenylethyl)amino]pentyl]-4-fluoro-α-(1-methylethyl)benezeneacetonitrile;
(+)-α-[3-[bis(phenylethyl)amino]butyl]-4-chloro-α-(1-methylethyl)benezeneacetonitrile;
(+)-α-[3-[bis(phenylethyl)amino]pentyl]-4-chloro-α-(1-methylethyl)benzeneacetonitrile;
(+)-α-[3-[bis(phenylethyl)amino]butyl]-4-bromo-α-(1-methylethyl)benezeneacetonitrile;
(+)-α-[3-[bis(phenylethyl)amino]pentyl]-4-bromo-α-(1-methylethyl)benzeneacetonitrile;
(+)-α-[3-[bis(phenylethyl)amino]butyl]-4-trifluoromethyl-α-(1-methylethyl)benzeneacetonitrile;
(+)-α-[3-[bis(phenylethyl)amino]pentyl]-4-trifluoromethyl-α-(1-methylethyl)benzeneacetonitrile;
(+)-α-[3-[bis(phenylethyl)amino]butyl]-4-fluoro-α-(1-cyclopropyl)benzeneacetonitrile;
(+)-α-[3-[bis(phenylethyl)amino]pentyl]-4-fluoro-α-(1-cyclopropyl)benzeneacetonitrile;
(+)-α-[3-[bis(phenylethyl)amino]butyl]-4-fluoro-α-(1-cyclobutyl)benzeneacetonitrile;
(+)-α-[3-[bis(phenylethyl)amino]pentyl]-4-fluoro-α-(1-cyclobutyl)benzeneacetonitrile;
(+)-α-[3-[bis(phenylethyl)amino]butyl]-4-fluoro-α-(1-cyclopentyl)benzeneacetonitrile;
(+)-α-[3-[bis(phenylethyl)amino]pentyl]-4-fluoro-α-(1-cyclopentyl)benzeneacetonitrile;
(+)-α-[3-[bis(phenylethyl)amino]butyl]-4-fluoro-α-(1-cyclohexyl)benzeneacetonitrile;
(+)-α-[3-[bis(phenylethyl)amino]pentyl]-4-fluoro-α-(1-cyclohexyl)benzeneacetonitrile;

A family of specific compounds of higher interest within Formula I consists of compounds and pharmaceutically-acceptable salts thereof, as follows:

(±)-3,4-difluoro-α-(1-methylethyl)-α-[3-[methyl(phenylmethyl)amino]propyl]benezeneacetonitrile;
(±)-4-fluoro-α-(1-methylethyl)-α-[3-[methyl(phenylmethyl)amino]propyl]benzeneacetonitrile;
(±)-4-fluoro-α-(1-methylethyl)-α-[3-[methyl(2-phenylethyl)amino]propyl]benzeneacetonitrile;
(±)-α-cyclopentyl-4-fluoro-α-[3-(methyl(phenylmethyl)amino]propyl]benzeneacetonitrile;
(±)-4-fluoro-α-(1-methylethyl)-α-[4-(methyl(phenylmethyl)amino]butyl]benzeneacetonitrile;
(±)-4-fluoro-α-(1-methylethyl)-α-[5-(methyl(phenylmethyl)amino]pentyl]benzeneacetonitrile;
(±)-α-(1-methylethyl)-α-[3-[methyl(2-phenylethyl)amino]propyl]-4-(trifluoromethyl)benzeneacetonitrile;
(±)-2-fluoro-α-(1-methylethyl)-α-[3-[methyl(phenylmethyl)amino]propyl]benzeneacetonitrile;
(±)-2,6-difluoro-α-(1-methylethyl)-α-[3-[methyl(phenylmethyl)amino]propyl]benzeneacetonitrile; and
(±)-α-[3-[bis(phenylmethyl)amino]propyl]-4-fluoro-α-(1-methylethyl)benzeneacetonitrile.

GENERAL SYNTHETIC PROCEDURES

Compounds embraced by Formula I may be prepared in accordance with Scheme I, which follows, wherein each of the R substituents are as defined in Formula I above, except where further noted.

Synthesis of the compounds of Formula I can be achieved by the reaction of bis-electrophile, sequentially, with two nucleophiles (Scheme I). The bis-electrophile can be, for example, an alkyl chain, substituted at the desired positions with a halogen or a sulfonic acid ester or the like or by a group that can be transformed into such an electrophile. It may be convenient, upon treatment with a nucleophile, that the two electrophilic groups have a differential reactivity toward nucleophilic substitution, e.g., a chloro group and a bromo group. Examples of bis-electrophiles are 3-bromo-chloropropane, 4-bromo-chlorobutane, 4-bromobutane-1-para-toluenesulfonate, 5-chloro-1-methyl-butane trifluoromethanesulfonate and the like. Examples of nucleophiles that can be reacted with the above bis-electrophiles are the anions of aryl-propionitriles (compound 1, scheme I) and aryl-acetic acid esters (compound 17, scheme IV), prepared using non-nucleophilic bases, and primary or secondary amines (compound 5, scheme I). Non-nucleophilic bases are, for example, sodium hydride, potassium hydride, lithium di-iso-propyl amide, lithium dicyclohexylamide and the like. Non-nucleophilic bases that are considered weaker bases then those discussed above include, for example, dimethylamino pyridine, potassium carbonate, silver oxide and diazabicycloundecane. Electrophilic groups are indicated in by $E_1$ and $E_2$.

Solvents useful for the preparation of thses compounds are dipolar aprotic solvents such as dimethylformamide (DMF), dimethylsufoxide (DMSO), acetonitrile, dimethyl acetamide, sulfolane, tetra-methyl urea, dimethyl acetamide and the like. Protic solvents such as methanol, ethanol, tert-butyl alcohol or nonprotic solvents such as diethyl ether, tetrahydrofuran, pyridine, lutidine, collidine, or benzofuran can also be used. Ketones such as acetone or methylethyl ketone are also useful especially when exchanging electrophiles as in the case of, for example, iodide for chlorine.

The preparations illustrated in Scheme I can be at temperatures of between 0° C. and about 200° C. Temperatures of between about room temperature and 100° C. are preferred since it is convenient to implement the conversions at the reflux temperature of the reaction solvent.

The aryl nitrile (1) can be alkylated with a protected aminoalkyl-$E_1$ reagent where $E_1$ represents halogen, tosylate or a similar electrophilic leaving group. A preferred protecting group (P) is a succinimide or a phthalimide as is illustrated in Step 2.

Bases that are useful in this step include alkyl lithium reagents such as tert-butyl lithium, lithium amides such as lithium dicyclohexyl amide (LDA), magnesium salts such as tert-butyl magnesium, alsoholates such as sodium ethoxide or potassium tert-butoxide, metal hydrides such as potassium hydride, sodium hydride or calcium hydride or, metal hydroxides such as potassium hydroxide or sodium hydroxide or tetra-substituted ammonium hydroxides or strong organic bases such as dimethylaminopyridines (DMAP).

Solvents for these alkylations can be protic solvents such as methanol, ethanol, tert-butyl alcohol or nonprotic solvents such as diethyl ether, tetrahydrofuran, pyridine, lutidine, collidine or benzofuran. In the case of alcohols, the solvents may be the same alcohol as is used to form the alcoholate anion used to form the anion of the starting material (1). A special class of useful solvents are the dipolar aprotic solvents such as dimethylformamide (DMF), dimethylsulfoxide (DMSO), acetonitrile, dimethyl acetamide, sulfolane, tetra-methyl urea, dimethyl acetamide and the like.

A preferred alkylation method is to use a phase transfer system. An example of a phase transfer system is a tetra substituted ammonium hydroxide such as tetra butyl ammonium chloride in water mixed with a partially miscible organic solvent such as methylene chloride, chloroform or tetrachloroethylene {W. P. Weber, G. W. Gokel, *Phase Transfer Catalysis in Organic Synthesis*, Springer-Verlag, Berlin Heidelberg, 1977}.

Mixtures of the abovesolvents may also be used to improve the solubility of reactants, reaction intermediates or products, control reaction temperatures at reflux or encourage precipitation of the desired product or an undesired impurity or reaction product and may be useful for the control of the reaction temperature.

The temperature of the reaction can vary from about −100° C. to about 285° C. Lower temperatures are preferred for reactions carried out using organic metal reagents, e.g., −100° to −30° C. whereas reflux tem-

SCHEME I

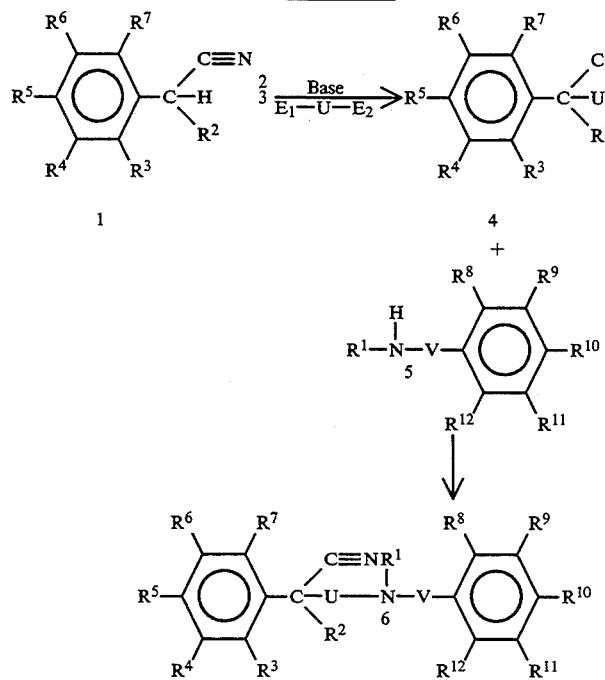

peratures are preferred for use with metal alcoholate bases, e.g., abot 65° C. for methanol, organic bases, e.g., about 170° C. for collidine, 153° C. for DMF or 285° C. for sulfolane, and for phase transfer reactions.

The preparation of the reagent used in step 2 is an example of a nucleophilic substitution reaction using a well known preformed potassium salt of a phthalimide that is an article of commerce. Preferred conditions for implementing a nucleophilic substitution are illustrated in Scheme I.

Production of the primary amines (8) or their acid addition salts, which are useful intermediates as well as immune modolation agents, by removal of the protecting group is illustrated in Step 3 of Scheme II. Hydrazines or a hydrazine hydrate are the preferred regents for accomplishing this type of transformation. Most preferred is hydrazine hydrate.

The intermediate primary amines (8, Scheme II), which may also be immune modulation agents, may be substituted on nitrogen by reductive alylation with an aldehyde, ketone or aldehyde or ketone equivalent as is illustrated in Scheme II. The preferred method of preparation of compound 9 is treatment of the amine with the required aldehyde in the presence of a metal cyanoborohydride reagent such as sodium cyanoborohydride or potassium cyanoborohydride substituted with an organic radical such as is disclosed in GB Patent number 1,390,214. Solvents useful in this reaction are alcohols such as methanol or ethanol or solvent mixtures such as an alcohol and tetrahydrofuran or dimethylformamide. A temperature range is room temperature to the reflux temperature of the solvent, e.g., 65° to 153° C. It should be noted that this reductive alkylation may be repeated with the same or a different aldehyde or ketone to provide the compounds in Scheme I. In addition, the Schiff base, imminium salt or enamine between 8 and an aldehyde or ketone may be prepared, with or without isolation, at an intermediate step and subsequently reduced as above is such an intermediate step is desired.

Acylation of 8 to produce an amide is a alternative procedure for the preparation of the compounds of this invention. Suitable acylating agents are the acid halide, mixed anhydride or anhydride of the carboxylic acid illustrated in Scheme II. The preparation of such intermediates are well known in the art or may be articles of commerce, c. f., discussion of Scheme II.

Non-protic solvents are preferred for the acylation reaction although alcohols such as methanol or isopropanol can be used especially at low temperatures. Examples are ethers such as THF or diethyl ether, ketones such as methylethyl ketone or acetone, dipolar aprotic solvents such as dimethylformamide (DMF), dimethylsulfoxide (DMSO), acetonitrile, dimethyl acetamide, sulfolane, tetra-methyl urea, dimethyl acetamide and the like, halogenated solvents such as methylene chloride, chloroform or methylene chloride or solvents such as heptane, toluene, or cyclohexane.

The acylation reaction illustrated in Scheme II can be carried out at room temperature or from about $-80°$ C. to the reflux temperature of the desired solvent, e.g., about 285° C. for sulfolane.

Reduction of the amide to give the product 9 of this invention as is shown in Scheme II is preferably carried out using a hydride donor such as lithium aluminum hydride, potassium borohydride, aluminum hydride or a borane complex or diborane.

Solvents preferred for this reduction are ethers such as THF of diethyl ether, halogenated solvents such as methylene chloride or tetrachloroethylene or mixtures of these solvents. If higher temperatures are required, high boiling alcohols such as hexanol, octanol, dodecanol or cyclohexanol may be used preferably with less reactive reagents such as potassium borohydride. Suitable temperatures for this reduction are from between about $-80°$ C. to about 260° C. Room temperature is preferred for reactions using, for example, the borane complex with THF in THF solvent as the reducing agent.

Product 6 can then be prepared by reacting the secondary amine (9) with electrophile (10) under similar conditions as illustrated in step 2 of Scheme I.

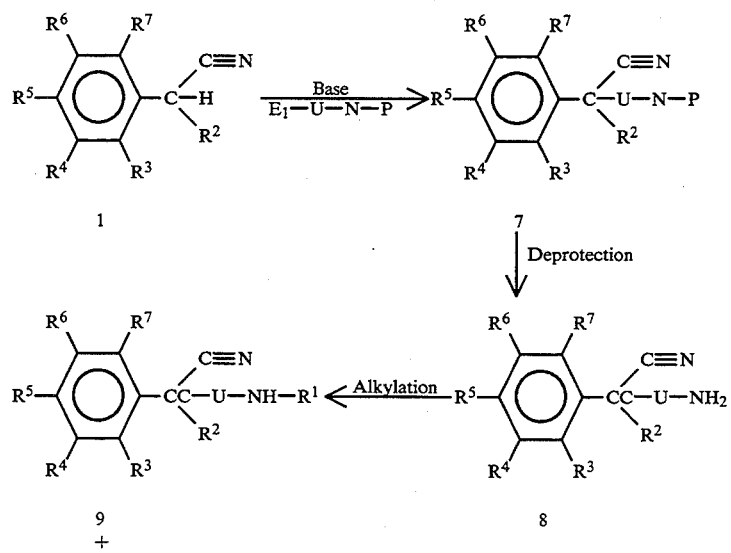

SCHEME II

-continued
SCHEME II

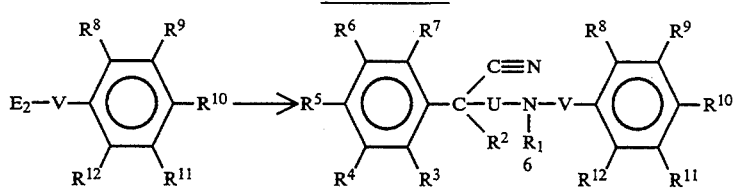

Step 1 in Scheme III can be carried out as in Step 1 in Scheme II. The choice of reagents, temperatures of the reaction and solvents for the reaction are the same as those exemplified in Scheme II. The product of this reaction is utilized in the same fashion to produce compound 11.

In Step 2 of scheme III, an alternative alkylating agent 12 is used as illustrated to prepare compound 11 wherein the electrophilic group $E_1$ is as defined above in Scheme I and Scheme II, $R^{26}$ and $R^{27}$ are defined above, and the carboxylate portion of the alkylating agent is protected as an ester. The alcohol portion of the ester function, represented as R, may be simple such as methyl or ethyl or more hindered such as tert-butyl or isoamyl. Other suitable alcohol functions are, for example, dimethylcyclohexyl, benzyl, substituted aryl, substituted benzyl.

The R group may be removed from compound 12 to give an intermediate carboxylic acid by a number of standard ways well known to those skilled in the art. For example, the ester may be hydrolyxed using an acid such as hydrochloric acid or a base such as sodium or potassium hydroxide at room temperature or with heating to reflux temperature. Some esters, for example benzyl esters and substituted benzyl esters, may be removed by catalytic hydrogenation. Suitable catalysts are Raney nickel, palladium and palladium on carbon, or platinum or platinum oxide in solvents such as methyl or ethyl alcohol or acetic acid at hydrogen pressures of from atmospheric pressure to about 1000 psi and reaction temperatures of from room temperature to about 200° C. High temperature and/or pressure reactions may require that the conversion be carried out in a special reaction vessel (bomb). Hydrogen exchange using, for example, cyclohexene with palladium on carbon at reflux is also useful.

The carboxylic acid or carboxylate salt product obtained from the above reactions may then be converted into and activated carboxylate derivative (13) such as when COX is an acid halide, an anhydride or a mixed anhydride. These conversions are well known to those skilled in the art, for example, acid chlorides obtained by teatment of the acid or salt with thionyl chloride or oxalyl chloride or mixed anhydrides obtained by treatment with isobutyl chloroformate. Anhydrides can be prepared by treatment of an acid chloride with an acid salt or the acid with phosphorus pentoxide.

Secondary or tertiary amide formation can be accomplished by treatment of an activated carboxyl group with a secondary or tertiary amine using methods well known to those skilled in the art. Typically, these condensations are carried out in solvents such as THF, diethyl ether, methylene chloride, acetone, pyridine or toluene at temperatures of between about −80° C. to 100° C. A base such as triethylamine, DMAP, N-methyl-morpholine, sodium carbonate, calcium carbonate or the like may be added to accept any protic acids formed during the reaction.

Amide formation can also take place using direct exchange of an amine for the ester alcohol. This type of exchange is preferably carried out at reflux in a solvent such as toluene or THF that will allow distillation or co-distillation or azeotrope formation with the product alcohol. Alternatively, molecular sieves may be used to remove the alcohol from the mixture as it is formed.

Reduction of the amides can be accomplished using hydride reagents. Thus, reduction of amide 14 gives the product 6 of this invention as is shown in Scheme III. This reduction is preferably carried out using a hydride donor such as lithium aluminum hydride, potassium borohydride, aluminum hydride, a borane complex or diborane.

SCHEME III

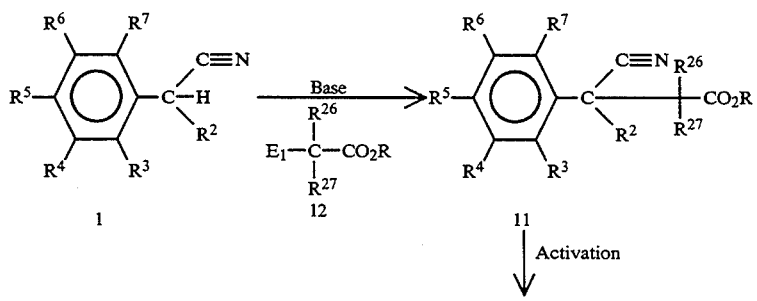

-continued
SCHEME III

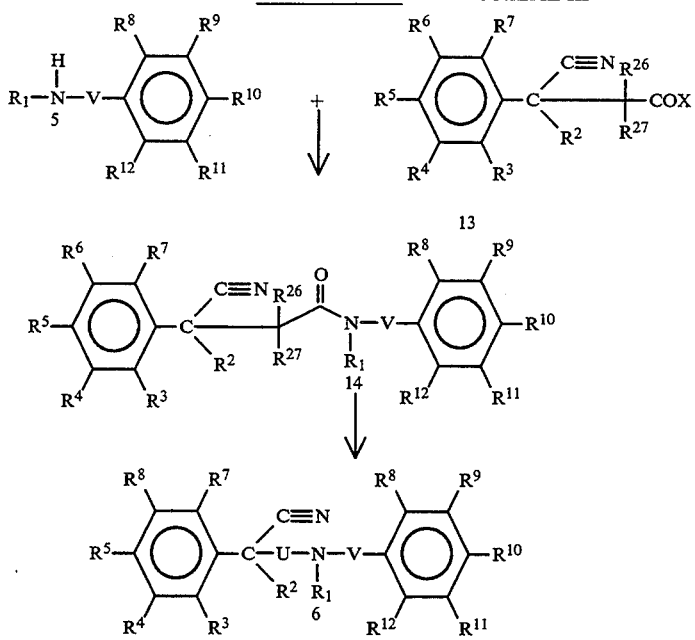

Solvents preferred for this reduction are ethers such as THF or diethyl ether, halogenated solvents such as methylene chloride or tetrachloroethylene or mixtures of these solvents. If higher temperatures are required, high boiling alcohols such as hexanol, octanol, dodecanol or cyclohexanol may be used preferably with less reactive reagents such as potassium borohydride. Suitable temperatures for this reduction are from between about −80° C. to about 260° C. Room temperature is preferred for reactions using, for example, the borane complex with THF as the reducing agent.

Scheme IV is an alternative method of preparation of the compounds of this invention. It is especially useful for providing novel, optical active intermediates for the synthesis of compound 6. Compounds 17, 18 or 19 can be resolved by crystallization or chromatographically when R is an optically active alcohol. The acid additions salts of the compounds where R=H and an optically active base can also be separated (resolved) to provide optically active acids upon protonation with an acid. In the latter case, re-esterification may be required.

The ester is alkylated following anion formation with a base with an electrophile (Step 1). The product is then alkylated a second time with a bis electrophile in Step 2 to give product.

Bases that are useful in these steps include alkyl lithium reagents such as tert-butyl lithium, lithium amides such as lithium dicyclohexyl amide (LDA), magnesium salts such as tert-butyl magnesium, alcoholates such as sodium ethoxide or potassium tert-butoxide, metal hydrides such as potassium hydride, sodium hydride or calcium hydride or, metal hydroxides such as anhydrous potassium hydroxide or sodium hydroxide or tetra-substituted ammonium hydroxides or stron organic bases such as dimethylaminopyridines (DMAP).

Solvents for these alkylations can be protic solvents such as methanol, ethanol, tert-butyl alcohol or nonprotic solvents such as diethyl ether, tetrahydrofuran, pyridine, lutidine, collidine or benzofuran. In the case of alcohols, the solvent may be the same alcohol as is used to form the alcoholate anion used to form the anion of the starting material 16. A special class of useful solvents are the dipolar aprotic solvents such as dimethylformamide (DMF), dimethylsulfoxide (DMSO), acetonitrile, dimethyl acetamide, sulfolane, tetra-methyl urea, dimethyl acetamide and the like.

Mixtures of the above solvents may also be used to improve the solubility of reactants, reaction intermediates or products, control reaction temperatures at refulx or encourage precipitation of the desired product or an undesired impurity or reaction product and may be useful for the contraol of the reaction temperatures.

The temperature of the reactions can vary from about −100° C. to about 285° C. Lower temperatures are preferred for reactions carried out using organic metal reagents, e.g., −100° to −30° C. with eventual warming to room temperature whereas refulx temperatures are preferred for use with metal alcoholate bases, e.g., about 65° C. for methanol, organic bases, e.g., about 170° C. for collidine, 153° C. for DMF or 285° C. for sulfolane.

The electrophiles for Step 3, Scheme IV are as illustrated in Scheme I.

Hydrolysis of compound 19 followed by activation of the carboxyl and treatment with ammonia provides product compound 20. Methods of hydrolysis, active carboxyl group formation and the subsequent formation of an amide are detailed for the preparation of the amides in Scheme III.

Dehydration of the amide 20 to the product (6) of this invention is shown in Step 8 of Scheme IV. Dehydration of the amide can be accomplished with, for example, phosphorus oxychloride, thionyl chloride or phosphorus pentoxide. Solvents for this reaction can be, for example, toluene, xylene, decalin, tetrachloroethane, methylene chloride, chloroform or the like. In the case of phosphorus oxychloride and thionyl chloride, it may be convenient to use the reagent as the reaction solvent. The temperature of the reaction can be varied from room temperature to about 200° C.

Other factors that can improve the yields and the quality of the products from the above reactions are the use of an inert gas atmosphere and/or a drying agent. Examples of inert gases are nitrogen, argon and helium. Examples of agents for drying the reaction atmosphere are calcium sulphate and calcium chloride. References for the discussion above are: 1. H. O. House, *Modern Synthetic Reactions*, 2nd ed., W. A. Benjamin, Inc., Philippines, 1972; 2. W. Carruthers, *Some Modern Methods Of Organic Synthesis*, 2nd ed., Cambridge University Press, Cambridge, 1978; 3. J. March, *Advanced Organic Chemistry*, 3rd ed., John Wilet & Sons, New York 1985.

scope of the invention. All parts are by weight unless otherwise indicated.

EXAMPLE 1

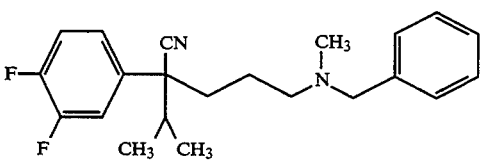

(±)-3,4-difluoro-α-(1-methylethyl)-α-[3-[methyl(-

SCHEME IV

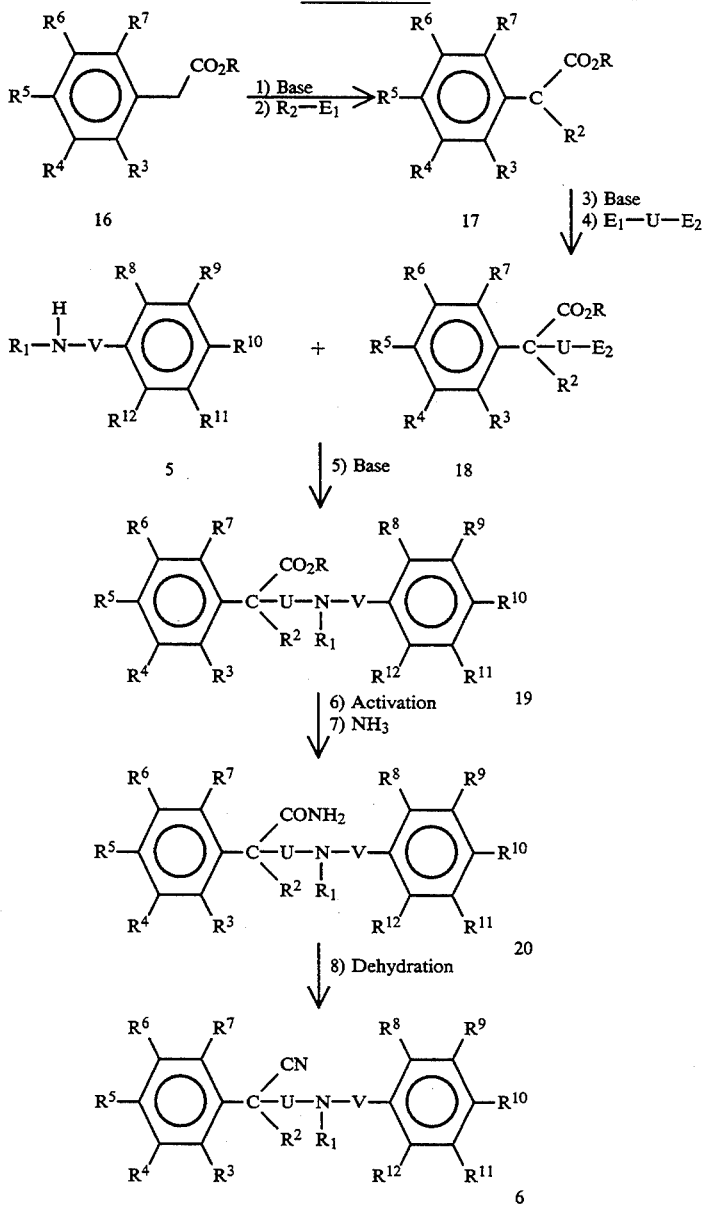

The following Examples 1–13 are detailed descriptions of the methods of preparation of compounds of Formula I. These detailed preparations fall within the scope of, and serve to exemplify, the above described Generic Procedures which form part of the invention. These Examples 1–13 are presented for illustrative purposes only and are not intended as a restriction on the phenylmethyl)amino]propyl]benzeneacetonitrile Step(a): Preparation of (±)-3,4-difluoro-α-(1-methylethyl)benzeneacetonitrile 3,4-difluorophenyl acetonitrile (25.0 g, 0.163 mole) was added to 50% sodium hydroxide (11.4 g, 0.143 mole). Sodium hydroxide pellets (1.6 g, 0.04 mole) and tetrabutylammonium chloride (8.1 g, 0.029 mole) were added and the mixture heated to 45° C. 2-Bromopropane (22.0 g, 0.190 mole) was added and the mixture was heated to 60° C. for 1 hr. and then 90° C. for 1 hr. The mixture was stirred for 48 hrs. at room temperature. Water (100 mL) was added followed by toluene (200 mL). The layers were separated and the aqueous layer was washed with toluene (50 mL). The toluene wash were combined with the separated toluene layer and then dried over anhydrous sodium sulfate, filtered and concentrated in vacuo to an oil. The title compound was purified by silica gel chromatography. The structure was supported by NMR infrared spectroscopy and elemental analysis (M.W.=195.21). Analysis: Calcd. for $C_{11}H_{11}NF_2$: C, 67.68; H, 5.68; N, 7.18; Found: C, 67.55; H, 5.73; N, 7.06.

Step (b): Preparation of (±)-3,4-difluoro-α-(1-methylethyl)-α-(3-chloropropyl)benzeneacetonitrile Potassium bis(trimethylsilyl)amide (0.5M in toluene, 202 mL, 0.101 mole) was added by syringe over 40 min. to a cold (−76° C.) solution of the product of Example 1, Step (a), in tetrahydrofuran (400 mL) keeping the temperature between −65° and −75° C. After stirring at −76° C. for 1 hr, 3-bromo-1-chloropropane was added and the reaction was allowed to come to room temperature. Water (100 mL) was added and the tetrahydrofuran was removed by rotary evaporator. Diethyl ether (300 mL) was added and the layers were separated. The aqueous layer was washed with diethyl ether (300 mL). The organic layer and washes were combined and dried over anhydrous sodium sulfate, filtered and concentrated in vacuo. The product was purified by vacuum distillation (125°-135° C., 0.1 mm Hg). The structure was supported by NMR, infrared spectroscopy and elemental analysis (M.W.=271.74). Analysis: Calcd, for $C_{14}H_{16}NF_2Cl$: C, 61.88; H, 5.93; N, 5.15; Cl, 13.05; Found: C, 61.87; H, 5.96; N, 5.07; Cl, 13.08.

Step (c): Preparation of (±)-3,4-difluoro-α-(1-methylethyl)-α-[3-[methyl(phenylmethyl)amino]propyl]benzeneacetonitrile The product of Example 1, Step (b), (0.54 g, 0.0020 mole), N-benzylmethylamine (0.29 g, 0.0024 mole) and potassium carbonate (0.33 g, 0.0024 mole) were stirred in dimethylformamide (25 mL) for 10 days at room temperature. The mixture was concentrated in vacuo. Water (25 mL) and ethyl acetate (25 mL) were added to the residue. The layers were separated and the aqueous layer was washed with ethyl acetate (25 mL). The ethyl acetate layer and washes were combined and dried over anhydrous sodium sulfate, filtered and concentrated in vacuo. The product was purified by silica gel chromatography to give an oil. The structure was supported by NMR, infrared spectroscopy and elemental analysis (M.W.=356.46+0.15 mole $H_2O$). Analysis: Calcd. for $C_{22}H_{26}N_2F_2$. 0.15M $H_2O$): C, 73.57; H, 7.38; N, 7.80; Found: C, 73.57; H, 7.33; N, 7.71.

EXAMPLE 2

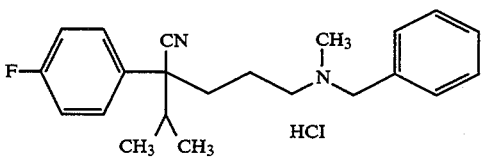

(±)-4-fluoro-α-(1-methylethyl)-α-[3-[methyl(phenylmethyl)amino]propyl]benzeneacetonitrile, monohydrochloride Step (a): Preparation of 4-fluoro-α-(1-methylethyl)benzeneacetonitrile.

To a stirred solution of 50% sodium hydroxide (5.2 g, 65.2 mmol) there was added 4-fluorophenylacetonitrile (10.0 g, 74.1 mmol), sodium hydroxide pellets (0.7 g, 18.5 mmol) and tetrabutylammonium chloride (3.3 g, 14.1 mmol) and the reaction mixture was heated to 45° C. To the reaction mixture there was added 2-bromopropane (10.0 g, 81.5 mmol) and the reaction mixture heated at 60°-65° C. for 1 hour, and then at 90°-95° C. for 1 hour. The reaction mixture was cooled to ambient temperature. The reaction mixture was diluted with a mixture of 1:1 diethyl ether/water (100 mL). The layers were separated and the aqueous layer was washed with diethyl ether (25 mL). The organic layers were combined, washed with brine (25 mL), dried over sodium sulfate, filtered, and concentrated. The residue was purified by flash chromatography (silica gel, 30/70 methylene chloride/hexane) to give 9.4 g (71% yield) of 4-fluoro-a-(1-methylethyl)benzeneacetonitrile as a white oil. $^1$H NMR (300 MHz, CDCl$_3$) d 7.31 (m, 2H), 7.08 (m, 2H), 3.65 (d, 1H), 2.12 (m, 1H), 1.07 (d, 3H), 1.03 (d, 3H).

Step (b): α-(3-chloropropyl)-4-fluoro-2-(1-methylethyl)benzeneacetonitrile n-Butyllithium (1.5M, 20.7 mL) was added to a chilled (0° C.) solution of diisopropylamine (4.34 mL, 31 mmol) in tetrahydrofuran (60 mL). After 2–3 minutes, the flask was cooled to −78° C., and a solution of the product from Example 2, Step (a) (5.0 g, 28.2 mmol) in tetrahydrofuran (6 mL) was added over a three minute period. After allowing the yellow anion to stir for 40 minutes, 1-bromo-3-chloro-propane (3.06 mL, 31 mmol) was added, the bath was removed, and the mixture was allowed to stir at ambient temperature for 1 hour. Solvent was removed by rotary evaporation. The crude product was diluted with ether (150 mL) and the ether layer was washed with water (20 mL). The ether layer was dried using MgSO$_4$ and concentrated. The residue was diluted with dichloromethane and filtered through a silica plug, rinsing with additional dichloromethane. Concentration afforded the title compound as an oil product characterized by NMR as follows: NMR(CDCl$_3$, 400 MHz, partial): 3.48 (m, 2 h), 1.21 (d, 3H, J=6 Hz), 0.78 (d, 3H, J=6 Hz); $^{13}$CNMR(CDCl$_3$, 100 MHz, partial): 52.8, 44.5, 38.0, 35.2, 28.5, 18.8, 18.5.

Step (C): Preparation of 4-fluoro-α-(1-methylethyl)-α-[3-[methyl(phenylmethyl)amino]-propyl]benzeneacetonitrile, monohydrochloride The product from Example 2, Step (b) (2.61 g, 10.3 mmol) was diluted with dimethylformamide (6 mL). N-benzylmethylamine (1.42 mL, 11 mmol), diisopropylethylamine (1.91 mL, 11 mmol) and tetrabutylammoniumbromide (300 mg) were added and the mixture was stirred at 57° C. overnight, then at 77° C. for an additional 24 hours. The mixture was diluted with water (10 ml) and extracted with ethylacetate (100 mL, then 2×10 mL). The combined organic layers were dried over MgSO$_4$, filtered through silica, and concentrated. Chromatography in silica gel afforded the free base, which was converted to the hydrochloride salt using hydrogen chloride gas in dichloromethane. The salt was recrystallized from a mixture of dichloromethane, methyl acetate and hexane, and characterized by NMR as follows: Analysis calcd. for C₂₂H₂₈ClFN₂: C, 70.48; H, 7.53; N, 7.47; Found: C, 70.09; H, 7.52; N, 7.33; ¹³CNMR free base (CDCl₃, 100 MHz, partial): 62.2, 56.5, 53.1, 42.1, 37.9, 35.5, 23.4, 18.8, 18.6.

EXAMPLE 3

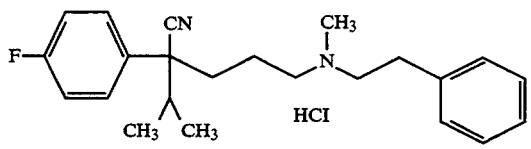

(±)-4-fluoro-α-(1-methylethyl)-α-[3-[methyl(2-phenylethyl)amino]propyl]benezeneacetonitrile, monohydrochloride Preparation of 4-fluoro-α-(1-methylethyl)-α-[3-methyl(phenylethyl)amino]-propyl]benzeneacetonitrile, monohydrochloride The product from Example 2, Step (b) (2.048 g, 8.06 mmol) was diluted with N,N-dimethylformamide (4.8 mL). N-methylphenethylamine (2.46 mL, 16.9 mmol) and tetrabutylammonium iodide (150 mg) were added, and the mixture was stirred under argon at 70° C. overnight. The reaction mixture was diluted with water (50 mL) and extracted with ethyl acetate (100 mL, then 2×20 mL). The combined organic layers were dried over MgSO₄, concentrated, and subjected to silica gel chromatography. The product was converted to its hydrochloride salt using hydrogen chloride gas in dichloromethane. A product compound was obtained by recrystallization from a mixture of dichloromethane/methylacetate/hexane, and characterized by NMR as follows: ¹³NMR free base (CDCl₃, 100 MHz, partial): 59.1, 56.8, 53.1, 41.9, 37.9, 35.5, 33.6, 23.4, 18.8, 18.6; Analysis calcd. for C₂₃H₃₀ClFN₂: C, 71.02; H, 7.77; N, 7.20; Found: C, 70.71; H, 7.85; N, 7.15.

EXAMPLE 4

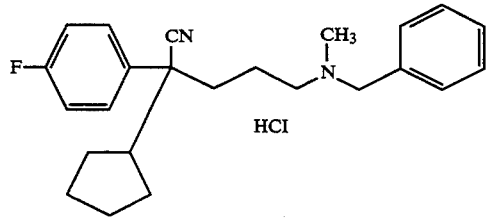

(±)-α-cyclopentyl-4-fluoro-α-[3-(methyl(phenylmethyl)amino]propyl]benzeneacetonitrile, monohydrochloride Step (a): Preparation of α-(4-Fluorophenyl)cyclopentaneacetonitrile 4-Fluorophenylacetonitrile (10 g, 74 mmol) was combined with tetrabutylammonium bromide (2.76 g), 50% sodium hydroxide (38 g), and sodium hydroxide pellets (8.5 g, 213 mmol). The flask was warmed to 50° C. (internal) and bromocyclopentane (8.57 mL, 80 mmol) was added over a 5 minute period. The temperature was raised to 100° C. and maintained for 30 minutes. Workup consisted of pouring the reaction mixture onto ice (100 mL) and extracting with ether (100 mL, then 2×50 mL). The combined ethereal extracts were washed with saturated with sodium chloride solution (20 mL), dried using MgSO₄, filtered through silica, and concentrated. The residue was subjected to vacuum distillation, affording the a product compound as an oil, which was characterized as follows: 13CNMR(CDCl₃, 100 MHz, partial): 45.3, 41.7, 30.9, 30.2, 24.9, 24.8. NMR(CDCl₃, 400 MHz, partial): 3.72 (d, 1H, J=7 Hz).

Step (b): Preparation of α-(3-chloropropyl)-α-(4-fluorophenyl)cyclopentaneacetonitrile n-Butyllithium (5.56 mL, 1.6M) was added to a chilled (0° C.) solution of diisopropylamine (1.25 mL, 8.90 mmol) in tetrahydrofuran (16 mL). After 2–3 minutes, the flask was cooled to −78° C., and the product from Example 4, Step 6 (1.61 g, 7.95 mmol) in tetrahydrofuran (ca. 4mL) was added over three minutes. The anion was allowed to form over 45 minutes. 1-bromo-3-chloro-propane (0.88 mL, 8.9 mmol) was added, the cooling bath was removed, and the reaction was stirred at ambient temperature for 1 hour. The mixture was concentrated, then diluted with dichloromethane and filtered through a silica gel plug. Final concentration afforded the a product compound as an oil, which was characterized by MNR as follows: NMR (CDCl₃, 300 MHz, partial): 3.50 (m, 2H).

Step (C): Preparation of α-4-fluorophenyl-α-[3-[methyl(phenylmethyl)amino]propyl]cyclopentaneacetonitrile, monohydrochloride.

The product from Example 4, Step (b) (1.99 g, 7.06 mmol) was combined with N-benzylmethylamine (1.82 mL, 14.1 mmol), N,N-dimethylformamide (3.5 mL) and tetrabutylammonium iodide (130 mg). The mixture was heated at 50° C. overnight, then diluted with water (25 mL) and extracted with ethyl acetate (100 mL, then 2×25 mL). The combined organic layers were dried over MgSO₄, filtered through silica, concentrated and subjected to chromatography. The product was converted to the hydrochloride salt using hydrogen chloride gas in methylene chloride. The salt was recrystallized from dichloromethane/methyl acetate/hexane, affording the a product compound which was characterized as follows: ¹³C NMR of free base (CDCl₃), 100 MHz, partial): 62.1, 56.5, 52.4, 50.1, 42.0, 37.2, 29.5, 29.2, 25.4, 24.8, 23.1; Analysis Cal'd. for C₂₄H₃₀ClFN₂. 0.25 H₂O: C, 71.09; H, 7.58; N, 6.91; Found: C, 70.92; H, 7.53; N, 6.84.

EXAMPLE 5

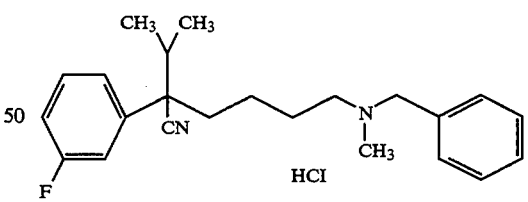

(±)-4-fluoro-α-(1-methylethyl)-α-[4-(methyl(phenylmethyl)amino]butyl]benzeneacetonitrile, monohydrochloride Step (a): Preparation of α-(4-chlorobutyl)-4-fluoro-α-(1-methylethyl)benzeneacetonitrile n-Butyllithium (1.5 m, 9.0 mL) was added to a chilled (0° C.) solution of diisopropylamine (1.90 mL, 13.5 mmol) in tetrahydrofuran (27 mL). After 2–3 minutes, the flask was cooled to −78° C. The product from Example 2, Step (a) (2.0 g, 11.3 mmol) in tetrahydrofuran (3 mL) was introduced over 3 minutes. The bright-yellow anion was allowed to form over a 40 minute period, at which point, 1-bromo-4-chloro-butane (1.38 mL, 12 mmol) was added and the bath was removed.

After 1 hour at ambient temperature, the reaction mixture was concentrated, diluted with ether (100 mL), and washed with water (15 mL). The organic layer was dried over MgSO4 and concentrated. The residue was diluted with 1:1 dichloromethane/hexane, filtered through silica, rinsing with additional solvent, and concentrated to afford a compound as an oil. The structure of the compound was characterized by NMR as follows: NMR(CDCl3, 400 MHz, partial): 3.43 (M, 2H), 1.20 (d, 3H, J=6 HZ); 0.78 (d, 3H, J=6 Hz).

Step (b): Preparation of 4-fluoro-α-(1-methylethyl)-α-[3-[methyl(phenylmethyl)-amino]butyl]benzeneacetonitrile, monohydrochloride The product from Example 5, Step (a) (0.471 g, 1.76 mmol) was combined with N,N-dimethylformamide (1 mL), N-benzylmethylamine (0.295 mL, 1.9 mmol), diisopropylethylamine (0.301 mL, 1.76 mmol), and tetrabutylammonium iodide (20 mg). The mixture was maintained at 60° overnight, stirred an additional 3 hours at 75° C. The crude product was diluted with ethyl acetate (100 mL) and washed with half-saturated sodium bicarbonate (20 mL). The aqueous layer was extracted with additional ethyl acetate (2×10 mL). The combined organic phases were dried over MgSO4, concentrated, and subjected to silica gel chromatography. The hydrochloride salt was prepared by dissolving the product in methylene chloride and introducing gaseous hydrogen chloride. A product compound was obtained by recrystallization from ethanol/ethyl acetate. The structure of the title compound was confirmed by NMR. Analysis calc'd. for C23H30ClFN2. 0.2H2O: C, 70.37; H, 7.81; N, 7.19; Found: C, 70.41; H, 7.84; N, 7.13.

EXAMPLE 6

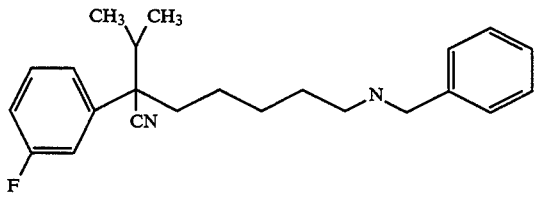

(±)-4-fluoro-α-(1-methylethyl)-α-[5-(methyl(phenylmethyl)amino]pentyl]benzeneacetonitrile Step (a): Preparation of α-(5-chloropentyl)-4-fluoro-α-(1-methylethyl)benzeneacetonitrile n-Butyllithium (1.6 m, 4.88 mL) was added to a chilled (0° C.) solution of diisopropylamine in tetrahydrofuran (10 mL). After 2-3 minutes, the flask was chilled to −78° C., and the product from example D (1.15 g, 6.50 mmol) in tetrahydrofuran (3 mL) was added over 3 minutes. After allowing 40 minutes at −78° C. for anion formation, 1-bromo-α-chloro-pentane (0.92 mL, 7.0 mmol) was introduced. The bath was removed and the mixture was stirred for 1 hour at ambient temperature. The crude product was concentrated, taken up into ether (100 mL), and the ethereal solution was washed with eater (15 mL). The organic layer was dried over MgSO4, concentration and then diluted with 1:1 dichloromethane/hexane. Filtration through silica was followed by concentration, affording a compound as an oil and a structure verified by NMR as a-(5-chloropentyl)-4-fluoro-α-(1-methylethyl)benzeneacetonitrile.

Step (b): Preparation of 4-fluoro-α-(1-methylethyl)-α-[3-[methyl(phenylmethyl)amino]-pentyl]benzeneacetonitrile The product from Example 6, Step (a) (0,538 g, 1.91 mmol) was combined with N-benzylmethylamine (0.28 mL, 2.2 mmol), N,N-dimethylformamide (1.3 mL), diisopropylethylamine (0.33 mL, 1.91 mmol), and tetrabutylammonium iodide, and the mixture was then stirred at 70° C. overnight. Upon cooling, the reaction product was diluted with ethyl acetate (50mL) and washed with half-saturated sodium bicarbonate (30 mL). The aqueous layer was extracted with additional ethyl acetate (2×30 mL). The combined organic was dried over MgSO4, and the crude product was concentrated. Silica gel chromatography, using diethyl ether as the eluent, followed by concentration, afforded a product compound as an oil which was characterized by NMR as follows: NMR (free base) (CDCl3, 400 MHz, partial): 3.91 (s, 2H); 2.13 (s, 3H); 1.18 (d, 3H, J=6 Hz); 0.75 (d, 3H, J=6 Hz); Analysis calc'd. for C24H31FN2: C, 78.64; H, 8.53; N, 7.64; Found: C, 78.54; H, 8.52; N, 7.84

EXAMPLE 7

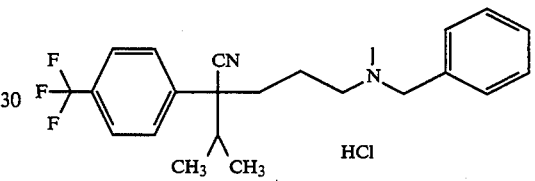

(±)-α-(1-methylethyl)-α-[3-[methyl(2-phenylethyl)amino]propyl]-4-(trifluoromethyl)benzeneacetonitrile, monohydrochloride Step (a): Preparation of 4-trifluoromethyl-α-(1-methylethyl)benzeneacetonitrile To a mixture of 4-trifluoromethyl-phenylacetonitrile (5.00 g, 27.0 mmoles), 50% aqueous sodium hydroxide solution (1.9 g), sodium hydroxide (270 mg), and tetra n-butylammonium chloride (1.2 g) stirring in a 60° oil bath was added 2-bromopropane (3.32 g, 27.0 mmoles). The resulting mixture was stirred at 80° for 0.5 hours, and then at 90°-95° for 1.0 hours longer. After cooling, the mixture was partitioned between toluene and water. The organic layer was washed with water, dried over anhydrous sodium sulfate, filtered and then evaporated. Chromatography of the residue over silica gel using 10% ethyl acetate-hexane as eluent gave the title compound (3.95 g) as an orange oil which was characterized by NMR as follows: 1H NMR (CDCl3) d 7.67 (d, 2H), 7.48 (d, 2H), 3.77 (d, 1H), 2.18 (m, 1H), 1.13 (d, 3H), 1.06 (d, 3H).

Step (b): (±)-4-trifluoromethyl-α-(1-methylethyl)-α-(3-chloro-propyl)benzeneacetonitrile To a solution consisting of a 0.5M solution of bis(-trimethylsilyl)amide in toluene (2.2 mL, (1.1 mmoles) and tetrahydrofuran (7.8 mL) stirring at −78° under an argon atmosphere was added dropwise a solution of the compound of Example 7, Step (a) (227 g, 1.00 mmole) in tetrahydrofuran (1.0 mL). After stirring for 1.0 hour at −78°, 3-bromo-1-chloropropane (236 mg 1.50 mmoles) was added in one portion, and the resulting mixture was stirred for 30 minutes at −78° and then 2.0 hours at room temperature. The mixture was partitioned between diethyl ether and water, the aqueous layer was extracted with ether, and the combined organic extracts were washed with water and then brine. After drying over sodium sulfate, the solution was filtered and then evaporated. A compound (271 mg) was obtained as a red oil which was characterized by NMR as follows: $^1$H NMR(CDCl$_3$) d 7.65 (d, 2H), 7.53 (d, 2H), 3.48 (m, 2H), 1.19 (d, 3H), 0.79 (d, 3H).

Step (c): Preparation of title compound.

A mixture of the product of Example7, Step (b) (271 mg, 0.89 mmole), methyl benzylamine (2.42 mg, 2.00 mmoles), tetra-n-butylammonium iodide (37 mg, 10 mmole %), and anhydrous potassium carbonate (2.76 mg, 2.00 mmoles) in 1.0 mL DMF was stirred overnight at 80°–86°. After cooling, the mixture was partitioned between diethyl ether and water. The aqueous layer was extracted with ether, the combined organic extracts were washed with brine, dried over magnesium sulfate, filtered and the solvent evaporated. Chromatography of the residue over silica gel using 20% ethyl acetate-hexane as eluent gave the title compound as the free base. A methanol solution of the free base was acidified with a solution of hydrochloric chloride in methanol, the solvent evaporated, and the residue crystallized from ethyl acetate-hexane to give a product compound (53 mg) as a white crystalline solid, characterized as follows: Analysis for C$_{23}$H$_{28}$ClF$_3$N$_2$¼ H$_2$O (mw 429.44): Calculated: C, 64.35; H, 6.69; N, 6.52; Found: C, 64.60; H, 6.70; N, 6.52.

EXAMPLE 8

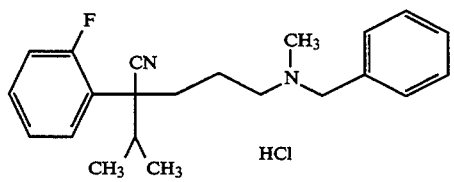

(±)-2-fluoro-α-(1-methylethyl)-α-[3-[methyl(phenylmethyl)amino]propyl]benzeneacetonitrile, monohydrochloride Step (a): Preparation of 2-fluoro-α-(1-methylethyl)benzeneacetonitrile A mixture of 2-fluorophenylacetonitrile (10.0 g, 74.1 mmoles), 50% aqueous sodium hydroxide (5.2 g), sodium hydroxide (741 mg), tetra-n-butylammonium chloride (3.3 g), and 2-bromopropane (10.0 g, 81.5 mmoles) was stirred rapidly while heating from room temperature to 60°–65°. The temperature was increased to 90°–95 and so maintained for 1.0 hour. After cooling, the mixture was partitioned between diethyl ether and water. The organic layer was washed with brine, dried over sodium sulfate, filtered, and the solvent evaporated. Chromatography of the residue over silica gel using 30% methylene chloride-hexane as eluent gave a compound (9.35 g) as a water-white oil which was characterized by NMR, as follows: $^1$H NMR(CDCl$_3$) d 7.51–7.00 (m, 4H), 3.99 (d, 1H), 2.22 (m, 1H), 1.06 (d, 1H).

Step (b): Preparation of (±)-2-fluoro-α-(1-methylethyl)-α-(3-chloropropyl)-benezeneacetonitrile To a mixture of a 0.5M solution of potassium bis(trimethylsilyl)amide (12.4 mL and tetrahydrofuran (44 mL) stirring at −78° under argon was added dropwise a solution of the title product of Example 8, Step (a) (1.00 g) in tetrahydrofuran (2 mL). After stirring at −78° for 0.5 hour, 1-bromo-3-chloropropane (1.3 g) was added, and the mixture was stirred while being permitted to warm to room temperature. The mixture was partitioned between diethyl ether and saturated aqueous ammonium chloride, the aqueous layer was extracted with two portions of ether, the combined organic extracts washed with brine, dried over magnesium sulfate, filtered and evaporated to give a compound (1.20 g) which was characterized by NMR, as follows: $^1$H NMR(CDCl$_3$) d 7.64–7.00 (m, 4H), 3.50 (t, 2H), 1.24 (d, 3H), 0.82 (d, 3H).

Step (C): Preparation of (±)-2-fluoro-α-(1-methylethyl)-α-[3-methyl[methyl(phenylmethyl)amino]-propyl]benzeneacetonitrile To a mixture of the product compound of Example 8, Step (b) (508 mg, 2.00 mmoles), methyl benzylamine (484 mg, 4.00 mmoles), and tetra-n-butylammonium iodide (74 mg) in dry dimethylformamide (2.0 mL) was added anhydrous potassium carbonate (552 mg, 4.00 mmol). The mixture was stirred overnight at 80°–85°. After cooling, the mixture was partitioned between diethyl ether and water, the aqueous layer was extracted with ether, the combined organic extracts were washed with brine, dried over sodium sulfate, filtered and the solvent evaporated. Chromatography of the residue over silica gel using 25% ethyl acetate-hexane as eluent gave a compound (540 mg) as an oil which was characterized by NMR, as follows: $^1$H NMR(CD$_2$Cl$_2$) d 7.63–6.95 (m, 9H), 1.22 (d, 3H), 0.82 (d, 3H).

Step (d):

A solution of the product of Example 8, Step (c) (470 mg) in methanol (10 mL) was acidified with a solution of hydrochloric acid in methanol. The solvent was evaporated, and the residue was dried by azeotropic distillation with toluene. Crystallization of the residue from ethyl acetate gave the title compound (333 mg) as a white, crystalline solid, m.p. 164° C., characterized as follows: Analysis for C$_{22}$H$_{28}$FN$_2$Cl (MW 374.93 ); Calc'd: C, 70.47; H, 7.53; N, 7.47; Found: C, 70.36; H, 7.54; N, 7.42.

EXAMPLE 9

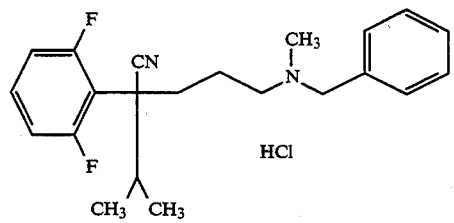

(±)-2,6-difluoro-α-(1-methylethyl)-α-[3-[methyl(phenylmethyl)amino]propyl]benzeneacetonitrile, monohydrochloride Step (a): Preparation of 2,6-difluoro-α-(1-methylethyl)-benzeneacetonitrile A mixture of 2,6-difluorophenylacetonitrile (10.0 g, 5.4 mmoles), 50% aqueous sodium hydroxide (4.6 g), sodium hydroxide (653 mg), tetra-n-butylammonium bromide (2.90 g and 2-bromopropane (8.85 g, 71.9 mmoles) was stirred while heating to 80°–85° over 1.0 hours, and then maintained at that temperature for 2.0 hours. After cooling, the mixture was partitioned between diethyl ether and water, the aqueous layer extracted with ether and the combined organic extracts washed with brine, dried over magnesium sulfate, filtered and the solvent evaporated. The residue was distilled to give a product compound (9.64 g) as a water-white liquid, b.p. 92°–94° (3 mm) which was characterized by NMR as follows: $^1$H NMR (CDCl)$_3$ d 7.32 (m, 1H), 6.95 (m, 2H), 3.84 (d, 1H), 2.32 (m, 1H), 1.24 (d, 3H), 0.89 (d, 3H).

Step (b): Preparation of (±)-2,6-difluoro-α-(1-methylethyl)-α-(3-chloro-propyl)benzeneacetonitrile To a mixture of a 0.5M solution of potassium bis(trimethylsilyl)amide in toluene (53.2 mL) and tetrahydrofuran (152 mL) stirring at −78° under argon was added dropwise a solution of the title product of Example 8, Step (a) (4.00 g, 20.5 mmoles) in tetrahydrofuran (10 mL). After stirring at −78° for 30 min. 1-bromo-3-chloro propane (4.8 g, 31 mmoles) was added, and stirring was continued while permitting the mixture to warm to room temperature. The mixture was washed with saturated aqueous ammonium chloride, the aqueous layer extracted with diethyl ether, the combined organic extracts washed with brine, dried over magnesium sulfate, filtered and the solvent evaporated to give a compound (4.16 g) as a water-white oil which was characterized by NMR, as follows: $^1$H NMR(CDCl$_3$) d 7.29 (m, 1H), 6.92 (m, 2H), 3.54 (m, 2H), 1.18 (d, 3H), 0.96 (d, 3H). Step (c): Preparation of title compound.

Step (c): Preparation of title compound.

To a mixture of the product compound of Example 8, Step (b) (508 mg, 1.87 mmoles, methyl benzylamine (484 mg, 4.00 mmoles), tetra-n-butylammonium iodide (74 mg), and dimethylformamide (2.0 mL) was added anhydrous potassium carbonate (552 mg, 4.00 mmoles. The resulting mixture was then stirred overnight at 80°–85° C. After cooling, the mixture was partitioned between diethyl ether and water, and the aqueous layer was extracted with ether. The combined organic extracts were washed with brine, dried over sodium sulfate, filtered, and the solvent evaporated. Chromatography of the residue over silica gel using 25% ethyl acetate-hexane as eluent gave the free base of the title compound. The free base was dissolved in methanol and acidified with a solution of hydrochloric acid in methanol. Evaporation of the solvent followed by trituration of the residue with diethyl ether gave the title compound (153 mg) as a white crystalline solid, m.p. 155° C., which was characterized as follows: Analysis for C$_{22}$H$_{37}$ClF$_2$N$_2$ (MW 392.92): Calc'd: C, 67.24; H, 6.93; N, 7.13; Found: C, 67.16; H, 6.98; N, 7.05.

EXAMPLE 10

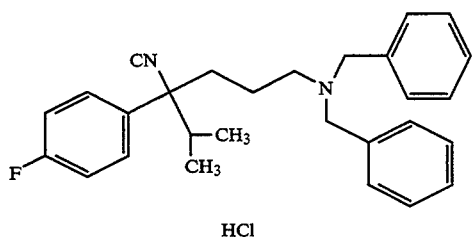

HCl (±)-α-[3-[bis(phenylmethyl)amino]propyl]-4-fluoro-α-(1-methylethyl)benzeneacetonitrile, monohydrochloride Step (a): Preparation of (±)-4-fluoro-α-(1-methylethyl)-α-[3-bis(phenylmethyl)amino]propyl]benzeneacetonitrile To a solution of the title product of Example 5, Step (a) (508 mg, 2.00 mmoles), dibenzylamine (788 mg, 4.00 mmoles), tetra-n-butylammonium iodide (74 mg), and dimethylformamide (2.0 mL) was added anhydrous potassium carbonate (552 mg, 4.00 mmoles). The resulting mixture was stirred overnight at 80°–85° C. After cooling, the mixture was partitioned between diethyl ether and water, the aqueous layer extracted with ether, combined organic extracts washed with brine, dried over sodium sulfate, filtered, and the solvent evaporated. Chromatography of the residue over silica gel using 5% ethyl acetate-hexane as eluent gave the title compound (264 mg) as an oil which was characterized by NMR as follows: $^1$H NMR(CD$_2$Cl$_2$) d 7.42–6.95 (m, 14H), 3.45 (s, 4H), 2.37 (t, 2H), 2.07 (m, 2H), 1.78 (ddd, 1H), 1.57 (m, 1H) 1.15 (d, 3H), 1.10 (m, 1H), 0.74 (d, 3H).

Step (b): Preparation of title compound.

A solution Of the title product of Example 10, Step (a) (264 mg) in methanol was acidified with a solution of hydrochloric acid in methanol. The solvent was evaporated and the residue was triturated with a mixture of diethyl ether and hexane to give the title compound (88 mg) as a white, crystalline solid m.p. 186° C., characterized as follows: Analysis for C$_{28}$H$_{32}$ClFN$_2$ (MW 451.03): Calc'd: C, 74.57; H, 7.15; N, 6.21; Found: C, 74.70; H, 7.26; N, 6.20.

EXAMPLE 11

Step (a): Preparation of (±)-4-Fluoro-α-(1-methylethyl)-α-[3-(methylamino)propyl]]benzeneacetonitrile

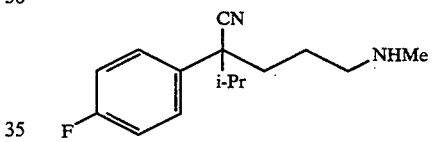

A solution of the title product of Example 2 step (a) (2.00 g, 7.87 mmoles) in toluene was treated with excess methylamine at 600 and 43 psi pressure for 48 hours. After cooling, the solvent was removed and the residue chromatographed over silica gel using 30% methanol-2.5% ammonium hydroxide-67.5% ethyl acetate as eluent to give the title compound (1.18 g) as a white solid. $^1$H NMR (300 MHz, CD$_2$Cl$_2$—CD$_3$OD) δ7.42 (m, 2H), 7.14 (m, 2H), 3.95 (m, 1H), 2.85 (m, 2H), 2.52 (s, 3H), 2.16 (m, 3H), 1.73 (m, 1H), 1.38 (m, 1H), 1.21 (d, 3H), 0.78 (d, 3H).

Step (b): Preparation of (±)-4-Fluoro-α-(1-methylethyl)-α-[3-(methylamino)propyl]]benzeneacetonitrile, hydrochloride

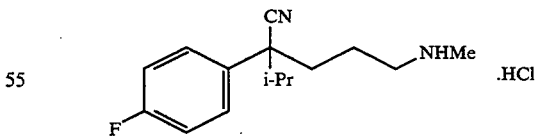

A solution of 250 mg of the title product of Example X+1 in methanol was acidified with a solution of hydrochloric acid in methanol. The solvent was removed and the residue triturated with diethyl ether to give the title compound (221 mg) as a white solid. Anal. Calcd. for C$_{15}$H$_{22}$ClFN$_2$. ¾ H$_2$O (MW 298.31): C, 60.41; H, 7.94; N, 9.39. Found: C, 60.24; H, 7.56; N, 9.58. $^1$H NMR (300 MHz, CD$_3$OD) δ7.49 (m, 2H), 7.19 (m, 2H), 2.97 (m, 2H), 2.62 (s, 3H), 2.23 (m, 2H), 2.07 (m, 1H), 1.68 (m, 1H), 1.32 (m, 1H), 1.22 (d, 3H), 0.78 (d, 3H).

EXAMPLE 12

(±)-4-fluoro-α-[3-[methyl(4-chlorophenylmethyl)amino]propyl]benzeneacetonitrile, hydrochloride

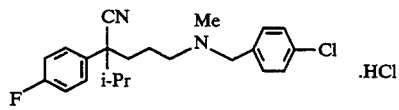

A mixture of the title product of Example 11 step (a) (450 mg, 1.81 moles), 4-chlorobenzylchloride (438 mg, 2.72 mmoles), and potassium carbonate (500 mg, 3.62 mmoles) in 3.6 ml of dimethylformamide was stirred overnight at ambient temperature. The mixture was partitioned between diethyl ether and water, extracted further with diethyl ether, the combined organic extracts dried over sodium sulfate, filtered, and the solvent removed. Chromatography of the residue over silica gel using 25% ethyl acetate-hexane as eluent gave the title product as the free base. A solution of the free amine in methanol was acidified with a solution of hydrochloric acid in methanol, and the solvent was removed. Trituration of the residue with diethyl ether gave the title compound as a white crystalline solid (498 mg). Anal. Calcd. for $C_{22}H_{27}Cl_2N_2$ (MW 409.38): C, 64.56; H, 6.65; N, 6.84. Found: C, 64.47; H, 6.72; N, 6.80. $^1$H NMR (400 MHz, $CD_2Cl_2$) δ7.64–7.34 (m, 6H), 7.13 (m, 2H), 4.13–3.95 (m, 1H), 3.02–2.67 (m, 2H), 2.54 (m, 3H), 2.25 (m, 1H), 2.11 (m, 1H), 1.98–1.66 (m, 3H), 1.51 (m, 1H), 1.17 (d, 3H), 0.75 (d, 3H).

EXAMPLE 13

(±)-4-fluoro-α-[3-[methyl(4-fluorophenylmethyl)amino]propyl]benzeneacetonitrile, hydrochloride

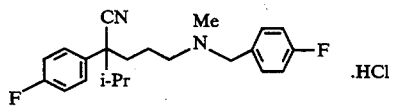

A mixture of the title product of Example 11 step (a) (418 mg, 1.69 mmoles), 4-fluorobenzyl bromide (284 mg, 2.53 mmoles) and potassium carbonate (465 mg, 3.37 mmoles) in 3.4 ml of dimethylformamide was stirred overnight at ambient temperature. The mixture was partitioned between diethyl ether and water, further extracted with diethyl ether, the combined organic extracts dried over sodium sulfate, filtered, and the solvent removed. Chromatography of the residue over silica gel using 40% ethyl acetate-hexane as eluent gave the title product as the free base. The free amine was dissolved in methanol, acidified with a solution of hydrochloric acid in methanol, the solvent removed, and the residue triturated with diethyl ether to give the title compound as a pure white crystalline solid (390 mg). Anal. Calcd. for $C_{22}H_{27}ClF_2N_2$ (MW 392.92): C, 67.24; H, 6.93; N, 7.13. Found: C, 67.10; H, 6.89; N, 7.00. $^1$H NMR (200 MHz, $CD_2Cl_2$) δ12.72 (m, 1H), 7.68–7.33 (m, 4H), 7.13 (m, 4H), 4.02 (m, 2H), 2.88 (m, 2H), 2.53 (m, 3H), 2.35–1.65 (m, 4H), 1.52 (m, 1H), 1.16 (d, 3H), 0.75 (d, 3H).

BIOLOGICAL EVALUATION

ASSAY A: Suppression of Mitogen-Stimulated Proliferation (Murine) (Culture Conditions I)

Lymphocyte activation can be polyclonally stimulated by plant lectins and other mitogens that induce blast transformation and mitosis. Certain mitogens like Concanavalin A (ConA), preferentially activate T-lymphocytes. Exposure to ConA results in polyclonal activation of T-cells and can be used as an in vitro index for general immunomodulation of pan T-cell activity. In this assay spleen cells harvested from female Balb/c mice were incubated at 37° C., in 95% air/5% $CO_2$ atmosphere in 96 well microtiter plates ($10^5$ cells/well) for 5 days with Iscove's modified Dulbecco's medium [25 mM HEPES 2 mM L-glutamine, 5% fetal bovine serum and 2-mercaptoethanol (40 μM)], concanavalin A (ConA)alone (Sigma, St. Louis, Mo.; 1.0 μg/ml) or ConA in the presence of test compounds (0.001–25 μM). Inhibition of ConA-stimulated proliferation was measured by addition of the colorimetric indicator of growth metabolic activity or viability, MTT (3-(4,5-dimethylthiazol-2-yl)-2 diphenyl tetrazolium bromide; (100 μl/well, 1 mg/ml) Sigma) [Mosmann, T., J. of Immunological Methods, 65, 55–63, 1988]. After four hours, plates were centrifuged (1200 rpm) media supernatants aspirated and dye loaded cells were solubilized in isopropanol (150 μl/well). The absorbance was measured on an ELISA plate reader with a test wavelength of 570 nm and a reference of 630nm. The $IC_{50}$ values for active immunosuppressant compounds were calculated by four parameter logistic regression analysis of the results [Delean et al, Am. J, Physiol., 235, 397 (1978)]. Results are shown in Table I.

Assay B: Suppression of Mitogen-Stimulated Proliferation(Murine) (Culture Conditions II.)

It is known that lymphocyte activation can be polyclonally stimulated by plant lectins and other mitogenic substances that induce blast transformation and mitosis. The plant lectin concanavalin A (conA) preferentially induces activation and proliferation of T lymphocytes. Exposure of T cells to conA results in polyclonal T cell activation, and this response can be used to determine the in vitro index of immunomodulatory effects of test compounds on pan-T cell activation. Spleen cells were harvested asceptically from female Balb/c mice, and cells were extruded by compression in phosphate buffered saline (pH 7.0). Cells were pelleted by centrifugation (300×g/5 min) and erythrocytes were lysed by resuspension of the splen cells in a hypotonic solution (5 ml per spleen) containing 0.14M $NH_4Cl$ and 0.017M Tris base, pH 7.2, and incubation for 5 min. An equal volume of freshly prepared medium [Iscove's modified Dulbecco's medium containing 2 mM L-glutamine, 5% heat inactivated (56° C./45 min) fetal bovine serum and 40 uM 2-mercaptoethanol] was added to stop cell lysis. The remaining cells were pelleted, resuspended in medium, filtered through a cotton plug to remove debris, and the leukocytes were then counted. Leukocytes ($10^5$ cells per 100 ul per well) were incubated at 37° C. in a 95% air/6% $CO_2$ atmosphere in 96 well microtiter plates for 3 days. At the start of culture conA (1 ug/ml, SIGMA Chemical Co., St. Louis, Mo.) alone or in combination with test compound (0.0001–60 uM final) or vehicle control (0.6% DMSO or ethanol). All test compounds were dissolved in 95% ethanol or 100% DMSO, and subsequent dilutions were prepared in media. Inhibition of conA stimulated T cell proliferation was measured using a colorimetric indicator of cell growth and proliferation, MTT [3-(4,5-dimethylthiazol-2-yl)-2 diphenyltetrazolium bromide; 100 ul of a 1 mg/ml solution per well, SIGMA] [Mosmann, T., 1988. J. Immunol. Methods 65, 55–63.] Cells were loaded with MTT dye at 37° C. for 4 hours; media supernatants were then aspirated from the cell pellets. MTT loaded cells were solubilized in isopropanol (150 ul per well). Light absorbance was measured at a test wavelength of 570 nM and a reference wavelength of 650 nM using a spectrophotometer. $EC_{50}$ values for immunosuppressive compounds were estimated by four parameter logistical regression analysis of the optical density data [Delean, A., Munson, P. J. and D. Robard, 1978. Am,. J. Physiol. 235:397.

Assay C: One-Way Mixed Lymphocyte Reaction (Human)

The mixed lymphocyte reaction (MLR) is an assay that measures T-cell activation and mitosis which occurs when lymphocytes from different major and minor histocompatibility complex (MHC) haplotypes are cocultured. This response is considered a "one-way MLR" when stimulator cells are made unresponsive by inhibition of DNA synthesis (treatment with mitomycin-C or gamma-irradiation) prior to coculture with responder cells. This assay can be used as an indicator of the cellular immunomodulation mechanisms involved in transplant rejection. In this assay, human peripheral blood mononuclear cells (PMNC) were used as the responder cell population and were isolated from normal donor blood as follows: Blood samples were collected in LeucoPREP ™ tubes (Becton Dickinson, Lincoln Park, N.J.) and the mononuclear cell preparation was obtained by following the manufacturers procedures. Isolated mononuclear cells were co-incubated at $6 \times 10^4$ cells/well with a stimulator cell line at $2 \times 10^4$ cells/well in RPMI 1640 medium containing 5% fetal bovine serum and 2-mercaptoethanol (40 $\mu$M). The stimulator cell line, Raji, which was derived from a human Burkitt lymphoma (American Type Culture Collection, Rockville Md.) was previously inactivated by mitomycin-C treatment (Sigma, St. Louis Mo., 25 $\mu$g/ml, 37° for 30 minutes). After repeated washings of mitomycin-C from the stimulator cell line, cocultures were incubated in 96 well microtiter plates at 37° C., in 95% air/5% $CO_2$ atmosphere for 120 hours in the presence or absence of test compounds (0.1-25 $\mu$M). Inhibition of proliferation was measured by reduced incorporation of $^3$H-thymidine (0.5 $\mu$Ci/well, added during the last 24 hours of the assay). The $IC_{50}$ values for the immunosuppressant compounds were calculated by four parameter logistic regression analysis of the results [Delean et al, Id.] Results are shown in Table I.

TABLE I

| In Vitro Suppression of Immune Response | | | |
|---|---|---|---|
| Test Compound of Example # | Assay A[1] $IC_{50}$ ($\mu$M) | Assay B[2] $IC_{50}$ ($\mu$M) | Assay C[3] $IC_{50}$ ($\mu$M) |
| 1 | NT | 2.41 | NT |
| 2 | 2.2 | 5.19 | 7.2 |
| 3 | 1.0 | 3.22 | 4.8 |
| 4 | 3.2 | 4.81 | 2.3 |
| 5 | 0.9 | 1.76 | 2.1 |
| 6 | 0.5 | 0.93 | NT |
| 7 | 1.4 | 1.98 | 2.4 |
| 8 | 1.4 | 3.35 | 2.9 |
| 9 | NT | 4.15 | NT |
| 10 | NT | 13.52 | NT |
| 11 | NT | NT | NT |
| 12 | NT | NT | NT |
| 13 | NT | NT | NT |

NT = Not Tested
[1]Assay A: Suppression of Mitogen-Stimulated Proliferation (Murine)(Culture Conditions I.)
[2]Assay B: Suppression of Human Mitogen Stimulated Proliferation (Murine)(Culture Conditions II.)
[3]Assay C: One-Way Mixed Lymphocyte Reaction (Human)

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of Formula III:

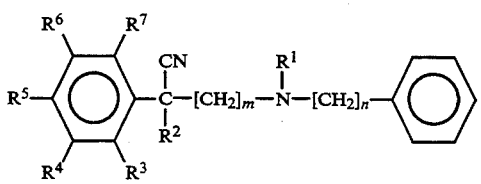

(III)

wherein m is a number selected from three to five, inclusive;
wherein n is one or two;
wherein R¹ is selected from methyl, ethyl, n-propyl, isopropyl, n-butyl, sec-butyl, tert-butyl, iso-butyl, n-pentyl, isopentyl, cyclopropyl, cyclobutyl, cyclopentyl, cyclohexyl, cyclopropylmethyl, cyclobutylmethyl, cyclopentylmethyl, cyclohexylmethyl, benzyl and phenethyl;
wherein R² is selected from methyl, ethyl, n-propyl, isopropyl, n-butyl, sec-butyl, tert-butyl, iso-butyl, n-pentyl, isopentyl, cyclopropyl, cyclobutyl, cyclopentyl, cyclohexyl, cyclopropylmethyl, cyclobutylmethyl, cyclopentylmethyl, cyclohexylmethyl, benzyl and phenethyl;
wherein each of R³ through R⁷ is selected from hydrido, fluoro, chloro, bromo, azide, trifluoromethyl, difluorochloromethyl, 1,1-difluoroethyl, 2,2,2-trifluoroethyl, perfluoroethyl and 2,2,3,3-tetrafluoropropyl;
with the proviso that at least one of R³ through R⁷ is selected from fluoro and trifluoromethyl;
or a tautomer thereof or a pharmaceutically-acceptable salt thereof.

2. Compound of claim 1 selected from compounds and their pharmaceutical salts of the group consisting of
(±)-3,4-difluoro-α-(1-methylethyl)-α-[3-[methyl(phenylmethyl)amino]propyl]benzeneacetonitrile;
(±)-4-fluoro-α-(1-methylethyl)-α-[3-[methyl(phenylmethyl)amino]propyl]benzeneacetonitrile;
(±)-4-fluoro-α-(1-methylethyl)-α-[3-[methyl(2-phenylethyl)amino]propyl]benzeneacetonitrile;
(±)-α-cyclopentyl-4-fluoro-α-[3-(methyl(phenylmethyl)amino]propyl]benzeneacetonitrile;
(±)-4-fluoro-α-(1-methylethyl)-α-[4-(methyl(phenylmethyl)amino]butyl]benzeneacetonitrile;
(±)-4-fluoro-α-(1-methylethyl)-α-[5-(methyl(phenylmethyl)amino]pentyl]benzeneacetonitrile;
(±)-α-(1-methylethyl)-α-[3-[methyl(2-phenylethyl)amino]propyl]-4-(trifluoromethyl)benzeneacetonitrile;
(±)-2-fluoro-α-(1-methylethyl)-α-[3-[methyl(phenylmethyl)amino]propyl]benzeneacetonitrile;
(±)-2,6-difluoro-α-(1-methylethyl)-α-[3-[methyl(phenylmethyl)amino]propyl]benezeneacetonitrile; and
(±)-α-[3-[bis(phenylmethyl)amino]propyl]-4-fluoro-α(1-methylethyl)benzeneacetonitrile.

3. A composition comprising a therapeutically-effective amount of an immunosuppressive compound and a pharmaceutically-acceptable carrier or diluent, said immunosuppressive compound selected from compounds of Formula III:

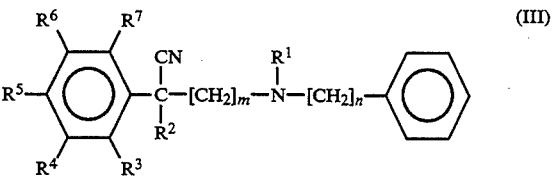

(III)

wherein m is a number selected from three to five, inclusive; wherein n is one or two;
wherein R¹ is selected from methyl, ethyl, n-propyl, isopropyl, n-butyl, sec-butyl, tert-butyl, iso-butyl, n-pentyl, isopentyl, cyclopropyl, cyclobutyl, cyclopentyl, cyclohexyl, cyclopropylmethyl, cyclobutylmethyl, cyclopentylmethyl, cyclohexylmethyl, benzyl and phenethyl;
wherein R² is selected from methyl, ethyl, n-propyl, isopropyl, n-butyl, sec-butyl, tert-butyl, iso-butyl, n-pentyl, isopentyl, cyclopropyl, cyclobutyl, cyclopentyl, cyclohexyl, cyclopropylmethyl, cyclobutylmethyl, cyclopentylmethyl, cyclohexylmethyl, benzyl and phenethyl;
wherein each of R³ through R⁷ is selected from hydrido, fluoro, chloro, bromo, azide, trifluoromethyl, difluorochloromethyl, 1,1-difluoroethyl, 2,2,2-trifluoroethyl, perfluoroethyl and 2,2,3,3-tetrafluoropropyl;
with the proviso that at least one of R³ through R⁷ is selected from fluoro and trifluoromethyl;
or a tautomer thereof or a pharmaceutically-acceptable salt thereof.

4. The composition of claim 3 wherein said immunosuppressive compound is selected from compounds and their pharmaceutical salts of the group consisting of
(±)-3,4-difluoro-α-(1-methylethyl)-α-[3-[methyl(phenylmethyl)amino]propyl]benzeneacetonitrile;
(±)-4-fluoro-α-(1-methylethyl)-α-[3-[methyl(phenylmethyl)amino]propyl]benzeneacetonitrile;
(±)-4-fluoro-α-(1-methylethyl-α-[3-[methyl(2-phenylethyl)amino]propyl]benzeneacetonitrile;
(±)-α-cyclopentyl-4-fluoro-α-[3-(methyl(phenylmethyl)amino]propyl]benzeneacetonitrile;
(±)-4-fluoro-α-(1-methylethyl)-α-[4-(methyl(phenylmethyl)amino]butyl]benzeneacetonitrile;
(±)-4-fluoro-α-(1-methylethyl-α-[5-(methyl(phenylmethyl)amino]pentyl]benzeneacetonitrile;
(±)-α-(1-methylethyl)-α-[3-[methyl(2-phenylethyl)amino]propyl]-4-(trifluoromethyl)benzeneacetonitrile;
(±)-2-fluoro-α-(1-methylethyl)-α-[3-[methyl(phenylmethyl)amino]propyl]benzeneacetonitrile;
(±)-2, 6-difluoro-α-(1-methylethyl)-α-[3-[methyl(phenylmethyl)amino]propyl]benzeneacetonitrile; and
(±)-α-[3-[bis(phenylmethyl)amino]propyl]-4-fluoro-α(1-methylethyl)benzeneacetonitrile.

* * * * *